(12) United States Patent
Garvey et al.

(10) Patent No.: US 7,595,313 B2
(45) Date of Patent: Sep. 29, 2009

(54) NITRIC OXIDE DONATING DIURETIC COMPOUNDS, COMPOSITIONS AND METHODS OF USE

(75) Inventors: David S. Garvey, Dover, MA (US); L. Gordon Letts, Dover, MA (US); Richard A. Earl, Westford, MA (US); Maiko Ezawa, Acton, MA (US); Xinqin Fang, Lexington, MA (US); Ricky D. Gaston, Malden, MA (US); Subhash P. Khanapure, Clinton, MA (US); Chia-En Lin, Concord, MA (US); Ramani R. Ranatunge, Lexington, MA (US); Cheri A. Stevenson, Haverhill, MA (US); Shiow-Jyi Wey, Billerica, MA (US)

(73) Assignee: NicOx, S.A. (FR)

( * ) Notice: Subject to any disclaimer, the term of this patent is extended or adjusted under 35 U.S.C. 154(b) by 0 days.

(21) Appl. No.: 12/136,531

(22) Filed: Jun. 10, 2008

(65) Prior Publication Data

US 2008/0255101 A1    Oct. 16, 2008

Related U.S. Application Data

(62) Division of application No. 11/360,599, filed on Feb. 24, 2006, now Pat. No. 7,396,829.

(60) Provisional application No. 60/655,414, filed on Feb. 24, 2005, provisional application No. 60/656,545, filed on Feb. 28, 2005, provisional application No. 60/685,027, filed on May 26, 2005, provisional application No. 60/692,228, filed on Jun. 21, 2005, provisional application No. 60/749,853, filed on Dec. 13, 2005.

(51) Int. Cl.
| | | |
|---|---|---|
| C07D 285/24 | (2006.01) | |
| C07D 417/04 | (2006.01) | |
| C07D 513/10 | (2006.01) | |
| A61K 31/549 | (2006.01) | |

(52) U.S. Cl. ........................................ 514/223.2; 544/6
(58) Field of Classification Search ..................... 544/6; 514/223.2
See application file for complete search history.

(56) References Cited

U.S. PATENT DOCUMENTS

| 3,252,975 | A | 5/1966 | de Stevens et al. |
|---|---|---|---|
| 3,254,076 | A | 5/1966 | Lund et al. |
| 4,559,340 | A | 12/1985 | Neustadt et al. |
| 4,675,324 | A | 6/1987 | Ueda et al. |
| 4,992,451 | A | 2/1991 | Koike et al. |
| 5,773,434 | A | 6/1998 | Larson et al. |
| 6,083,947 | A | 7/2000 | Granger et al. |
| 6,166,008 | A | 12/2000 | Johnson et al. |
| 6,811,965 | B2 | 11/2004 | Vodovotz et al. |
| 6,818,647 | B2 | 11/2004 | Wolff et al. |
| 6,864,280 | B2 | 3/2005 | Igarashi et al. |
| 2004/0043987 | A1 | 3/2004 | Gouliaev et al. |
| 2004/0053974 | A1 | 3/2004 | Takaoka et al. |
| 2004/0105818 | A1 | 6/2004 | Every et al. |
| 2004/0254176 | A1 | 12/2004 | Grigorieff et al. |
| 2005/0004145 | A1 | 1/2005 | Widder et al. |
| 2005/0038017 | A1 | 2/2005 | Wolff et al. |

FOREIGN PATENT DOCUMENTS

| EP | 0598770 | 7/1992 |
|---|---|---|
| EP | 1336602 | 8/2003 |
| EP | 1595540 | 11/2005 |
| FR | 6869 | 12/1966 |
| GB | 863474 | 3/1961 |
| GB | 899037 | 6/1962 |
| GB | 1129360 | 10/1968 |
| JP | 2-180867 | 7/1990 |
| WO | WO-97/26884 | 7/1997 |
| WO | WO-97/49692 | 12/1997 |
| WO | WO-98/09948 | 3/1998 |
| WO | WO-98/12185 | 3/1998 |
| WO | WO-99/21422 | 5/1999 |

(Continued)

OTHER PUBLICATIONS

Allen et al., J. Med Chem., 21: 838-840 (1978).
Braghiroli et al., J. Med. Chem., 45: 2355-2357 (2002).
Carter et al., Hypertension., 43: 4-9 (2004).
Costa et al., Clin. Exp. Pharmacol Physiol., 28: 528-532 (2001).
Cotter et al., Lancet, 351: 389-393 (1998).
Domanski et al., J. Am. Col. Cardiol., 42: 705-708(2003).
Feit et al., J. Med Chem 13: 1071-1075 (1970).

(Continued)

*Primary Examiner*—Kahsay T Habte
(74) *Attorney, Agent, or Firm*—Wilmer Cutler Pickering Hale and Dorr LLP

(57) ABSTRACT

The invention describes novel compositions and kits comprising at least one nitric oxide enhancing diuretic compound, or pharmaceutically acceptable salts thereof, and, optionally, at least one nitric oxide enhancing compound and/or at least one therapeutic agent. The invention also provides methods for (a) treating conditions resulting from excessive water and/or electrolyte retention; (b) treating cardiovascular diseases; (c) treating renovascular diseases; (d) treating diabetes; (e) treating diseases resulting from oxidative stress; (f) treating endothelial dysfunctions; (g) treating diseases caused by endothelial dysfunctions; (h) treating cirrhosis; (j) treating pre-eclampsia; (k) treating osteoporosis; (l) treating nephropathy; (m) treating peripheral vascular diseases; (n) treating portal hypertension; (o) treating central nervous system disorders; (p) treating metabolic syndrome; (q) treating sexual dysfunctions; and (r) hyperlipidemia. The nitric oxide enhancing diuretic compounds comprise at least one nitric oxide enhancing group linked to the diuretic compound through one or more sites such as carbon, oxygen and/or nitrogen via a bond or moiety that cannot be hydrolyzed.

12 Claims, 2 Drawing Sheets

FOREIGN PATENT DOCUMENTS

| | | |
|---|---|---|
| WO | WO-99/42456 | 8/1999 |
| WO | WO-99/67231 | 12/1999 |
| WO | WO-01/70694 | 9/2001 |
| WO | WO-01/70709 | 9/2001 |
| WO | WO-02/24207 | 3/2002 |
| WO | WO-03/081246 | 10/2003 |
| WO | WO-2004/056360 | 7/2004 |
| WO | WO-2004/060375 | 7/2004 |
| WO | WO-2005/014043 | 2/2005 |

OTHER PUBLICATIONS

Feit et al., J. Med Chem 15: 79-83 (1971).
Feit et al., J. Med Chem 16: 127-130 (1973).
Feit et al., J. Med Chem 17: 572-578 (1974).
Feit et al., J. Med Chem 19: 402-406 (1976).
Feit, J. Clin. Pharmacol., 21: 531-536 (1981).
Hernandez et al., J. Am. Col. Cardiol., 42: 709-711 (2003).
Hoefle et al., J. Am. Chem. Soc., 11:974-976 (1970).
Holdrege et al., J. Am. Chem. Soc., 4807-4810 (1959).
Jul. 29, 2005. International Search Report from PCT Application No. PCT/US2004/026911.
Lee et al., J. Med Chem 27: 1579-1587 (1984).
Lund et al., Acta. Pharmacol et toxicol., 16: 297-324 (1960).
Neilson et al., J. Med Chem 16: 1170-1177 (1973).
Nielson et al., J. Med Chem 18: 41-50 (1975).
Novello et al., J. Org. Chem., 25: 970-981 (1959).
Robertson et al., J. Med. Chem.,8: 90-95 (1965).
Sakaguchi et al., Chem. Pharm. Bull., 40: 202-211 (1992).
Shani et al., Pharmacology., 26: 172-180 (1983).
Shetty et al., J. Med. Chem., 13: 886-895 (1970).
Taylor et al., J. Med & Pharm Chem., 5: 312-320 (1962).
Topliss et al., J. Org. Chem., 26: 3842-3850 (1961).
Wangemann et al., Pflugers Arch 407: (Suppl 2): S128-141 (1986).
Werner et al., J. Am. Chem. Soc., 1161-1166 (1960).
Whitehead et al., J. Org. Chem., 2809-2813 (1961).
Woltersdorf et al., J. Med Chem 27: 840-845 (1984).

NITRIC OXIDE DONATING DIURETIC COMPOUNDS, COMPOSITIONS AND METHODS OF USE

RELATED APPLICATIONS

This application is a divisional of U.S. patent application Ser. No. 11/360,599, filed Feb. 24, 2006, issued as U.S. Pat. No 7,396,829, which claims priority under 35 USC § 119 to U.S. Application No. 60/655,414 filed Feb. 24, 2005; U.S. Application No. 60/656,545 filed Feb. 28, 2005; U.S. Application No. 60/685,027 filed May 26, 2005; U.S. Application No. 60/692,228 filed Jun. 21. 2005; and to U.S. Application No. 60/749,853 filed Dec. 13, 2005.

FIELD OF THE INVENTION

The invention describes novel compositions and kits comprising at least one nitric oxide enhancing diuretic compound, or pharmaceutically acceptable salts thereof, and, optionally, at least one nitric oxide enhancing compound and/or at least one therapeutic agent. The invention also provides methods for (a) treating conditions resulting from excessive water and/or electrolyte retention; (b) treating cardiovascular diseases; (c) treating renovascular diseases; (d) treating diabetes; (e) treating diseases resulting from oxidative stress; (f) treating endothelial dysfunctions; (g) treating diseases caused by endothelial dysfunctions; (h) treating cirrhosis; (j) treating pre-eclampsia; (k) treating osteoporosis; (l) treating nephropathy; (m) treating peripheral vascular diseases; (n) treating portal hypertension; (o) treating central nervous system disorders; (p) treating metabolic syndrome; (q) treating sexual dysfunctions; and (r) hyperlipidemia. The nitric oxide enhancing diuretic compounds comprise at least one nitric oxide enhancing group linked to the diuretic compound through one or more sites such as carbon, oxygen and/or nitrogen via a bond or moiety that cannot be hydrolyzed.

BACKGROUND OF THE INVENTION

The decline in cardiovascular morbidity and mortality in the United States over the past three decades has been the result of significant advances in research on cardiovascular disease mechanisms and therapeutic strategies. The incidence and prevalence of myocardial infarction and death from myocardial infarction, as well as that from cerebrovascular accident, have decreased significantly over this period largely owing to advances in prevention, early diagnosis, and treatment of these very common diseases.

The compounds administered for the treatment of diuresis, cardiovascular diseases, and diseases resulting from oxidative and/or endothelial dysfunctions often result in toxic, chronic and/or debilitating side effects. Cardiovascular compounds such as ACE inhibitors, beta-adrenergic blockers, antithrombotic and vasodilator compounds or anti-hyperlipidemic compounds, show, for example, respiratory toxicity resulting in asthma and/or bronchitis. Hence there is a need in the art for compounds that have improved efficacy, lower toxicity and that can be used at low dosages. The invention is directed to these, as well as other, important ends.

SUMMARY OF THE INVENTION

The invention provides novel nitric oxide enhancing diuretic compounds, and pharmaceutically acceptable salts thereof, comprising at least one nitric oxide enhancing group selected from an —ONO group, an —SNO group, an —NNO group, an —ONO$_2$ group, an —SNO$_2$ group, an —NNO$_2$ group, an —(N$_2$O$_2$—).M$_1^+$ group, a heterocyclic nitric oxide donor group and a nitroxide group; where the nitric oxide enhancing group is directly or indirectly linked to the diuretic compound through one or more sites such as carbon, oxygen and/or nitrogen via a bond or moiety that cannot be hydrolyzed. The heterocyclic nitric oxide donors are preferably furoxans, sydnonimines, oxatriazole-5-ones and/or oxatriazole-5-imines. The nitric oxide enhancing diuretic compounds are not pro-drugs of the parent diuretic compound. The invention also provides compositions comprising the novel compounds described herein in a pharmaceutically acceptable carrier.

The invention is also based on the discovery that administering at least one diuretic compound comprising at least one nitric oxide enhancing group selected from an —ONO group, an —SNO group, an —NNO group, an —ONO$_2$ group, an —SNO$_2$ group, an —NNO$_2$ group, an —(N$_2$O$_2$—).M$_1^+$ group, a heterocyclic nitric oxide donor group and a nitroxide group; wherein the nitric oxide enhancing group is directly or indirectly linked to the diuretic compound through one or more sites such as carbon, oxygen and/or nitrogen via a bond or moiety that cannot be hydrolyzed, or a pharmaceutically acceptable salt thereof, and, optionally, at least one nitric oxide enhancing compound improves the properties of the diuretic compound. Nitric oxide enhancing compounds include, for example, S-nitrosothiols, nitrites, nitrates, N-oxo-N-nitrosamines, furoxans, sydnonimines, SPM 3672, SPM 4757, SPM 5185, SPM 5186 and analogues thereof, substrates of the various isozymes of nitric oxide synthase, and nitroxides. Thus, another embodiment of the invention provides compositions comprising at least one nitric oxide enhancing diuretic compound and at least one nitric oxide enhancing compound. The invention also provides for such compositions in a pharmaceutically acceptable carrier.

The invention provides compositions comprising at least one nitric oxide enhancing diuretic compound, and, optionally, at least one nitric oxide enhancing compound and/or at least one therapeutic agent, including, but not limited to, aldosterone antagonists, alpha-adrenergic receptor antagonists, angiotensin II antagonists, angiotensin-converting enzyme (ACE) inhibitors, antidiabetic compounds, anti-hyperlipidemic compounds, antioxidants, antithrombotic and vasodilator compounds, β-adrenergic antagonists, calcium channel blockers, digitalis, diuretics, endothelin antagonists, hydralazine compounds, H$_2$ receptor antagonists, neutral endopeptidase inhibitors, nonsteroidal antiinflammatory compounds (NSAIDs), phosphodiesterase inhibitors, potassium channel blockers, platelet reducing agents, proton pump inhibitors, renin inhibitors, selective cyclooxygenase-2 (COX-2) inhibitors, and combinations of two or more thereof. In one embodiment the at least one therapeutic agent is selected from the group consisting of an aldosterone antagonist, an angiotensin II antagonist, an angiotensin-converting enzyme (ACE) inhibitors, a β-adrenergic antagonist, a digitalis, a diuretic, and a hydralazine compound. The invention also provides for such compositions in a pharmaceutically acceptable carrier.

Another embodiment of the invention provides compositions comprising an effective amount of at least one nitric oxide enhancing diuretic compound, and at least one therapeutic agent selected from the group consisting of an aldosterone antagonist, an angiotensin II antagonist, an angiotensin-converting enzyme (ACE) inhibitor, a β-adrenergic antagonist, a calcium channel blocker, a diuretic, a hydralazine compound and a renin inhibitor. The invention also provides for such compositions in a pharmaceutically acceptable carrier.

The invention provides methods for (a) treating conditions resulting from excessive water and/or electrolyte retention; (b) treating cardiovascular diseases; (c) treating renovascular diseases; (d) treating diabetes; (e) treating diseases resulting from oxidative stress; (f) treating endothelial dysfunctions; (g) treating diseases caused by endothelial dysfunctions; (h) treating cirrhosis; (j) treating pre-eclampsia; (k) treating osteoporosis; (l) treating nephropathy; (m) treating peripheral vascular diseases; (n) treating portal hypertension; (o) treating central nervous system disorders; (p) treating metabolic syndrome; (q) treating sexual dysfunctions; and (r) hyperlipidemia in a patient in need thereof comprising administering to the patient an effective amount of at least one nitric oxide enhancing diuretic compound, and, optionally, at least one therapeutic agent, such as, for example, aldosterone antagonists, alpha-adrenergic receptor antagonists, angiotensin II antagonists, angiotensin-converting enzyme (ACE) inhibitors, antidiabetic compounds, anti-hyperlipidemic compounds, antioxidants, antithrombotic and vasodilator compounds, β-adrenergic antagonists, calcium channel blockers, digitalis, diuretics, endothelin antagonists, hydralazine compounds, $H_2$ receptor antagonists, neutral endopeptidase inhibitors, nonsteroidal antiinflammatory compounds (NSAIDs), phosphodiesterase inhibitors, potassium channel blockers, platelet reducing agents, proton pump inhibitors, renin inhibitors, selective cyclooxygenase-2 (COX-2) inhibitors, and combinations of two or more thereof. The methods can optionally further comprise the administration of at least one nitric oxide enhancing compound. In this embodiment of the invention, the methods can involve (i) administering the nitric oxide enhancing diuretic compounds, (ii) administering the nitric oxide enhancing diuretic compounds, and nitric oxide enhancing compounds, (iii) administering the nitric oxide enhancing diuretic compounds and therapeutic agents, or (iv) administering the nitric oxide enhancing diuretic compounds, nitric oxide enhancing compounds, and therapeutic agents. In one embodiment the at least one therapeutic agent is selected from the group consisting of an aldosterone antagonist, an angiotensin II antagonist, an angiotensin-converting enzyme (ACE) inhibitor, a β-adrenergic antagonist, a calcium channel blocker, a diuretic, a hydralazine compound and a renin inhibitor. The nitric oxide enhancing diuretic compounds, nitric oxide donors, and/or therapeutic agents can be administered separately or as components of the same composition in one or more pharmaceutically acceptable carriers.

Another embodiment of the invention provides kits comprising at least one nitric oxide enhancing diuretic compound, and, optionally, at least one nitric oxide enhancing compound. The kit can further comprise at least one therapeutic agent, such as, for example, aldosterone antagonists, alpha-adrenergic receptor antagonists, angiotensin II antagonists, angiotensin-converting enzyme (ACE) inhibitors, antidiabetic compounds, anti-hyperlipidemic compounds, antioxidants, antithrombotic and vasodilator compounds, β-adrenergic antagonists, calcium channel blockers, digitalis, diuretics, endothelin antagonists, hydralazine compounds, $H_2$ receptor antagonists, neutral endopeptidase inhibitors, nonsteroidal antiinflammatory compounds (NSAIDs), phosphodiesterase inhibitors, potassium channel blockers, platelet reducing agents, proton pump inhibitors, renin inhibitors, selective cyclooxygenase-2 (COX-2) inhibitors, and combinations of two or more thereof. The nitric oxide enhancing diuretic compound, the nitric oxide enhancing compound and/or therapeutic agent, can be separate components in the kit or can be in the form of a composition in one or more pharmaceutically acceptable carriers.

These and other aspects of the invention are described in detail herein.

DETAILED DESCRIPTION OF THE INVENTION

Figure 1:
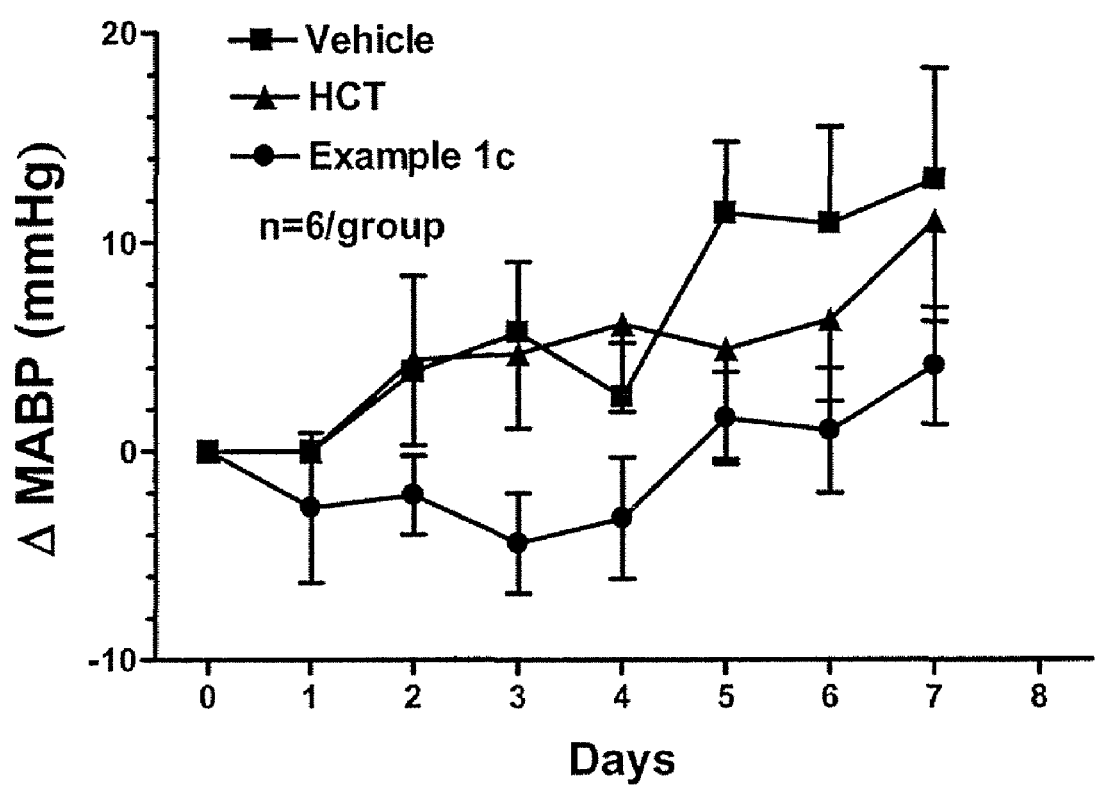
FIG. 1 shows the blood pressure lowering effects of hydrochlorothiazide and Example 1b in Dahl Salt sensitive rats.

As used throughout the disclosure, the following terms, unless otherwise indicated, shall be understood to have the following meanings.

"Conditions resulting from excessive water and/or electrolyte retention" include but are not limited to lower extremity swelling, fatigue, body fluid retention, cardiac enlargement, pulmonary edema, cerebral edema, edema associated at least in part with a cause selected from the group consisting of heart failure, cirrhosis of the liver, poor blood circulation, lymphatic system failure, chronic nephritis, malnutrition, use of birth control pills, premenstrual syndrome, sunburn, hypertension, Meniere's disease, glaucoma, cystic fibrosis and/or an imbalance of sodium and potassium, and the like.

"Cardiovascular disease or disorder" refers to any cardiovascular disease or disorder known in the art, including, but not limited to, heart failure, restenosis, hypertension (e.g. pulmonary hypertension, labile hypertension, idiopathic hypertension, low-renin hypertension, salt-sensitive hypertension, low-renin, salt-sensitive hypertension, thromboembolic pulmonary hypertension; pregnancy-induced hypertension; renovascular hypertension; hypertension-dependent end-stage renal disease, hypertension associated with cardiovascular surgical procedures, hypertension with left ventricular hypertrophy, and the like), diastolic dysfunction, coronary artery disease, myocardial infarctions, cerebral infarctions, atherosclerosis, atherogenesis, cerebrovascular disease, angina, (including chronic, stable, unstable and variant (Prinzmetal) angina pectoris), aneurysm, ischemic heart disease, cerebral ischemia, myocardial ischemia, thrombosis, platelet aggregation, platelet adhesion, smooth muscle cell proliferation, vascular or non-vascular complications associated with the use of medical devices, wounds associated with the use of medical devices, vascular or non-vascular wall damage, peripheral vascular disease, neointimal hyperplasia following percutaneous transluminal coronary angiograph, vascular grafting, coronary artery bypass surgery, thromboembolic events, post-angioplasty restenosis, coronary plaque inflammation, hypercholesterolemia, embolism, stroke, shock, arrhythmia, atrial fibrillation or atrial flutter, thrombotic occlusion and reclusion cerebrovascular incidents, left ventricular dysfunction and hypertrophy, and the like.

"Heart failure" includes, but is not limited to congestive heart failure, compensated heart failure, decompensated heart failure, and the like.

"Thromboembolic events" include, but are not limited to, ischemic stroke, transient ischemic stroke, myocardial infarction, angina pectoris, thrombosis (for example, restenosis, arterial thrombosis, coronary thrombosis, heart valve thrombosis, coronary stenosis, stent thrombosis, graft thrombosis, and first and subsequent thrombotic stroke, and the like), thromboembolism (for example, pulmonary thromboembolism, cerebral thromboembolism, and the like), thrombophlebitis, thrombocytopenia, bleeding disorders, thrombotic occlusion and reocclusion and acute vascular events. Patients who are at risk of developing thromboembolic events, may include those with a familial history of, or genetically predisposed to, thromboembolic disorders, who have had ischemic stroke, transient ischemic stroke, myocardial infarction, and those with unstable angina pectoris or chronic stable angina pectoris and patients with altered prostacyclin/thromboxane $A_2$ homeostasis or higher than normal thromboxane $A_2$ levels leading to increase risk for thromboembolism, including patients with diabetes and rheumatoid arthritis.

"Diseases resulting from oxidative stress" refers to any disease that involves the generation of free radicals or radical compounds, such as, for example, atherogenesis, atheromatosis, arteriosclerosis, atherosclerosis, vascular hypertrophy associated with hypertension, hyperlipoproteinaemia, normal vascular degeneration through aging, parathyroidal reactive hyperplasia, renal disease (e.g., acute or chronic), neoplastic diseases, inflammatory diseases, neurological and acute bronchopulmonary disease, tumorigenesis, ischemia-reperfusion syndrome, arthritis, sepsis, cognitive dysfunction, endotoxic shock, endotoxin-induced organ failure, and the like.

"Renovascular diseases" refers to any disease or dysfunction of the renal system including, but not limited to, renal failure (e.g., acute or chronic), renal insufficiency, nephrotic edema, acute glomerulonephritis, oliguric renal failure, renal deterioration associated with severe hypertension, unilateral perechymal renal disease, polycystic kidney disease, chronic pyelonephritis, renal diseases associated with renal insufficiency, complications associated with dialysis or renal transplantation, renovascular hypertension, nephropathy, glomerulonephritis, scleroderma, glomerular sclerosis, and the like "Endothelial dysfunction" refers to the impaired ability in any physiological processes carried out by the endothelium, in particular, production of nitric oxide regardless of cause. It may be evaluated by, such as, for example, invasive techniques, such as, for example, coronary artery reactivity to acetylcholine or methacholine, and the like, or by noninvasive techniques, such as, for example, blood flow measurements, brachial artery flow dilation using cuff occlusion of the arm above or below the elbow, brachial artery ultrasonography, imaging techniques, measurement of circulating biomarkers, such as, asymmetric dimethylarginine (ADMA), and the like. For the latter measurement the endothelial-dependent flow-mediated dialation will be lower in patients diagnosed with an endothelial dysfunction.

"Methods for treating endothelial dysfunction" include, but are not limited to, treatment prior to the onset/diagnosis of a disease that is caused by or could result from endothelial dysfunction, such as, for example, atherosclerosis, hypertension, diabetes, heart failure, and the like.

"Methods for treating diseases caused by endothelial dysfunction" include, but are not limited to, the treatment of any disease resulting from the dysfunction of the endothelium, such as, for example, arteriosclerosis, heart failure, hypertension, cardiovascular diseases, cerebrovascular diseases, renovascular diseases, mesenteric vascular diseases, pulmonary vascular diseases, ocular vascular diseases, peripheral vascular diseases, peripheral ischemic diseases, and the like.

"Central nervous system disorders" include, but are not limited to, any disorder that is responsive to the positive modulation of the AMPA receptor, such as, for example, neurodegenerative disorders, cognitive or memory dysfunctions, memory and learning disorders, attention disorders, Alzheimer's disease, depression, schizophrenia, memory loss, dementia, senile dementia, learning deficit, attention deficit, cognitive deficit, psychotic disorders, intellectual impairment disorders, autism, disorders resulting from neurotoxic agents, alcohol intoxication or substance abuse, and the like.

"Metabolic syndrome" also known as "insulin-resistance syndrome" or "syndrome X" refers to a condition characterized by an increased amount of adipose tissue inside the abdominal cavity, insulin resistance with increased risk of developing senile diabetes, i.e. diabetes type II, high levels of blood fats and high blood pressure.

"Sexual dysfunction" refers to and includes male erectile dysfunction and female sexual dysfunction. Sexual dysfunction includes, but is not limited to, for example, sexual pain disorders, sexual desire disorders, sexual arousal dysfunction, orgasmic dysfunction, dyspareunia, vaginismus, and the like.

"Therapeutic agent" includes any therapeutic agent that can be used to treat or prevent the diseases described herein. "Therapeutic agents" include, for example, aldosterone antagonists, alpha-adrenergic receptor antagonists, angiotensin II antagonists, angiotensin-converting enzyme (ACE) inhibitors, antidiabetic compounds, anti-hyperlipidemic compounds, antioxidants, antithrombotic and vasodilator compounds, β-adrenergic antagonists, calcium channel blockers, digitalis, diuretics, endothelin antagonists, hydralazine compounds, $H_2$ receptor antagonists, neutral endopeptidase inhibitors, nonsteroidal antiinflammatory compounds (NSAIDs), phosphodiesterase inhibitors, potassium channel blockers, platelet reducing agents, proton pump inhibitors, renin inhibitors, selective cyclooxygenase-2 (COX-2) inhibitors, and the like. Therapeutic agent includes the pharmaceutically acceptable salts thereof, pro-drugs, and pharmaceutical derivatives thereof including, but not limited to, the corresponding nitrosated and/or nitrosylated and/or heterocyclic nitric oxide donor derivatives and/or nitroxide derivative. Although nitric oxide enhancing compounds have therapeutic activity, the term "therapeutic agent" does not include the nitric oxide enhancing compounds described herein, since nitric oxide enhancing compounds are separately defined.

"Prodrug" refers to a compound that is made more active in vivo.

"Antioxidant" refers to and includes any compound that can react and quench a free radical.

"Angiotensin converting enzyme (ACE) inhibitor" refers to compounds that inhibit an enzyme which catalyzes the conversion of angiotensin I to angiotensin II. ACE inhibitors include, but are not limited to, amino acids and derivatives thereof, peptides, including di- and tri-peptides, and antibodies to ACE which intervene in the renin-angiotensin system by inhibiting the activity of ACE thereby reducing or eliminating the formation of the pressor substance angiotensin II.

"Angiotensin II antagonists" refers to compounds which interfere with the function, synthesis or catabolism of angiotensin II. Angiotensin II antagonists include peptide compounds and non-peptide compounds, including, but not limited to, angiotensin II antagonists, angiotensin II receptor antagonists, agents that activate the catabolism of angiotensin II, and agents that prevent the synthesis of angiotensin I from angiotensin II. The renin-angiotensin system is involved in the regulation of hemodynamics and water and electrolyte balance. Factors that lower blood volume, renal perfusion pressure, or the concentration of sodium in plasma tend to activate the system, while factors that increase these parameters tend to suppress its function.

"Anti-hyperlipidemic compounds" refers to any compound or agent that has the effect of beneficially modifying serum cholesterol levels such as, for example, lowering serum low density lipoprotein (LDL) cholesterol levels, or inhibiting oxidation of LDL cholesterol, whereas high density lipoprotein (HDL) serum cholesterol levels may be lowered, remain the same, or be increased. Preferably, the anti-hyperlipidemic compound brings the serum levels of LDL cholesterol and HDL cholesterol (and, more preferably, triglyceride levels) to normal or nearly normal levels.

"Diuretic compound" refers to and includes any compound or agent that increases the amount of urine excreted by a patient.

"Neutral endopeptidase inhibitors" refers to and includes compounds that are antagonists of the renin angiotensin aldosterone system including compounds that are dual inhibitors of neutral endopeptidases and angiotensin converting (ACE) enzymes.

"Renin inhibitors" refers to compounds which interfere with the activity of renin.

"Phosphodiesterase inhibitor" or "PDE inhibitor" refers to any compound that inhibits the enzyme phosphodiesterase. The term refers to selective or non-selective inhibitors of cyclic guanosine 3',5'-monophosphate phosphodiesterases (cGMP-PDE) and cyclic adenosine 3',5'-monophosphate phosphodiesterases (cAMP-PDE).

"Platelet reducing agents" refers to compounds that prevent the formation of a blood thrombus via any number of potential mechanisms. Platelet reducing agents include, but are not limited to, fibrinolytic agents, anti-coagulant agents and any inhibitors of platelet function. Inhibitors of platelet function include agents that impair the ability of mature platelets to perform their normal physiological roles (i.e., their normal function, such as, for example, adhesion to cellular and non-cellular entities, aggregation, release of factors such as growth factors) and the like.

"Proton pump inhibitor" refers to any compound that reversibly or irreversibly blocks gastric acid secretion by inhibiting the $H^+/K^+$-ATPase enzyme system at the secretory surface of the gastric parietal cell.

"NSAID" refers to a nonsteroidal anti-inflammatory compound or a nonsteroidal anti-inflammatory drug. NSAIDs inhibit cyclooxygenase, the enzyme responsible for the biosyntheses of the prostaglandins and certain autocoid inhibitors, including inhibitors of the various isozymes of cyclooxygenase (including but not limited to cyclooxygenase-1 and -2), and as inhibitors of both cyclooxygenase and lipoxygenase.

"Cyclooxygenase-2 (COX-2) selective inhibitor" refers to a compound that selectively inhibits the cyclooxygenase-2 enzyme over the cyclooxygenase-1 enzyme. In one embodiment, the compound has a cyclooxygenase-2 $IC_{50}$ of less than about 2 μM and a cyclooxygenase-1 $IC_{50}$ of greater than about 5 μM, in the human whole blood COX-2 assay (as described in Brideau et al., *Inflamm Res.*, 45: 68-74 (1996)) and also has a selectivity ratio of cyclooxygenase-2 inhibition over cyclooxygenase-1 inhibition of at least 10, and preferably of at least 40. In another embodiment, the compound has a cyclooxygenase-1 $IC_{50}$ of greater than about 1 μM, and preferably of greater than 20 μM. The compound can also inhibit the enzyme, lipoxygenase. Such selectivity may indicate an ability to reduce the incidence of common NSAID-induced side effects.

"Patient" refers to animals, preferably mammals, most preferably humans, and includes males and females, and children and adults.

"Transdermal" refers to the delivery of a compound by passage through the skin and into the blood stream.

"Transmucosal" refers to delivery of a compound by passage of the compound through the mucosal tissue and into the blood stream.

"Penetration enhancement" or "permeation enhancement" refers to an increase in the permeability of the skin or mucosal tissue to a selected pharmacologically active compound such that the rate at which the compound permeates through the skin or mucosal tissue is increased.

"Carriers" or "vehicles" refers to carrier materials suitable for compound administration and include any such material known in the art such as, for example, any liquid, gel, solvent, liquid diluent, solubilizer, or the like, which is non-toxic and which does not interact with any components of the composition in a deleterious manner.

"Sustained release" refers to the release of an active compound and/or composition such that the blood levels of the active compound are maintained within a desirable therapeutic range over a period of time. The sustained release formulation can be prepared using any conventional method known to one skilled in the art to obtain the desired release characteristics.

"Nitric oxide enhancing" refers to compounds and functional groups which, under physiological conditions can increase endogenous nitric oxide. Nitric oxide enhancing compounds include, but are not limited to, nitric oxide releasing compounds, nitric oxide donating compounds, nitric oxide donors, radical scavenging compounds and/or reactive oxygen species scavenger compounds. In one embodiment the radical scavenging compound contains a nitroxide group.

"Nitroxide group" refers to compounds that have the ability to mimic superoxide dimutase and catalase and act as radical scavengers, or react with superoxide or other reactive oxygen species via a stable aminoxyl radical i.e. N-oxide.

"Nitric oxide adduct" or "NO adduct" refers to compounds and functional groups which, under physiological conditions, can donate, release and/or directly or indirectly transfer any of the three redox forms of nitrogen monoxide ($NO^+$, $NO^-$, NO.), such that the biological activity of the nitrogen monoxide species is expressed at the intended site of action.

"Nitric oxide releasing" or "nitric oxide donating" refers to methods of donating, releasing and/or directly or indirectly transferring any of the three redox forms of nitrogen monoxide ($NO^+$, NO—, NO.), such that the biological activity of the nitrogen monoxide species is expressed at the intended site of action.

"Nitric oxide donor" or "NO donor" refers to compounds that donate, release and/or directly or indirectly transfer a nitrogen monoxide species, and/or stimulate the endogenous production of nitric oxide or endothelium-derived relaxing factor (EDRF) in vivo and/or elevate endogenous levels of nitric oxide or EDRF in vivo and/or are oxidized to produce nitric oxide and/or are substrates for nitric oxide synthase and/or cytochrome P450. "NO donor" also includes compounds that are precursors of L-arginine, inhibitors of the enzyme arginase and nitric oxide mediators.

"Heterocyclic nitric oxide donor" refers to a trisubstituted 5-membered ring comprising two or three nitrogen atoms and at least one oxygen atom. The heterocyclic nitric oxide donor is capable of donating and/or releasing a nitrogen monoxide species upon decomposition of the heterocyclic ring. Exemplary heterocyclic nitric oxide donors include oxatriazol-5-ones, oxatriazol-5-imines, sydnonimines, furoxans, and the like.

"Alkyl" refers to a lower alkyl group, a substituted lower alkyl group, a haloalkyl group, a hydroxyalkyl group, an alkenyl group, a substituted alkenyl group, an alkynyl group, a bridged cycloalkyl group, a cycloalkyl group or a heterocyclic ring, as defined herein. An alkyl group may also comprise one or more radical species, such as, for example a cycloalkylalkyl group or a heterocyclicalkyl group.

"Lower alkyl" refers to branched or straight chain acyclic alkyl group comprising one to about ten carbon atoms (preferably one to about eight carbon atoms, more preferably one to about six carbon atoms). Exemplary lower alkyl groups include methyl, ethyl, n-propyl, isopropyl, n-butyl, isobutyl, sec-butyl, t-butyl, pentyl, neopentyl, iso-amyl, hexyl, octyl, and the like.

"Substituted lower alkyl" refers to a lower alkyl group, as defined herein, wherein one or more of the hydrogen atoms have been replaced with one or more $R^{100}$ groups, wherein each $R^{100}$ is independently a hydroxy, an ester, an amidyl, an oxo, a carboxyl, a carboxamido, a halo, a cyano, a nitrate, a nitrite, a thionitrate, a thionitrite or an amino group, as defined herein.

"Haloalkyl" refers to a lower alkyl group, an alkenyl group, an alkynyl group, a bridged cycloalkyl group, a cycloalkyl group or a heterocyclic ring, as defined herein, to which is appended one or more halogens, as defined herein. Exemplary haloalkyl groups include trifluoromethyl, chloromethyl, 2-bromobutyl, 1-bromo-2-chloro-pentyl, and the like.

"Alkenyl" refers to a branched or straight chain $C_2$-$C_{10}$ hydrocarbon (preferably a $C_2$-$C_8$ hydrocarbon, more preferably a $C_2$-$C_6$ hydrocarbon) that can comprise one or more carbon-carbon double bonds. Exemplary alkenyl groups include propylenyl, buten-1-yl, isobutenyl, penten-1-yl, 2,2-methylbuten-1-yl, 3-methylbuten-1-yl, hexan-1-yl, hepten-1-yl, octen-1-yl, and the like.

"Lower alkenyl" refers to a branched or straight chain $C_2$-$C_4$ hydrocarbon that can comprise one or two carbon-carbon double bonds.

"Substituted alkenyl" refers to a branched or straight chain $C_2$-$C_{10}$ hydrocarbon (preferably a $C_2$-$C_8$ hydrocarbon, more preferably a $C_2$-$C_6$ hydrocarbon) which can comprise one or more carbon-carbon double bonds, wherein one or more of the hydrogen atoms have been replaced with one or more $R^{100}$ groups, wherein each $R^{100}$ is independently a hydroxy, an oxo, a carboxyl, a carboxamido, a halo, a cyano or an amino group, as defined herein.

"Alkynyl" refers to an unsaturated acyclic $C_2$-$C_{10}$ hydrocarbon (preferably a $C_2$-$C_8$ hydrocarbon, more preferably a $C_2$-$C_6$ hydrocarbon) that can comprise one or more carbon-carbon triple bonds. Exemplary alkynyl groups include ethynyl, propynyl, butyn-1-yl, butyn-2-yl, pentyl-1-yl, pentyl-2-yl, 3-methylbutyn-1-yl, hexyl-1-yl, hexyl-2-yl, hexyl-3-yl, 3,3-dimethyl-butyn-1-yl, and the like.

"Bridged cycloalkyl" refers to two or more cycloalkyl groups, heterocyclic groups, or a combination thereof fused via adjacent or non-adjacent atoms. Bridged cycloalkyl groups can be unsubstituted or substituted with one, two or three substituents independently selected from alkyl, alkoxy, amino, alkylamino, dialkylamino, hydroxy, halo, carboxyl, alkylcarboxylic acid, aryl, amidyl, ester, alkylcarboxylic ester, carboxamido, alkylcarboxamido, oxo and nitro. Exemplary bridged cycloalkyl groups include adamantyl, decahydronapthyl, quinuclidyl, 2,6-dioxabicyclo(3.3.0)octane, 7-oxabicyclo(2.2.1)heptyl, 8-azabicyclo(3,2,1)oct-2-enyl and the like.

"Cycloalkyl" refers to a saturated or unsaturated cyclic hydrocarbon comprising from about 3 to about 10 carbon atoms. Cycloalkyl groups can be unsubstituted or substituted with one, two or three substituents independently selected from alkyl, alkoxy, amino, alkylamino, dialkylamino, arylamino, diarylamino, alkylarylamino, aryl, amidyl, ester, hydroxy, halo, carboxyl, alkylcarboxylic acid, alkylcarboxylic ester, carboxamido, alkylcarboxamido, oxo, alkylsulfinyl, and nitro. Exemplary cycloalkyl groups include cyclopropyl, cyclobutyl, cyclopentyl, cyclohexyl, cyclohexenyl, cyclohepta-1,3-dienyl, and the like.

"Heterocyclic ring or group" refers to a saturated or unsaturated cyclic hydrocarbon group having about 2 to about 10 carbon atoms (preferably about 4 to about 6 carbon atoms) where 1 to about 4 carbon atoms are replaced by one or more nitrogen, oxygen and/or sulfur atoms. Sulfur may be in the thio, sulfinyl or sulfonyl oxidation state. The heterocyclic ring or group can be fused to an aromatic hydrocarbon group. Heterocyclic groups can be unsubstituted or substituted with one, two or three substituents independently selected from alkyl, alkoxy, amino, alkylthio, aryloxy, arylthio, arylalkyl, hydroxy, oxo, thial, halo, carboxyl, carboxylic ester, alkylcarboxylic acid, alkylcarboxylic ester, aryl, arylcarboxylic acid, arylcarboxylic ester, amidyl, ester, alkylcarbonyl, arylcarbonyl, alkylsulfinyl, carboxamido, alkylcarboxamido, arylcarboxamido, sulfonic acid, sulfonic ester, sulfonamide nitrate and nitro. Exemplary heterocyclic groups include pyrrolyl, furyl, thienyl, 3-pyrrolinyl,4,5,6-trihydro-2H-pyranyl, pyridinyl, 1,4-dihydropyridinyl, pyrazolyl, triazolyl, pyrimidinyl, pyridazinyl, oxazolyl, thiazolyl, imidazolyl, indolyl, thiophenyl, furanyl, tetrahydrofuranyl, tetrazolyl, pyrrolinyl, pyrrolindinyl, oxazolindinyl 1,3-dioxolanyl, imidazolinyl, imidazolindinyl, pyrazolinyl, pyrazolidinyl, isoxazolyl, isothiazolyl, 1,2,3-oxadiazolyl, 1,2,3-triazolyl, 1,3,4-thiadiazolyl, 2H-pyranyl, 4H-pyranyl, piperidinyl, 1,4-dioxanyl, morpholinyl, 1,4-dithianyl, thiomorpholinyl, pyrazinyl, piperazinyl, 1,3,5-triazinyl, 1,3,5-trithianyl, benzo(b) thiophenyl, benzimidazolyl, benzothiazolinyl, quinolinyl, 2,6-dioxabicyclo(3.3.0)octane, and the like.

"Heterocyclic compounds" refer to mono- and polycyclic compounds comprising at least one aryl or heterocyclic ring.

"Aryl" refers to a monocyclic, bicyclic, carbocyclic or heterocyclic ring system comprising one or two aromatic rings. Exemplary aryl groups include phenyl, pyridyl, napthyl, quinoyl, tetrahydronaphthyl, furanyl, indanyl, indenyl, indoyl, and the like. Aryl groups (including bicyclic aryl groups) can be unsubstituted or substituted with one, two or three substituents independently selected from alkyl, alkoxy, alkylthio, amino, alkylamino, dialkylamino, arylamino, diarylamino, alkylarylamino, halo, cyano, alkylsulfinyl, hydroxy, carboxyl, carboxylic ester, alkylcarboxylic acid, alkylcarboxylic ester, aryl, arylcarboxylic acid, arylcarboxylic ester, alkylcarbonyl, arylcarbonyl, amidyl, ester, carboxamido, alkylcarboxamido, carbomyl, sulfonic acid, sulfonic ester, sulfonamido and nitro. Exemplary substituted aryl groups include tetrafluorophenyl, pentafluorophenyl, sulfonamide, alkylsulfonyl, arylsulfonyl, and the like.

"Cycloalkenyl" refers to an unsaturated cyclic $C_2$-$C_{10}$ hydrocarbon (preferably a $C_2$-$C_8$ hydrocarbon, more preferably a $C_2$-$C_6$ hydrocarbon) which can comprise one or more carbon-carbon double bonds.

"Alkylaryl" refers to an alkyl group, as defined herein, to which is appended an aryl group, as defined herein. Exemplary alkylaryl groups include benzyl, phenylethyl, hydroxybenzyl, fluorobenzyl, fluorophenylethyl, and the like.

"Arylalkyl" refers to an aryl radical, as defined herein, attached to an alkyl radical, as defined herein. Exemplary arylalkyl groups include benzyl, phenylethyl, 4-hydroxybenzyl, 3-fluorobenzyl, 2-fluorophenylethyl, and the like.

"Arylalkenyl" refers to an aryl radical, as defined herein, attached to an alkenyl radical, as defined herein. Exemplary arylalkenyl groups include styryl, propenylphenyl, and the like.

"Cycloalkylalkyl" refers to a cycloalkyl radical, as defined herein, attached to an alkyl radical, as defined herein.

"Cycloalkylalkoxy" refers to a cycloalkyl radical, as defined herein, attached to an alkoxy radical, as defined herein.

"Cycloalkylalkylthio" refers to a cycloalkyl radical, as defined herein, attached to an alkylthio radical, as defined herein.

"Heterocyclicalkyl" refers to a heterocyclic ring radical, as defined herein, attached to an alkyl radical, as defined herein.

"Arylheterocyclic ring" refers to a bi- or tricyclic ring comprised of an aryl ring, as defined herein, appended via two adjacent carbon atoms of the aryl ring to a heterocyclic ring, as defined herein. Exemplary arylheterocyclic rings include dihydroindole, 1,2,3,4-tetra-hydroquinoline, and the like.

"Alkylheterocyclic ring" refers to a heterocyclic ring radical, as defined herein, attached to an alkyl radical, as defined herein. Exemplary alkylheterocyclic rings include 2-pyridylmethyl, 1-methylpiperidin-2-one-3-methyl, and the like.

"Alkoxy" refers to $R_{50}O$—, wherein $R_{50}$ is an alkyl group, as defined herein (preferably a lower alkyl group or a haloalkyl group, as defined herein). Exemplary alkoxy groups include methoxy, ethoxy, t-butoxy, cyclopentyloxy, trifluoromethoxy, and the like.

"Aryloxy" refers to $R_{55}O$—, wherein $R_{55}$ is an aryl group, as defined herein. Exemplary arylkoxy groups include napthyloxy, quinolyloxy, isoquinolizinyloxy, and the like.

"Alkylthio" refers to $R_{50}S$—, wherein $R_{50}$ is an alkyl group, as defined herein.

"Lower alkylthio" refers to a lower alkyl group, as defined herein, appended to a thio group, as defined herein.

"Arylalkoxy" or "alkoxyaryl" refers to an alkoxy group, as defined herein, to which is appended an aryl group, as defined herein. Exemplary arylalkoxy groups include benzyloxy, phenylethoxy, chlorophenylethoxy, and the like.

"Arylalklythio" refers to an alkylthio group, as defined herein, to which is appended an aryl group, as defined herein. Exemplary arylalklythio groups include benzylthio, phenylethylthio, chlorophenylethylthio, and the like.

"Arylalklythioalkyl" refers to an arylalkylthio group, as defined herein, to which is appended an alkyl group, as defined herein. Exemplary arylalklythioalkyl groups include benzylthiomethyl, phenylethylthiomethyl, chlorophenylethylthioethyl, and the like.

"Alkylthioalkyl" refers to an alkylthio group, as defined herein, to which is appended an alkyl group, as defined herein. Exemplary alkylthioalkyl groups include allylthiomethyl, ethylthiomethyl, trifluoroethylthiomethyl, and the like.

"Alkoxyalkyl" refers to an alkoxy group, as defined herein, appended to an alkyl group, as defined herein. Exemplary alkoxyalkyl groups include methoxymethyl, methoxyethyl, isopropoxymethyl, and the like.

"Alkoxyhaloalkyl" refers to an alkoxy group, as defined herein, appended to a haloalkyl group, as defined herein. Exemplary alkoxyhaloalkyl groups include 4-methoxy-2-chlorobutyl and the like.

"Cycloalkoxy" refers to $R_{54}O$—, wherein $R_{54}$ is a cycloalkyl group or a bridged cycloalkyl group, as defined herein. Exemplary cycloalkoxy groups include cyclopropyloxy, cyclopentyloxy, cyclohexyloxy, and the like.

"Cycloalkylthio" refers to $R_{54}S$—, wherein $R_{54}$ is a cycloalkyl group or a bridged cycloalkyl group, as defined herein. Exemplary cycloalkylthio groups include cyclopropylthio, cyclopentylthio, cyclohexylthio, and the like.

"Haloalkoxy" refers to an alkoxy group, as defined herein, in which one or more of the hydrogen atoms on the alkoxy group are substituted with halogens, as defined herein. Exemplary haloalkoxy groups include 1,1,1-trichloroethoxy, 2-bromobutoxy, and the like.

"Hydroxy" refers to —OH.

"Oxy" refers to —O—

"Oxo" refers to =O.

"Oxylate" refers to —O⁻$R_{77}^+$ wherein $R_{77}$ is an organic or inorganic cation.

"Thiol" refers to —SH.

"Thio" refers to —S—.

"Oxime" refers to =N—$OR_{81}$ wherein $R_{81}$ is a hydrogen, an alkyl group, an aryl group, an alkylsulfonyl group, an arylsulfonyl group, a carboxylic ester, an alkylcarbonyl group, an arylcarbonyl group, a carboxamido group, an alkoxyalkyl group or an alkoxyaryl group.

"Hydrazone" refers to =N—N($R_{81}$)($R'_{81}$) wherein $R'_{81}$ is independently selected from $R_{81}$, and $R_{81}$ is as defined herein.

"Hydrazino" refers to $H_2N$—N(H)—.

"Organic cation" refers to a positively charged organic ion. Exemplary organic cations include alkyl substituted ammonium cations, and the like.

"Inorganic cation" refers to a positively charged metal ion. Exemplary inorganic cations include Group I metal cations such as for example, sodium, potassium, magnesium, calcium, and the like.

"Hydroxyalkyl" refers to a hydroxy group, as defined herein, appended to an alkyl group, as defined herein.

"Nitrate" refers to —O—$NO_2$ i.e. oxidized nitrogen.

"Nitrite" refers to —O—NO i.e. oxidized nitrogen.

"Thionitrate" refers to —S—$NO_2$.

"Thionitrite" and "nitrosothiol" refer to —S—NO.

"Nitro" refers to the group —$NO_2$ and "nitrosated" refers to compounds that have been substituted therewith.

"Nitroso" refers to the group —NO and "nitrosylated" refers to compounds that have been substituted therewith.

"Nitrile" and "cyano" refer to —CN.

"Halogen" or "halo" refers to iodine (I), bromine (Br), chlorine (Cl), and/or fluorine (F).

"Imine" refers to —C(=N—$R_{51}$)— wherein $R_{51}$ is a hydrogen atom, an alkyl group, an aryl group or an arylheterocyclic ring, as defined herein "Amine" refers to any organic compound that contains at least one basic nitrogen atom.

"Amino" refers to —$NH_2$, an alkylamino group, a dialkylamino group, an arylamino group, a diarylamino group, an alkylarylamino group or a heterocyclic ring, as defined herein.

"Alkylamino" refers to $R_{50}NH$—, wherein $R_{50}$ is an alkyl group, as defined herein. Exemplary alkylamino groups include methylamino, ethylamino, butylamino, cyclohexylamino, and the like.

"Arylamino" refers to $R_{55}NH$—, wherein $R_{55}$ is an aryl group, as defined herein.

"Dialkylamino" refers to $R_{52}R_{53}N$—, wherein $R_{52}$ and $R_{53}$ are each independently an alkyl group, as defined herein. Exemplary dialkylamino groups include dimethylamino, diethylamino, methyl propargylamino, and the like.

"Diarylamino" refers to $R_{55}R_{60}N$—, wherein $R_{55}$ and $R_{60}$ are each independently an aryl group, as defined herein.

"Alkylarylamino" or "arylalkylamino" refers to $R_{52}R_{55}N$—, wherein $R_{52}$ is an alkyl group, as defined herein, and $R_{55}$ is an aryl group, as defined herein.

"Alkylarylalkylamino" refers to $R_{52}R_{79}N-$, wherein $R_{52}$ is an alkyl group, as defined herein, and $R_{79}$ is an arylalkyl group, as defined herein.

"Alkylcycloalkylamino" refers to $R_{52}R_{80}N-$, wherein $R_{52}$ is an alkyl group, as defined herein, and $R_{80}$ is a cycloalkyl group, as defined herein.

"Aminoalkyl" refers to an amino group, an alkylamino group, a dialkylamino group, an arylamino group, a diarylamino group, an alkylarylamino group or a heterocyclic ring, as defined herein, to which is appended an alkyl group, as defined herein. Exemplary aminoalkyl groups include dimethylaminopropyl, diphenylaminocyclopentyl, methylaminomethyl, and the like.

"Aminoaryl" refers to an aryl group to which is appended an alkylamino group, an arylamino group or an arylalkylamino group. Exemplary aminoaryl groups include anilino, N-methylanilino, N-benzylanilino, and the like.

"Sulfinyl" refers to $-S(O)-$.

"Methanthial" refers to $-C(S)-$.

"Thial" refers to $=S$.

"Sulfonyl" refers to $-S(O)_2^-$.

"Sulfonic acid" refers to $-S(O)_2OR_{76}$, wherein $R_{76}$ is a hydrogen, an organic cation or an inorganic cation, as defined herein.

"Alkylsulfonic acid" refers to a sulfonic acid group, as defined herein, appended to an alkyl group, as defined herein.

"Arylsulfonic acid" refers to a sulfonic acid group, as defined herein, appended to an aryl group, as defined herein.

"Sulfonic ester" refers to $-S(O)_2OR_{58}$, wherein $R_{58}$ is an alkyl group, an aryl group, or an aryl heterocyclic ring, as defined herein.

"Sulfonamido" refers to $-S(O)_2-N(R_{51})(R_{57})$, wherein $R_{51}$ and $R_{57}$ are each independently a hydrogen atom, an alkyl group, an aryl group or an arylheterocyclic ring, as defined herein, or $R_{51}$ and $R_{57}$ when taken together are a heterocyclic ring, a cycloalkyl group or a bridged cycloalkyl group, as defined herein.

"Alkylsulfonamido" refers to a sulfonamido group, as defined herein, appended to an alkyl group, as defined herein.

"Arylsulfonamido" refers to a sulfonamido group, as defined herein, appended to an aryl group, as defined herein.

"Alkylthio" refers to $R_{50}S-$, wherein $R_{50}$ is an alkyl group, as defined herein (preferably a lower alkyl group, as defined herein).

"Arylthio" refers to $R_{55}S-$, wherein $R_{55}$ is an aryl group, as defined herein.

"Arylalkylthio" refers to an aryl group, as defined herein, appended to an alkylthio group, as defined herein.

"Alkylsulfinyl" refers to $R_{50}-S(O)-$, wherein $R_{50}$ is an alkyl group, as defined herein.

"Alkylsulfonyl" refers to $R_{50}-S(O)_2-$, wherein $R_{50}$ is an alkyl group, as defined herein.

"Alkylsulfonyloxy" refers to $R_{50}-S(O)_2-O-$, wherein $R_{50}$ is an alkyl group, as defined herein.

"Arylsulfinyl" refers to $R_{55}-S(O)-$, wherein $R_{55}$ is an aryl group, as defined herein.

"Arylsulfonyl" refers to $R_{55}-S(O)_2-$, wherein $R_{55}$ is an aryl group, as defined herein.

"Arylsulfonyloxy" refers to $R_{55}-S(O)_2-O-$, wherein $R_{55}$ is an aryl group, as defined herein.

"Amidyl" refers to $R_{51}C(O)N(R_{57})-$ wherein $R_{51}$ and $R_{57}$ are each independently a hydrogen atom, an alkyl group, an aryl group or an arylheterocyclic ring, as defined herein.

"Ester" refers to $R_{51}C(O)R_{82}-$ wherein $R_{51}$ is a hydrogen atom, an alkyl group, an aryl group or an arylheterocyclic ring, as defined herein and $R_{82}$ is oxygen or sulfur.

"Carbamoyl" refers to $-O-C(O)N(R_{51})(R_{57})$, wherein $R_{51}$ and $R_{57}$ are each independently a hydrogen atom, an alkyl group, an aryl group or an arylheterocyclic ring, as defined herein, or $R_{51}$ and $R_{57}$ taken together are a heterocyclic ring, a cycloalkyl group or a bridged cycloalkyl group, as defined herein.

"Carboxyl" refers to $-C(O)OR_{76}$, wherein $R_{76}$ is a hydrogen, an organic cation or an inorganic cation, as defined herein.

"Carbonyl" refers to $-C(O)-$.

"Alkylcarbonyl" refers to $R_{52}-C(O)-$, wherein $R_{52}$ is an alkyl group, as defined herein.

"Arylcarbonyl" refers to $R_{55}-C(O)-$, wherein $R_{55}$ is an aryl group, as defined herein.

"Arylalkylcarbonyl" refers to $R_{55}-R_{52}-C(O)-$, wherein $R_{55}$ is an aryl group, as defined herein, and $R_{52}$ is an alkyl group, as defined herein.

"Alkylarylcarbonyl" refers to $R_{52}-R_{55}-C(O)-$, wherein $R_{55}$ is an aryl group, as defined herein, and $R_{52}$ is an alkyl group, as defined herein.

"Heterocyclicalkylcarbonyl" refer to $R_{78}C(O)-$ wherein $R_{78}$ is a heterocyclicalkyl group, as defined herein.

"Carboxylic ester" refers to $-C(O)OR_{58}$, wherein $R_{58}$ is an alkyl group, an aryl group or an aryl heterocyclic ring, as defined herein.

"Alkylcarboxylic acid" and "alkylcarboxyl" refer to an alkyl group, as defined herein, appended to a carboxyl group, as defined herein.

"Alkylcarboxylic ester" refers to an alkyl group, as defined herein, appended to a carboxylic ester group, as defined herein.

"Alkyl ester" refers to an alkyl group, as defined herein, appended to an ester group, as defined herein.

"Arylcarboxylic acid" refers to an aryl group, as defined herein, appended to a carboxyl group, as defined herein.

"Arylcarboxylic ester" and "arylcarboxyl" refer to an aryl group, as defined herein, appended to a carboxylic ester group, as defined herein.

"Aryl ester" refers to an aryl group, as defined herein, appended to an ester group, as defined herein.

"Carboxamido" refers to $-C(O)N(R_{51})(R_{57})$, wherein $R_{51}$ and $R_{57}$ are each independently a hydrogen atom, an alkyl group, an aryl group or an arylheterocyclic ring, as defined herein, or $R_{51}$ and $R_{57}$ when taken together are a heterocyclic ring, a cycloalkyl group or a bridged cycloalkyl group, as defined herein.

"Alkylcarboxamido" refers to an alkyl group, as defined herein, appended to a carboxamido group, as defined herein.

"Arylcarboxamido" refers to an aryl group, as defined herein, appended to a carboxamido group, as defined herein.

"Urea" refers to $-N(R_{59})-C(O)N(R_{51})(R_{57})$ wherein $R_{51}$, $R_{57}$, and $R_{59}$ are each independently a hydrogen atom, an alkyl group, an aryl group or an arylheterocyclic ring, as defined herein, or $R_{51}$ and $R_{57}$ taken together are a heterocyclic ring, a cycloalkyl group or a bridged cycloalkyl group, as defined herein.

"Phosphoryl" refers to $-P(R_{70})(R_{71})(R_{72})$, wherein $R_{70}$ is a lone pair of electrons, thial or oxo, and $R_{71}$ and $R_{72}$ are each independently a covalent bond, a hydrogen, a lower alkyl, an alkoxy, an alkylamino, a hydroxy, an oxy or an aryl, as defined herein.

"Phosphoric acid" refers to $-P(O)(OR_{51})OH$ wherein $R_{51}$ is a hydrogen atom, an alkyl group, an aryl group or an arylheterocyclic ring, as defined herein.

"Phosphinic acid" refers to $-P(O)(R_{51})OH$ wherein $R_{51}$ is a hydrogen atom, an alkyl group, an aryl group or an arylheterocyclic ring, as defined herein.

"Silyl" refers to —Si(R$_{73}$)(R$_{74}$)(R$_{75}$), wherein R$_{73}$, R$_{74}$ and R$_{75}$ are each independently a covalent bond, a lower alkyl, an alkoxy, an aryl or an arylalkoxy, as defined herein.

The compounds and compositions of the invention are diuretics, including, but are not limited to, thiazides (such as, for example, althiazide, bendroflumethiazide, benzclortriazide, benzhydrochlorothiazide, benzthiazide, buthiazide, chlorothiazide, cyclopenethiazide, cyclothiazide, epithiazide, ethiazide, hydrobenzthiazide, hydrochlorothiazide, hydroflumethiazide, methylclothiazide, methylcyclothiazide, penflutazide, polythiazide, teclothiazide, trichlormethiazide, triflumethazide, and the like); alilusem, ambuside, amiloride, aminometradine, azosemide, bemetizide, bumetanide, butazolamide, butizide, canrenone, carperitide, chloraminophenamide, chlorazanil, chlormerodrin, chlorthalidone, cicletanide, clofenamide, clopamide, clorexolone, conivaptan, daglutril, dichlorophenamide, disulfamide, ethacrynic acid, ethoxzolamide, etozolon, fenoldopam, fenquizone, furosemide, indapamide, mebutizide, mefruside, meralluride, mercaptomerin sodium, mercumallylic acid, mersalyl, methazolamide, meticane, metolazone, mozavaptan, muzolimine, N-(5-1,3,4-thiadiazol-2-yl)acetamide, nesiritide, pamabrom, paraflutizide, piretanide, protheobromine, quinethazone, scoparius, spironolactone, theobromine, ticrynafen, torsemide, torvaptan, triamterene, tripamide, ularitide, xipamide, potassium, AT 189000, AY 31906, BG 9928, BG 9791, C 2921, DTI 0017, JDL 961, KW 3902, MCC 134, SLV 306, SR 121463, WAY 140288, ZP 120, and the like. The contemplated diuretic compounds are described more fully in the literature, such as in Goodman and Gilman, The Pharmacological Basis of Therapeutics (9th Edition), McGraw-Hill, (1996); Merck Index on CD-ROM, 13$^{th}$ Edition; STN Express, file phar and file registry, the disclosures of each of which are incorporated by reference herein in their entirety.

In one embodiment, the diuretic compounds of the invention comprise at least one nitric oxide enhancing group selected from the group consisting of an —ONO group, an —SNO group, an —NNO group, an —ONO$_2$ group, an —SNO$_2$ group, an —NNO$_2$ group, an —(N$_2$O$_2$—).M$_1^+$ group, a heterocyclic group (e.g., furoxan, sydnonimine, oxatriazole-5-one, oxatriazole-5-imine) and a nitroxide group; wherein the nitric oxide (NO) enhancing group is directly or indirectly linked to the diuretic compound through one or more sites such as carbon, oxygen and/or nitrogen by a bond or moiety that cannot be hydrolyzed. The nitric oxide enhancing diuretic compounds may be represented by Formula (A):

(diuretic compound)-(nonhydrolyzable bond)-(linking group)$_{aa}$-(NO enhancing group)     (A)

wherein:

the diuretic compound can be any known in the art. In one embodiment, the diuretic compound is althiazide, bendroflumethiazide, benzthiazide, buthiazide, chlorothiazide, cyclothiazide, ethiazide, fenquizone, hydrochlorothiazide, hydroflumethiazide, methyclothiazide, metolazone, paraflutizide, polythiazide, quinethazone, teclothiazide, or trichlormethiazide;

the nitric oxide enhancing group is selected from the group consisting of an —ONO group, an —SNO group, an —NNO group, an —ONO$_2$ group, an —SNO$_2$ group, an —NNO$_2$ group, an —(N$_2$O$_2$—).M$_1^+$ group, a heterocyclic group (e.g., furoxan, sydnonimine, oxatriazole-5-one, oxatriazole-5-imine) and a nitroxide group;

aa is 0 or 1;

when aa is 0, the nitric oxide enhancing group is directly linked to the angiotensin II antagonist compound via a bond that cannot be hydrolyzed;

when aa is 1, the linking group can be any known in the art;

the linking group may optionally comprise one or more hydrolyzable bonds; however, the hydrolyzable bond cannot be directly adjacent the diuretic compound. In other words, at least one atom or moiety in the linking group directly adjacent to the diuretic compound must form a non-hydrolyzable bond with the diuretic compound.

In another embodiment, the invention described nitric oxide enhancing diuretic compounds of Formula (I) and pharmaceutically acceptable salts thereof:

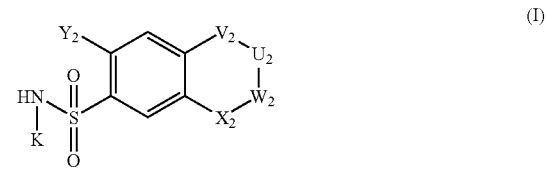

(I)

wherein:

X$_2$ is —C(O)— or —S(O)$_2$;

Y$_2$ is chlorine or CF$_3$;

—V$_2$—U$_2$—W$_2$— is:

(i) —NH—(C(R$_q$)(R$_r$))—NR$_q$—; or (ii) —NH—C(R$_q$)=N—;

R$_q$ and R$_r$ at each occurrence are independently a hydrogen, a lower alkyl group, a substituted alkyl group, a benzyl group, an aryl group, an alkylaryl group, —CH$_2$—S—CH—CH=CH$_2$; —CH$_2$—S—CF$_3$, —CH$_2$—S—CH$_2$—C$_6$H$_5$ or K';

K' is -G-E$_c$-(C(R$_e$)(R$_f$))$_x$—W$_d$—(C(R$_e$)(R$_f$))$_y$—W$_i$-E$_j$-W$_g$—(C(R$_e$)(R$_f$))$_z$—V$_4$;

K is —(W)$_a$-E$_b$-(C(R$_e$)(R$_f$))$_{p1}$-E$_c$-(C(R$_e$)(R$_f$))$_x$—(W)$_d$—(C(R$_e$)(R$_f$))$_y$—(W)$_i$-E$_j$-(W)$_g$—(C(R$_e$)(R$_f$))$_z$—V$_4$;

a, b, c, d, g, i and j are each independently an integer from 0 to 3;

p$_1$, x, y and z are each independently an integer from 0 to 10;

G is a heterocyclic ring, —CH$_2$, oxygen or nitrogen;

V$_4$ is V$_3$, R$_e$, —U$_3$—V$_5$ or V$_6$;

V$_3$ is:

(1)

(2)

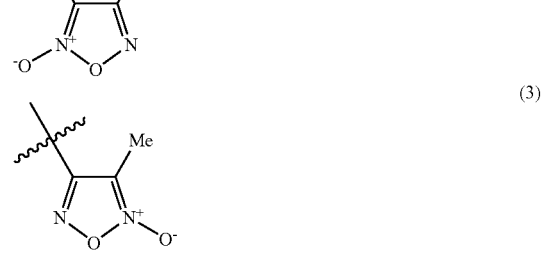

(3)

-continued
(4) 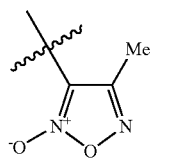
(5) 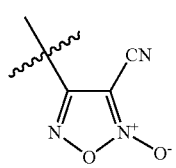
(6) 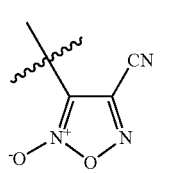
(7) 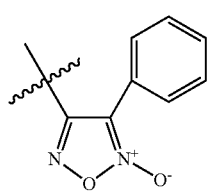
(8) 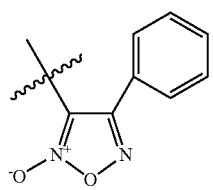
(9) 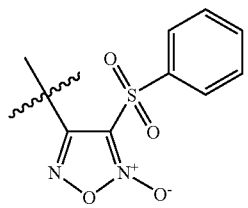
(10) 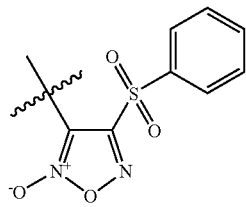
(11) 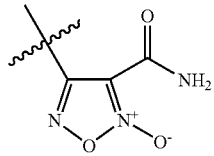
-continued
(12) 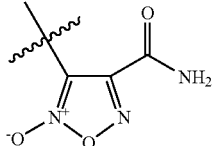
(13) 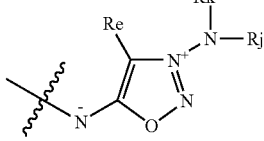
(14) 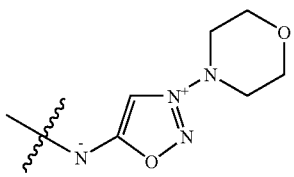
(15) 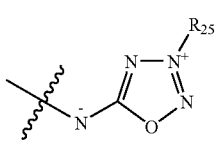
(16) 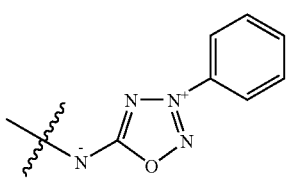
(17) 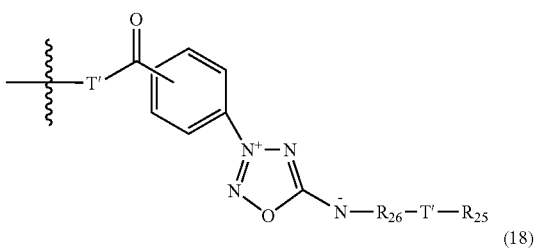
(18) 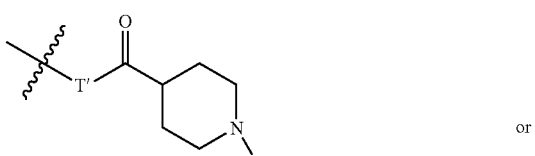
or
(19) 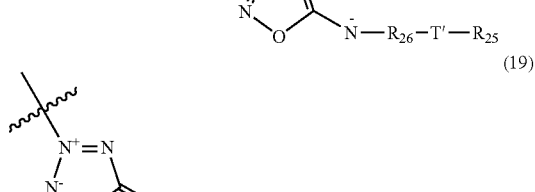
$R_{24}$ is —$C_6H_4R_{29}$, —CN, —$S(O)_2$—$C_6H_4R_{29}$, —C(O)—N($R_a$)($R_i$), —$NO_2$, —C(O)—$OR_{25}$ or —$S(O)_2$—$R_{25}$;
$R_{25}$ is an aryl group, a lower alkyl group, a haloalkyl group, a hydroxyalkyl group or an arylalkyl group;

$R_{26}$ is —C(O)— or —S(O)$_2$—;

$R_{29}$ is a hydrogen, —CN, —S(O)$_2$—R$_{25}$, —C(O)—N(R$_a$)(R$_i$), —NO$_2$ or —C(O)—OR$_{25}$;

T' is oxygen, sulfur or NR$_6$;

R$_6$ is a hydrogen, a lower alkyl group, or an aryl group;

V$_6$ is:

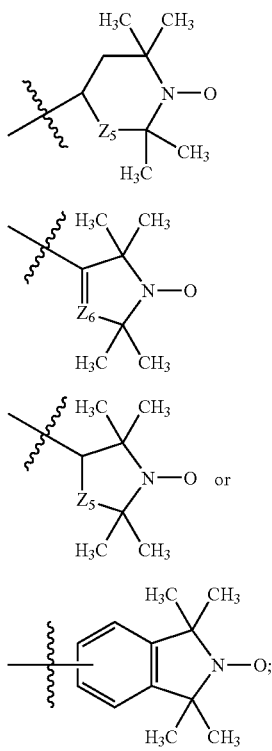

Z$_5$ is —CH$_2$ or oxygen;

Z$_6$ is —CH or nitrogen;

k$_1$ is an integer from 1 to 3;

W at each occurrence is independently —C(O)—, —C(S)—, -T$_3$-, —(C(R$_e$)(R$_f$))$_h$—, —N(R$_a$)R$_i$, an alkyl group, an aryl group, a heterocyclic ring, an arylheterocyclic ring, —(CH$_2$CH$_2$O)$_{q1}$— or a heterocyclic nitric oxide donor;

E at each occurrence is independently -T$_3$-, an alkyl group, an aryl group, —(C(R$_e$)(R$_f$))$_h$—, a heterocyclic ring, an arylheterocyclic ring, —(CH$_2$CH$_2$O)$_{q1}$— or Y$_4$;

Y$_4$ is:

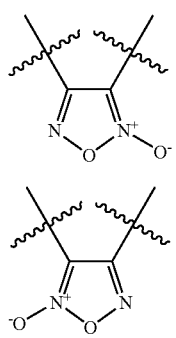

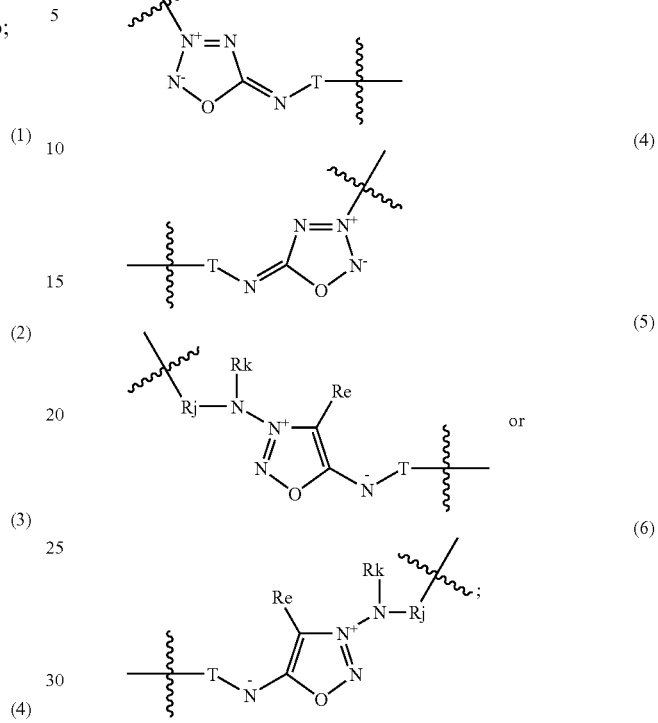

T is a —S(O)$_o$—; a carbonyl or a covalent bond;

o is an integer from 0 to 2;

R$_j$ and R$_k$ are independently selected from an alkyl group, an aryl group, or R$_j$ and R$_k$ taken together with the nitrogen atom to which they are attached are a heterocylic ring;

T$_3$ at each occurrence is independently a covalent bond, a carbonyl, an oxygen, —S(O)$_o$— or —N(R$_a$)R$_i$;

h is an integer form 1 to 10;

q$_1$ is an integer from 1 to 5;

R$_e$ and R$_f$ are each independently a hydrogen, an alkyl, a cycloalkoxy, a halogen, a hydroxy, an hydroxyalkyl, an alkoxyalkyl, an arylheterocyclic ring, an alkylaryl, an alkylcycloalkyl, an alkylheterocyclic ring, a cycloalkylalkyl, a cycloalkylthio, an arylalklythio, an arylalklythioalkyl, an alkylthioalkyl, a cycloalkenyl, an heterocyclicalkyl, an alkoxy, a haloalkoxy, an amino, an alkylamino, a dialkylamino, an arylamino, a diarylamino, an alkylarylamino, an alkoxyhaloalkyl, a sulfonic acid, a sulfonic ester, an alkylsulfonic acid, an arylsulfonic acid, an arylalkoxy, an alkylthio, an arylthio, a cyano, an aminoalkyl, an aminoaryl, an aryl, an arylalkyl, an alkylaryl, a carboxamido, an alkylcarboxamido, an arylcarboxamido, an amidyl, a carboxyl, a carbamoyl, an alkylcarboxylic acid, an arylcarboxylic acid, an alkylcarbonyl, an arylcarbonyl, an ester, a carboxylic ester, an alkylcarboxylic ester, an arylcarboxylic ester, a sulfonamido, an alkylsulfonamido, an arylsulfonamido, an alkylsulfonyl, an alkylsulfonyloxy, an arylsulfonyl, arylsulphonyloxy, a sulfonic ester, an alkyl ester, an aryl ester, a urea, a phosphoryl, a nitro, —U$_3$—V$_5$, V$_6$, —(C(R$_o$)(R$_p$))$_{k1}$—U$_3$—V$_5$, —(C(R$_o$)(R$_p$))$_{k1}$—U$_3$—V$_3$, —(C(R$_o$)(R$_p$))$_{k1}$—U$_3$—V$_6$, —(C(R$_o$)(R$_p$))$_{k1}$—U$_3$—C(O)—V$_6$, or R$_e$ and R$_f$ taken together with the carbons to which they are attached form a carbonyl, a methanthial, a heterocyclic ring, a cycloalkyl group, an aryl group, an oxime, an imine, a hydrazone, a bridged cycloalkyl group,

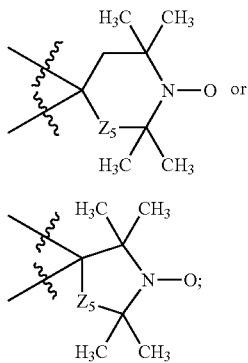

(1)

(2)

$R_o$ and $R_p$ are each independently a hydrogen, an alkyl, a cycloalkoxy, a halogen, a hydroxy, an hydroxyalkyl, an alkoxyalkyl, an arylheterocyclic ring, an alkylaryl, an alkylcycloalkyl, an alkylheterocyclic ring, a cycloalkylalkyl, a cycloalkylthio, an arylalklythio, an arylalklythioalkyl, an alkylthioalkyl a cycloalkenyl, an heterocyclicalkyl, an alkoxy, a haloalkoxy, an amino, an alkylamino, a dialkylamino, an arylamino, a diarylamino, an alkylarylamino, an alkoxyhaloalkyl, a sulfonic acid, a sulfonic ester, an alkylsulfonic acid, an arylsulfonic acid, an arylalkoxy, an alkylthio, an arylthio, a cyano an aminoalkyl, an aminoaryl, an aryl, an arylalkyl, an alkylaryl, a carboxamido, an alkylcarboxamido, an arylcarboxamido, an amidyl, a carboxyl, a carbamoyl, an alkylcarboxylic acid, an arylcarboxylic acid, an alkylcarbonyl, an arylcarbonyl, an ester, a carboxylic ester, an alkylcarboxylic ester, an arylcarboxylic ester, a sulfonamido, an alkylsulfonamido, an arylsulfonamido, an alkylsulfonyl, an alkylsulfonyloxy, an arylsulfonyl, arylsulphonyloxy, a sulfonic ester, an alkyl ester, an aryl ester, a urea, a phosphoryl, a nitro, $-U_3-V_5$, $V_6$, or $R_o$ and $R_p$ taken together with the carbons to which they are attached form a carbonyl, a methanthial, a heterocyclic ring, a cycloalkyl group, an aryl group, an oxime, an imine, a hydrazone a bridged cycloalkyl group,

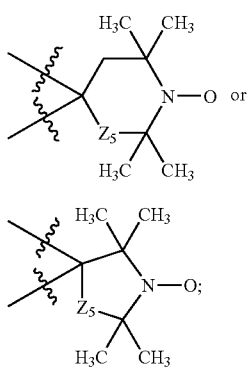

(1)

(2)

$U_3$ is an oxygen, sulfur or $-N(R_a)R_i$;
$V_5$ is $-NO$ or $-NO_2$ (i.e. an oxidized nitrogen);
$k_1$ is an integer from 1 to 3;
$R_a$ is a lone pair of electrons, a hydrogen or an alkyl group;

$R_i$ is a hydrogen, an alkyl, an aryl, an alkylcarboxylic acid, an arylcarboxylic acid, an alkylcarboxylic ester, an arylcarboxylic ester, an alkylcarboxamido, an arylcarboxamido, an alkylaryl, an alkylsulfinyl, an alkylsulfonyl, an alkylsulfonyloxy, an arylsulfinyl, an arylsulfonyl, an arylsulphonyloxy, a sulfonamido, a carboxamido, a carboxylic ester, an aminoalkyl, an aminoaryl, $-CH_2-C-(U_3-V_5)(R_e)(R_f)$, a bond to an adjacent atom creating a double bond to that atom or $-(N_2O_2-).M_1^+$, wherein $M_1^+$ is an organic or inorganic cation; and with the proviso that the compounds of Formula (I) must contain at least one nitric oxide enhancing group selected from a $-ONO$ group, a $-SNO$ group, a $-NNO$ group, a $-ONO_2$ group, a $-SNO_2$ group, a $-NNO_2$ group, a $-(N_2O_2-).M_1^+$ group, a heterocyclic nitric oxide donor group and a nitroxide group where the nitric oxide enhancing group is linked to the diuretic compound through one or more sites such as carbon, oxygen and/or nitrogen via a bond or moiety that cannot be hydrolyzed.

In cases where multiple designations of variables which reside in sequence are chosen as a "covalent bond" or the integer chosen is 0, the intent is to denote a single covalent bond connecting one radical to another. For example, $E_0$ would denote a covalent bond, while $E_2$ denotes (E-E) and $(C(R_4)(R_4))_2$ denotes $-C(R_4)(R_4)-C(R_4)(R_4)-$.

In other embodiments of the invention the compound of Formula (I) is a nitric oxide enhancing althiazide, a nitric oxide enhancing bendroflumethiazide, a nitric oxide enhancing benzthiazide, a nitric oxide enhancing buthiazide, a nitric oxide enhancing chlorothiazide, a nitric oxide enhancing cyclothiazide, a nitric oxide enhancing ethiazide, a nitric oxide enhancing fenquizone, a nitric oxide enhancing hydrochlorothiazide, a nitric oxide enhancing hydroflumethiazide, a nitric oxide enhancing methyclothiazide, a nitric oxide enhancing metolazone, a nitric oxide enhancing paraflutizide, a nitric oxide enhancing polythiazide, a nitric oxide enhancing quinethazone, a nitric oxide enhancing teclothiazide, a nitric oxide enhancing trichlormethiazide; and pharmaceutically acceptable salts thereof.

In other embodiments of the invention the compound of Formula (I) is a compound of Formula (II) to Formula (XXVII), or a pharmaceutically acceptable salt thereof, wherein the compound of Formula (II) to Formula (XXVII) is:

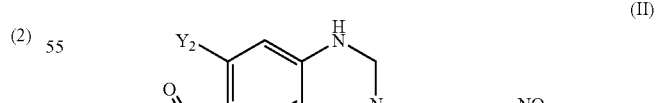

(II)

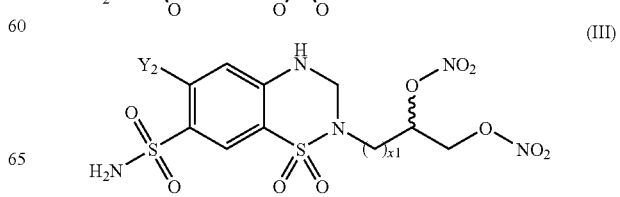

(III)

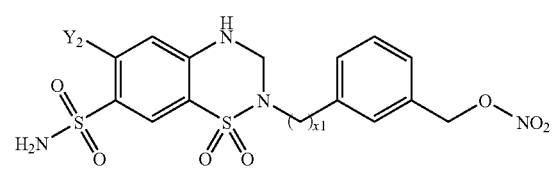
(IV)
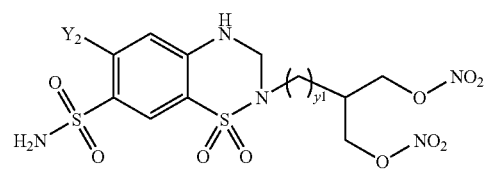
(V)
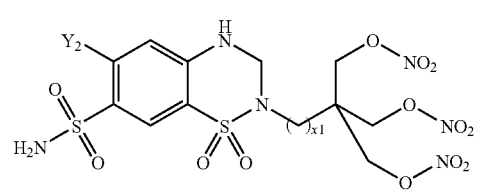
(VI)
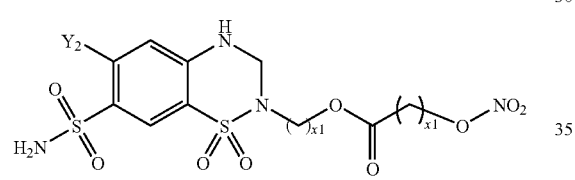
(VII)
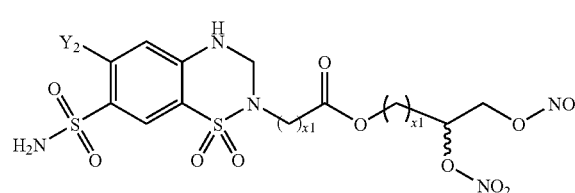
(VIII)
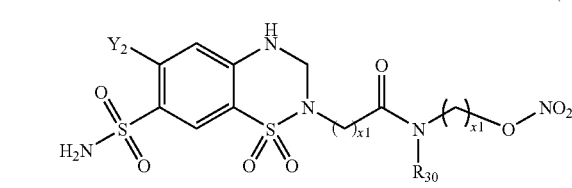
(IX)
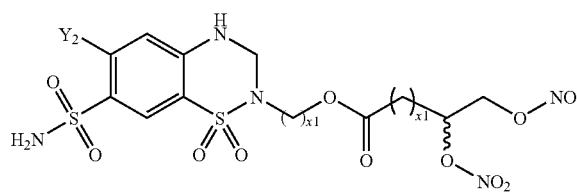
(X)
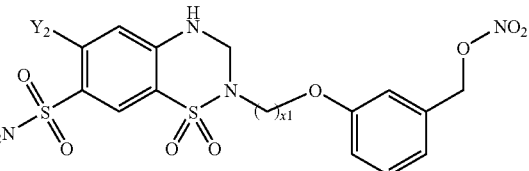
(XI)
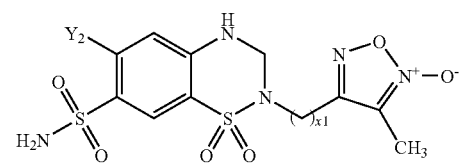
(XII)
(XIII)
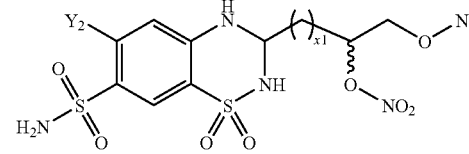
(XIV)
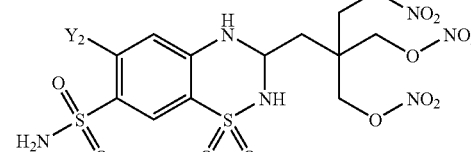
(XV)
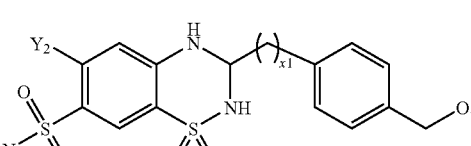
(XVI)
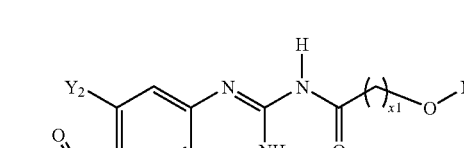
(XVII)
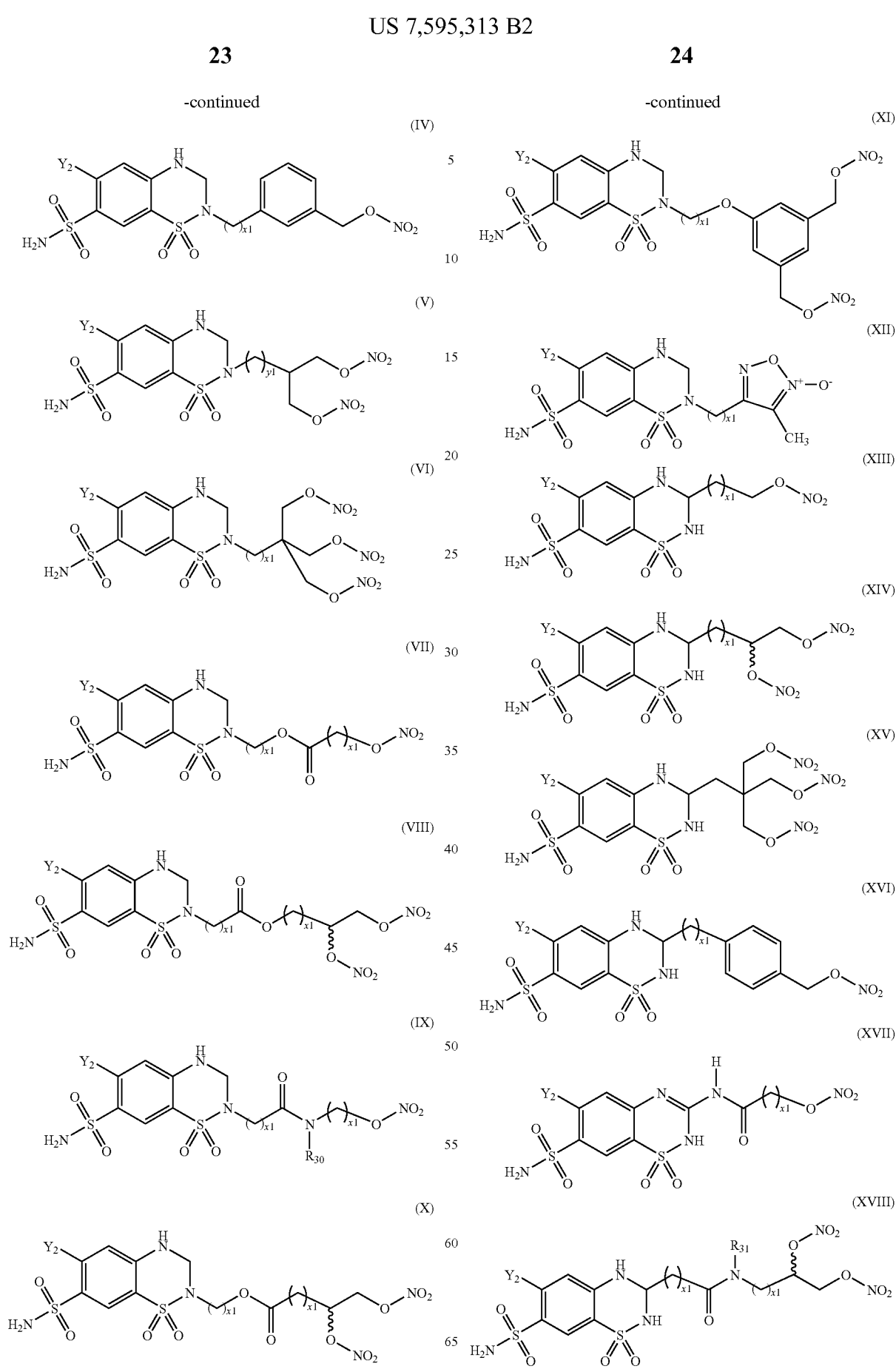
(XVIII)

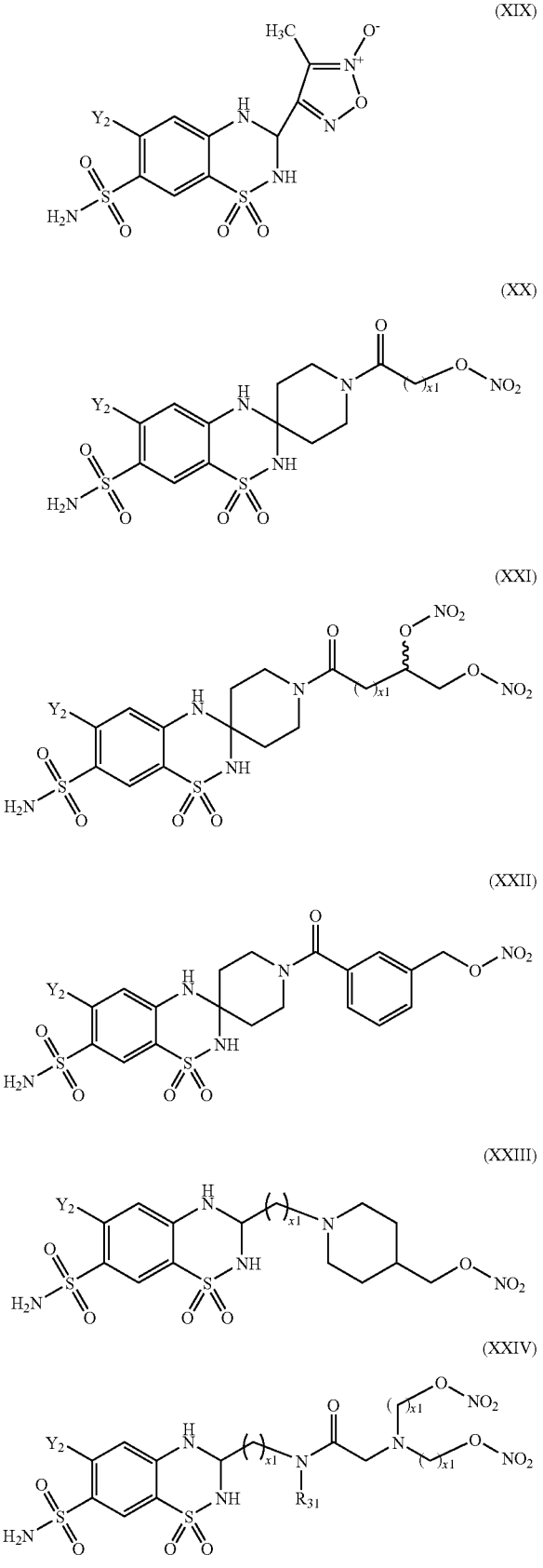
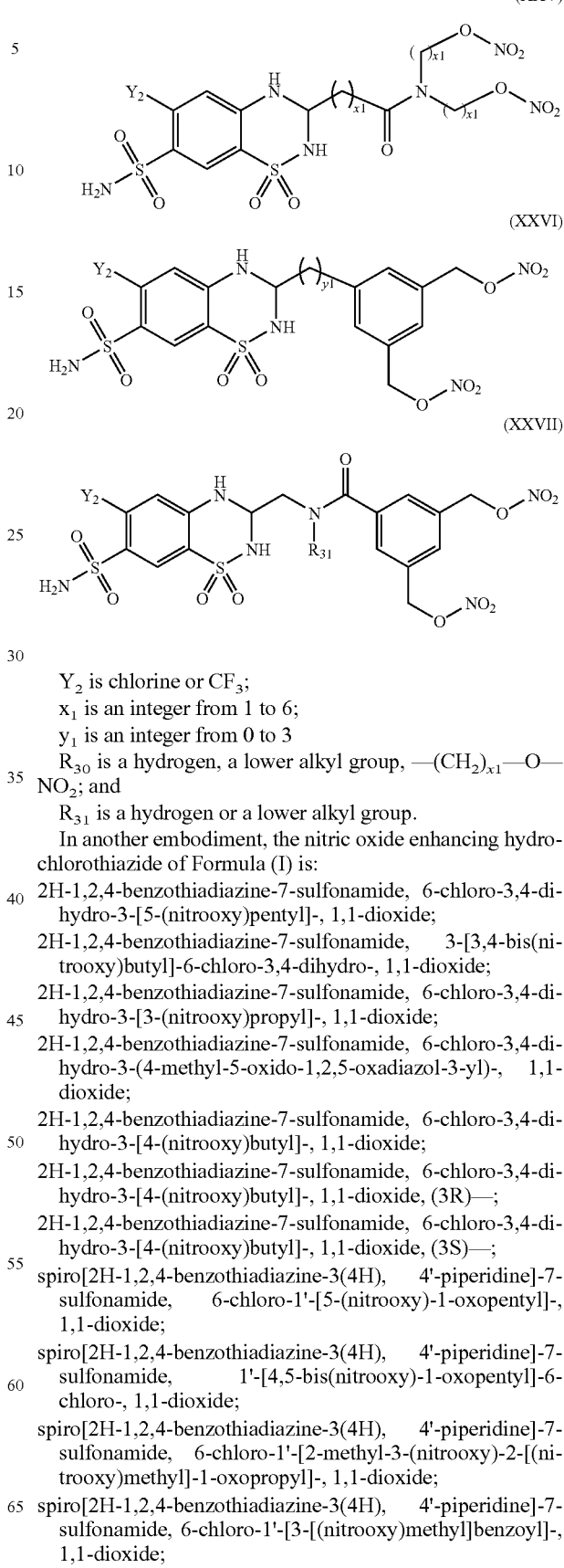

$Y_2$ is chlorine or $CF_3$;

$x_1$ is an integer from 1 to 6;

$y_1$ is an integer from 0 to 3

$R_{30}$ is a hydrogen, a lower alkyl group, —$(CH_2)_{x1}$—O—$NO_2$; and $R_{31}$ is a hydrogen or a lower alkyl group.

In another embodiment, the nitric oxide enhancing hydrochlorothiazide of Formula (I) is:

2H-1,2,4-benzothiadiazine-7-sulfonamide, 6-chloro-3,4-dihydro-3-[5-(nitrooxy)pentyl]-, 1,1-dioxide;

2H-1,2,4-benzothiadiazine-7-sulfonamide, 3-[3,4-bis(nitrooxy)butyl]-6-chloro-3,4-dihydro-, 1,1-dioxide;

2H-1,2,4-benzothiadiazine-7-sulfonamide, 6-chloro-3,4-dihydro-3-[3-(nitrooxy)propyl]-, 1,1-dioxide;

2H-1,2,4-benzothiadiazine-7-sulfonamide, 6-chloro-3,4-dihydro-3-(4-methyl-5-oxido-1,2,5-oxadiazol-3-yl)-, 1,1-dioxide;

2H-1,2,4-benzothiadiazine-7-sulfonamide, 6-chloro-3,4-dihydro-3-[4-(nitrooxy)butyl]-, 1,1-dioxide;

2H-1,2,4-benzothiadiazine-7-sulfonamide, 6-chloro-3,4-dihydro-3-[4-(nitrooxy)butyl]-, 1,1-dioxide, (3R)—;

2H-1,2,4-benzothiadiazine-7-sulfonamide, 6-chloro-3,4-dihydro-3-[4-(nitrooxy)butyl]-, 1,1-dioxide, (3S)—;

spiro[2H-1,2,4-benzothiadiazine-3(4H), 4'-piperidine]-7-sulfonamide, 6-chloro-1'-[5-(nitrooxy)-1-oxopentyl]-, 1,1-dioxide;

spiro[2H-1,2,4-benzothiadiazine-3(4H), 4'-piperidine]-7-sulfonamide, 1'-[4,5-bis(nitrooxy)-1-oxopentyl]-6-chloro-, 1,1-dioxide;

spiro[2H-1,2,4-benzothiadiazine-3(4H), 4'-piperidine]-7-sulfonamide, 6-chloro-1'-[2-methyl-3-(nitrooxy)-2-[(nitrooxy)methyl]-1-oxopropyl]-, 1,1-dioxide;

spiro[2H-1,2,4-benzothiadiazine-3(4H), 4'-piperidine]-7-sulfonamide, 6-chloro-1'-[3-[(nitrooxy)methyl]benzoyl]-, 1,1-dioxide;

spiro[2H-1,2,4-benzothiadiazine-3(4H), 4'-piperidine]-7-sulfonamide, 6-chloro-1'-[6-(nitrooxy)-1-oxohexyl]-, 1,1-dioxide;

2H-1,2,4-benzothiadiazine-2-acetic acid, 7-(aminosulfonyl)-6-chloro-3,4-dihydro-, (2R)-2,3-bis(nitrooxy)propyl ester, 1,1-dioxide;

2H-1,2,4-benzothiadiazine-7-sulfonamide, 6-chloro-3,4-dihydro-2-[[3-[(nitrooxy)methyl]phenyl]methyl]-, 1,1-dioxide;

2H-1,2,4-benzothiadiazine-2-acetamide, 7-(aminosulfonyl)-6-chloro-3,4-dihydro-N-[3-(nitrooxy)propyl]-, 1,1-dioxide;

2H-1,2,4-benzothiadiazine-7-sulfonamide, 6-chloro-3,4-dihydro-2-[3-(nitrooxy)propyl]-, 1,1-dioxide;

2H-1,2,4-benzothiadiazine-7-sulfonamide, 6-chloro-3,4-dihydro-3-[[4-[2-(nitrooxy)ethyl]-1-piperidinyl]methyl]-, 1,1-dioxide;

2H-1,2,4-benzothiadiazine-7-sulfonamide, 6-chloro-3,4-dihydro-3-[[4-[2-(nitrooxy)ethyl]-1-piperidinyl]methyl]-, 1,1-dioxide, 2-hydroxy-1,2,3-propanetricarboxylate (1:1) (salt);

2H-1,2,4-benzothiadiazine-7-sulfonamide, 6-chloro-3,4-dihydro-2-[(4-methyl-5-oxido-1,2,5-oxadiazol-3-yl)methyl]-, 1,1-dioxide;

2H-1,2,4-benzothiadiazine-2-acetamide, 7-(aminosulfonyl)-6-chloro-3,4-dihydro-N-methyl-N-[2-(nitrooxy)ethyl]-, 1,1-dioxide;

2H-1,2,4-benzothiadiazine-2-acetamide, 7-(aminosulfonyl)-6-chloro-3,4-dihydro-N,N-bis[2-(nitrooxy)ethyl]-, 1,1-dioxide;

2H-1,2,4-benzothiadiazine-7-sulfonamide, 6-chloro-3,4-dihydro-2-[4-(nitrooxy)butyl]-, 1,1-dioxide;

pentanoic acid, 4,5-bis(nitrooxy)-, 2-[7-(aminosulfonyl)-6-chloro-3,4-dihydro-1,1-dioxido-2H-1,2,4-benzothiadiazin-2-yl]ethyl ester;

2H-1,2,4-benzothiadiazine-7-sulfonamide, 2-[4,5-bis(nitrooxy)pentyl]-6-chloro-3,4-dihydro-, 1,1-dioxide;

pentanoic acid, 5-(nitrooxy)-, 2-[7-(aminosulfonyl)-6-chloro-3,4-dihydro-1,1-dioxido-2H-1,2,4-benzothiadiazin-2-yl]ethyl ester;

2H-1,2,4-benzothiadiazine-7-sulfonamide, 6-chloro-3,4-dihydro-3-[[methyl[2-(nitrooxy)ethyl]amino]methyl]-, 1,1-dioxide;

2H-1,2,4-benzothiadiazine-7-sulfonamide, 6-chloro-3,4-dihydro-2-[5-(nitrooxy)pentyl]-, 1,1-dioxide;

2H-1,2,4-benzothiadiazine-7-sulfonamide, 6-chloro-3,4-dihydro-3-[6-(nitrooxy)hexyl]-, 1,1-dioxide;

2H-1,2,4-benzothiadiazine-7-sulfonamide, 2-[(3S)-3,4-bis(nitrooxy)butyl]-6-chloro-3,4-dihydro-1,1-dioxide;

2H-1,2,4-benzothiadiazine-3-acetamide, 7-(aminosulfonyl)-6-chloro-3,4-dihydro-N,N-bis[2-(nitrooxy)ethyl]-, 1,1-dioxide;

2H-1,2,4-benzothiadiazine-7-sulfonamide, 3-[3,5-bis[(nitrooxy)methyl]phenyl]-6-chloro-3,4-dihydro-, 1,1-dioxide;

2H-1,2,4-benzothiadiazine-7-sulfonamide, 6-chloro-3,4-dihydro-2-[2-(nitrooxy)ethyl]-, 1,1-dioxide;

2H-1,2,4-benzothiadiazine-7-sulfonamide, 6-chloro-3,4-dihydro-4-nitro-2-[2-(nitrooxy)ethyl]-, 1,1-dioxide;

2H-1,2,4-benzothiadiazine-7-sulfonamide, 6-chloro-3,4-dihydro-3-[4-(nitrooxy)-3,3-bis[(nitrooxy)methyl]butyl]-, 1,1-dioxide;

2H-1,2,4-benzothiadiazine-7-sulfonamide, 6-chloro-3,4-dihydro-2-[5-(nitrooxy)-4,4-bis[(nitrooxy)methyl]pentyl]-, 1,1-dioxide;

acetamide, N—[[7-(aminosulfonyl)-6-chloro-3,4-dihydro-1,1-dioxido-2H-1,2,4-benzothiadiazin-3-yl]methyl]-2-[bis[2-(nitrooxy)ethyl]amino]-;

2H-1,2,4-benzothiadiazine-7-sulfonamide, 6-chloro-3,4-dihydro-2-[6-(nitrooxy)hexyl]-, 1,1-dioxide;

acetamide, N—[[7-(aminosulfonyl)-6-chloro-3,4-dihydro-1,1-dioxido-2H-1,2,4-benzothiadiazin-3-yl]methyl]-2-[bis[2-(nitrooxy)ethyl]amino]-N-methyl-;

(5-{[{[{[7-(aminosulfonyl)-6-chloro-1,1-dioxido-3,4-dihydro-2H-1,2,4-benzothiadiazin-3-yl]methyl}(methyl)amino]carbonyl}-1,3-phenylene)bis(methylene) dinitrate;

2H-1,2,4-benzothiadiazine-7-sulfonamide, 6-chloro-3,4-dihydro-2-[(2E)-4-(nitrooxy)-2-butenyl], 1,1-dioxide;

2H-1,2,4-benzothiadiazine-7-sulfonamide, 2-[[3-(4-bromobutoxy)-5-[(nitrooxy)methyl]phenyl]methyl]-6-chloro-3,4-dihydro-, 1,1-dioxide;

2H-1,2,4-benzothiadiazine-7-sulfonamide, 2-[4-[3,5-bis[(nitrooxy)methyl]phenoxy]butyl]-6-chloro-3,4-dihydro-, 1,1-dioxide;

2H-1,2,4-benzothiadiazine-7-sulfonamide, 2-[3-[3,5-bis[(nitrooxy)methyl]phenoxy]propyl]-6-chloro-3,4-dihydro-, 1,1-dioxide;

2H-1,2,4-benzothiadiazine-7-sulfonamide, 2-[2-[3,5-bis[(nitrooxy)methyl]phenoxy]ethyl]-6-chloro-3,4-dihydro-, 1,1-dioxide;

2H-1,2,4-benzothiadiazine-2-acetamide, 7-(aminosulfonyl)-6-chloro-3,4-dihydro-N,N-bis[3-(nitrooxy)propyl]-, 1,1-dioxide;

2H-1,2,4-benzothiadiazine-7-sulfonamide, 2-[(3R)-3,4-bis(nitrooxy)butyl]-6-chloro-3,4-dihydro-1,1-dioxide;

2H-1,2,4-benzothiadiazine-7-sulfonamide, 6-chloro-3,4-dihydro-3-[2-(nitrooxy)ethyl]-, 1,1-dioxide;

2H-1,2,4-benzothiadiazine-7-sulfonamide, 2-[2,3-bis(nitrooxy)propyl]-6-chloro-3,4-dihydro-, 1,1-dioxide;

2H-1,2,4-benzothiadiazine-7-sulfonamide, 2-[(2R)-2,3-bis(nitrooxy)propyl]-6-chloro-3,4-dihydro-, 1,1-dioxide;

2H-1,2,4-benzothiadiazine-7-sulfonamide, 2-[(2S)-2,3-bis(nitrooxy)propyl]-6-chloro-3,4-dihydro-, 1,1-dioxide;

2H-1,2,4-benzothiadiazine-7-sulfonamide, 2-[2,3-bis(nitrooxy)propyl]-6-chloro-3,4-dihydro-4-nitro-, 1,1-dioxide;

2H-1,2,4-benzothiadiazine-7-sulfonamide, 6-chloro-3,4-dihydro-2-[2-hydroxy-3-(nitrooxy)propyl]-4-nitro-, 1,1-dioxide;

1-piperidinyloxy, 4-[[7-(aminosulfonyl)-6-chloro-3,4-dihydro-1,1-dioxido-2H-1,2,4-benzothiadiazin-3-yl]methyl]-2,2,6,6-tetramethyl-;

2H-1,2,4-benzothiadiazine-7-sulfonamide, 6-chloro-3,4-dihydro-3-[(1-hydroxy-2,2,6,6-tetramethyl-4-piperidinyl)methyl]-, 1,1-dioxide;

2H-1,2,4-benzothiadiazine-7-sulfonamide, 3-[2-[3,5-bis[(nitrooxy)methyl]phenyl]ethyl]-6-chloro-3,4-dihydro-, 1,1-dioxide;

2H-1,2,4-benzothiadiazine-7-sulfonamide, 6-chloro-3,4-dihydro-4-methyl-3-[4-(nitrooxy)butyl]-1,1-dioxide;

2H-1,2,4-benzothiadiazine-7-sulfonamide, 3-[(1R)-1,2-bis(nitrooxy)ethyl]-6-chloro-3,4-dihydro-4-methyl-, 1,1-dioxide;

2H-1,2,4-benzothiadiazine-7-sulfonamide, 3-[(1S)-1,2-bis(nitrooxy)ethyl]-6-chloro-3,4-dihydro-4-methyl-, 1,1-dioxide;

1-pyrrolidinyloxy, 3-[7-(aminosulfonyl)-6-chloro-3,4-dihydro-1,1-dioxido-2H-1,2,4-benzothiadiazin-3-yl]-2,2,5,5-tetramethyl-;

spiro[2H-1,2,4-benzothiadiazine-3(4H), 4'-piperidin]-1'-yloxy, 7-(aminosulfonyl)-6-chloro-2',2',6',6'-tetramethyl-1,1-dioxido-;

2H-1,2,4-benzothiadiazine-7-sulfonamide, 6-chloro-3,4-dihydro-2-[3-(nitrooxy)-2-[(nitrooxy)methyl]propyl]-, 1,1-dioxide; and pharmaceutically acceptable salts thereof.

In another embodiment, the nitric oxide enhancing hydroflumethiazide of Formula (I) is:

2H-1,2,4-benzothiadiazine-7-sulfonamide, 3,4-dihydro-3-[5-(nitrooxy)pentyl]-6-(trifluoromethyl)-, 1,1-dioxide;

2H-1,2,4-benzothiadiazine-7-sulfonamide, 3,4-dihydro-3-[3-(nitrooxy)propyl]-6-(trifluoromethyl)-, 1,1-dioxide;

2H-1,2,4-benzothiadiazine-7-sulfonamide, 3-[3,4-bis(nitrooxy)butyl]-3,4-dihydro-6-(trifluoromethyl)-, 1,1-dioxide;

2H-1,2,4-benzothiadiazine-7-sulfonamide, 3,4-dihydro-3-(4-methyl-5-oxido-1,2,5-oxadiazol-3-yl)-6-(trifluoromethyl)-, 1,1-dioxide;

spiro[2H-1,2,4-benzothiadiazine-3(4H), 4'-piperidine]-7-sulfonamide, 1'-[5-(nitrooxy)-1-oxopentyl]-6-(trifluoromethyl)-, 1,1-dioxide;

spiro[2H-1,2,4-benzothiadiazine-3(4H), 4'-piperidine]-7-sulfonamide, 1'-[3-[(nitrooxy)methyl]benzoyl]-6-(trifluoromethyl)-, 1,1-dioxide;

spiro[2H-1,2,4-benzothiadiazine-3(4H), 4'-piperidine]-7-sulfonamide, 1'-[2-methyl-3-(nitrooxy)-2-[(nitrooxy)methyl]-1-oxopropyl]-6-(trifluoromethyl)-, 1,1-dioxide;

spiro[2H-1,2,4-benzothiadiazine-3(4H), 4'-piperidine]-7-sulfonamide, 1'-[2,2-dimethyl-3-(nitrooxy)-1-oxopropyl]-6-(trifluoromethyl)-, 1,1-dioxide;

2H-1,2,4-benzothiadiazine-7-sulfonamide, 3-[3,5-bis[(nitrooxy)methyl]phenyl]-3,4-dihydro-6-(trifluoromethyl)-, 1,1-dioxide;

2H-1,2,4-benzothiadiazine-7-sulfonamide, 3,4-dihydro-3-[4-(nitrooxy)butyl]-6-(trifluoromethyl)-, 1,1-dioxide;

spiro[2H-1,2,4-benzothiadiazine-3(4H), 4'-piperidine]-7-sulfonamide, 1'-[6 (nitrooxy)-1-oxohexyl]-6-(trifluoromethyl)-, 1,1-dioxide; and pharmaceutically acceptable salts thereof.

In another embodiment, the nitric oxide enhancing chlorothiazide of Formula (I) is:

pentanamide, N-[7-(aminosulfonyl)-6-chloro-1,1-dioxido-2H-1,2,4-benzothiadiazin-3-yl]-5-(nitrooxy)-;

hexanamide, N-[7-(aminosulfonyl)-6-chloro-1,1-dioxido-2H-1,2,4-benzothiadiazin-3-yl]-6-(nitrooxy)-;

4H-1,2,4-benzothiadiazine-3-butanamide, 7-(aminosulfonyl)-N-[(2R)-2,3-bis(nitrooxy)propyl]-6-chloro-, 1,1-dioxide;

4H-1,2,4-benzothiadiazine-3-propanamide, 7-(aminosulfonyl)-6-chloro-N-[2-[2-(nitrooxy)ethoxy]ethyl]-, 1,1-dioxide;

4H-1,2,4-benzothiadiazine-3-butanamide, 7-(aminosulfonyl)-6-chloro-N-[2-(nitrooxy)ethyl]-, 1,1-dioxide;

4H-1,2,4-benzothiadiazine-7-sulfonamide, 6-chloro-3-[5-(nitrooxy)pentyl]-, 1,1-dioxide;

4H-1,2,4-benzothiadiazine-3-butanamide, 7-(aminosulfonyl)-N-[(2S)-2,3-bis(nitrooxy)propyl]-6-chloro-, 1,1-dioxide;

4H-1,2,4-benzothiadiazine-7-sulfonamide, 6-chloro-3-[4-(nitrooxy)butyl]-, 1,1-dioxide;

N-(5-chloro-2,4-disulfamoylphenyl)-2-{4-[(nitrooxy)methyl]phenyl}acetamide;

4H-1,2,4-benzothiadiazine-7-sulfonamide, 6-chloro-3-[[4-[(nitrooxy)methyl]phenyl]methyl]-, 1,1-dioxide; and pharmaceutically acceptable salts thereof.

In another embodiment, the nitric oxide enhancing hydrochlorothiazide of Formula (I) is:

2H-1,2,4-benzothiadiazine-7-sulfonamide, 6-chloro-3,4-dihydro-2-[2-(nitrooxy)ethyl]-, 1,1-dioxide;

2H-1,2,4-benzothiadiazine-7-sulfonamide, 2-[(2R)-2,3-bis(nitrooxy)propyl]-6-chloro-3,4-dihydro-, 1,1-dioxide;

2H-1,2,4-benzothiadiazine-7-sulfonamide, 2-[(2S)-2,3-bis(nitrooxy)propyl]-6-chloro-3,4-dihydro-, 1,1-dioxide;

2H-1,2,4-benzothiadiazine-7-sulfonamide, 6-chloro-3,4-dihydro-3-[4-(nitrooxy)butyl]-, 1,1-dioxide, (3R)—;

2H-1,2,4-benzothiadiazine-7-sulfonamide, 6-chloro-3,4-dihydro-3-[4-(nitrooxy)butyl]-, 1,1-dioxide, (3S)—; and pharmaceutically acceptable salts thereof.

Compounds of the invention that have one or more asymmetric carbon atoms may exist as the optically pure enantiomers, pure diastereomers, mixtures of enantiomers, mixtures of diastereomers, racemic mixtures of enantiomers, diastereomeric racemates or mixtures of diastereomeric racemates. It is to be understood that the invention anticipates and includes within its scope all such isomers and mixtures thereof.

Another embodiment of the invention describes the metabolites of the nitric oxide enhancing diuretic compounds and pharmaceutically acceptable salts thereof. These metabolites, include but are not limited to, degradation products, hydrolysis products, gluconoride adducts and the like, of the nitric oxide enhancing diuretic compounds and pharmaceutically acceptable salts thereof. The metabolites of the nitric oxide enhancing diuretic compounds, include, but are not limited to, 2H-1,2,4-benzothiadiazine-7-sulfonamide, 6-chloro-3,4-dihydro-3-(5-hydroxypentyl)-, 1,1-dioxide;

2H-1,2,4-benzothiadiazine-7-sulfonamide, 3,4-dihydro-3-(5-hydroxypentyl)-6-(trifluoromethyl)-1,1-dioxide;

2H-1,2,4-benzothiadiazine-7-sulfonamide, 6-chloro-3,4-dihydro-3-(4-hydroxybutyl)-, 1,1-dioxide;

pentanamide, N-[2,4-bis(aminosulfonyl)-5-chlorophenyl]-5-(nitrooxy)-;

2H-1,2,4-benzothiadiazine-7-sulfonamide, 6-chloro-3,4-dihydro-2-(2-hydroxyethyl)-, 1,1-dioxide;

2H-1,2,4-benzothiadiazine-2-acetic acid, 7-(aminosulfonyl)-6-chloro-3,4-dihydro-, ethyl ester, 1,1-dioxide;

2H-1,2,4-benzothiadiazine-7-sulfonamide, 6-chloro-3,4-dihydro-2-(4-hydroxybutyl)-, 1,1-dioxide;

2H-1,2,4-benzothiadiazine-2-acetic acid, 7-(aminosulfonyl)-6-chloro-3,4-dihydro-, methyl ester, 1,1-dioxide;

2H-1,2,4-benzothiadiazine-3-acetic acid, 7-(aminosulfonyl)-6-chloro-3,4-dihydro-, 1,1-dioxide;

2H-1,2,4-benzothiadiazine-2-butanoic acid, 7-(aminosulfonyl)-6-chloro-3,4-dihydro-, 1,1-dioxide;

2H-1,2,4-benzothiadiazine-7-sulfonamide, 3-(aminomethyl)-6-chloro-3,4-dihydro-, 1,1-dioxide;

2H-1,2,4-benzothiadiazine-7-sulfonamide, 6-chloro-3,4-dihydro-2-(3-hydroxypropyl)-, 1,1-dioxide;

2H-1,2,4-benzothiadiazine-7-sulfonamide, 6-chloro-3,4-dihydro-2-(5-hydroxypentyl)-, 1,1-dioxide;

2H-1,2,4-benzothiadiazine-7-sulfonamide, 3,4-dihydro-3-(4-hydroxybutyl)-6-(trifluoromethyl)-, 1,1-dioxide;

2H-1,2,4-benzothiadiazine-7-sulfonamide, 6-chloro-3,4-dihydro-3-[(methylamino)methyl]-, 1,1-dioxide;

2H-1,2,4-benzothiadiazine-7-sulfonamide, 6-chloro-3,4-dihydro-2-(6-hydroxyhexyl)-, 1,1-dioxide;

2H-1,2,4-benzothiadiazine-7-sulfonamide, 2-[4-[3,5-bis(hydroxymethyl)phenoxy]butyl]-6-chloro-3,4-dihydro-, 1,1-dioxide;

2H-1,2,4-benzothiadiazine-7-sulfonamide, 2-[3-[3,5-bis(hydroxymethyl)phenoxy]propyl]-6-chloro-3,4-dihydro-, 1,1-dioxide;

2H-1,2,4-benzothiadiazine-7-sulfonamide, 2-[2-[3,5-bis(hydroxymethyl)phenoxy]ethyl]-6-chloro-3,4-dihydro-, 1,1-dioxide;

2H-1,2,4-benzothiadiazine-7-sulfonamide, 6-chloro-2-(2,3-dihydroxypropyl)-3,4-dihydro-, 1,1-dioxide;

2H-1,2,4-benzothiadiazine-7-sulfonamide, 6-chloro-3,4-dihydro-2-[2-hydroxy-1-(hydroxymethyl)ethyl]-, 1,1-dioxide;

2H-1,2,4-benzothiadiazine-7-sulfonamide, 3-[2-[3,5-bis(hydroxymethyl)phenyl]ethyl]-6-chloro-3,4-dihydro-, 1,1-dioxide;

and pharmaceutically acceptable salts thereof.

Another embodiment of the invention provides processes for making the novel compounds of the invention and to the intermediates useful in such processes. The reactions are performed in solvents appropriate to the reagents and materials used are suitable for the transformations being effected. It is understood by one skilled in the art of organic synthesis that the functionality present in the molecule must be consistent with the chemical transformation proposed. This will, on occasion, necessitate judgment by the routineer as to the order of synthetic steps, protecting groups required, and deprotection conditions. Substituents on the starting materials may be incompatible with some of the reaction conditions required in some of the methods described, but alternative methods and substituents compatible with the reaction conditions will be readily apparent to one skilled in the art. The use of sulfur and oxygen protecting groups is well known for protecting thiol and alcohol groups against undesirable reactions during a synthetic procedure and many such protecting groups are known and described by, for example, Greene and Wuts, *Protective Groups in Organic Synthesis*, Third Edition, John Wiley & Sons, New York (1999).

The chemical reactions described herein are generally disclosed in terms of their broadest application to the preparation of the compounds of this invention. Occasionally, the reactions may not be applicable as described to each compound included within the disclosed scope. The compounds for which this occurs will be readily recognized by one skilled in the art. In all such cases, either the reactions can be successfully performed by conventional modifications known to one skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily prepared from known starting materials.

The compounds of Formulas (I) can be synthesized by one skilled in the art following the methods and examples described herein. Some of the parent diuretic compounds (i.e. diuretic compounds that do not contain a nitric oxide enhancing group) are commercially available. The synthesis of the parent diuretic compounds are also disclosed in, for example, U.S. Pat. Nos. 2,809,194, 2,976,289, 3,055,904, 3,058,882, 3,255,241, 3,360,518, 3,392,168, 3,565,911, 3,665,002, 3,758,506, 3,806,534, 4,010,273, 4,018,020, 6,767,917 and in JP 7305,585 and in DE 1,163,332, and in J. Am. Chem. Soc. 82: 1132 (1960), the disclosures of each of which are incorporated by reference herein in their entirety. The parent diuretic compounds are substituted to contain a nitric oxide enhancing group linked to the diuretic compound through one or more sites such as carbon and/or nitrogen using conventional methods known to one skilled in the art. Known methods for linking the heterocyclic nitric oxide donor group to compounds are described in WO 99/64417, WO 94/01422; EP 0 574 726 A1, EP 0 683 159 A1; and in *J. Med. Chem.*, 47: 2688-2693 (2004); *J. Med. Chem.*, 47: 1840-1846 (2004); *J. Med. Chem.*, 46: 3762-3765 (2003); *J. Med. Chem.*, 46: 747-754 (2003); *Chem. Rev.*, 102: 1091-1134 (2002); *J. Med. Chem.*, 42: 1941-1950 (1999); *J. Med. Chem.*, 41: 5393-5401 (1998); *J. Med. Chem.*, 38: 4944-4949 (1995); *Arzneim. Forsch. Drug Res.*, 47 (II): 847-854 (1997); the disclosures of each of which are incorporated by reference herein in their entirety. The methods of linking the heterocyclic nitric oxide donor group to compounds described in these references can be applied by one skilled in the art to produce any of the diuretic compounds comprising a heterocyclic nitric oxide donor group described herein.

Known methods of linking the nitroxide group to compounds are described in U.S. Pat. Nos. 6,448,267, 6,455,542, 6,759,430, and in WO 2004/050084, WO 03/088961, the disclosures of each of which are incorporated by reference herein in their entirety.

Nitric oxide enhancing diuretic compounds comprising at least one —ONO group, —SNO group, —NNO group, —ONO$_2$ group, —SNO$_2$ group, —NNO$_2$ group and/or —(N$_2$O$_2$—).M$_1^+$ group can be synthesized using conventional methods known to one skilled in the art. Known methods for attaching a —ONO group, —SNO group, —NNO group, —ONO$_2$ group, —SNO$_2$ group, —NNO$_2$ group and/or —(N$_2$O$_2$—).M$_1^+$ group to compounds are described in U.S. Pat. Nos. 5,380,758, 5,859,053, 5,703,073 and 6,297,260; and in WO 94/03421, WO 94/04484, WO 94/12463, WO 95/09831, WO 95/19952, WO 95/30641, WO 97/27749, WO 98/09948, WO 98/19672, WO 98/21193, WO 00/51988, WO 00/61604, WO 00/72838, WO 01/00563, WO 01/04082, WO 01/10814, WO 01/12584, WO 01/45703, WO 00/61541, WO 00/61537, WO 02/11707, WO 02/30866 and in Oae et al, *Org. Prep. Proc. Int.*, 15(3):165-198 (1983), the disclosures of each of which are incorporated by reference herein in their entirety. The methods of for attaching a —ONO group, —SNO group, —NNO group, —ONO$_2$ group, —SNO$_2$ group, —NNO$_2$ group and/or —(N$_2$O$_2$—).M$_1^+$ group to compounds described in these references can be applied by one skilled in the art to produce any of the nitric oxide enhancing diuretic compounds described herein.

Compounds contemplated for use in the invention, e.g., nitric oxide enhancing diuretic compounds comprising at least one nitric oxide enhancing group selected from an —ONO group, an —SNO group, an —NNO group, an —ONO$_2$ group, an —SNO$_2$ group, an —NNO$_2$ group, a —(N$_2$O$_2$—).M$_1^+$ group, a heterocyclic nitric oxide donor group and a nitroxide group; where the nitric oxide enhancing group is directly or indirectly linked to the angiotensin II antagonist compound through one or more sites such as carbon, oxygen, nitrogen and/or sulfur via a bond or moiety that cannot be hydrolyzed, are, optionally, used in combination with nitric oxide enhancing compounds that release nitric oxide, increase endogeneous levels of nitric oxide or otherwise directly or indirectly deliver or transfer a biologically active form of nitrogen monoxide to a site of its intended activity, such as on a cell membrane in vivo.

Nitrogen monoxide can exist in three forms: NO— (nitroxyl), NO. (nitric oxide) and NO$^+$ (nitrosonium). NO. is a highly reactive short-lived species that is potentially toxic to cells. This is critical because the pharmacological efficacy of NO depends upon the form in which it is delivered. In contrast to the nitric oxide radical (NO.), nitrosonium (NO$^+$) does not react with $O_2$ or $O_2$— species, and functionalities capable of transferring and/or releasing $NO^+$ and NO— are also resistant to decomposition in the presence of many redox metals. Consequently, administration of charged NO equivalents (positive and/or negative) does not result in the generation of toxic by-products or the elimination of the active NO group.

The term "nitric oxide" encompasses uncharged nitric oxide (NO.) and charged nitrogen monoxide species, preferably charged nitrogen monoxide species, such as nitrosonium ion ($NO^+$) and nitroxyl ion (NO—). The reactive form of nitric oxide can be provided by gaseous nitric oxide. The nitrogen monoxide releasing, delivering or transferring compounds have the structure F—NO, wherein F is a nitrogen monoxide releasing, delivering or transferring group, and include any and all such compounds which provide nitrogen monoxide to its intended site of action in a form active for its intended purpose.

The term "NO adducts" encompasses any nitrogen monoxide releasing, delivering or transferring compounds, including, for example, S-nitrosothiols, nitrites, nitrates, S-nitrothiols, sydnonimines, 2-hydroxy-2-nitrosohydrazines, (NONOates), (E)-alkyl-2-((E)-hydroxyimino)-5-nitro-3-hexeneamide (FK-409), (E)-alkyl-2-((E)-hydroxyimino)-5-nitro-3-hexeneamines, N-((2Z,3E)-4-ethyl-2-(hydroxyimino)-6-methyl-5-nitro-3-heptenyl)-3-pyridinecarboxamide (FR 146801), N-nitrosoamines, N-hydroxyl nitrosamines, nitrosimines, diazetine dioxides, oxatriazole 5-imines, oximes, hydroxylamines, N-hydroxyguanidines, hydroxyureas, benzofuroxanes, furoxans as well as substrates for the endogenous enzymes which synthesize nitric oxide.

Suitable NONOates include, but are not limited to, (Z)-1-(N-methyl-N-(6-(N-methyl-ammoniohexyl)amino))diazen-1-ium-1,2-diolate ("MAHMA/NO"), (Z)-1-(N-(3-ammoniopropyl)-N-(n-propyl)amino)diazen-1-ium-1,2-diolate ("PAPA/NO"), (Z)-1-(N-(3-aminopropyl)-N-(4-(3-aminopropylammonio)butyl)-amino) diazen-1-ium-1,2-diolate (spermine NONOate or "SPER/NO") and sodium(Z)-1-(N,N-diethylamino)diazenium-1,2-diolate (diethylamine NONOate or "DEA/NO") and derivatives thereof. NONOates are also described in U.S. Pat. Nos. 6,232,336, 5,910,316 and 5,650,447, the disclosures of which are incorporated herein by reference in their entirety. The "NO adducts" can be mono-nitrosylated, poly-nitrosylated, mono-nitrosated and/or poly-nitrosated at a variety of naturally susceptible or artificially provided binding sites for biologically active forms of nitrogen monoxide.

Suitable furoxanes include, but are not limited to, CAS 1609, C93-4759, C92-4678, S35b, CHF 2206, CHF 2363, and the like.

Suitable sydnonimines include, but are not limited to, molsidomine (N-ethoxycarbonyl-3-morpholinosydnonimine), SIN-1 (3-morpholinosydnonimine) CAS 936 (3-(cis-2,6-dimethylpiperidino)-N-(4-methoxybenzoyl)-sydnonimine, pirsidomine), C87-3754 (3-(cis-2,6-dimethylpiperidino)sydnonimine, linsidomine, C4144 (3-(3,3-dimethyl-1,4-thiazane-4-yl)sydnonimine hydrochloride), C89-4095 (3-(3,3-dimethyl-1,1-dioxo-1,4-thiazane-4-yl)sydnonimine hydrochloride, and the like.

Suitable oximes, include, but are not limited to, NOR-1, NOR-3, NOR-4, and the like.

One group of NO adducts is the S-nitrosothiols, which are compounds that include at least one —S—NO group. These compounds include S-nitroso-polypeptides (the term "polypeptide" includes proteins and polyamino acids that do not possess an ascertained biological function, and derivatives thereof); S-nitrosylated amino acids (including natural and synthetic amino acids and their stereoisomers and racemic mixtures and derivatives thereof); S-nitrosylated sugars; S-nitrosylated, modified and unmodified, oligonucleotides (preferably of at least 5, and more preferably 5-200 nucleotides); straight or branched, saturated or unsaturated, aliphatic or aromatic, substituted or unsubstituted S-nitrosylated hydrocarbons; and S-nitroso heterocyclic compounds. S-nitrosothiols and methods for preparing them are described in U.S. Pat. Nos. 5,380,758 and 5,703,073; WO 97/27749; WO 98/19672; and Oae et al, Org. Prep. Proc. Int., 15(3): 165-198 (1983), the disclosures of each of which are incorporated by reference herein in their entirety.

Another embodiment of the invention is S-nitroso amino acids where the nitroso group is linked to a sulfur group of a sulfur-containing amino acid or derivative thereof. Such compounds include, for example, S-nitroso-N-acetylcysteine, S-nitroso-captopril, S-nitroso-N-acetylpenicillamine, S-nitroso-homocysteine, S-nitroso-cysteine, S-nitroso-glutathione, S-nitroso-cysteinyl-glycine, and the like.

Suitable S-nitrosylated proteins include thiol-containing proteins (where the NO group is attached to one or more sulfur groups on an amino acid or amino acid derivative thereof) from various functional classes including enzymes, such as tissue-type plasminogen activator (TPA) and cathepsin B; transport proteins, such as lipoproteins; heme proteins, such as hemoglobin and serum albumin; and biologically protective proteins, such as immunoglobulins, antibodies and cytokines. Such nitrosylated proteins are described in WO 93/09806, the disclosure of which is incorporated by reference herein in its entirety. Examples include polynitrosylated albumin where one or more thiol or other nucleophilic centers in the protein are modified.

Other examples of suitable S-nitrosothiols include:

(i) $HS(C(R_e)(R_f))_m SNO$;

(ii) $ONS(C(R_e)(R_f))_m R_e$; or (iii) $H_2N$—$CH(CO_2H)$—$(CH_2)_m$—$C(O)NH$—$CH(CH_2SNO)$—$C(O)NH$—$CH_2$—$CO_2H$;

wherein m is an integer from 2 to 20;

$R_e$ and $R_f$ are each independently a hydrogen, an alkyl, a cycloalkoxy, a halogen, a hydroxy, an hydroxyalkyl, an alkoxyalkyl, an arylheterocyclic ring, an alkylaryl, an alkylcycloalkyl, an alkylheterocyclic ring, a cycloalkylalkyl, a cycloalkylthio, an arylalklythio, an arylalklythioalkyl, an alkylthioalkyl, a cycloalkenyl, an heterocyclicalkyl, an alkoxy, a haloalkoxy, an amino, an alkylamino, a dialkylamino, an arylamino, a diarylamino, an alkylarylamino, an alkoxyhaloalkyl, a sulfonic acid, a sulfonic ester, an alkylsulfonic acid, an arylsulfonic acid, an arylalkoxy, an alkylthio, an arylthio, a cyano, an aminoalkyl, an aminoaryl, an aryl, an arylalkyl, an alkylaryl, a carboxamido, an alkylcarboxamido, an arylcarboxamido, an amidyl, a carboxyl, a carbamoyl, an alkylcarboxylic acid, an arylcarboxylic acid, an alkylcarbonyl, an arylcarbonyl, an ester, a carboxylic ester, an alkylcarboxylic ester, an arylcarboxylic ester, a sulfonamido, an alkylsulfonamido, an arylsulfonamido, an alkylsulfonyl, an alkylsulfonyloxy, an arylsulfonyl, arylsulphonyloxy, a sulfonic ester, an alkyl ester, an aryl ester, a urea, a phosphoryl, a nitro, —$U_3$—$V_5$, $V_6$, —$(C(R_o)(R_p))_{k1}$—$U_3$—$V_5$, —$(C(R_o)(R_p))_{k1}$—$U_3$—$V_3$, —$(C(R_o)(R_p))_{k1}$—$U_3$—$V_6$, —$(C(R_o)(R_p))_{k1}$—$U_3$—$C(O)$—$V_6$, or $R_e$ and $R_f$ taken together with the carbons to which they are attached form a carbonyl, a methanthial, a heterocyclic ring, a cycloalkyl group, an aryl group, an oxime, an imine, a hydrazone, a bridged cycloalkyl group,

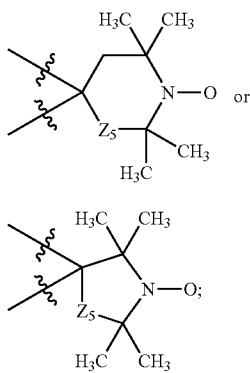

R$_o$ and R$_p$ are each independently a hydrogen, an alkyl, a cycloalkoxy, a halogen, a hydroxy, an hydroxyalkyl, an alkoxyalkyl, an arylheterocyclic ring, an alkylaryl, an alkylcycloalkyl, an alkylheterocyclic ring, a cycloalkylalkyl, a cycloalkylthio, an arylalkylthio, an arylalklythioalkyl, an alkylthioalkyl a cycloalkenyl, an heterocyclicalkyl, an alkoxy, a haloalkoxy, an amino, an alkylamino, a dialkylamino, an arylamino, a diarylamino, an alkylarylamino, an alkoxyhaloalkyl, a sulfonic acid, a sulfonic ester, an alkylsulfonic acid, an arylsulfonic acid, an arylalkoxy, an alkylthio, an arylthio, a cyano an aminoalkyl, an aminoaryl, an aryl, an arylalkyl, an alkylaryl, a carboxamido, an alkylcarboxamido, an arylcarboxamido, an amidyl, a carboxyl, a carbamoyl, an alkylcarboxylic acid, an arylcarboxylic acid, an alkylcarbonyl, an arylcarbonyl, an ester, a carboxylic ester, an alkylcarboxylic ester, an arylcarboxylic ester, a sulfonamido, an alkylsulfonamido, an arylsulfonamido, an alkylsulfonyl, an alkylsulfonyloxy, an arylsulfonyl, arylsulphonyloxy, a sulfonic ester, an alkyl ester, an aryl ester, a urea, a phosphoryl, a nitro, —U$_3$—V$_5$, V$_6$, or R$_o$ and R$_p$ taken together with the carbons to which they are attached form a carbonyl, a methanthial, a heterocyclic ring, a cycloalkyl group, an aryl group, an oxime, an imine, a hydrazone a bridged cycloalkyl group,

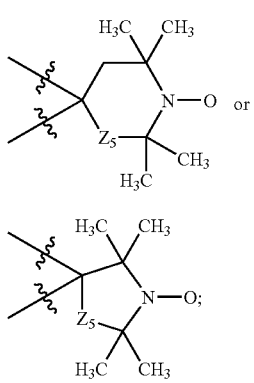

Z$_5$ is —CH$_2$ or oxygen;
Z$_6$ is —CH or nitrogen;
U$_3$ is an oxygen, sulfur or —N(R$_a$)R$_i$;
V$_5$ is —NO or —NO$_2$ (i.e. an oxidized nitrogen);
k$_1$ is an integer from 1 to 3;
R$_a$ is a lone pair of electrons, a hydrogen or an alkyl group;
R$_i$ is a hydrogen, an alkyl, an aryl, an alkylcarboxylic acid, an arylcarboxylic acid, an alkylcarboxylic ester, an arylcarboxylic ester, an alkylcarboxamido, an arylcarboxamido, an alkylaryl, an alkylsulfinyl, an alkylsulfonyl, an alkylsulfonyloxy, an arylsulfinyl, an arylsulfonyl, an arylsulphonyloxy, a sulfonamido, a carboxamido, a carboxylic ester, an aminoalkyl, an aminoaryl, —CH$_2$—C—(U$_3$—V$_5$)(R$_e$)(R$_f$), a bond to an adjacent atom creating a double bond to that atom or —(N$_2$O$_2$—).M$_1^+$, wherein M$_1^+$ is an organic or inorganic cation; and V$_3$ and V$_6$ are as defined herein.

In cases where R$_e$ and R$_f$ are independently a heterocyclic ring or taken together R$_e$ and R$_f$ are a heterocyclic ring, then R$_i$ can be a substituent on any disubstituted nitrogen contained within the radical wherein R$_i$ is as defined herein.

Nitrosothiols can be prepared by various methods of synthesis. In general, the thiol precursor is prepared first, then converted to the S-nitrosothiol derivative by nitrosation of the thiol group with NaNO$_2$ under acidic conditions (pH is about 2.5) which yields the S-nitroso derivative. Acids which can be used for this purpose include aqueous sulfuric, acetic and hydrochloric acids. The thiol precursor can also be nitrosylated by reaction with an organic nitrite such as tert-butyl nitrite, or a nitrosonium salt such as nitrosonium tetrafluoroborate in an inert solvent.

Another group of NO adducts for use in the invention, where the NO adduct is a compound that donates, transfers or releases nitric oxide, include compounds comprising at least one ON—O— or ON—N— group. The compounds that include at least one ON—O— or ON—N— group are preferably ON—O— or ON—N-polypeptides (the term "polypeptide" includes proteins and polyamino acids that do not possess an ascertained biological function, and derivatives thereof); ON—O— or ON—N-amino acids (including natural and synthetic amino acids and their stereoisomers and racemic mixtures); ON—O— or ON—N-sugars; ON—O— or —ON—N— modified or unmodified oligonucleotides (comprising at least 5 nucleotides, preferably 5-200 nucleotides); ON—O— or ON—N— straight or branched, saturated or unsaturated, aliphatic or aromatic, substituted or unsubstituted hydrocarbons; and ON—O—, ON—N— or ON—C-heterocyclic compounds. Examples of compounds comprising at least one ON—O— or ON—N— group include butyl nitrite, isobutyl nitrite, tert-butyl nitrite, amyl nitrite, isoamyl nitrite, N-nitrosamines, N-nitrosamides, N-nitrosourea, N-nitrosoguanidines, N-nitrosocarbamates, N-acyl-N-nitroso compounds (such as, N-methyl-N-nitrosourea); N-hydroxy-N-nitrosamines, cupferron, alanosine, dopastin, 1,3-disubstitued nitrosiminobenzimidazoles, 1,3,4-thiadiazole-2-nitrosimines, benzothiazole-2 (3H)-nitrosimines, thiazole-2-nitrosimines, oligonitroso sydnonimines, 3-alkyl-N-nitroso-sydnonimines, and 2H-1,3,4-thiadiazine nitrosimines.

Another group of NO adducts for use in the invention include nitrates that donate, transfer or release nitric oxide, such as compounds comprising at least one O$_2$N—O—, O$_2$N—N— or O$_2$N—S— group. Among these compounds are O$_2$N—O—, O$_2$N—N— or O$_2$N—S-polypeptides (the term "polypeptide" includes proteins and also polyamino acids that do not possess an ascertained biological function, and derivatives thereof); O$_2$N—O—, O$_2$N—N— or O$_2$N—S-amino acids (including natural and synthetic amino acids and their stereoisomers and racemic mixtures); O$_2$N—O—, O$_2$N—N— or O$_2$N—S— sugars; O$_2$N—O—, O$_2$N—N— or O$_2$N—S— modified and unmodified oligonucleotides (comprising at least 5 nucleotides, preferably 5-200 nucleotides); O$_2$N—O—, O$_2$N—N— or O$_2$N—S— straight or branched, saturated or unsaturated, aliphatic or aromatic, substituted or unsubstituted hydrocarbons; and O$_2$N—O—, O$_2$N—N— or O₂N—S— heterocyclic compounds. Examples of compounds comprising at least one O₂N—O—, O₂N—N— or O₂N—S— group include isosorbide dinitrate, isosorbide mononitrate, clonitrate, erythrityl tetranitrate, mannitol hexanitrate, nitroglycerin, pentaerythritoltetranitrate, pentrinitrol, propatylnitrate and organic nitrates with a sulfhydryl-containing amino acid such as, for example SPM 3672, SPM 4757, SPM 5185, SPM 5186 and those disclosed in U.S. Pat. Nos. 5,284,872, 5,428,061, 5,661,129, 5,807,847 and 5,883,122 and in WO 97/46521, WO 00/54756 and in WO 03/013432, the disclosures of each of which are incorporated by reference herein in their entirety.

Another group of NO adducts are N-oxo-N-nitrosoamines that donate, transfer or release nitric oxide and are represented by the formula: $R^{1''}R^{2''}N$—$N(O-M^+)$—$NO$, where $R^{1''}$ and $R^{2''}$ are each independently a polypeptide, an amino acid, a sugar, a modified or unmodified oligonucleotide, a straight or branched, saturated or unsaturated, aliphatic or aromatic, substituted or unsubstituted hydrocarbon, or a heterocyclic group, and where $M_1^+$ is an organic or inorganic cation, such, as for example, an alkyl substituted ammonium cation or a Group I metal cation.

The invention is also directed to compounds that stimulate endogenous NO or elevate levels of endogenous endothelium-derived relaxing factor (EDRF) in vivo or are oxidized to produce nitric oxide and/or are substrates for nitric oxide synthase and/or cytochrome P450. Such compounds include, for example, L-arginine, L-homoarginine, and N-hydroxy-L-arginine, N-hydroxy-L-homoarginine, N-hydroxydebrisoquine, N-hydroxypentamidine including their nitrosated and/or nitrosylated analogs (e.g., nitrosated L-arginine, nitrosylated L-arginine, nitrosated N-hydroxy-L-arginine, nitrosylated N-hydroxy-L-arginine, nitrosated and nitrosylated L-homoarginine), N-hydroxyguanidine compounds, amidoxime, ketoximes, aldoxime compounds, that can be oxidized in vivo to produce nitric oxide. Compounds that may be substrates for a cytochrome P450, include, for example, imino(benzylamino)methylhydroxyl amine, imino(((4-methylphenyl)methyl)amino)methylhydroxylamine, imino(((4-methoxyphenyl)methyl)amino) methylhydroxylamine, imino(((4-(trifluoromethyl)phenyl)methyl)amino) methylhydroxylamine, imino(((4-nitrophenyl) methyl)amino)methylhydroxylamine, (butylamino)iminomethylhydroxylamine, imino (propylamino) methylhydroxylamine, imino(pentylamino)methylhydroxylamine, imino (propylamino)methylhydroxylamine, imino((methylethyl)amino)methylhydroxylamine, (cyclopropylamino)iminomethylhydroxylamine, imino-2-1,2,3,4-tetrahydroisoquinolyl methylhydroxylamine, imino(1-methyl(2-1,2,3,4-tetrahydroisoquinolyl)) methylhydroxylamine, (1,3-dimethyl(2-1,2,3,4-tetrahydroisoquinolyl)) iminomethylhydroxylamine, (((4-chlorophenyl)methyl)amino)iminomethylhydroxylamine, ((4-chlorophenyl)amino) iminomethylhydroxylamine, (4-chlorophenyl)(hydroxyimino)methylamine, and 1-(4-chlorophenyl)-1-(hydroxyimino) ethane, and the like, precursors of L-arginine and/or physiologically acceptable salts thereof, including, for example, citrulline, ornithine, glutamine, lysine, polypeptides comprising at least one of these amino acids, inhibitors of the enzyme arginase (e.g., N-hydroxy-L-arginine and 2(S)-amino-6-boronohexanoic acid), nitric oxide mediators and/or physiologically acceptable salts thereof, including, for example, pyruvate, pyruvate precursors, α-keto acids having four or more carbon atoms, precursors of α-keto acids having four or more carbon atoms (as disclosed in WO 03/017996, the disclosure of which is incorporated herein in its entirety), and the substrates for nitric oxide synthase, cytokines, adenosin, bradykinin, cal-reticulin, bisacodyl, and phenolphthalein. EDRF is a vascular relaxing factor secreted by the endothelium, and has been identified as nitric oxide (NO) or a closely related derivative thereof (Palmer et al, *Nature,* 327:524-526 (1987); Ignarro et al, *Proc. Natl. Acad. Sci. USA,* 84:9265-9269 (1987)).

The invention is also directed to nitric oxide enhancing compounds that can increase endogenous nitric oxide. Such compounds, include for example, nitroxide containing compounds, include, but are not limited to, substituted 2,2,6,6-tetramethyl-1-piperidinyloxy compounds, substituted 2,2,5,5-tetramethyl-3-pyrroline-1-oxyl compounds, substituted 2,2,5,5-tetramethyl-1-pyrrolidinyloxyl compounds, substituted 1,1,3,3-tetramethylisoindolin-2-yloxyl compounds, substituted 2,2,4,4-tetramethyl-1-oxazolidinyl-3-oxyl compounds, substituted 3-imidazolin-1-yloxy, 2,2,5,5-tetramethyl-3-imidazolin-1-yloxyl compounds, OT-551, 4-hydroxy-2,2,6,6-tetramethyl-1-piperidinyloxy (tempol), and the like. Suitable substituents, include, but are not limited to, aminomethyl, benzoyl, 2-bromoacetamido, 2-(2-(2-bromoacetamido)ethoxy)ethylcarbamoyl, carbamoyl, carboxy, cyano, 5-(dimethylamino)-1-naphthalenesulfonamido, ethoxyfluorophosphinyloxy, ethyl, 5-fluoro-2,4-dinitroanilino, hydroxy, 2-iodoacetamido, isothiocyanato, isothiocyanatomethyl, methyl, maleimido, maleimidoethyl, 2-(2-maleimidoethoxy)ethylcarbamoyl, maleimidomethyl, maleimido, oxo, phosphonooxy, and the like.

The invention is also based on the discovery that compounds and compositions of the invention may be used in conjunction with other therapeutic agents for co-therapies, partially or completely, in place of other therapeutic agents, such as, for example, aldosterone antagonists, alpha-adrenergic receptor antagonists, angiotensin II antagonists, angiotensin-converting enzyme (ACE) inhibitors, antidiabetic compounds, anti-hyperlipidemic compounds, antioxidants, antithrombotic and vasodilator compounds, β-adrenergic antagonists, calcium channel blockers, digitalis, diuretics, endothelin antagonists, hydralazine compounds, H₂ receptor antagonists, neutral endopeptidase inhibitors, nonsteroidal antiinflammatory compounds (NSAIDs), phosphodiesterase inhibitors, potassium channel blockers, platelet reducing agents, proton pump inhibitors, renin inhibitors, selective cyclooxygenase-2 (COX-2) inhibitors, and combinations of two or more thereof. The therapeutic agent may optionally be nitrosated and/or nitrosylated and/or contain at least one heterocyclic nitric oxide donor group and/or at least one nitroxide group.

Suitable aldosterone antagonists include, but are not limited to, canrenone, potassium canrenoate, drospirenone, spironolactone, eplerenone (INSPRA®), epoxymexrenone, fadrozole, pregn-4-ene-7,21-dicarboxylic acid, 9,11-epoxy-17-hydroxy-3-oxo, γ-lactone, methyl ester, (7α,11α,17β)-; pregn-4-ene-7,21-dicarboxylic acid, 9,11-epoxy-17-hydroxy-3-oxo-dimethyl ester, (7α,11α,17β.)-; 3'H-cyclopropa (6,7)pregna-4,6-diene-21-carboxylic acid, 9,11-epoxy-6,7-dihydro-17-hydroxy-3-oxo-, γ-lactone, (6β,7β,11α,17β)-; pregn-4-ene-7,21-dicarboxylic acid, 9,11-epoxy-17-hydroxy-3-oxo-, 7-(1-methylethyl) ester, monopotassium salt, (7α,11α,17β.)-; pregn-4-ene-7,21-dicarboxylic acid, 9,11,-epoxy-17-hydroxy-3-oxo-, 7-methyl ester, monopotassium salt, (7α,11α,17β.)-; 3'H-cyclopropa(6,7) pregna-1,4,6-triene-21-carboxylic acid, 9,11-epoxy-6,7-dihydro-17-hydroxy-3-oxo-, γ-lactone, (6β,7β,11α)-; 3'H-cyclopropa(6,7) pregna-4,6-diene-21-carboxylic acid, 9,11-epoxy-6,7-dihydro-17-hydroxy-3-oxo-, methyl ester, (6β,7β,11α,17β)-; 3'H-cyclopropa (6,7)pregna-4,6-diene-21-carboxylic acid, 9,11-epoxy-6,7-dihydro-17-hydroxy-3-oxo-, monopotassium salt, (6β,7β,11α,17β)-; 3'H-cyclopropa(6,7)pregna-1,4, 6-triene-21-carboxylic acid, 9,11-epoxy-6,7-dihydro-17-hydroxy-3-oxo-, γ-lactone, (6β,7β,11α,17β)-; pregn-4-ene-7,21-dicarboxylic acid, 9,11-epoxy-17-hydroxy-3-oxo-, γ-lactone, ethyl ester, (7α,11α,17β)-; pregn-4-ene-7,21-dicarboxylic acid, 9,11-epoxy-17-hydroxy-3-oxo-, γ-lactone, 1-methylethyl ester, (7α,11α,17β)-; RU-28318, and the like. Suitable aldosterone antagonists are described more fully in the literature, such as in Goodman and Gilman, The Pharmacological Basis of Therapeutics (9th Edition), McGraw-Hill, 1995; and the Merck Index on CD-ROM, 13$^{th}$ Edition; and on STN Express, file phar and file registry.

In some embodiments the aldosterone antagonists is eplerenone or spironolactone (a potassium sparing diuretic that acts like an aldosterone antagonist). In more particular embodiments eplerenone is administered in an amount of about 25 milligrams to about 300 milligrams as a single dose or as multiple doses per day; the spironolactone is administered in an amount of about 25 milligrams to about 150 milligrams as a single dose or as multiple doses per day.

Suitable alpha-adrenergic receptor antagonists include but are not limited to, phentolamine, tolazoline, idazoxan, deriglidole, RX 821002, BRL 44408, BRL 44409, BAM 1303, labetelol, ifenprodil, rauwolscine, corynathine, raubascine, tetrahydroalstonine, apoyohimbine, akuammigine, β-yohimbine, yohimbol, yohimbine, pseudoyohimbine, epi-3α-yohimbine, 10-hydroxy-yohimbine, 11-hydroxy-yohimbine, tamsulosin, benoxathian, atipamezole, BE 2254, WB 4101, HU-723, tedisamil, mirtazipine, setiptiline, reboxitine, delequamine, naftopil, saterinone, SL 89.0591, ARC 239, urapidil, 5-methylurapidil, monatepi, haloperidol, indoramin, SB 216469, moxisylyte, trazodone, dapiprozole, efaroxan, Recordati 15/2739, SNAP 1069, SNAP 5089, SNAP 5272, RS 17053, SL 89.0591, KMD 3213, spiperone, AH 11110A, chloroethylclonidine, BMY 7378, niguldipine, and the like. Suitable alpha-adrenergic receptor antagonists are described more fully in the literature, such as in Goodman and Gilman, The Pharmacological Basis of Therapeutics (9th Edition), McGraw-Hill, 1995; and the Merck Index on CD-ROM, Thirteenth Edition; and on STN Express, file phar and file registry.

Suitable angiotensin II antagonists include, but are not limited to, angiotensin, abitesartan, candesartan, candesartan cilexetil, elisartan, embusartan, enoltasosartan, eprosartan, fonsartan, forasartan, glycyllosartan, irbesartan, losartan, olmesartan, milfasartan, medoxomil, ripisartan, pomisartan, pratosartan, saprisartan, saralasin, sarmesin, tasosartan, telmisartan, valsartan, zolasartan, 3-(2'(tetrazole-5-yl)-1,1'-biphen-4-yl)methyl-5,7-dimethyl-2-ethyl-3H-imidazo[4,5-b]pyridine, antibodies to angiotensin II, A-81282, A-81988, BAY 106734, BIBR-363, BIBS-39, BIBS-222, BMS-180560, BMS-184698, BMS-346567, CGP-38560A, CGP-42112A, CGP-48369, CGP-49870, CGP-63170, CI-996, CP-148130, CL-329167, CV-11194, DA-2079, DE-3489, DMP-811, DuP-167, DuP-532, DuP-753, E-1477, E-4177, E-4188, EMD-66397, EMD-666R4, EMD-73495, EMD-66684, EXP-063, EXP-929, EXP-3174, EXP-6155, EXP-6803, EXP-7711, EXP-9270, EXP-9954, FK-739, FRI 153332, GA-0050, GA-0056, HN-65021, HOE-720, HR-720, ICI-D6888, ICI-D7155, ICI-D8731, KRI-1177, KT3-671, KT-3579, KW-3433, L-158809, L-158978, L-159282, L-159689, L-159874, L-161177, L-162154, L-162234, L-162441, L-163007, L-163017, LF-70156, LRB-057, LRB-081, LRB-087, LY-235656, LY-266099, LY-285434, LY-301875, LY-302289, LY-315995, ME-3221, MK-954, MK 996, PD-123177, PD-123319, PD-126055, PD-150304, RG-13647, RWJ-38970, RWJ-46458, S-8307, S-8308, SC-51757, SC-54629, SC-52458, SC-52459, SK 1080, SL-910102, SR-47436, TAK-536, UP-2696, U-96849, U-97018, UK-77778, UP-275-22, WAY-126227, WK-1260, WK-1360, WK-1492, WY 126227, YH-1498, YM-358, YM-31472, X-6803, XH-148, XR-510, ZD-6888, ZD-7155, ZD-8731, ZD 8131, the compounds of ACS registry numbers 124750-92-1, 133240-46-7, 135070-05-2, 139958-16-0, 145160-84-5, 147403-03-0, 153806-29-2, 439904-54-8P, 439904-55-9P, 439904-56-0P, 439904-57-1P, 439904-58-2P, 155918-60-8P, 155918-61-9P, 272438-16-1P, 272446-75-0P, 223926-77-0P, 169281-89-4, 439904-65-1P, 165113-01-9P, 165113-02-0P, 165113-03-1P, 165113-03-2P, 165113-05-3P, 165113-06-4P, 165113-07-5P, 165113-08-6P, 165113-09-7P, 165113-10-0P, 165113-11-1P, 165113-12-2P, 165113-17-7P, 165113-18-8P, 165113-19-9P, 165113-20-2P, 165113-13-3P, 165113-14-4P, 165113-15-5P, 165113-16-6P, 165113-21-3P, 165113-22-4P, 165113-23-5P, 165113-24-6P, 165113-25-7P, 165113-26-8P, 165113-27-9P, 165113-28-0P, 165113-29-1P, 165113-30-4P, 165113-31-5P, 165113-32-6P, 165113-33-7P, 165113-34-8P, 165113-35-9P, 165113-36-0P, 165113-37-1P, 165113-38-2P, 165113-39-3P, 165113-40-6P, 165113-41-7P, 165113-42-8P, 165113-43-9P, 165113-44-0P, 165113-45-1P, 165113-46-2P, 165113-47-3P, 165113-48-4P, 165113-49-5P, 165113-50-8P, 165113-51-9P, 165113-52-0P, 165113-53-1P, 165113-54-2P, 165113-55-3P, 165113-56-4P, 165113-57-5P, 165113-58-6P, 165113-59-7P, 165113-60-0P, 165113-61-1P, 165113-62-2P, 165113-63-3P, 165113-64-4P, 165113-65-5P, 165113-66-6P, 165113-67-7P, 165113-68-8P, 165113-69-9P, 165113-70-2P, 165113-71-3P, 165113-72-4P, 165113-73-5P, 165113-74-6P, 114798-27-5, 114798-28-6, 114798-29-7, 124749-82-2, 114798-28-6, 124749-84-4, 124750-88-5, 124750-91-0, 124750-93-2, 161946-65-2P, 161947-47-3P, 161947-48-4P, 161947-51-9P, 161947-52-0P, 161947-55-3P, 161947-56-4P, 161947-60-0P, 161947-61-1P, 161947-68-8P, 161947-69-9P, 161947-70-2P, 161947-71-3P, 161947-72-4P, 161947-74-6P, 161947-75-7P, 161947-81-5P, 161947-82-6P, 161947-83-7P, 161947-84-8P, 161947-85-9P, 161947-86-0P, 161947-87-1P, 161947-88-2P, 161947-89-3P, 161947-90-6P, 161947-91-7P, 161947-92-8P, 161947-93-9P, 161947-94-0P, 161947-95-1P, 161947-96-2P, 161947-97-3P, 161947-98-4P, 161947-99-5P, 161948-00-1P, 161948-01-2P, 161948-02-3P, 168686-32-6P, 167301-42-0P, 166813-82-7P, 166961-56-4P, 166961-58-6P, 158872-96-9P, 158872-97-0P, 158807-14-8P, 158807-15-9P, 158807-16-0P, 158807-17-1P, 158807-18-2P, 158807-19-3P, 158807-20-6P, 155884-08-5P, 154749-99-2, 167371-59-7P, 244126-99-6P, 177848-35-OP and 141309-82-2P, and the like. Suitable angiotensin II antagonists are described more fully in the literature, such as in Goodman and Gilman, The Pharmacological Basis of Therapeutics (9th Edition), McGraw-Hill, 1995; and the Merck Index on CD-ROM, 13$^{th}$ Edition; and on STN Express, file phar and file registry.

In some embodiments the angiotensin II antagonists are candesartan, eprosartan, irbesartan, losartan, omlesartan, telmisartan or valsartan. In more particular embodiments the candesartan is administered as candesartan cilexetil in an amount of about 15 milligrams to about 100 milligrams as a single dose or as multiple doses per day; the eprosartan, is administered as eprosartan mesylate in an amount of about 400 milligrams to about 1600 milligrams as a single dose or as multiple doses per day; the irbesartan is administered in an amount of about 75 milligrams to about 1200 milligrams as a single dose or as multiple doses per day; the losartan is administered as losartan potassium in an amount of about 25 milligrams to about 100 milligrams as a single dose or as multiple doses per day; the omlesartan is administered as omlesartan medoxomil in an amount of about 5 milligrams to about 40 milligrams as a single dose or as multiple doses per day; the telmisartan is administered in an amount of about 20 milligrams to about 80 milligrams as a single dose or as multiple doses per day; the valsartan is administered in an amount of about 80 milligrams to about 320 milligrams as a single dose or as multiple doses per day.

Suitable angiotensin-converting enzyme inhibitors (ACE inhibitors) include, but are not limited to, alacepril, benazepril (LOTENSIN®, CIBACEN®), benazeprilat, captopril, ceronapril, cilazapril, delapril, duinapril, enalapril, enalaprilat, fasidotril, fosinopril, fosinoprilat, gemopatrilat, glycopril, idrapril, imidapril, lisinopril, moexipril, moveltipril, naphthopidil, omapatrilat, pentopril, perindopril, perindoprilat, quinapril, quinaprilat, ramipril, ramiprilat, rentipril, saralasin acetate, spirapril, temocapril, trandolapril, trandolaprilat, urapidil, zofenopril, acylmercapto and mercaptoalkanoyl pralines, carboxyalkyl dipeptides, carboxyalkyl dipeptide, phosphinylalkanoyl pralines, registry no. 796406, AVE 7688, BP1.137, CHF 1514, E 4030, ER 3295, FPL-66564, MDL 100240, RL 6134, RL 6207, RL 6893, SA 760, S-5590, Z 13752A, and the like. Suitable angiotensin-converting enzyme inhibitors are described more fully in the literature, such as in Goodman and Gilman, The Pharmacological Basis of Therapeutics (9th Edition), McGraw-Hill, 1995; and the Merck Index on CD-ROM, Twelfth Edition, Version 12:1, 1996; and on STN Express, file phar and file registry.

In some embodiments the angiotensin-converting enzyme inhibitors are benazepril, captopril, enalapril, fosinopril, lisinopril, moexipril, quinapril, ramipril, trandolapril or trandolaprilat. In more particular embodiments the benazepril is administered as benazepril hydrochloride in an amount of about 5 milligrams to about 80 milligrams as a single dose or as multiple doses per day; the captopril is administered in an amount of about 12.5 milligrams to about 450 milligrams as a single dose or as multiple doses per day; the enalapril is administered as enalapril maleate in an amount of about 2.5 milligrams to about 40 milligrams as a single dose or as multiple doses per day; the fosinopril is administered as fosinopril sodium in an amount of about 5 milligrams to about 60 milligrams as a single dose or as multiple doses per day; the lisinopril is administered in an amount of about 2.5 milligrams to about 75 milligrams as a single dose or as multiple doses per day; the moexipril is administered as moexipril hydrochloride in an amount of about 7.5 milligrams to about 45 milligrams as a single dose or as multiple doses per day; the quinapril is administered as quinapril hydrochloride in an amount of about 5 milligrams to about 40 milligrams as single or multiple doses per day; the ramipril hydrochloride in an amount of about 1.25 milligrams to about 40 milligrams as single or multiple doses per day; the trandolapril is administered as in an amount of about 0.5 milligrams to about 4 milligrams as single or multiple doses per day; the trandolaprilat is administered as in an amount of about 0.5 milligrams to about 4 milligrams as single or multiple doses per day.

Suitable antidiabetic compounds include but are not limited to, acarbose, acetohexamide, buformin, carbutamide, chlorpropamide, glibornuride, gliclazide, glimepiride, glipizide, gliquidone, glisoxepid, glyburide, glybuthiazol(e), glybuzole, glyhexamide, glymidine, glypinamide, insulin, metformin, miglitol, nateglinide, phenbutamide, phenformin, pioglitazone, repaglinide, rosiglitazone, tolazamide, tolbutamide, tolcyclamide, troglitazone, voglibose, and the like. Suitable antidiabetic compounds are described more fully in the literature, such as in Goodman and Gilman, The Pharmacological Basis of Therapeutics (9th Edition), McGraw-Hill, 1995; and the Merck Index on CD-ROM, Thirteenth Edition; and on STN Express, file phar and file registry.

Suitable anti-hyperlipidemic compounds include, but are not limited to, statins or HMG-CoA reductase inhibitors, such as, for example, atorvastatin (LIPITOR®), bervastatin, cerivastatin (BAYCOL®), dalvastatin, fluindostatin (Sandoz XU-62-320), fluvastatin, glenvastatin, lovastatin (MEVACOR®), mevastatin, pravastatin (PRAVACHOL®), rosuvastatin (CRESTRO®), simvastatin (ZOCOR®), velostatin (also known as synvinolin), VYTORIN™ (ezetimibe/simvastatin), GR-95030, SQ 33,600, BMY 22089, BMY 22,566, CI 980, and the like; gemfibrozil, cholystyramine, colestipol, niacin, nicotinic acid, bile acid sequestrants, such as, for example, cholestyramine, colesevelam, colestipol, poly(methyl-(3-trimethylaminopropyl) imino-trimethylene dihalide) and the like; probucol; fibric acid agents or fibrates, such as, for example, bezafibrate (Bezalip™), beclobrate, binifibrate, ciprofibrate, clinofibrate, clofibrate, etofibrate, fenofibrate (Lipidil™, Lipidil Micro™), gemfibrozil (Lopid™.), nicofibrate, pirifibrate, ronifibrate, simfibrate, theofibrate and the like; cholesterol ester transfer protein (CETP) inhibitors, such as for example, CGS 25159, CP-529414 (torcetrapid), JTT-705, substituted N-[3-(1,1,2,2-tetrafluoroethoxy)benzyl]-N-(3-phenoxyphenyl)-trifluoro-3-amino-2-propanols, N,N-disubstituted trifluoro-3-amino-2-propanols, PD 140195 (4-phenyl-5-tridecyl-4H-1,2,4-triazole-3-thiol), SC-794, SC-795, SCH 58149, and the like.

In some embodiments the anti-hyperlipidemic compounds are atorvastatin, fluvastatin, lovastatin, pravastatin, rosuvastatin or simvastatin. In more particular embodiments the atorvastatin is administered in an amount of about 10 milligrams to about 80 milligrams as a single dose or as multiple doses per day; the fluvastatin is administered in an amount of about 20 milligrams to about 80 milligrams as a single dose or as multiple doses per day; the lovastatin is administered in an amount of about 10 milligrams to about 80 milligrams as a single dose or as multiple doses per day; the pravastatin is administered in an amount of about 10 milligrams to about 80 milligrams as a single dose or as multiple doses per day; the rosuvastatin is administered in an amount of about 5 milligrams to about 40 milligrams as a single dose or as multiple doses per day; the simvastatin is administered in an amount of about 5 milligrams to about 80 milligrams as a single dose or as multiple doses per day.

Suitable antioxidants include, but are not limited to, small-molecule antioxidants and antioxidant enzymes. Suitable small-molecule antioxidants include, but are not limited to, hydralazine compounds, glutathione, vitamin C, vitamin E, cysteine, N-acetyl-cysteine, β-carotene, ubiquinone, ubiquinol-10, tocopherols, coenzyme Q, superoxide dismutase mimetics, such as, for example, 2,2,6,6-tetramethyl-1-piperidinyloxy (TEMPO), DOXYL, PROXYL nitroxide compounds; 4-hydroxy-2,2,6,6-tetramethyl-1-piperidinyloxy (Tempol), M-40401, M-40403, M-40407, M-40419, M-40484, M-40587, M-40588, and the like. Suitable antioxidant enzymes include, but are not limited to, superoxide dismutase, catalase, glutathione peroxidase, NADPH oxidase inhibitors, such as, for example, apocynin, aminoguanidine, ONO 1714, S17834 (benzo[b]pyran-4-one derivative), and the like; xanthine oxidase inhibitors, such as, for example, allopurinol, oxypurinol, amflutizole, diethyldithiocarbamate, 2-styrylchromones, chrysin, luteolin, kaempferol, quercetin, myricetin, isorhamnetin, benzophenones such as 2,2',4,4'-tetrahydroxybenzophenone, 3,4,5,2',3',4'-hexahydroxybenzophenone and 4,4'-dihydroxybenzophenone; benzothiazinone analogues such as 2-amino-4H-1,3-benzothiazine-4-one, 2-guanidino-4H-1,3-benzothiazin-4-one and rhodanine; N-hydroxyguanidine derivative such as, PR5 (1-(3,4-dimethoxy-2-chlorobenzylideneamino)-3-hydroxyguanidine); 6-formylpterin, and the like. The antioxidant enzymes can be delivered by gene therapy as a viral vertor and/or a non-viral vector. Suitable antioxidants are described more fully in the literature, such as in Goodman and Gilman, The Pharmacological Basis of Therapeutics (9th Edition), McGraw-Hill, 1995; and the Merck Index on CD-ROM, Thirteenth Edition; and on STN Express, file phar and file registry.

In some embodiments the antioxidants are apocynin, hydralazine compounds and superoxide dimutase mimetics.

Suitable antithrombotic and vasodilator compounds include, but are not limited to, abciximab, acetorphan, acetylsalicylic acid, argatroban, bamethan, benfurodil, benziodarone, betahistine, bisaramil, brovincamine, bufeniode, citicoline, clobenfurol, clopidogrel, cyclandelate, dalteparin, dipyridamol, droprenilamine, enoxaparin, fendiline, ifenprodil, iloprost, indobufen, isobogrel, isoxsuprine, heparin, lamifiban, midrodine, nadroparin, nicotinoyl alcohol, nylidrin, ozagrel, perhexyline, phenylpropanolamine, prenylamine, papaveroline, reviparin sodium salt, ridogrel, suloctidil, tinofedrine, tinzaparin, trifusal, vintoperol, xanthinal niacinate, and the like. Suitable antithrombotic and vasodilator compounds are described more fully in the literature, such as in Goodman and Gilman, The Pharmacological Basis of Therapeutics (9th Edition), McGraw-Hill, 1995; and the Merck Index on CD-ROM, Thirteenth Edition; and on STN Express, file phar and file registry.

Suitable calcium channel blockers include, but are not limited to, amlodipine (NORVASC®), anipamil, aranidipine, aminone, azelnidipine, barnidipine, bencyclane, benidipine, bepridil, cilnidipine, cinnarizine, clentiazem, diltiazem, dotarizine, efonidipine, elgodipine, fantofarone, felodipine, fendiline, flunarizine, fluspirilene, furnidipine, gallopamil, ipenoxazone, isradipine, lacidipine, lemildipine, lercanidipine, lomerizine, manidipine, mibefradil, monatepil, nicardipine, nifedipine, niguldipine, niludipine, nilvadipine, nimodipine, nisoldipine, nitrendipine, nivaldipine, oxodipine, perhexylene, phenyloin, phenylprenylamine, pranidipine, ranolazine, ryosidine, semotiadil, tamolarizine, temiverine hydrochloride, terodiline, tiapamil, vatanidipine hydrochloride, verapamil, ziconotide, AE-0047, CAI, JTV-519, CHF-1521, L-651582, NS-7, NW-1015, RO-2933, SB-237376, SL-34.0829-08, S-312d, SD-3212, TA-993, YM-430, and the like. Suitable calcium channel blockers are described more fully in the literature, such as in Goodman and Gilman, The Pharmacological Basis of Therapeutics (9th Edition), McGraw-Hill, 1995; and the Merck Index on CD-ROM, Thirteenth Edition; and on STN Express, file phar and file registry.

In some embodiments the calcium channel blockers are amlodipine, diltiazem, isradipine, nicardipine, nifedipine, nimodipine, nisoldipine, nitrendipine, verapamil.

Suitable digitals include but are not limited to digoxin and digoxitin. In some embodiments the digoxin is administered to achieve a steady state blood serum concentration of at least about 0.7 nanograms per ml to about 2.0 nanograms per ml.

Suitable diuretics include but are not limited to, thiazides (such as, for example, althiazide, bendroflumethiazide, benzclortriazide, benzhydrochlorothiazide, benzthiazide, buthiazide, chlorothiazide, cyclopenethiazide, cyclothiazide, epithiazide, ethiazide, hydrobenzthiazide, hydrochlorothiazide, hydroflumethiazide, methylclothiazide, methylcyclothiazide, penflutazide, polythiazide, teclothiazide, trichlormethiazide, triflumethazide, and the like); alilusem, ambuside, amiloride, aminometradine, azosemide, bemetizide, bumetanide, butazolamide, butizide, canrenone, carperitide, chloraminophenamide, chlorazanil, chlormerodrin, chlorthalidone, cicletanide, clofenamide, clopamide, clorexolone, conivaptan, daglutril, dichlorophenamide, disulfamide, ethacrynic acid, ethoxzolamide, etozolon, fenoldopam, fenquizone, furosemide, indapamide, mebutizide, mefruside, meralluride, mercaptomerin sodium, mercumallylic acid, mersalyl, methazolamide, meticane, metolazone, mozavaptan, muzolimine, N-(5-1,3,4-thiadiazol-2-yl)acetamide, nesiritide, pamabrom, paraflutizide, piretanide, protheobromine, quinethazone, scoparius, spironolactone, theobromine, ticrynafen, torsemide, torvaptan, triamterene, tripamide, ularitide, xipamide or potassium, AT 189000, AY 31906, BG 9928, BG 9791, C 2921, DTI 0017, JDL 961, KW 3902, MCC 134, SLV 306, SR 121463, WAY 140288, ZP 120, and the like. Suitable diuretics are described more fully in the literature, such as in Goodman and Gilman, The Pharmacological Basis of Therapeutics (9th Edition), McGraw-Hill, 1995; and the Merck Index on CD-ROM, 13$^{th}$ Edition; and on STN Express, file phar and file registry.

Depending on the diuretic employed, potassium may also be administered to the patient in order to optimize the fluid balance while avoiding hypokalemic alkalosis. The administration of potassium can be in the form of potassium chloride or by the daily ingestion of foods with high potassium content such as, for example, bananas or orange juice. The method of administration of these compounds is described in further detail in U.S. Pat. No. 4,868,179, the disclosure of which is incorporated by reference herein in its entirety.

In some embodiments the diuretics are amiloride, furosemide, chlorthalidone, hydrochlorothiazide or triamterene. In more particular embodiments the amiloride is administered as amiloride hydrochloride in an amount of about 5 milligrams to about 15 milligrams as a single dose or as multiple doses per day; the furosemide is administered in an amount of about 10 milligrams to about 600 milligrams as a single dose or as multiple doses per day; the chlorthalidone is administered in an amount of about 15 milligrams to about 150 milligrams as a single dose or as multiple doses per day; the hydrochlorothiazide is administered in an amount of about 12.5 milligrams to about 300 milligrams as a single dose or as multiple doses per day; the triamterene is administered in an amount of about 35 milligrams to about 225 milligrams as a single dose or as multiple doses per day.

Suitable endothelin antagonists include, but are not limited to, atrasentan, bosentan, darusentan, endothelin, enrasentan, sitaxsentan, sulfonamide endothelin antagonists, tezosentan, BMS 193884, BQ-123, SQ 28608, and the like. Suitable endothelin antagonists are described more fully in the literature, such as in Goodman and Gilman, The Pharmacological Basis of Therapeutics (9th Edition), McGraw-Hill, 1995; and the Merck Index on CD-ROM, Thirteenth Edition; and on STN Express, file phar and file registry.

Suitable hydralazine compounds include, but are not limited to, compounds having the formula:

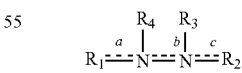

wherein a, b and c are independently a single or double bond; $R_1$ and $R_2$ are each independently a hydrogen, an alkyl, an ester or a heterocyclic ring, wherein alkyl, ester and heterocyclic rind are as defined herein; $R_3$ and $R_4$ are each independently a lone pair of electrons or a hydrogen, with the proviso that at least one of $R_1$, $R_2$, $R_3$ and $R_4$ is not a hydrogen. Exemplary hydralazine compounds include budralazine, cadralazine, dihydralazine, endralazine, hydralazine, pildralazine, todralazine, and the like. Suitable hydralazine compounds are described more fully in the literature, such as in Goodman and Gilman, The Pharmacological Basis of Therapeutics (9th Edition), McGraw-Hill, 1995; and the Merck Index on CD-ROM, Thirteenth Edition; and on STN Express, file phar and file registry.

In some embodiments the hydralazine compound is hydralazine or a pharmaceutically acceptable salt thereof such as hydralazine hydrochloride. In more particular embodiments the hydralazine is administered as hydralazine hydrochloride in an amount of about 10 milligrams to about 300 milligrams as a single dose or as multiple doses per day.

Suitable $H_2$ receptor antagonists include, but are not limited to, burimamide, cimetidine, ebrotidin, famotidine, nizatidine, roxatidine, rantidine, tiotidine, and the like. Suitable $H_2$ receptor antagonists are described more fully in the literature, such as in Goodman and Gilman, The Pharmacological Basis of Therapeutics (9th Edition), McGraw-Hill, 1995, Pgs. 901-915; the Merck Index on CD-ROM, 13$^{th}$ Edition; and in WO 00/28988 assigned to NitroMed. Inc., the disclosures of which are incorporated herein by reference in their entirety.

Suitable neutral endopeptidase inhibitors include, but are not limited to, atrial natriuretic peptides, diazapins, azepinones, ecadotril, fasidotril, fasidotrilat, omapatrilat, sampatrilat, BMS 189,921, Z 13752 A, and the like. Neutral endopeptidase inhibitors are described more fully in the literature, such as in Goodman and Gilman, The Pharmacological Basis of Therapeutics (9th Edition), McGraw-Hill, 1995; and the Merck Index on CD-ROM, Thirteenth Edition; and on STN Express, file phar and file registry.

Suitable NSAIDs include, but are not limited to, acetaminophen, acemetacin, aceclofenac, alminoprofen, amfenac, bendazac, benoxaprofen, bromfenac, bucloxic acid, butibufen, carprofen, cinmetacin, clopirac, diclofenac, etodolac, felbinac, fenclozic acid, fenbufen, fenoprofen, fentiazac, flunoxaprofen, flurbiprofen, ibufenac, ibuprofen, indomethacin, isofezolac, isoxepac, indoprofen, ketoprofen, lonazolac, loxoprofen, metiazinic acid, mofezolac, miroprofen, naproxen, oxaprozin, pirozolac, pirprofen, pranoprofen, protizinic acid, salicylamide, sulindac, suprofen, suxibuzone, tiaprofenic acid, tolmetin, xenbucin, ximoprofen, zaltoprofen, zomepirac, aspirin, acemetcini, bumadizon, carprofenac, clidanac, diflunisal, enfenamic acid, fendosal, flufenamic acid, flunixin, gentisic acid, ketorolac, meclofenamic acid, mefenamic acid, mesalamine, prodrugs thereof, and the like. Suitable NSAIDs are described more fully in the literature, such as in Goodman and Gilman, The Pharmacological Basis of Therapeutics (9th Edition), McGraw-Hill, 1995, Pgs. 617-657; the Merck Index on CD-ROM, 13$^{th}$ Edition; and in U.S. Pat. Nos. 6,057,347 and 6,297,260 assigned to NitroMed Inc., the disclosures of which are incorporated herein by reference in their entirety.

In some embodiments the NSAIDs are acetaminophen, diclofenac, flurbiprofen, ibuprofen, indomethacin, ketoprofen, naproxen or aspirin. In more particular embodiments the acetaminophen is administered in an amount of about 325 milligrams to about 4 grams as a single dose or as multiple doses per day; the diclofenac is administered in an amount of about 50 milligrams to about 250 milligrams as a single dose or as multiple doses per day; the flurbiprofen is administered in an amount of about 100 milligrams to about 300 milligrams as a single dose or as multiple doses per day; the ibuprofen is administered in an amount of about 400 milligrams to about 3.2 grams as a single dose or as multiple doses per day; the indomethacin is administered in an amount of about 25 milligrams to about 200 milligrams as a single dose or as multiple doses per day; the ketoprofen is administered in an amount of about 50 milligrams to about 300 milligrams as a single dose or as multiple doses per day; the naproxen is administered in an amount of about 250 milligrams to about 1.5 grams as a single dose or as multiple doses per day; the aspirin is administered in an amount of about 10 milligrams to about 2 grams as a single dose or as multiple doses per day.

Suitable phosphodiesterase inhibitors, include but are not limited to, filaminast, piclamilast, rolipram, Org 20241, MCI-154, roflumilast, toborinone, posicari, lixazinone, zaprinast, sildenafil, pyrazolopyrimidinones, motapizone, pimobendan, zardaverine, siguazodan, CI 930, EMD 53998, imazodan, saterinone, loprinone hydrochloride, 3-pyridinecarbonitrile derivatives, acefylline, albifylline, bamifylline, denbufyllene, diphylline, doxofylline, etofylline, torbafylline, theophylline, nanterinone, pentoxofylline, proxyphylline, cilostazol, cilostamide, MS 857, piroximone, milrinone, aminone, tolafentrine, dipyridamole, papaveroline, E4021, thienopyrimidine derivatives, triflusal, ICOS-351, tetrahydropiperazino (1,2-b)beta-carboline-1,4-dione derivatives, carboline derivatives, 2-pyrazolin-5-one derivatives, fused pyridazine derivatives, quinazoline derivatives, anthranilic acid derivatives, imidazoquinazoline derivatives, tadalafil, vardenafil, and in Goodman and Gilman, The Pharmacological Basis of Therapeutics (9th Ed.), McGraw-Hill, Inc. (1995), The Physician's Desk Reference (49th Ed.), Medical Economics (1995), Drug Facts and Comparisons (1993 Ed), Facts and Comparisons (1993), and the Merck Index on CD-ROM, 13$^{th}$ Edition; and the like. Phosphodiesterase inhibitors and their nitrosated and/or nitrosylated derivatives are also disclosed in U.S. Pat. Nos. 5,932,538, 5,994,294, 5,874,437, 5,958,926 reissued as U.S. Pat. Nos. RE 03772346, 172,060, 6,197,778, 6,177,428, 6,172,068, 6,221,881, 6,232,321, 6,197,782, 6,133,272, 6,211,179, 6,316,457 and 6,331,542, the disclosures of each of which are incorporated herein by reference in their entirety.

Suitable potassium channel blockers include but are not limited to, nicorandil, pinacidil, cromakalim (BRL 34915), aprikalim, bimakalim, emakalim, lemakalim, minoxidil, diazoxide, 9-chloro-7-(2-chlorophenyl)-5H-pyrimido(5,4,-d)(2)-benzazepine, Ribi, CPG-11952, CGS-9896, ZD 6169, diazixide, Bay X 9227, P1075, Bay X 9228, SDZ PCO 400, WAY-120,491, WAY-120,129, Ro 31-6930, SR 44869, BRL 38226, S 0121, SR 46142A, CGP 42500, SR 44994, artilide fumarate, lorazepam, temazepam, rilmazafone, nimetazepam, midazolam, lormetazepam, loprazolam, ibutilide fumarate, haloxazolam, flunitrazepam, estazolam, doxefazepam, clonazepam, cinolazepam, brotizolam, and the like. Suitable potassium channel blockers are described more fully in the literature, such as in Goodman and Gilman, The Pharmacological Basis of Therapeutics (9th Edition), McGraw-Hill, 1995; and the Merck Index on CD-ROM, Thirteenth Edition; and on STN Express, file phar and file registry.

Suitable platelet reducing agents include but are not limited to, fibrinolytic agents such as for example, ancrod, anistreplase, bisobrin lactate, brinolase, Hageman factor (i.e. factor XII) fragments, plasminogen activators such as, for example, streptokinase, tissue plasminogen activators (TPA), urokinase, pro-Urokinase, recombinant TPA, plasmin, plasminogen, and the like; anti-coagulant agents including but are not limited to, inhibitors of factor Xa, factor TFPI, factor VIIa, factor IXc, factor Va, factor VIIIa, inhibitors of other coagulation factors, and the like; vitamin K antagonists, such as, for example, coumarin, coumarin derivatives (e.g., warfarin sodium); glycosoaminoglycans such as, for example, heparins both in unfractionated form and in low molecular weight form; ardeparin sodium, bivalirudin, bromindione, coumarin, dalteparin sodium, danaparoid sodium; dazoxiben hydrochloride, desirudin, dicumarol, efegatran sulfate, enoxaparin sodium, ifetroban, ifetroban sodium, lyapolate sodium, nafamostat mesylate, phenprocoumon, sulfatide, tinzaparin sodium, retaplase; trifenagrel, warfarin, dextrans and the like; abciximab, acadesine, anipamil, argatroban, aspirin, clopidogrel, diadenosine 5',5'''-P1,P4-tetraphosphate (Ap4A) analogs, difibrotide, dilazep dihydrochloride, dipyridamole, dopamine, 3-methoxytyramine, glucagon, glycoprotein IIb/IIIa antagonists, such as, for example, Ro-43-8857, L-700,462, iloprost, isocarbacyclin methyl ester, itazigrel, ketanserin, BM-13.177, lamifiban, lifarizine, molsidomine, nifedipine, oxagrelate, prostaglandins, platelet activating factor antagonists such as, for example, lexipafant, prostacyclins, pyrazines, pyridinol carbamate, ReoPro (i.e., abciximab), sulfinpyrazone, synthetic compounds BN-50727, BN-52021, CV-4151, E-5510, FK-409, GU-7, KB-2796, KBT-3022, KC-404, KF-4939, OP-41483, TRK-100, TA-3090, TFC-612, ZK-36374, 2,4,5,7-tetrathiaoctane, 2,4,5,7-tetrathiaoctane 2,2-dioxide, 2,4,5-trithiahexane, theophyllin pentoxifyllin, thromboxane and thromboxane synthetase inhibitors such as, for example, picotamide, sulotroban, ticlopidine, tirofiban, trapidil, ticlopidine, trifenagrel, trilinolein, 3-substituted 5,6-bis(4-methoxyphenyl)-1,2,4-triazines; antibodies to glycoprotein IIb/IIIa; antiserotonin drugs, such as, for example, clopridogrel; sulfinpyrazone and the like; aspirin; dipyridamole; clofibrate; pyridinol carbamate; glucagon, caffeine; theophyllin pentoxifyllin; ticlopidine, and the like.

Suitable proton pump inhibitors include, but are not limited to, disulprazole, esomeprazole, lansoprazole, leminoprazole, omeprazole, pantoprazole, rabeprazole, timoprazole, tenatoprazole, 2-(2-benzimidazolyl)-pyridine, tricyclic imidazole, thienopydidine benzimidazole, fluoroalkoxy substituted benzimidazole, dialkoxy benzimidazole, N-substituted 2-(pyridylalkenesulfinyl)benzimidazole, cycloheptenepyridine, 5-pyrrolyl-2-pyridylmethylsulfinyl benzimidazole, alkylsulfinyl benzimidazole, fluoro-pyridylmethylsulfinyl benzimidazole, imidazo[4,5-b]pydridine, RO 18-5362, IY 81149, 4-amino-3-carbonyl quinoline, 4-amino-3-acylnaphthyride, 4-aminoquinoline, 4-amino-3-acylquinoline, 3-butyryl-4-(2-methylphenylamino)-8-(2-hydroxyethoxy)quinoline, quinazoline, tetrahydroisoquinolin-2-yl pyrimidine, YH 1885, 3-substituted 1,2,4-thiadiazolo(4,5-a) benzimidazole, 3-substituted imidazo(1,2-d)-thiadiazole, 2-sulfinylnicotinamide, pyridylsulfinylbenz imidazole, pyridylsulfinyl thieno imidazole, theinoimidazole-toluidine, 4,5-dihydrooxazole, thienoimidazole-toluidine, Hoe-731, imidazo[1,2-a]pyridine, pyrrolo[2,3-b]pyridine, and the like. Suitable proton pump inhibitors are described more fully in the literature, such as in Goodman and Gilman, The Pharmacological Basis of Therapeutics (9th Edition), McGraw-Hill, 1995; the Merck Index on CD-ROM, 13$^{th}$ Edition; and in WO 00/50037 assigned to NitroMed. Inc., the disclosures of which are incorporated herein by reference in their entirety.

Suitable renin inhibitors include, but are not limited to, aliskiren (SPP-100), ditekiren, enalkrein (A-64662), medullipin, terlkiren, tonin, zankiren, RO 42-5892 (remikiren), A 62198, A 64662, A 65317, A 69729, A 72517 (zankiren), A 74273, CP 80794, CGP 29287, CGP-38560A, EMD 47942, ES 305, ES 1005, ES 8891, FK 906, FK 744, H 113, H-142, KRI 1314, pepstatinA, RO 44-9375 (ciprokiren), RO 42-5892, RO 66-1132, RO 66-1168, SP 500, SP 800, SR-43845, SQ 34017, U 71038, YM-21095, YM-26365, urea derivatives of peptides, amino acids connected by nonpeptide bonds, di- and tri-peptide derivatives (e.g., Act-A, Act-B, Act-C, ACT-D, and the like), amino acids and derivatives thereof, diol sulfonamides and sulfinyls, modified peptides, peptidyl beta-aminoacyl aminodiol carbamates, monoclonal antibodies to renin. Suitable renin inhibitors are described more fully in U.S. Pat. Nos. 5,116,835, 5,114,937, 5,106,835, 5,104,869, 5,095,119, 5,098,924), 5,095,006, 5,089,471, 5,075,451, 5,066,643, 5,063,208, 4,845,079, 5,055,466, 4,980,283, 4,885,292), 4,780,401, 5,071,837, 5,064,965, 5,063,207, 5,036,054, 5,036,053, 5,034,512, and 4,894,437, the disclosures of each of which are incorporated herein by reference in their entirety; and in the literature, such as in Goodman and Gilman, The Pharmacological Basis of Therapeutics (9th Edition), McGraw-Hill, 1995; and the Merck Index on CD-ROM, Thirteenth Edition; and on STN Express, file phar and file registry.

Suitable COX-2 inhibitors include, but are not limited to, nimesulide, celecoxib (CELEBREX®), etoricoxib (ARCOXIA®), flosulide, lumiracoxib (PREXIG®, COX-189), parecoxib (DYNSTAT®), rofecoxib (VIOXX®), tiracoxib (JTE-522), valdecoxib (BEXTRA®), ABT 963, BMS 347070, CS 502, DuP 697, GW-406381, NS-386, SC-57666, SC-58125, SC-58635, and the like, and mixtures of two or more thereof. Suitable COX-2 inhibitors are in U.S. Pat. Nos. 5,344,991, 5,380,738, 5,393,790, 5,409,944, 5,434,178, 5,436,265, 5,466,823, 5,474,995, 5,510,368, 5,536,752, 5,550,142, 5,552,422, 5,604,253, 5,604,260, 5,639,780, 5,932,598 and 6,633,272, and in WO 94/03387, WO 94/15723, WO 94/20480, WO 94/26731, WO 94/27980, WO 95/00501, WO 95/15316, WO 96/03387, WO 96/03388, WO 96/06840, WO 96/21667, WO 96/31509, WO 96/36623, WO 97/14691, WO 97/16435, WO 01/45703 and WO 01/87343, the disclosures of each of which are incorporated herein by reference in their entirety; and in the literature, such as in Goodman and Gilman, The Pharmacological Basis of Therapeutics (9th Edition), McGraw-Hill, 1995; and the Merck Index on CD-ROM, Thirteenth Edition; and on STN Express, file phar and file registry.

In some embodiments the COX-2 inhibitors are celecoxib, etoracoxib, lumiracoxib, paracoxib, rofecoxib or valdecoxib. In more particular embodiments the celecoxib is administered in an amount of about 100 milligrams to about 800 milligrams as a single dose or as multiple doses per day; the etoricoxib is administered in an amount of about 50 milligrams to about 200 milligrams as a single dose or as multiple doses per day; the lumiracoxib is administered in an amount of about 40 milligrams to about 1200 milligrams as a single dose or as multiple doses per day; the paracoxib is administered in an amount of about 20 milligrams to about 100 milligrams as a single dose or as multiple doses per day; the rofecoxib is administered in an amount of about 12.5 milligrams to about 50 milligrams as a single dose or as multiple doses per day; the valdecoxib is administered in an amount of about 10 milligrams to about 40 milligrams as a single dose or as multiple doses per day.

The invention provides compositions comprising (i) a nitric oxide enhancing diuretic compound or pharmaceutically acceptable salt thereof, and (ii) at least one compound selected from the group consisting of aldosterone antagonists, angiotensin II antagonists, angiotensin-converting enzyme (ACE) inhibitors, β-adrenergic antagonists, diuretics, and hydralazine compounds in one or more pharmaceutically acceptable carriers. In other embodiments of the invention the aldosterone antagonist is eplerenone or spironolactone; the angiotensin II antagonist is candesartan cilexetil, eprosartan mesylate, irbesartan, losartan potassium, medoxomil, telmisartan, trandolapril, trandolaprilat or valsartan; the angiotensin-converting enzyme inhibitor is benazepril hydrochloride, captopril, enalapril maleate, fosinopril sodium, lisinopril, moexipril hydrochloride, quinapril hydrochloride, ramipril; the β-adrenergic antagonist is bisoprolol fumarate, carvedilol, metoprolol tartrate, propranolol hydrochloride or timolol maleate; the calcium channel blockers is amlodipine, diltiazem, isradipine, nicardipine, nifedipine, nimodipine, nisoldipine, nitrendipine, verapamil; the diuretic is amiloride hydrochloride, chlorthalidone, hydrochlorothiazide or triamterene; the hydralazine compound is hydralazine hydrochloride; and the rennin inhibitor is aliskiren, ciprokiren, ditekiren, enalkrein, medullipin, remikiren, terlkiren, tonin or zankiren.

The invention provides compositions comprising (i) a nitric oxide enhancing diuretic compound or pharmaceutically acceptable salt thereof, (ii) a nitric oxide enhancing compound, such as, isosorbide dinitrate and/or isosorbide mononitrate (preferably isosorbide dinitrate), and (i) a hydralazine compound (such as hydralazine hydrochloride). In one embodiment, the hydralazine hydrochloride can be administered in an amount of about 30 milligrams per day to about 400 milligrams per day; the isosorbide dinitrate can be administered in an amount of about 10 milligrams per day to about 200 milligrams per day; or the isosorbide mononitrate can be administered in an amount of about 5 milligrams per day to about 120 milligrams per day. In another embodiment, the hydralazine hydrochloride can be administered in an amount of about 50 milligrams per day to about 300 milligrams per day; the isosorbide dinitrate can be administered in an amount of about 20 milligrams per day to about 160 milligrams per day; or the isosorbide mononitrate can be administered in an amount of about 15 milligrams per day to about 100 milligrams per day. In yet another embodiment, the hydralazine hydrochloride can be administered in an amount of about 37.5 milligrams to about 75 milligrams one to four times per day; the isosorbide dinitrate can be administered in an amount of about 20 milligrams to about 40 milligrams one to four times per day; or the isosorbide mononitrate can be administered in an amount of about 10 milligrams to about 20 milligrams one to four times per day. In another embodiment of the methods of the invention, the patient can be administered a composition comprising about 225 mg hydralazine hydrochloride and about 120 mg isosorbide dinitrate once per day (i.e., q.d.). In another embodiment of the methods of the invention, the patient can be administered a composition comprising about 112.5 mg hydralazine hydrochloride and about 60 mg isosorbide dinitrate twice per day (i.e., b.i.d.). In another embodiment of the methods of the invention, the patient can be administered a composition comprising about 56.25 mg hydralazine hydrochloride and about 30 mg isosorbide dinitrate twice per day (i.e., b.i.d.). In another embodiment of the methods of the invention, the patient can be administered a composition comprising about 75 mg hydralazine hydrochloride and about 40 mg isosorbide dinitrate three times per day (i.e., t.i.d.). In another embodiment of the methods of the invention, the patient can be administered a composition comprising about 37.5 mg hydralazine hydrochloride and about 20 mg isosorbide dinitrate three times per day (i.e., t.i.d.). The particular amounts of hydralazine and isosorbide dinitrate or isosorbide mononitrate can be administered as a single dose once a day; or in multiple doses several times throughout the day; or as a sustained-release oral formulation; or as an injectable formulation.

The invention provides methods for treating conditions resulting from excess water and/or electrolyte retention by administering to the patient in need thereof an effective amount of the compounds and/or compositions described herein. For example, the patient can be administered an effective amount of at least one nitric oxide enhancing diuretic compound. In another embodiment, the patient can be administered an effective amount of at least one nitric oxide enhancing diuretic compound, and at least one nitric oxide enhancing compound. In yet another embodiment, the patient can be administered an effective amount of at least one nitric oxide enhancing diuretic compound, and, at least one therapeutic agent, including but not limited to, such as, for example, aldosterone antagonists, alpha-adrenergic receptor antagonists, angiotensin II antagonists, angiotensin-converting enzyme (ACE) inhibitors, antidiabetic compounds, anti-hyperlipidemic compounds, antioxidants, antithrombotic and vasodilator compounds, β-adrenergic antagonists, calcium channel blockers, digitalis, diuretics, endothelin antagonists, hydralazine compounds, $H_2$ receptor antagonists, neutral endopeptidase inhibitors, nonsteroidal antiinflammatory compounds (NSAIDs), phosphodiesterase inhibitors, potassium channel blockers, platelet reducing agents, proton pump inhibitors, renin inhibitors, selective cyclooxygenase-2 (COX-2) inhibitors, and combinations of two or more thereof. In another embodiment, the patient can be administered an effective amount of at least one nitric oxide enhancing diuretic compound, and, at least one therapeutic agent, and, at least one nitric oxide enhancing compound. In one embodiment the condition resulting from excess water and/or electrolyte retention is lower extremity swelling, fatigue, body fluid retention, cardiac enlargement, and/or edema. The nitric oxide enhancing diuretic compounds, nitric oxide enhancing compounds, and/or therapeutic agents can be administered separately or as components of the same composition in one or more pharmaceutically acceptable carriers.

The invention provides methods for treating cardiovascular disorders by administering to the patient in need thereof an effective amount of the compounds and/or compositions described herein. For example, the patient can be administered an effective amount of at least one nitric oxide enhancing diuretic compound. In another embodiment, the patient can be administered an effective amount of at least one nitric oxide enhancing diuretic compound, and at least one nitric oxide enhancing compound. In yet another embodiment, the patient can be administered an effective amount of at least one nitric oxide enhancing diuretic compound, and, at least one therapeutic agent, including but not limited to, such as, for example, aldosterone antagonists, alpha-adrenergic receptor antagonists, angiotensin II antagonists, angiotensin-converting enzyme (ACE) inhibitors, antidiabetic compounds, anti-hyperlipidemic compounds, antioxidants, antithrombotic and vasodilator compounds, β-adrenergic antagonists, calcium channel blockers, digitalis, diuretics, endothelin antagonists, hydralazine compounds, $H_2$ receptor antagonists, neutral endopeptidase inhibitors, nonsteroidal antiinflammatory compounds (NSAIDs), phosphodiesterase inhibitors, potassium channel blockers, platelet reducing agents, proton pump inhibitors, renin inhibitors, selective cyclooxygenase-2 (COX-2) inhibitors, and combinations of two or more thereof. In another embodiment, the patient can be administered an effective amount of at least one nitric oxide enhancing diuretic compound, and, at least one therapeutic agent, and, at least one nitric oxide enhancing compound. In one embodiment the cardiovascular disorder is hypertension, heart failure and/or diastolic dysfunction. The nitric oxide enhancing diuretic compounds, nitric oxide enhancing compounds, and/or therapeutic agents can be administered separately or as components of the same composition in one or more pharmaceutically acceptable carriers.

The invention provides methods for treating renovascular diseases by administering to the patient in need thereof an effective amount of the compounds and/or compositions described herein. For example, the patient can be administered an effective amount of at least one nitric oxide enhancing diuretic compound. In another embodiment, the patient can be administered an effective amount of at least one nitric oxide enhancing diuretic compound, and at least one nitric oxide enhancing compound. In yet another embodiment, the patient can be administered an effective amount of at least one nitric oxide enhancing diuretic compound, and, at least one therapeutic agent, including but not limited to, such as, for example, aldosterone antagonists, alpha-adrenergic receptor antagonists, angiotensin II antagonists, angiotensin-converting enzyme (ACE) inhibitors, antidiabetic compounds, antihyperlipidemic compounds, antioxidants, antithrombotic and vasodilator compounds, β-adrenergic antagonists, calcium channel blockers, digitalis, diuretics, endothelin antagonists, hydralazine compounds, $H_2$ receptor antagonists, neutral endopeptidase inhibitors, nonsteroidal antiinflammatory compounds (NSAIDs), phosphodiesterase inhibitors, potassium channel blockers, platelet reducing agents, proton pump inhibitors, renin inhibitors, selective cyclooxygenase-2 (COX-2) inhibitors, and combinations of two or more thereof. In another embodiment, the patient can be administered an effective amount of at least one nitric oxide enhancing diuretic compound, and, at least one therapeutic agent, and, at least one nitric oxide enhancing compound. In one embodiment the renovascular disease is renal failure, renal insufficiency, renal deterioration associated with severe hypertension or renovascular hypertension. The nitric oxide enhancing diuretic compounds, nitric oxide enhancing compounds, and/or therapeutic agents can be administered separately or as components of the same composition in one or more pharmaceutically acceptable carriers.

The invention provides methods for treating diabetes; treating diseases resulting from oxidative stress; treating endothelial dysfunctions; treating diseases caused by endothelial dysfunctions; treating cirrhosis; treating pre-eclampsia; treating osteoporosis; treating nephropathy; treating peripheral vascular diseases; treating portal hypertension; treating central nervous system disorders; treating metabolic syndrome; treating sexual dysfunctions; and treating hyperlipidemia by administering to the patient in need thereof an effective amount of the compounds and/or compositions described herein. For example, the patient can be administered an effective amount of at least one nitric oxide enhancing diuretic compound. In another embodiment, the patient can be administered an effective amount of at least one nitric oxide enhancing diuretic compound, and at least one nitric oxide enhancing compound. In yet another embodiment, the patient can be administered an effective amount of at least one nitric oxide enhancing diuretic compound, and, at least one therapeutic agent, including but not limited to, such as, for example, aldosterone antagonists, alpha-adrenergic receptor antagonists, angiotensin II antagonists, angiotensin-converting enzyme (ACE) inhibitors, antidiabetic compounds, antihyperlipidemic compounds, antioxidants, antithrombotic and vasodilator compounds, β-adrenergic antagonists, calcium channel blockers, digitalis, diuretics, endothelin antagonists, hydralazine compounds, $H_2$ receptor antagonists, neutral endopeptidase inhibitors, nonsteroidal antiinflammatory compounds (NSAIDs), phosphodiesterase inhibitors, potassium channel blockers, platelet reducing agents, proton pump inhibitors, renin inhibitors, selective cyclooxygenase-2 (COX-2) inhibitors, and combinations of two or more thereof. In another embodiment, the patient can be administered an effective amount of at least one nitric oxide enhancing diuretic compound, and, at least one therapeutic agent, and, at least one nitric oxide enhancing compound. The nitric oxide enhancing diuretic compounds, nitric oxide enhancing compounds, and/or therapeutic agents can be administered separately or as components of the same composition in one or more pharmaceutically acceptable carriers.

When administered separately, the nitric oxide enhancing diuretic compound, nitric oxide enhancing compound and/or therapeutic agent can be administered about the same time as part of the overall treatment regimen, i.e., as a combination therapy. "About the same time" includes administering the at least one nitric oxide enhancing diuretic compound, simultaneously, sequentially, at the same time, at different times on the same day, or on different days, as long as they are administered as part of an overall treatment regimen, i.e., combination therapy or a therapeutic cocktail.

When administered in vivo, the compounds and compositions of the invention can be administered in combination with pharmaceutically acceptable carriers and in dosages described herein. When the compounds and compositions of the invention are administered as a combination of at least one nitric oxide enhancing diuretic compound and/or at least one nitric oxide enhancing compound and/or therapeutic agent, they can also be used in combination with one or more additional compounds which are known to be effective against the specific disease state targeted for treatment. The nitric oxide enhancing compounds, therapeutic agents and/or other additional compounds can be administered simultaneously with, subsequently to, or prior to administration of the nitric oxide enhancing diuretic compounds.

The compounds and compositions of the invention can be administered by any available and effective delivery system including, but not limited to, orally, bucally, parenterally, by inhalation, by topical application, by injection, transdermally, or rectally (e.g., by the use of suppositories) in dosage unit formulations containing conventional nontoxic pharmaceutically acceptable carriers, adjuvants, and vehicles, as desired. Parenteral includes subcutaneous injections, intravenous, intramuscular, intrasternal injection, or infusion techniques. In one embodiment of the invention the nitric oxide enhancing diuretic compound is administered orally, parentally or by inhalation.

Transdermal compound administration, which is known to one skilled in the art, involves the delivery of pharmaceutical compounds via percutaneous passage of the compound into the systemic circulation of the patient. Topical administration can also involve the use of transdermal administration such as transdermal patches or iontophoresis devices. Other components can be incorporated into the transdermal patches as well. For example, compositions and/or transdermal patches can be formulated with one or more preservatives or bacteriostatic agents including, but not limited to, methyl hydroxybenzoate, propyl hydroxybenzoate, chlorocresol, benzalkonium chloride, and the like. Dosage forms for topical administration of the compounds and compositions can include creams, sprays, lotions, gels, ointments, eye drops, nose drops, ear drops, and the like. In such dosage forms, the compositions of the invention can be mixed to form white, smooth, homogeneous, opaque cream or lotion with, for example, benzyl alcohol 1% or 2% (wt/wt) as a preservative, emulsifying wax, glycerin, isopropyl palmitate, lactic acid, purified water and sorbitol solution. In addition, the compositions can contain polyethylene glycol 400. They can be mixed to form ointments with, for example, benzyl alcohol 2% (wt/wt) as preservative, white petrolatum, emulsifying wax, and tenox II (butylated hydroxyanisole, propyl gallate, citric acid, propylene glycol). Woven pads or rolls of bandaging material, e.g., gauze, can be impregnated with the compositions in solution, lotion, cream, ointment or other such form can also be used for topical application. The compositions can also be applied topically using a transdermal system, such as one of an acrylic-based polymer adhesive with a resinous crosslinking agent impregnated with the composition and laminated to an impermeable backing.

The compositions can also be applied topically using a transdermal system, such as one of an acrylic-based polymer adhesive with a resinous crosslinking agent impregnated with the composition and laminated to an impermeable backing. In a particular embodiment, the compositions of the invention are administered as a transdermal patch, more particularly as a sustained-release transdermal patch. The transdermal patches of the invention can include any conventional form such as, for example, adhesive matrix, polymeric matrix, reservoir patch, matrix or monolithic-type laminated structure, and are generally comprised of one or more backing layers, adhesives, penetration enhancers, an optional rate controlling membrane and a release liner which is removed to expose the adhesives prior to application. Polymeric matrix patches also comprise a polymeric-matrix forming material. Suitable transdermal patches are described in more detail in, for example, U.S. Pat. Nos. 5,262,165, 5,948,433, 6,010,715 and 6,071,531, the disclosure of each of which are incorporated herein in their entirety.

Solid dosage forms for oral administration can include capsules, sustained-release capsules, tablets, sustained release tablets, chewable tablets, sublingual tablets, effervescent tablets, pills, powders, granules and gels. In such solid dosage forms, the active compounds can be admixed with at least one inert diluent such as sucrose, lactose or starch. Such dosage forms can also comprise, as in normal practice, additional substances other than inert diluents, e.g., lubricating agents such as magnesium stearate. In the case of capsules, tablets, effervescent tablets, and pills, the dosage forms can also comprise buffering agents. Soft gelatin capsules can be prepared to contain a mixture of the active compounds or compositions of the invention and vegetable oil. Hard gelatin capsules can contain granules of the active compound in combination with a solid, pulverulent carrier such as lactose, saccharose, sorbitol, mannitol, potato starch, corn starch, amylopectin, cellulose derivatives of gelatin. Tablets and pills can be prepared with enteric coatings.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents.

Suppositories for vaginal or rectal administration of the compounds and compositions of the invention can be prepared by mixing the compounds or compositions with a suitable nonirritating excipient such as cocoa butter and polyethylene glycols which are solid at room temperature but liquid at rectal temperature, such that they will melt in the rectum and release the drug.

Injectable preparations, for example, sterile injectable aqueous or oleaginous suspensions can be formulated according to the known art using suitable dispersing agents, wetting agents and/or suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be used are water, Ringer's solution, and isotonic sodium chloride solution. Sterile fixed oils are also conventionally used as a solvent or suspending medium.

The compositions of this invention can further include conventional excipients, i.e., pharmaceutically acceptable organic or inorganic carrier substances suitable for parenteral application which do not deleteriously react with the active compounds. Suitable pharmaceutically acceptable carriers include, for example, water, salt solutions, alcohol, vegetable oils, polyethylene glycols, gelatin, lactose, amylose, magnesium stearate, talc, surfactants, silicic acid, viscous paraffin, perfume oil, fatty acid monoglycerides and diglycerides, petroethral fatty acid esters, hydroxymethyl-cellulose, polyvinylpyrrolidone, and the like. The pharmaceutical preparations can be sterilized and if desired, mixed with auxiliary agents, e.g., lubricants, preservatives, stabilizers, wetting agents, emulsifiers, salts for influencing osmotic pressure, buffers, colorings, flavoring and/or aromatic substances and the like which do not deleteriously react with the active compounds. For parenteral application, particularly suitable vehicles consist of solutions, preferably oily or aqueous solutions, as well as suspensions, emulsions, or implants. Aqueous suspensions may contain substances which increase the viscosity of the suspension and include, for example, sodium carboxymethyl cellulose, sorbitol and/or dextran. Optionally, the suspension may also contain stabilizers.

The composition, if desired, can also contain minor amounts of wetting agents, emulsifying agents and/or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, magnesium carbonate, and the like.

Various delivery systems are known and can be used to administer the compounds or compositions of the invention, including, for example, encapsulation in liposomes, microbubbles, emulsions, microparticles, microcapsules and the like. The required dosage can be administered as a single unit or in a sustained release form.

The bioavailability of the compositions can be enhanced by micronization of the formulations using conventional techniques such as grinding, milling, spray drying and the like in the presence of suitable excipients or agents such as phospholipids or surfactants.

Sustained release dosage forms of the invention may comprise microparticles and/or nanoparticles having a therapeutic agent dispersed therein or may comprise the therapeutic agent in pure, preferably crystalline, solid form. For sustained release administration, microparticle dosage forms comprising pure, crystalline, therapeutic agents. The therapeutic dosage forms of this aspect of the invention may be of any configuration suitable for sustained release.

Nanoparticle sustained release therapeutic dosage forms are preferably biodegradable and, optionally, bind to the vascular smooth muscle cells and enter those cells, primarily by endocytosis. The biodegradation of the nanoparticles occurs over time (e.g., 30 to 120 days; or 10 to 21 days) in prelysosomic vesicles and lysosomes. Larger microparticle therapeutic dosage forms of the invention release the therapeutic agents for subsequent target cell uptake with only a few of the smaller microparticles entering the cell by phagocytosis. A practitioner in the art will appreciate that the precise mechanism by which a target cell assimilates and metabolizes a dosage form of the invention depends on the morphology, physiology and metabolic processes of those cells. The size of the particle sustained release therapeutic dosage forms is also important with respect to the mode of cellular assimilation. For example, the smaller nanoparticles can flow with the interstitial fluid between cells and penetrate the infused tissue. The larger microparticles tend to be more easily trapped interstitially in the infused primary tissue, and thus are useful to deliver anti-proliferative therapeutic agents.

Particular sustained release dosage forms of the invention comprise biodegradable microparticles or nanoparticles. More particularly, biodegradable microparticles or nanoparticles are formed of a polymer containing matrix that bio degrades by random, nonenzymatic, hydrolytic scissioning to release therapeutic agent, thereby forming pores within the particulate structure.

In a particular embodiment, the compositions of the invention are orally administered as a sustained release tablet or a sustained release capsule. For example, the sustained release formulations can comprise an effective amount of at least one nitric oxide enhancing diuretic compound or a pharmaceutically acceptable salt thereof, and, optionally at least one nitric oxide donor, or the sustained release formulations can comprise an effective amount of at least one nitric oxide enhancing diuretic compound or a pharmaceutically acceptable salt thereof, and at least one nitric oxide donor, and, optionally at least one therapeutic agent The compounds and compositions of the invention can be formulated as pharmaceutically acceptable salt forms. Pharmaceutically acceptable salts include, for example, alkali metal salts and addition salts of free acids or free bases. The nature of the salt is not critical, provided that it is pharmaceutically-acceptable. Suitable pharmaceutically-acceptable acid addition salts may be prepared from an inorganic acid or from an organic acid. Examples of such inorganic acids include, but are not limited to, hydrochloric, hydrobromic, hydroiodic, nitric, carbonic, sulfuric and phosphoric acid and the like. Appropriate organic acids include, but are not limited to, aliphatic, cycloaliphatic, aromatic, heterocyclic, carboxylic and sulfonic classes of organic acids, such as, for example, formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, stearic, algenic, β-hydroxybutyric, cyclohexylaminosulfonic, galactaric and galacturonic acid and the like. Suitable pharmaceutically-acceptable base addition salts include, but are not limited to, metallic salts made from aluminum, calcium, lithium, magnesium, potassium, sodium and zinc or organic salts made from primary, secondary and tertiary amines, cyclic amines, N,N'-dibenzylethylenediamine, chloroprocaine, choline, diethanolamine, ethylenediamine, meglumine (N-methylglucamine) and procaine and the like. All of these salts may be prepared by conventional means from the corresponding compound by reacting, for example, the appropriate acid or base with the compound. In one embodiment, the pharmaceutically acceptable salts of the compounds of the invention include the nitrate salt.

While individual needs may vary, determination of optimal ranges for effective amounts of the compounds and/or compositions is within the skill of the art. Generally, the dosage required to provide an effective amount of the compounds and compositions, which can be adjusted by one of ordinary skill in the art, will vary depending on the age, health, physical condition, sex, diet, weight, extent of the dysfunction of the recipient, frequency of treatment and the nature and scope of the dysfunction or disease, medical condition of the patient, the route of administration, pharmacological considerations such as the activity, efficacy, pharmacokinetic and toxicology profiles of the particular compound used, whether a drug delivery system is used, and whether the compound is administered as part of a drug combination.

The amount of a given nitric oxide enhancing diuretic compound that will be effective in the treatment of a particular disorder or condition will depend on the nature of the disorder or condition, and can be determined by standard clinical techniques, including reference to Goodman and Gilman, supra; The Physician's Desk Reference, Medical Economics Company, Inc., Oradell, N.J., 1995; and Drug Facts and Comparisons, Inc., St. Louis, Mo., 1993. The precise dose to be used in the formulation will also depend on the route of administration, and the seriousness of the disease or disorder, and should be decided by the physician and the patient's circumstances.

The invention also provides pharmaceutical kits comprising one or more containers filled with one or more of the ingredients of the pharmaceutical compounds and/or compositions of the invention, including, at least, one or more of the novel nitric oxide enhancing diuretic compound, and one or more of the nitric oxide enhancing compounds described herein. Associated with such kits can be additional therapeutic agents or compositions (e.g., aldosterone antagonists, alpha-adrenergic receptor antagonists, angiotensin II antagonists, angiotensin-converting enzyme (ACE) inhibitors, antidiabetic compounds, anti-hyperlipidemic compounds, antioxidants, antithrombotic and vasodilator compounds, β-adrenergic antagonists, calcium channel blockers, digitalis, diuretics, endothelin antagonists, hydralazine compounds, $H_2$ receptor antagonists, neutral endopeptidase inhibitors, nonsteroidal antiinflammatory compounds (NSAIDs), phosphodiesterase inhibitors, potassium channel blockers, platelet reducing agents, proton pump inhibitors, renin inhibitors, selective cyclooxygenase-2 (COX-2) inhibitors, and the like, and combinations of two or more thereof), devices for administering the compositions, and notices in the form prescribed by a governmental agency regulating the manufacture, use or sale of pharmaceuticals or biological products which reflects approval by the agency of manufacture, use or sale for humans.

EXAMPLES

Example 1

2H-1,2,4-Benzothiadiazine-7-sulfonamide, 6-chloro-3,4-dihydro-3-[5-(nitrooxy)pentyl]-, 1,1-dioxide 1a. 1,6-Hexanediol, mononitrate

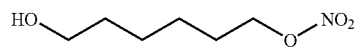

6-Bromohexan-1-ol (10 g, 55.2 mmol) was dissolved in acetonitrile (200 mL). To this solution was added silver nitrate (12.19 g, 71.76 mmol, 1.3 equivalents) and the reaction mixture was refluxed under nitrogen atmosphere for 2 hours. After removal of the solid by filtration, the solvent was evaporated under reduced pressure. The residue was extracted with ethyl acetate, then washed with water, brine, dried over sodium sulfate, filtered through a small pad of silica gel and then evaporated under reduced pressure to give the title compound as a pale yellow oil (8.28 g, 92% yield). $^1$H NMR (400 MHz, CDCl$_3$) δ 4.47 (t, J=6.7 Hz, 2H), 3.67 (t, J=6.5 Hz, 2H), 2.04 (s, 1H), 1.82-1.73 (m, 2H), 1.65-1.57 (m, 2H), 1.52-1.40 (m, 4H).

1b. Hexanal, 6-(nitrooxy)-

The product of Example 1a (8.19 g, 42 mmol) was dissolved in dichloromethane (200 mL). To this solution were added successively Dess-Martin periodinane reagent (Lancaster Synthesis, 17.8 g, 42 mmol) followed by water (0.8 mL) and the reaction mixture was stirred at room temperature for 2 hours. The solid precipitate was filtered off and filtrate was dried over sodium sulfate and then filtered through a pad of silica gel, and then evaporated at reduced pressure to give the title compound in nearly quantitative yield. $^1$H NMR (400 MHz, CDCl$_3$) δ 9.79 (s, 1H), 4.45 (t, J=6.8 Hz, 2H), 2.47 (t, J=7.2 Hz, 2H), 1.80-1.63 (m, 4H), 1.55-1.40 (m, 2H).

1c. 2H-1,2,4-Benzothiadiazine-7-sulfonamide, 6-chloro-3,4-dihydro-3-[5-(nitrooxy)pentyl]-, 1,1-dioxide

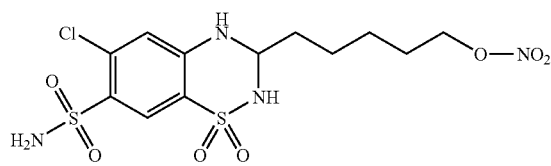

The crude product of Example 1b (42 mmol) and 2-amino-6-chloro-1,3-benzenedisulfonamide (Aldrich Chemical Co., 10.85 g, 38 mmol) were mixed together in dioxane (300 mL) and concentrated hydrochloric acid (9 mL). The reaction mixture was refluxed for 1 hour. It was then cooled to room temperature, washed with saturated brine, then the organic layer was separated and the solvent was evaporated at reduced pressure. The residue obtained was treated with ethyl acetate, washed with saturated aqueous sodium carbonate, water, brine, dried over sodium sulfate, filtered, and the filtrate was concentrated in vacuo to give the crude product. Purification by column chromatography over silica gel, eluting with 4% methanol in dichloromethane gave an oil (7.7 g) that was triturated with 20% ethyl acetate in hexane to give the title compound (6.7 g, 41% yield) as a white solid: mp 158-161° C.; $^1$H NMR (400 MHz, d$_6$-DMSO) δ 7.99 (s, 1H), 7.89 (s, 1H), 7.78 (br s, 1H), 7.50 (s, 2H), 6.98 (s, 1H), 4.75 (br s, 1H), 4.54 (t, J=6.5 Hz, 2H), 1.90-1.65 (m, 4H), 1.55-1.40 (m, 4H); Mass Spectrum (API-TIS) m/z 429 (MH)$^+$, 446 (MNH$_4$)$^+$.

Example 2

2H-1,2,4-Benzothiadiazine-7-sulfonamide, 3,4-dihydro-3-[5-(nitrooxy)pentyl]-6-(trifluoromethyl)-, 1,1-dioxide

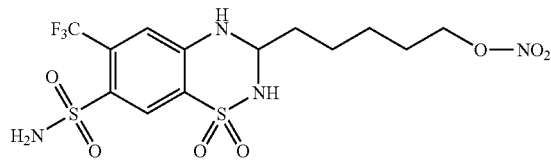

The title compound was prepared by reaction of the product of the Example 1b (5 mmol) and 2-amino-6-(trifluoromethyl)-1,3-benzenedisulfonamide (Fluka chemicals, 1.6 g, 5 mmol) following the procedure described in Example 1c. The title compound was obtained as a white solid (0.95 g, 41% yield): mp 171-189° C.; $^1$H NMR (400 MHz, d$_6$-DMSO) δ 8.21 (s, 1H), 8.12 (s, 1H), 7.87 (s, 1H), 7.57 (s, 2H), 7.34 (s, 1H), 4.80 (s, 1H), 4.54 (t, J=6.3 Hz, 2H), 1.90-1.68 (m, 4H), 1.60-1.35 (m, 4H); Mass Spectrum (API-TIS) m/z 463 (MH)$^+$, 480 (MNH$_4$)$^+$.

Example 3

2H-1,2,4-Benzothiadiazine-7-sulfonamide, 3,4-dihydro-3-[3-(nitrooxy)propyl]-6-(trifluoromethyl)-, 1,1-dioxide

3a. 1,4-Butanediol, acetate nitrate

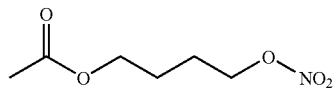

A solution of silver nitrate (7.87 g, 46.3 mmol) and 4-bromobutyl acetate (4.40 g, 22.6 mmol) in acetonitrile (100 mL) was stirred at room temperature overnight and then for an additional 1 hour at 70° C. The mixture was cooled to room temperature and then stirred with brine (150 mL) for 1 hour. The resulted mixture was filtered through Celite and washed with acetonitrile. The filtrate was concentrated and then extracted with ethyl acetate (50 mL×2). The combined organic extracts were washed with water and brine, dried over Na$_2$SO$_4$, filtered, concentrated and dried under vacuum to give the title compound as a yellow oil (3.58 g, 89% yield). The product, >95% purity from NMR analysis, was use in the next step without further purification. $^1$H NMR (300 MHz, CDCl$_3$) δ 4.53 (t, J=6.2 Hz, 2H), 4.11 (t, J=6.1 Hz, 2H), 2.06 (s, 3H), 1.85-1.75 (m, 4H); $^{13}$C NMR (75 MHz, CDCl$_3$) δ 170.8, 72.5, 63.3, 24.8, 23.5, 20.7.

3b. 1,4-Butanediol, mononitrate

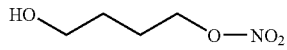

The crude product of Example 3a (1.03 g, 5.8 mmol) and 2N NaOH (2.6 mL, 5.2 mmol) in MeOH (20 mL) was stirred at room temperature for 2 hours. The reaction mixture was acidified with 3N HCl and then concentrated under reduced pressure. The residue was partitioned between 3N HCl and CH$_2$Cl$_2$. The organic extract was washed with water and brine, dried over Na$_2$SO$_4$, filtered, concentrated and dried under vacuum to give the title compound as a yellow oil (0.47 g, 70% yield). The product, >95% purity from NMR analysis, was use in the next step without purification. $^1$H NMR (300 MHz, CDCl$_3$) δ 4.49 (t, J=6.3 Hz, 2H), 3.71 (t, J=6.3 Hz, 2H), 1.90-1.80 (m, 2H), 1.80-1.65 (m, 2H); $^{13}$C NMR (75 MHz, CDCl$_3$) δ 73.1, 61.7, 28.5, 23.3.

3c. Butanal, 4-(nitrooxy)-

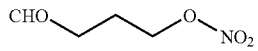

The product of the Example 3b (0.33 g, 2 mmol) was treated with Dess-Martin periodinane reagent (0.85 g, 2 mmol) in dichloromethane (10 mL) and water (50 µL) following the procedure for Example 1b to give the title compound in nearly quantitative yield. The crude product obtained was used as such in the next step without further purification.

3d. 2H-1,2,4-Benzothiadiazine-7-sulfonamide, 3,4-dihydro-3-[3-(nitrooxy)propyl]-6-(trifluoromethyl)-, 1,1-dioxide

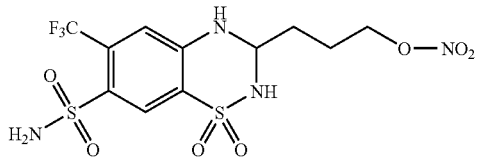

The product of Example 3c (2 mmol) was dissolved in dioxane (20 mL) and treated with 2-amino-6-(trifluoromethyl)-1,3-benzenedisulfonamide (0.64 g, 2 mmol) and concentrated hydrochloric acid (0.4 mL) following the procedure for Example 1c. The product was purified by silica gel flash chromatography eluting with 3% methanol in dichloromethane to give the title compound (0.54 g, 62% yield) as a white solid: mp 165° C. (with decomposition); $^1$H NMR (400 MHz, $d_6$-DMSO) δ 8.00 (s, 1H), 7.89 (s, 1H), 7.97 (br s, 1H), 7.85 (d, J=11.6 Hz, 1H), 7.51 (s, 1H), 6.98 (s, 1H), 4.82 (m, 1H), 4.60 (br s, 2H), 1.88 (br s, 4H); Mass Spectrum (API-TIS) m/z 435 (MH)$^+$, 452 (MNH$_4$)$^+$.

Example 4

Pentanamide, N-[7-(aminosulfonyl)-6-chloro-1,1-dioxido-2H-1,2,4-benzothiadiazin-3-yl]-5-(nitrooxy)-

4a. Pentanoic acid, 5-(nitrooxy)-

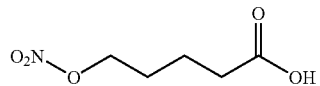

AgNO$_3$ (14 g, 82.8 mmol) was added to a solution of 5-bromovaleric acid (10 g, 55 mmol) in acetonitrile (70 mL). The reaction mixture was stirred at room temperature for 2 days. The residue after filtration and evaporation was chromatographed on silica gel eluting with EtOAc:Hexane (1:1) to give the title compound (8 g, 89% yield) as a colorless oil. $^1$H NMR (300 MHz, CDCl$_3$) δ 10.80 (br s, 1H), 4.51 (t, J=5.9 Hz, 2H), 2.47 (t, J=6.9 Hz, 2H), 1.87-1.76 (m, 4H); $^{13}$C NMR (75 MHz, CDCl$_3$) δ 179.7, 72.8, 33.4, 26.2, 20.9. Mass spectrum (API-TIS) m/z 181 (MNH$_4^+$).

4b. 2H-1,2,4-Benzothiadiazine-7-sulfonamide, 3-amino-6-chloro-, 1,1-dioxide

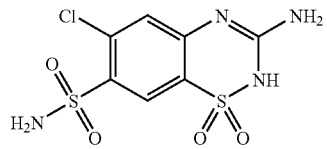

The title compound was synthesized by following the procedure in GB Patent No. 847,176, using 4-chloro-6-aminobenzene-1,3-disulfonamide (10 g, 35 mmol) and guanidine carbonate (5 g, 28 mmol). A white solid was obtained (0.9 g): mp>260° C.; $^1$H NMR (300 MHz, $d_6$-DMSO) δ 11.13 (s, 1H), 8.15 (s, 1H), 7.74 (s, 2H), 7.41 (br s, 2H), 7.40 (s, 1H); Mass spectrum (API-TIS) m/z 311 (MH$^+$). Anal. calcd for C$_7$H$_7$ClN$_4$O$_4$S$_2$: C, 27.06; H, 2.27; N, 18.03; Cl, 11.41. Found: C, 26.75; H, 2.38; N, 18.15; Cl, 11.37.

4c. Pentanamide, N-[7-(aminosulfonyl)-6-chloro-1,1-dioxido-2H-1,2,4-benzothiadiazin-3-yl]-5-(nitrooxy)-

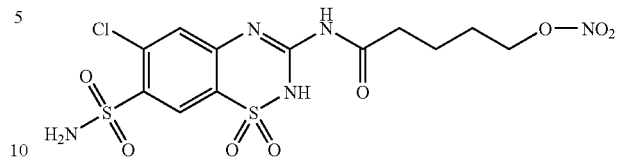

A mixture of the product of Example 4b (0.25 g, 0.8 mmol), the product of Example 4a (0.13 g, 0.8 mmol) and N,N-dimethylaminopyridine (DMAP, 98 mg, 0.8 mmol) in DMF (2 mL) at 0° C. was treated with 1-(3-(dimethylamino)propyl)-3-ethylcarbodiimide hydrochloride (0.19 g, 1 mmol). The reaction mixture was stirred at room temperature for 16 hours. The residue after evaporation of the solvent was chromatographed on silica gel, eluting with CH$_2$Cl$_2$:EtOAc:MeOH (1:1:0.1) to CH$_2$Cl$_2$:MeOH (1:0.5) to give the title compound (0.1 g, 27% yield) as a white solid: mp 222-225° C.; $^1$H NMR (400 MHz, $d_4$-MeOH) δ 8.49 (s, 1H), 7.26 (s, 1H), 4.46 (t, J=6.4 Hz, 2H), 2.24 (t, J=7.2 Hz, 2H), 1.60-1.68 (m, 4H). $^{13}$C NMR (100 MHz, $d_4$-MeOH) δ 181.0, 152.8, 138.6, 137.2, 135.2, 126.7, 119.7, 118.3, 73.1, 38.0, 26.0, 21.9. Mass spectrum (API-TIS) m/z 454 (M-H).

Example 5

Hexanamide, N-[7-(aminosulfonyl)-6-chloro-1,1-dioxido-2H-1,2,4-benzothiadiazin-3-yl]-6-(nitrooxy)-

5a Hexanoic acid, 6-(nitrooxy)-

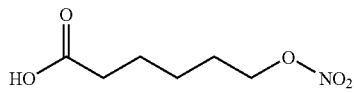

AgNO$_3$ (13 g, 76.9 mmol) was added to a solution of 6-bromohexanoic acid (10 g, 51 mmol) in acetonitrile (50 mL). The reaction mixture was stirred at room temperature for 2 days. The residue after filtration and evaporation was chromatographed on silica gel, eluting with CH$_2$Cl$_2$:EtOAc (1:1) to give the title compound (9 g, 99% yield) as a low melting solid. $^1$H NMR (300 MHz, CDCl$_3$) δ 10.70 (br s, 1H), 4.46 (t, J=6.5 Hz, 2H), 2.39 (t, J=7.2 Hz, 2H), 1.64-1.78 (m, 4H), 1.44-1.52 (m, 2H). $^{13}$C NMR (75 MHz, CDCl$_3$) δ 180.3, 73.1, 33.7, 26.4, 25.1, 24.1. Mass spectrum (API-TIS) m/z 177 (M$^+$).

5b. Hexanamide, N-[7-(aminosulfonyl)-6-chloro-1,1-dioxido-2H-1,2,4-benzothiadiazin-3-yl]-6-(nitrooxy)-

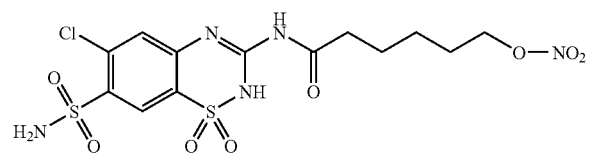

The title compound was prepared as a white solid (0.1 g, 26% yield) from the product of Example 4b (0.25 g, 0.8 mmol), the product of Example 5a (0.19 g, 1.1 mmol), N,N- dimethylaminopyridine (DMAP, 98 mg, 0.8 mmol) and 1-(3-(dimethylamino)propyl)-3-ethylcarbodiimide hydrochloride (0.19 g, 1 mmol) in DMF (2 mL) by following the procedure for Example 4c: Mp 177-179° C.; $^1$H NMR (400 MHz, d$_6$-DMSO) δ 11.10 (br s, 1H), 8.15 (s, 1H), 7.25 (br s, 2H), 7.19 (s, 1H), 4.47 (t, J=6.4 Hz, 2H), 1.92-2.00 (m, 2H), 1.58-1.64 (m, 2H), 1.40-1.49 (m, 2H), 1.22-1.30 (m, 2H); $^{13}$C NMR (100 MHz, d$_6$-DMSO) δ 177.5, 152.6, 134.2, 126.5, 120.5, 118.3, 74.3, 38.8, 26.4, 25.5, 25.3; Mass spectrum (API-TIS) m/z 470 (MH$^+$), 487 (MNH$_4$$^+$).

Example 6

2H-1,2,4-Benzothiadiazine-7-sulfonamide, 3-[3,4-bis(nitrooxy)butyl]-6-chloro-3,4-dihydro-, 1,1-dioxide 6a. Pentanal, 4,5-bis(nitrooxy)-

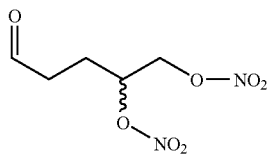

4,5-Bis(nitrooxy)pentan-1-ol was prepared by following the procedure described in WO 2005/030135 A2 (Example 27d) on a 5 mmol scale. The product was oxidized using Dess-Martin periodinane reagent following the procedure described in Example 1b. The crude product obtained was used without further purification. $^1$H NMR (400 MHz, CDCl$_3$) δ 9.81 (s, 1H), 5.47-5.35 (m, 1H), 4.80 (d, J=11.5 Hz, 1H), 4.48 (dd, J=2.8 and 11.5 Hz, 1H), 2.71 (t, J=7.0 Hz, 2H), 2.20-2.10 (m, 1H), 2.10-2.00 (m, 1H).

6b. 2H-1,2,4-Benzothiadiazine-7-sulfonamide, 3-[3,4-bis(nitrooxy)butyl]-6-chloro-3,4-dihydro-, 1,1-dioxide

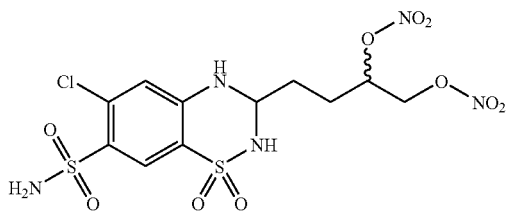

The product of Example 6a (2.5 mmol) was dissolved in dioxane (25 mL) and treated with 2-amino-6-chloro-1,3-benzenedisulfonamide (0.64 g, 2 mmol) and hydrochloric acid (0.5 mL) following the procedure for Example 1c. The resulting product was purified by silica gel flash chromatography, eluting with 3% methanol in dichloromethane, to give the title compound as an oil that was recrystallized from ethyl acetate/hexane (40:60) to give the pure product as a white solid (0.780 g) in 82% yield: mp 153-155° C.; $^1$H NMR (400 MHz, d$_6$-DMSO) δ 7.99 (s, 1H), 7.98 (s, 1H), 7.87 (dd, J=3.6 and 11.5 Hz, 1H), 7.52 (s, 2H), 6.90 (s, 1H), 5.50 (br s, 1H), 5.00 (m, 1H), 4.90-4.70 (m, 2H), 2.00-1.95 (m, 4H); Mass Spectrum (API-TIS) m/z 493 (MNH$_4$$^+$).

Example 7

2H-1,2,4-benzothiadiazine-7-sulfonamide, 3-[3,4-bis(nitrooxy)butyl]-3,4-dihydro-6-(trifluoromethyl)-, 1,1-dioxide

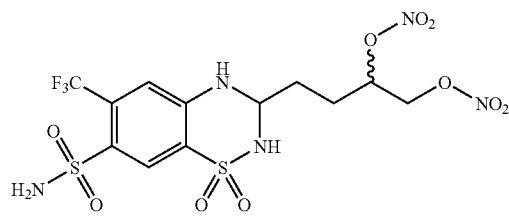

The product of Example 6a (2.5 mmol) was dissolved in dioxane (25 mL) and treated with 2-amino-6-(trifluoromethyl)-1,3-benzenedisulfonamide (0.64 g, 2 mmol) and concentrated hydrochloric acid (0.5 mL) following the procedure for Example 1c. The product was purified by silica gel flash chromatography, eluting with 3% methanol in dichloromethane, to give the title compound as an oil that was recrystallized from ethyl acetate/hexane (40:60) to give the pure product as a white solid (0.75 g, 74% yield): mp 157-160° C. (with decomposition); $^1$H NMR (400 MHz, d$_6$-DMSO) δ 8.25 (s, 2H), 8.00 (d, J=11.5 Hz, 1H), 7.65 (s, 2H), 7.35 (s, 1H), 5.52 (br s, 1H), 5.00-4.70 (m, 3H), 2.00 (br s, 4H); Mass Spectrum (API-TIS) m/z 527 (MNH$_4$)$^+$.

Example 8

2H-1,2,4-Benzothiadiazine-7-sulfonamide, 6-chloro-3,4-dihydro-3-[3-(nitrooxy)propyl]-, 1,1-dioxide

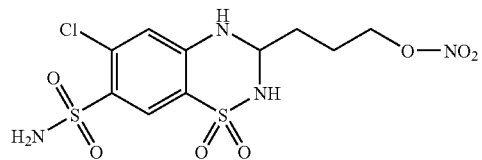

The title compound was prepared from the product of the Example 3c (2.5 mmol) and 2-amino-6-chloro-1,3-benzenedisulfonamide (0.57 g, 2 mmol) following the procedure for Example 1c. The title compound was obtained as a white solid (0.49 g, 61% yield): mp 178-181° C.; $^1$H NMR (400 MHz, d$_6$-DMSO) δ 7.99 (s, 1H), 7.96 (s, 1H), 7.85 (dd, J=3.4 and 11.6 Hz, 1H), 7.50 (br s, 2H), 6.97 (s, 1H), 4.9-4.80 (m, 1H), 4.59 (br s, 2H), 1.87 (br s, 4H); Mass Spectrum (API-TIS) m/z 401 (MH)$^+$, 403 [(MH)+2]$^+$, 418 (MNH$_4$)$^+$, 420 [(MNH$_4$)+2]$^+$.

Example 9

2H-1,2,4-Benzothiadiazine-7-sulfonamide, 6-chloro-3,4-dihydro-3-(4-methyl-5-oxido-1,2,5-oxadiazol-3-yl)-, 1,1-dioxide 9a. 1,2,5-Oxadiazole-3-carboxaldehyde, 4-methyl-, 5-oxide

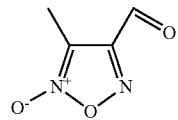

This title compound was synthesized as described by Fruttero et al, *J. Heterocyclic Chem.*, 26: 1345-1347 (1989). Low melting solid. $^1$H NMR (300 MHz, CDCl$_3$) δ 10.12 (s, 1H), 2.40 (s, 3H); $^{13}$C NMR (75 MHz, CDCl$_3$) δ 183.3, 154.3, 109.5, 8.2; Mass spectrum (API-TIS) m/z 127 (M-H).

9b. 2H-1,2,4-Benzothiadiazine-7-sulfonamide, 6-chloro-3,4-dihydro-3-(4-methyl-5-oxido-1,2,5-oxadiazol-3-yl)-, 1,1-dioxide

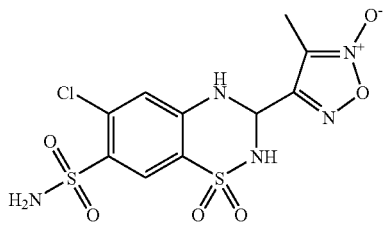

To a mixture of 4-chloro-6-aminobenzene-1,3-disulfonamide (0.3 g, 1.05 mmol) and the product of Example 9a (0.23 g, 1.8 mmol) in dioxane (9 mL), was added concentrated HCl (1 mL) dropwise. The reaction mixture was heated at 60° C. for 1 hour and then cooled to room temperature. The crude reaction mixture was chromatographed on silica gel, eluting with MeOH:CH$_2$Cl$_2$ (0.5:9.5 to 1:9 to 1.5:8.5), to give the title compound (0.24 g, 58% yield) as a white solid: mp 242-243° C. (with decomposition); $^1$H NMR (400 MHz, d$_6$-DMSO) δ 8.92 (br d, J=8.4 Hz, 1H), 8.72 (br s, 1H), 8.02 (s, 1H), 7.57 (br s, 2H), 7.23 (s, 1H), 6.41-6.43 (m, 1H), 2.20 (s, 3H); $^{13}$C NMR (100 MHz, d$_6$-DMSO) δ 156.6, 146.2, 135.3, 129.8, 125.7, 118.9, 118.2, 113.1, 61.4, 8.6. Mass spectrum (API-TIS) m/z 394 (M-H), 413 (MNH$_4^+$). Anal. calcd for C$_{10}$H$_{10}$ClN$_5$O$_6$S$_2$: C, 30.34; H, 2.55; N, 17.69. Found: C, 30.25; H, 2.49; N, 17.42.

Example 10

2H-1,2,4-Benzothiadiazine-7-sulfonamide, 3,4-dihydro-3-(4-methyl-5-oxido-1,2,5-oxadiazol-3-yl)-6-(trifluoromethyl)-, 1,1-dioxide

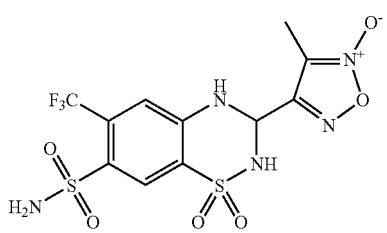

The title compound was prepared as a white solid (0.16 g, 40% yield) from 4-amino-6-trifluoromethylbenzene-1,3-disulfonamide (0.3 g, 0.94 mmol), the product of Example 9a (0.32 g, 2.5 mmol) and concentrated HCl (1 mL) by following the procedure of Example 9b. Mp 160° C. $^1$H NMR (400 MHz, d$_6$-DMSO) δ 9.00 (br s, 1H), 8.92 (s, 1H), 8.24 (s, 1H), 7.63 (s, 2H), 7.58 (s, 1H), 6.47 (bs, 1H), 2.19 (s, 3H); $^{13}$C NMR (100 MHz, d$_6$-DMSO) δ 156.5, 145.4, 130.2, 126.8, 124.0, 122.0, 121.3, 116.6, 113.1, 61.5, 8.5; Mass spectrum (API-TIS) m/z 428 (M-H). Anal. calcd for C$_{11}$H$_{10}$F$_3$N$_5$O$_6$S$_2$: C, 30.75; H, 2.34; N, 16.30; F, 13.33. Found: C, 30.89; H, 2.33; N, 16.04; F, 13.27.

Example 11

4H-1,2,4-Benzothiadiazine-3-butanamide, 7-(aminosulfonyl)-N-[(2R)-2,3-bis(nitrooxy)propyl]-6-chloro-, 1,1-dioxide

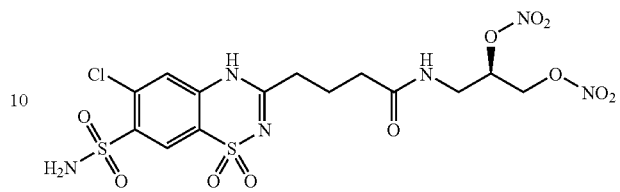

4-(6-Chloro-1,1-dioxo-7-sulfamoyl-4H-benzo[e]1,2,4-thiadiazin-3-yl)butanoic acid (2 mmol, prepared following the procedure in U.S. Pat. No. 3,287,360) was dissolved in a mixture of dimethylformamide (3 mL) and dichloromethane (2 mL). In a separate flask (2R)-2,3-bis(nitrooxy)propylamine-nitric acid salt (2 mmol, prepared as described in U.S. 2005/0059655 Al, Example 12a) was treated with triethylamine (0.25 mL) in dichloromethane (10 mL) to generate (2R)-2,3-bis(nitrooxy)propylamine. Both solutions were then mixed together and stirred at room temperature. To the resulting mixture were added 1-ethyl-3-(3-dimethylaminopropyl) carbamide hydrochloride (EDAC, 0.38 g, 2 mmol) and dimethyl aminopyridine (DMAP, 0.24 g, 2 mmol) under a nitrogen atmosphere. The resulting reaction mixture was then stirred at room temperature overnight. The solvent was evaporated under vacuo and the residue was extracted with ethyl acetate, washed with water, brine, dried over sodium sulfate, filtered, and evaporated. The product was purified by column chromatography over silica gel, eluting with 5% methanol in dichloromethane, to give the title compound (0.38 g, 35% yield) as a white solid: mp>220° C.; $^1$H NMR (400 MHz, d$_6$-DMSO) δ 12.25 (br s, 1H), 8.26 (s, 1H), 8.22 (t, J=4.0 Hz, 1H), 7.88 (s, 2H), 7.48 (s, 1H), 5.50-5.40 (m, 1H), 5.49 (dd, J=2.8 and 12.8 Hz, 1H), 4.70 (dd, J=6.8 and 12.8 Hz, 1H), 3.65-3.50 (m, 1H), 3.40 (m, 1H), 2.60 (t, J=7.6 Hz, 2H), 2.20 (t, J=7.0 Hz, 2H), 1.95-1.85 (m, 2H); Mass Spectrum (API-TIS) m/z 545 (MH)$^+$.

Example 12

Spiro[2H-1,2,4-benzothiadiazine-3(4H), 4'-piperidine]-7-sulfonamide, 1'-[5-(nitrooxy)-1-oxopentyl]-6-(trifluoromethyl)-, 1,1-dioxide 12a. Spiro[2H-1,2,4-benzothiadiazine-3(4H), 4'-piperidine]-1'-carboxylic acid, 7-(aminosulfonyl)-6-(trifluoromethyl)-, 1,1-dimethylethyl ester, 1,1-dioxide

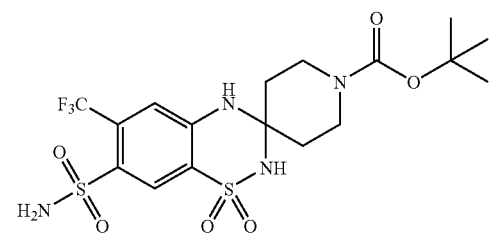

A solution of 4-amino-6-(trifluoromethyl)benzene-1,3-disulfonamide (11.94 g, 37.4 mmol) and 1-Boc-4-piperidone (8.19 g, 41.1 mmol, Fluka) in DMF (160 mL) was heated at reflux under ambient atmosphere for 5-7 hours until the first reactant was consumed as indicated by TLC. After cooling to room temperature, the mixture was poured into water, and extracted with EtOAc. The organic layer was washed with aqueous NaCl, dried over $Na_2SO_4$, filtered, and concentrated to give a yellow solid. Chromatography (silica gel, THF1:1 EtOAc:Hexane) gave the title compound (16.95 g, 91% yield) as a white solid. Mass spectrum (API-TIS) m/z 501.3 ($MH^+$), 518.4 ($MNH_4^+$).

12b. Spiro[2H-1,2,4-benzothiadiazine-3(4H), 4'-piperidine]-7-sulfonamide, 6-(trifluoromethyl)-, 1,1-dioxide, monohydrochloride

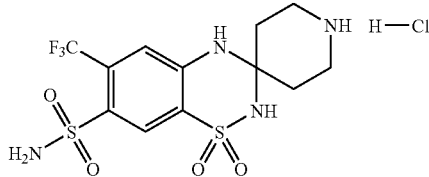

To a stirred solution of the product of Example 12a (7.70 g, 15.4 mmol) in 1,4-dioxane (50 mL) was added hydrogen chloride in 1,4-dioxane (4 M, 200 mL) in one portion, resulting is a cloudy solution. After 2 hours, the reaction mixture was concentrated to half the original volume. The solid was collected by filtration, washed with hexane, air-dried, and vacuum-dried to give the title compound (5.10 g, 76% yield) as a white solid: mp>260° C. $^1$H NMR (400 MHz, $d_6$-DMSO) δ 9.36 (br s, 1H), 9.12 (br s, 1H), 8.92 (s, 1H), 8.43 (s, 1H), 8.22 (s, 1H), 7.61 (s, 2H), 7.48 (s, 1H), 3.45-3.34 (m, 2H), 3.07 (br q, 2H), 2.40 (br d, 2H), 2.13 (br t, 2H); Mass spectrum (API-TIS) m/z 401.2 ($MH^+$).

12c. Spiro[2H-1,2,4-benzothiadiazine-3(4H), 4'-piperidine]-7-sulfonamide, 1'-[5-(nitrooxy)-1-oxopentyl]-6-(trifluoromethyl)-, 1,1-dioxide

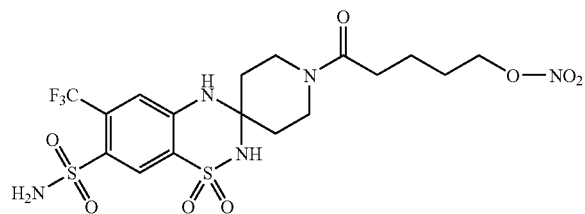

To a stirred mixture of 5-(nitrooxy)pentanoic acid (0.33 g, 2 mmol, prepared by as described by Breschi, M. C. et al. *J. Med. Chem.* 2004, 47, 5597-5600), N-(3-dimethylaminopropyl)-N'-ethylcarbodiimide hydrochloride (0.768 g, 4 mmol), 1-hydroxybenzotriazole hydrate (0.541 g, 4 mmol), and the product of Example 12b (0.80 g, 1.8 mmol) in acetonitrile (50 mL) was added triethylamine (5 mL). The resulting mixture was stirred at room temperature for 18 hours, concentrated, dissolved in EtOAc, washed with water, and then aqueous $Na_2CO_3$. The organic layer was dried over $MgSO_4$, filtered, and concentrated to give a solid. The solid was dissolved in THF and purified by chromatography (silica gel, EtOAc) to give the title compound (0.90 g, 92% yield) as a white solid: mp 178° C. (with decomposition); $^1$H NMR (400 MHz, $d_6$-DMSO) δ 8.27 (br s, 1H), 8.20 (s, 1H), 7.57 (br s, 2H), 7.28 (s, 1H), 4.52 (t, J=6 Hz, 2H), 4.12 (m, 3H), 3.73 (m, 1H), 3.00 (m, 1H), 2.39 (t, J=7.2 Hz, 2H), 2.28 (m, 1H), 2.20 (m, 1H), 1.70-1.59 (m, 6H); Mass spectrum (API-TIS) m/z 546 ($MH^+$).

Example 13

4H-1,2,4-Benzothiadiazine-3-propanamide, 7-(aminosulfonyl)-6-chloro-N-[2-[2-(nitrooxy)ethoxy]ethyl]-, 1,1-dioxide

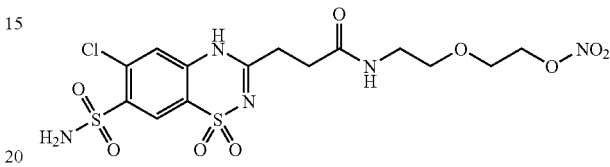

To a solution of 3-(6-chloro-1,1-dioxo-7-sulfamoyl-4H-benzo[e]1,2,4-thiadiazin-3-yl)propanoic acid (0.74 g, 2.0 mmol, prepared according to U.S. Pat. No. 3,287,360, Example 2) and 2-[2-(nitrooxy)ethoxy]ethylamine, nitric acid salt (0.46 g, 2.2 mmol, prepared as described in WO 2005/030135 A2 Example 11a) in DMF (10 mL) and dichloromethane (10 mL) was added DMAP (49 mg, 0.4 mmol) and EDAC (0.46 g, 2.4 mmol). Triethylamine (0.31 mL, 0.22 g, 2.2 mmol) was then added dropwise. After stirring at room temperature for 2 hours, the reaction mixture was partitioned between water and dichloromethane. The aqueous layer was washed twice with dichloromethane, and the combined organic layers were washed with water, brine, and dried over magnesium sulfate. The solvent was removed under vacuum, and the crude product was purified via column chromatography on silica gel, 10% methanol/dichloromethane. The crude solid was recrystallized from ethyl acetate/hexane to give the title compound (0.35 g, 35% yield) as a white solid: mp 175-178° C.; $^1$H NMR (400 MHz, $d_6$-DMSO) δ 12.42 (s, 1H), 8.25 (s, 1H), 8.07 (t, J=5.6 Hz, 1H), 7.87 (s, 2H), 7.48 (s, 1H), 4.65 (m, 2H), 3.69 (m, 2H), 3.43 (t, J=5.8 Hz, 2H), 3.20 (q, J=5.8 Hz, 2H), 2.83 (t, J=7.2 Hz, 2H), 2.56 (t, J=7.2 Hz, 2H); Mass spectrum (API-TIS) m/z 500 ($MH^+$), 999 (2 $MH^+$).

Example 14

4H-1,2,4-Benzothiadiazine-3-butanamide, 7-(aminosulfonyl)-6-chloro-N-[2-(nitrooxy)ethyl]-, 1,1-dioxide

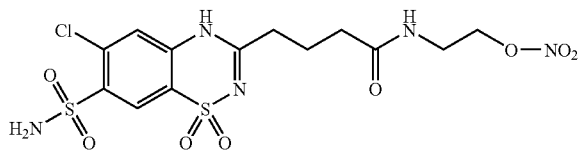

The title compound was prepared by the reaction of 2-(nitrooxy)ethylamine-nitric acid salt (2 mmol) (prepared as described in U.S. Patent No. 2004/0024057, Example 22a) and 4-(6-chloro-1,1-dioxo-7-sulfamoyl-4H-benzo[e]1,2,4-thiadiazin-3-yl)butanoic acid (2 mmol) by following the procedure for Example 11. The product was purified by column chromatography over silica gel, eluting with 5% methanol in dichloromethane to give the title compound (0.29 g, 31% yield) as a white solid: mp 168-170° C.; $^1$H NMR (400 MHz, d$_6$-DMSO) δ 12.28 (br s, 1H), 8.29 (br s, 1H), 8.20 (s, 1H), 7.79 (s, 2H), 7.46 (s, 1H), 4.51 (t, J=4.8 Hz, 2H), 3.40 (t, J=5.2 Hz, 2H), 2.60 (t, J=7.4 Hz, 2H), 2.21 (t, J=7.0 Hz, 2H), 2.21-1.91 (m, 2H); Mass Spectrum (API-TIS) m/z 470 (MH)$^+$, 472 (MH+2)$^+$.

Example 15

Spiro[2H-1,2,4-benzothiadiazine-3(4H), 4'-piperidine]-7-sulfonamide, 1'-[3-[(nitrooxy)methyl]benzoyl]-6-(trifluoromethyl)-, 1,1-dioxide 15a. Benzoyl chloride, 3-[(nitrooxy)methyl]-

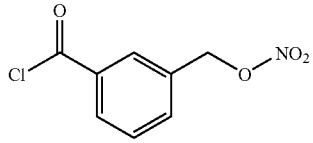

Oxalyl chloride (0.3 mL, 3.4 mmol) was added to a solution of 3-[(nitrooxy)methyl]benzoic acid, (prepared as described in U.S. Patent No. 2004/0024057, Example 43a, 0.53 g, 2.7 mmol) in CH$_2$Cl$_2$ (50 mL) and DMF (50 μL) and stirred at room temperature for 1.5 hours. The reaction mixture was evaporated to dryness and dried under vacuum to give the title compound as a white solid. The product was use in the next step without further purification. $^1$H NMR (300 MHz, CDCl$_3$) δ 8.15-8.10 (m, 2H), 7.77-7.74 (m, 1H), 7.65-7.55 (m, 1H), 5.52 (s, 2H); $^{13}$C NMR (75 MHz, CDCl$_3$) δ 167.7, 135.5, 133.7, 133.6, 132.1, 131.4, 129.6, 73.3.

15b. Spiro[2H-1,2,4-benzothiadiazine-3(4H), 4'-piperidine]-7-sulfonamide, 1'-[3-[(nitrooxy)methyl]benzoyl]-6-(trifluoromethyl)-, 1,1-dioxide

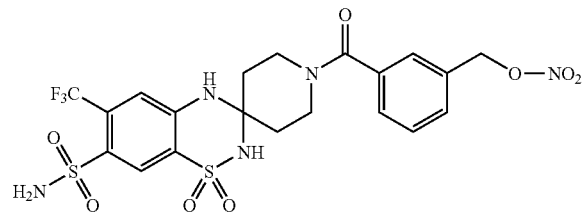

To a stirred mixture of the product of Example 15a (2.58 mmol), and the product of Example 12b (1.13 g, 2.58 mmol) in DMF (20 mL) was added triethylamine (5 mL) dropwise. After 1 hour, the mixture was diluted with EtOAc, and washed with aqueous NaHCO$_3$ twice. The organic layer was dried over Na$_2$SO4, filtered, and concentrated. Chromatography of the residue (silica gel, 1:5 THF:EtOAc) gave the title compound (1.21 g, 81% yield) as a white solid. $^1$H NMR (400 MHz, d$_6$-DMSO) δ 8.30 (s, 2H), 8.22 (s, 1H), 7.59-7.46 (m, 4H), 7.31 (s, 1H), 5.62 (s, 2H), 4.25 (m, 2H), 3.80 (m, 1H), 3.67 (m, 1H), 3.47 (m, 1H), 3.32 (m, 1H), 2.40-2.20 (m, 2H), 1.77-1.69 (m, 2H). Mass spectrum (API-TIS) m/z 580 (MH$^+$).

Example 16

Spiro[2H-1,2,4-benzothiadiazine-3(4H), 4'-piperidine]-7-sulfonamide, 1'-[2-methyl-3-(nitrooxy)-2-[(nitrooxy)methyl]-1-oxopropyl]-6-(trifluoromethyl)-, 1,1-dioxide 16a. Propanoic acid, 2-methyl-3-(nitrooxy)-2-[(nitrooxy)methyl]-

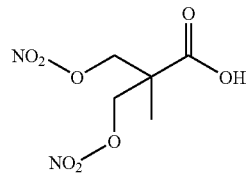

Fuming nitric acid (90%; 6 mL, 143 mmol) was added to ice-cold acetic anhydride (30 mL) and stirred in the ice bath for 10 minutes. Then 2,2-bis(hydroxymethyl)-propionoic acid (Aldrich, 2.59 g, 19.3 mmol) in ethyl acetate (30 mL) was added and the resulting mixture stirred at room temperature for 20 minutes and then evaporated to dryness under vacuum at 45° C. The residue was partitioned between 3N HCl (100 mL) and ethyl acetate (100 mL). The organic extract was washed with water, NaCl, dried over Na$_2$SO$_4$, filtered, concentrated and dried under vacuum. The crude material was dissolved in ethyl ether (3 mL) and triturated with hexane (100 mL). The solid was collected and dried under vacuum to give the title compound as a white solid (2.89 g, 67% yield): mp 66-69° C.; $^1$H NMR (300 MHz, CDCl$_3$) δ 5.2-50 (br s, 1H), 4.8-4.6 (m, 4H), 1.35 (s, 3H); $^{13}$C NMR (75 MHz, CDCl$_3$) δ 174.3, 74.3, 46.1, 18.2; Mass spectrum (API-TIS) m/z 223 (M-H).

16b. Propanoyl chloride, 2-methyl-3-(nitrooxy)-2-[(nitrooxy)methyl]-

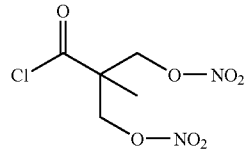

Oxalyl chloride (150 μL, 1.7 mmol) was added to a solution of the product of Example 16a (0.32 g, 1.4 mmol) in CH$_2$Cl$_2$ (10 mL) and DMF (10 μL) and stirred at room temperature for 2.5 hours. The reaction mixture was evaporated to dryness and dried under vacuum to give the title compound as a light colored oil. The product was use in the next step without purification. $^1$H NMR (400 MHz, CDCl$_3$) δ 4.8-4.65 (m, 4H), 1.52 (s, 3H); $^{13}$C NMR (100 MHz, CDCl$_3$) δ 173.6, 71.5, 54.3, 17.8.

16c. Spiro[2H-1,2,4-benzothiadiazine-3(4H), 4'-piperidine]-7-sulfonamide, 1'-[2-methyl-3-(nitrooxy)-2-[(nitrooxy)methyl]-1-oxopropyl]-6-(trifluoromethyl)-, 1,1-dioxide

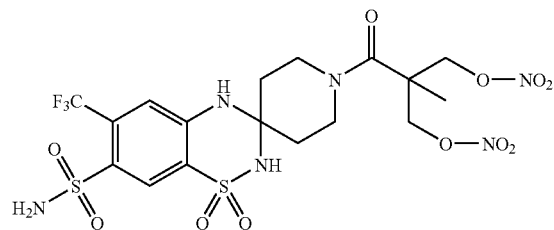

Triethylamine (0.36 mL, 2.6 mmol) was added to a mixture of the crude product of Example 16b and the product of Example 12b (0.57 g, 1.3 mmol) in acetonitrile (20 mL) and stirred at room temperature overnight. The reaction mixture was evaporated to dryness under reduced pressure. The residue was partitioned between 3N HCl (10 mL) and ethyl acetate (150 mL). The organic extract was washed with water, brine, dried over $Na_2SO_4$, filtered, concentrated and dried under vacuum. The crude product was dissolved in ethyl acetate (3 mL) and triturated with $CHCl_3$ (50 mL). The solid was collected and dried under vacuum to obtained the title compound as a white solid (0.59 g, 75% yield): mp>140° C. (with decomposition); $^1$H NMR (400 MHz, $d_4$-MeOH) δ 8.35 (s, 1H), 7.25 (s, 1H), 4.85-4.7 (m, 4H), 4.24 (br d, 2H), 3.38 (br t, 2H), 2.48 (br d, 2H), 1.80-1.70 (m, 2H), 1.48 (s, 3H); $^{13}$C NMR (100 MHz, $CDCl_3$) δ 170.7, 146.1, 133.2, 132.3 (q, $J_{CF}$=33 Hz), 130.0, 128.8, 123.7 (q, $J_{CF}$=275 Hz), 122.4, 117.3 (q, $J_{CF}$=7 Hz), 75.1, 71.1, 47.1, 42.3, 37.2, 18.0; Mass Spectrum (API-TIS) m/z 607 (MH$^+$). Anal. calcd for $C_{17}H_{21}F_3N_6O_{11}S_2$: C, 33.67; H, 3.49; N, 13.86; Found: C, 33.42; H, 3.32; N, 13.60.

Example 17

2H-1,2,4-Benzothiadiazine-7-sulfonamide, 6-chloro-3,4-dihydro-3-[4-(nitrooxy)butyl]-, 1,1-dioxide 17a. Pentanal, 5-(nitrooxy)-

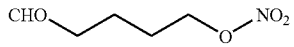

5-(Nitrooxy)pentan-1-ol (50 mmol) (prepared as described in WO 2004/012659, Example 3b) was oxidized using Dess-Martin periodinane following the procedure for Example 1b to give the title compound. The crude product obtained was used as such in the next step without further purification. $^1$H NMR (400 MHz, $CDCl_3$) δ 9.73 (s, 1H), 4.43 (t, J=6.4 Hz, 2H), 2.51-2.48 (m, 2H), 1.77-1.69 (m, 4H).

17b. 2H-1,2,4-Benzothiadiazine-7-sulfonamide, 6-chloro-3,4-dihydro-3-[4-(nitrooxy)butyl]-, 1,1-dioxide

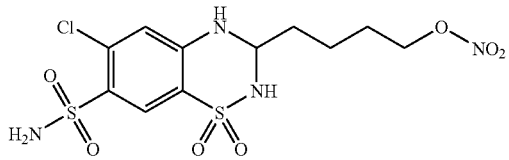

The title compound was prepared by reaction of the product of the Example 17a and 2-amino-6-chloro-1,3-benzenedisulfonamide (14.35 g, 50 mmol) following the procedure for Example 1c. The product was purified by column chromatography over silica gel, eluting with 4% methanol in dichloromethane to give the title compound (8.1 g, 39% yield) as a white solid: mp 171-179° C.; $^1$H NMR (400 MHz, $d_6$-DMSO) δ 8.01 (s, 1H), 7.82 (s, 1H), 7.71 (d, J=11.2 Hz, 1H), 7.38 (s, 2H), 6.95 (s, 1H), 4.74 (m, 1H), 4.52 (t, J=6.4 Hz, 2H), 1.97-1.74 (m, 4H), 1.59-1.51 (m, 2H); Mass Spectrum (API-TIS) m/z 432 (MNH$_4$)$^+$.

17c. 2H-1,2,4-benzothiadiazine-7-sulfonamide, 6-chloro-3,4-dihydro-3-[4-(nitrooxy)butyl]-, 1,1-dioxide, (3R)-(enantiomer 1) and 2H-1,2,4-benzothiadiazine-7-sulfonamide, 6-chloro-3,4-dihydro-3-[4-(nitrooxy)butyl]-, 1,1-dioxide, (3S)-(enantiomer 2)

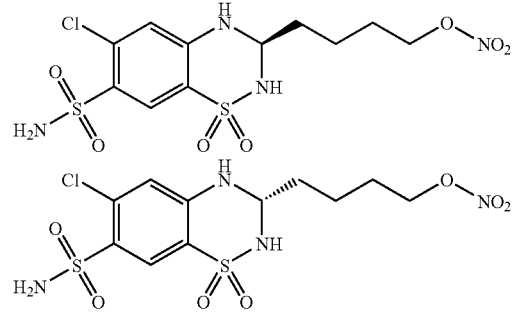

The product of Example 17b was separated into the enantiomers by super fluid critical chiral chromatography on CHIRACEL OJ-H column using liquid $CO_2$:methanol (70:30) at 280 nM UV detection. The purity of each isomer was determined by analytical chiral column OJ-H (150×4.6 mm) using isocratic solvent system of methanol:water (60:40) at a flow rate of 1 mL/minute. Retention times for the enantiomer 1 and 2 were 12.26 and 14.76 minutes respectively.

Example 18

Spiro[2H-1,2,4-benzothiadiazine-3(4H), 4'-piperidine]-7-sulfonamide, 6-chloro-1'-[5-(nitrooxy)-1-oxopentyl]-, 1,1-dioxide 18a. Spiro[2H-1,2,4-benzothiadiazine-3(4H), 4'-piperidine]-7-sulfonamide, 6-chloro-, 1,1-dioxide, monohydrochloride

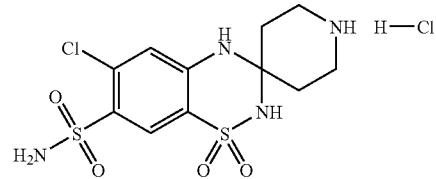

A mixture of 4-amino-6-chloro-1,3-benzenedisulfonamide (Aldrich, Wisconsin; 40.7 g, 0.142 mol), 4-piperidone monohydrate hydrochloride (Aldrich, Wisconsin; 24.1 g, 0.16 mol), N,N-dimethylacetamide (120 mL), toluene (600 mL) and p-toluenesulfonic acid monohydrate (Aldrich, Wisconsin; 1.0 g, 5.26 mmol, 0.04 eq) was heated at reflux (180-200° C.) for 3-4 hours until water had ceased distilling over. The reaction mixture was cooled to ambient temperature, the solids removed by filtration and then washed with toluene to give the crude product (70 g). The crude product was ground with a mortar and pestle and then re-crystallized from hot (70° C.) water. The solid was removed by filtration and washed with water (50 mL) to give the title compound (43.9 g, 76.4% yield) as a white solid: mp 265° C. (with decomposition); $^1$H NMR (400 MHz, $d_6$-DMSO) δ 9.08 (br s, 1H), 8.82 (br s, 1H), 8.49 (br s, 1H), 8.28 (s, 1H), 7.97 (s, 1H), 7.51 (s, 2H), 7.04 (s, 1H), 3.30-3.26 (m, 2H), 3.08-3-20 (m, 2H), 2.36 (m, 2H), 2.02-1.96 (m, 2H). Mass spectrum (API-TIS) m/z 367 (MH+).

18b. Spiro[2H-1,2,4-benzothiadiazine-3(4H), 4'-piperidine]-7-sulfonamide, 6-chloro-1'-[5-(nitrooxy)-1-oxopentyl]-, 1,1-dioxide

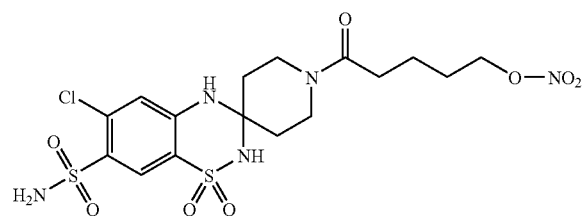

To a stirred mixture of 5-(nitrooxy)pentanoic acid (5.35 g, 32.8 mmol, prepared as described by Breschi, M. C. et al, *J. Med. Chem.* 47, 5597-5600, 2004), N-(3-dimethylaminopropyl)-N'-ethylcarbodiimide hydrochloride (6.29 g, 32.8 mmol), 1-hydroxybenzotriazole hydrate (4.44 g, 32.8 mmol), and the product of Example 18a (8.82 g, 21.9 mmol) in acetonitrile (180 mL) was added triethylamine (15.3 mL, 110 mmol). The resulting mixture was stirred at room temperature for 5 hours, concentrated to remove the volatiles, taken up with EtOAc, washed with water, aqueous NaHCO$_3$, and aqueous NaCl. The organic layer was dried over Na$_2$SO$_4$, filtered, and concentrated to give a solid. Chromatography (silica gel, THF for loading, EtOAc for eluting) of the crude product gave the title compound (698 mg, 6.2% yield) as a white solid: mp 155° C. (with decomposition); $^1$H NMR (400 MHz, d$_4$-MeOH) δ 8.19 (s, 1H), 6.94 (s, 1H), 4.54 (t, J=6.4 Hz, 2H), 4.40 (d, J=13.6 Hz, 1H), 3.90 (d, J=14.4 Hz, 1H), 3.51 (td, J=12 Hz and 2.4 Hz, 1H), 3.12 (td, J=12.4 Hz and 2.4 Hz, 1H), 2.56-2.49 (m, 3H), 2.35 (dd, J=14, 2.4 Hz, 1H), 1.82-1.75 (m, 6H). Mass spectrum (API-TIS) m/z 512 and 514 (MH+ for $^{35}$Cl and $^{37}$Cl respectively).

Example 19

Spiro[2H-1,2,4-benzothiadiazine-3(4H), 4'-piperidine]-7-sulfonamide, 1'-[2,2-dimethyl-3-(nitrooxy)-1-oxopropyl]-6-(trifluoromethyl)-, 1,1-dioxide 19a. Propanoyl chloride, 2,2-dimethyl-3-(nitrooxy)-

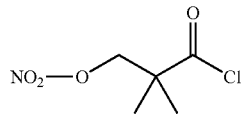

To 2,2-dimethyl-3-(nitrooxy)propanoic acid (1.11 g, 6.82 mmol, prepared as described U.S. Pat. No. 5,428,061, Example 3) in methylene chloride (15 mL) was added oxalyl chloride (1.0 mL, 11.5 mmol) and DMF (50 μL). The reaction mixture was stirred at room temperature for half an hour, concentrated to dryness, and dried in vacuum for 40 minutes to give the title compound (1.28 g, 100% yield). $^1$H NMR (300 MHz, CDCl$_3$) δ 4.59 (s, 2H), 1.43 (s, 6H). $^{13}$C NMR (75 MHz, CDCl$_3$) δ 176.8, 76.4, 51.8, 22.2.

19b. Spiro[2H-1,2,4-benzothiadiazine-3(4H), 4'-piperidine]-7-sulfonamide, 1'-[2,2-dimethyl-3-(nitrooxy)-1-oxopropyl]-6-(trifluoromethyl)-, 1,1-dioxide

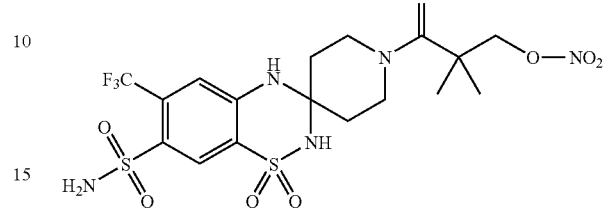

The product of Example 12b (176.3 mg, 0.40 mmol) in DMF (1 mL) was added to the product of Example 19a (120.4 mg, 0.643 mmol) followed by triethyl amine (0.5 mL, 3.6 mmol). The reaction mixture was stirred at room temperature for one hour, concentrated to dryness under vacuum. The crude product was chromatographed on silica gel eluting with methanol:dichloromethane (0:100, then 2:98, then 5:95) to give the title compound (135.2 mg, 61% yield): mp 152-156° C. (with decomposition): $^1$H NMR (400 MHz, d$_4$-MeOH) δ 8.35 (s, 1H), 7.23 (s, 1H), 4.58 (s, 2H), 4.26-4.22 (m, 2H), 3.37-3.31 (m, 2H), 2.47-2.43 (m, 2H), 1.76-1.70 (m, 2H), 1.39 (s, 6H); $^{13}$C NMR (100 MHz, d$_4$-MeOH) δ 174.9, 146.1, 132.7, 132.4, 132.1, 131.8, 129.9, 128.8, 125.1, 122.3, 117.47, 117.41, 117.34, 117.28, 80.5, 71.2, 43.4, 42.3, 37.3, 22.6; Mass spectrum (API-TIS) m/z 546 (MH+), 563 (MNH$_4^+$), 568 (MNa+).

Example 20

4H-1,2,4-Benzothiadiazine-7-sulfonamide, 6-chloro-3-[5-(nitrooxy)pentyl]-, 1,1-dioxide 20a. Hexanoyl chloride, 6-(nitrooxy)-

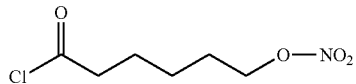

Oxalyl chloride (1.9 mL, 2.69 g, 21.2 mmol) was added dropwise to a solution of the product of Example 5a (2.5 g, 14.1 mmol) in CH$_2$Cl$_2$ (7 mL) at 0° C. To this solution DMF (35 μL) was added dropwise. The reaction mixture was stirred at 0° C. for 10 minutes and then at room temperature for 30 minutes. The residue, after evaporation of the solvent, was dried under vacuo to give the title compound as a semi-solid. The product was used immediately without further purification. $^1$H NMR (400 MHz, CDCl$_3$) δ 4.46 (t, J=6.4 Hz, 2H), 2.93 (t, J=7.2 Hz, 2H), 1.70-1.83 (m, 4H), 1.42-1.55 (m, 2H). $^{13}$C NMR (100 MHz, CDCl$_3$) δ 73.6, 72.8, 46.8, 26.5, 24.8, 24.7. Mass spectrum (API-TIS) m/z 212 (MNH$_4^+$).

20b. Hexanamide, N-[2,4-bis(aminosulfonyl)-5-chlorophenyl]-6-(nitrooxy)-

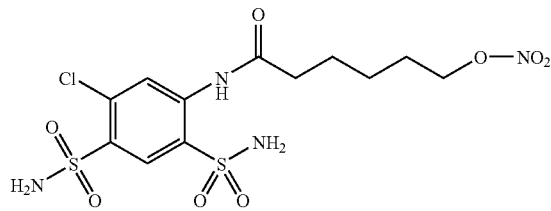

A mixture of 4-chloro-6-aminobenzene-1,3-disulfonamide (3.22 g, 11.3 mmol) and the product of Example 20a (14.1 mmol) in dioxane (30 mL) was refluxed at 110° C. for 30 minutes. The reaction mixture was cooled to room temperature. The residue, after evaporation of the solvent, was washed with EtOAc and dried under vacuum to give the title compound (2.3 g, 46% yield) as a white solid: mp 180-182° C. $^1$H NMR (400 MHz, $d_6$-DMSO) δ 9.45 (br s, 1H), 8.55 (s, 1H), 8.41 (s, 1H), 7.90-8.15 (br s, 2H), 7.73 (br s, 2H), 4.50 (t, J=6.4 Hz, 2H), 2.44-2.52 (m, 2H), 1.60-1.72 (m, 4H), 1.35-1.42 (m, 2H). $^{13}$C NMR (100 MHz, $d_6$-DMSO) δ 172.2, 138.7, 135.6, 135.0, 129.9, 129.4, 124.1, 74.1, 37.1, 26.2, 24.9, 24.2. Mass spectrum (API-TIS) m/z 443 (M-H), 445 (MH$^+$), 462 (MNa$^+$). Anal. calcd for $C_{12}H_{17}ClN_4O_8S_2$: C, 32.40; H, 3.85; N, 12.59. Found: C, 32.32; H, 3.69; N, 12.42.

20c. 4H-1,2,4-Benzothiadiazine-7-sulfonamide, 6-chloro-3-[5-(nitrooxy)pentyl]-, 1,1-dioxide

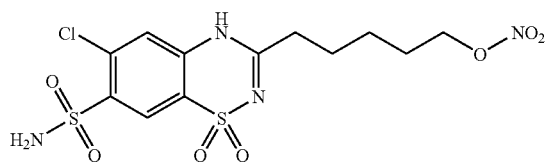

To a suspension of the product of Example 20b (1.3 g, 2.9 mmol) in water (15 mL) was added dropwise, an aqueous solution (w/w) of NaOH (0.45 g, 11.2 mmol) at 0° C. The reaction mixture was stirred at 0° C. for 15 minutes and then at room temperature for 3 hours. The clear solution was cooled to 0° C., acidified with 1 N HCl. The white precipitate was filtered, washed with water, dried under vacuum to give the title compound (0.7 g, 56% yield) as a white solid: mp 170-172° C. $^1$H NMR (400 MHz, $d_6$-DMSO) δ 12.30 (br s, 1H), 8.27 (s, 1H), 7.88 (s, 2H), 7.48 (s, 1H), 4.53 (t, J=6.8 Hz, 2H), 2.61 (t, J=7.6 Hz, 2H), 1.65-1.74 (m, 4H), 1.41-1.45 (m, 2H). $^{13}$C NMR (100 MHz, $d_6$-DMSO) δ 161.6, 138.83, 138.81, 134.7, 125.3, 120.5, 119.4, 74.0, 35.6, 26.1, 25.6, 24.7. Mass spectrum (API-TIS) m/z 425 (M-H), 427 (MH$^+$), 444 (MNH$_4^+$). Anal. calcd for $C_{12}H_{15}ClN_4O_7S_2$: C, 33.77; H, 3.54; N, 13.13; S, 15.02; Cl, 8.31. Found: C, 33.55; H, 3.28; N, 12.93; S, 14.83; Cl, 8.46.

Example 21

4H-1,2,4-Benzothiadiazine-3-butanamide, 7-(aminosulfonyl)-N-[(2S)-2,3-bis(nitrooxy)propyl]-6-chloro-, 1,1-dioxide

21a. 1,2-Propanediol, 3-amino-, dinitrate (ester), (2S)—, nitrate (1:1) (salt)

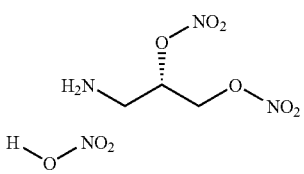

To (S)(−)-3-amino-1,2-propanediol (5.0 g, 54.9 mmol, prepared as described in HD 382, Example 12a), was added fuming nitric acid (2.75 mL) and the nitrating reagent (41.5 mL acetic anhydride and 11.6 mL fuming nitric acid) to give the title compound (light green solid) in quantitative yield: $^1$H NMR (CDCl$_3$, 400 MHz) δ 8.16 (s, 3H), 5.68-5.62 (m, 1H), 4.98 (dd, J=3.2 and 12.8 Hz, 1H), 4.80 (dd, J=5.2 and 12.8 Hz, 1H), 3.39-3.36 (m, 1H), 3.24-3.21 (m, 1H); Mass Spectrum (API-TIS) m/z 182 (MH—HNO$_3$)$^+$.

21b. 4H-1,2,4-Benzothiadiazine-3-butanamide, 7-(aminosulfonyl)-N-[(2S)-2,3-bis(nitrooxy)propyl]-6-chloro-, 1,1-dioxide

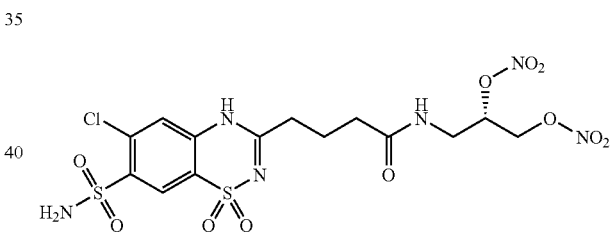

4-(6-Chloro-1,1-dioxo-7-sulfamoyl-4H-benzo[e]1,2,4-thiadiazin-3-yl)butanoic acid (3 mmol, prepared as described in U.S. Pat. No. 3,287,360) was dissolved in anhydrous DMF (3 mL). In a separate flask, the product of Example 21a (0.73 g, 3 mmol) was treated with triethylamine (0.42 mL) in anhydrous CH$_2$Cl$_2$ (10 mL) to generate (2S)-2,3-bis(nitrooxy)propylamine. Both solutions were combined followed by the addition of 1-ethyl-3-(3-dimethylaminopropyl) carbamide hydrochloride (EDAC) (0.58 g, 3 mmol) and dimethylamino pyridine (DMAP) (0.37 g, 3 mmol). The resulting mixture was stirred at room temperature overnight under nitrogen. The solvent was evaporated under high vacuum and the residue was purified by silica gel flash column chromatography eluting with 5% MeOH in CH$_2$Cl$_2$ to give the title compound (0.85 g, 52% yield) as a white solid: mp 140° C. (with decomposition); $^1$H NMR (400 MHz, $d_6$-DMSO) δ 12.35 (s, 1H), 8.27 (s, 1H), 8.24 (t, J=4.0 Hz, 1H), 7.88 (s, 2H), 7.48 (s, 1H), 5.45-5.40 (m, 1H), 4.90 (dd, J=2.8 and 12.8 Hz, 1H), 4.70 (dd, J=6.0 and 14.0 Hz, 1H), 3.60-3.53 (m, 1H), 3.43-3.35 (m, 1H), 2.62 (t, J=8.0 Hz, 2H), 2.23 (t, J=7.8 Hz, 2H), 1.94-1.82 (m, 2H); Mass Spectrum (API-TIS) m/z 545 (MH)$^+$, 562 (MNH$_4$)$^+$.

Example 22

Spiro[2H-1,2,4-benzothiadiazine-3(4H), 4'-piperidine]-7-sulfonamide, 1'-[4,5-bis(nitrooxy)-1-oxopentyl]-6-chloro-, 1,1-dioxide

22a. Pentanoic acid, 4,5-bis(nitrooxy)-

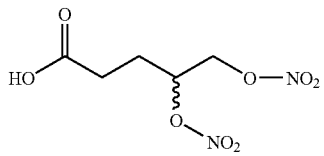

To a solution of 4,5-bis(nitrooxy)pentan-1-ol (1.21 g, 5.76 mmol, prepared as described in WO 2005/030135 A2, Example. 27d) in 20 mL of acetone was added Jones Reagent (1M, 12 mL, 12 mmol, prepared as described in Fieser, L. F. and Fieser, M. "Reagents for Organic Synthesis" Vol. 1, p. 142, 1967) dropwise, with stirring. A blue-green precipitate formed immediately. After the orange color persisted, the reaction mixture was stirred for an additional 30 minutes. The excess Jones Reagent was decomposed with isopropyl alcohol, followed by sodium hydrosulfite. The reaction mixture was filtered through Celite, and the filtrate was evaporated under vacuum. The residue was dissolved in ether, washed with water, brine, and dried over magnesium sulfate. Removal of solvent under vacuum gave the title compound (1.28 g, 5.74 mmol, 98% yield) as a colorless oil: $^1$H NMR (400 MHz, CDCl$_3$) δ 10.92 (br s, 1H), 5.39 (m, 1H), 4.78 (dd, J=3.2, 12.9 Hz, 1H), 4.51 (dd, J=6.0, 12.9 Hz, 1H), 2.57 (t, J=7.7 Hz, 2H), 2.15-1.95 (m, 2H); $^{13}$C NMR (100 MHz, CDCl$_3$) δ 177.9, 77.8, 71.0, 29.1, 24.3; Mass spectrum (API-TIS) m/z 447 (2M-H$^+$).

22b. Spiro[2H-1,2,4-benzothiadiazine-3(4H), 4'-piperidine]-7-sulfonamide, 1'-[4,5-bis(nitrooxy)-1-oxopentyl]-6-chloro-, 1,1-dioxide

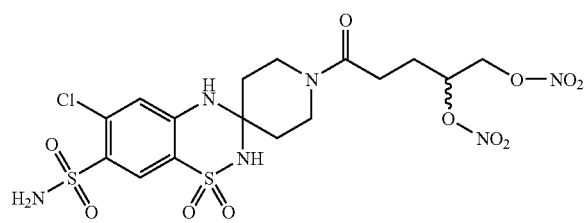

To a solution of the product of Example 18a (1.01 g, 2.5 mmol) and the product of Example 22a (0.83 g, 3.7 mmol) in 20 mL of DMF was added DMAP (0.06 g, 0.5 mmol) and EDAC (0.709 g, 3.7 mmol). Triethylamine (1.04 mL, 7.5 mmol) was then added dropwise. After stirring at room temperature overnight, the solvent was removed under vacuum. The residue was re-dissolved in ethyl acetate/methanol, and partitioned between water and ethyl acetate. The organic layer was washed with water, brine, and dried over magnesium sulfate. The solvent was removed under vacuum, and the crude product was purified via column chromatography on silica gel, 5% methanol/ethyl acetate. Evaporation of the solvent gave the title compound (0.53 g, 0.93 mmol, 37% yield) as a white amorphous solid: $^1$H NMR (400 MHz, d$_6$-DMSO) δ 8.13 (s, 1H), 8.02 (s, 1H), 7.98 (s, 1H), 7.50 (s, 2H), 6.95 (s, 1H), 5.47 (m, 1H), 4.94 (m, 1H), 4.73 (m, 1H), 4.13 (m, 1H), 3.75 (m, 1H), 3.36 (m, 1H), 2.98 (m, 1H), 2.52 (m, 2H), 2.25 (m, 2H), 1.98 (m, 2H), 1.62 (m, 2H); $^{13}$C NMR (100 MHz, d$_6$-DMSO) δ 170.0, 145.8, 135.0, 128.8, 126.0, 117.9, 117.8, 80.3, 72.4, 70.2, 41.3, 37.7, 36.4, 35.8, 28.0, 24.6; Mass spectrum (API-TIS) m/z 573 (MH$^+$), 590 (MNH$_4^+$), 1147 (2 MH$^+$).

Example 23

Spiro[2H-1,2,4-benzothiadiazine-3(4H), 4'-piperidine]-7-sulfonamide, 6-chloro-1'-[2-methyl-3-(nitrooxy)-2-[(nitrooxy)methyl]-1-oxopropyl]-, 1,1-dioxide

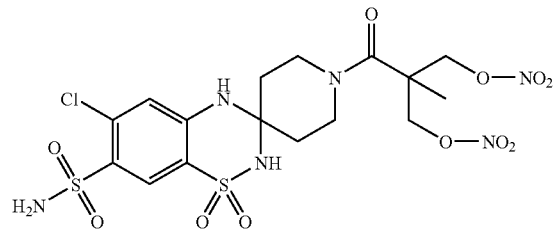

Triethylamine (0.70 mL, 5.0 mmol) was added to a mixture of the crude product of Example 16b and the product of Example 18a (1.03 g, 2.5 mmol) in acetonitrile (30 mL) and stirred at room temperature overnight. The reaction mixture was evaporated to dryness under reduced pressure. The residue was partitioned between 3N HCl (10 mL) and ethyl acetate (150 mL). The organic extract was washed with water, brine, dried over Na$_2$SO$_4$, filtered, concentrated and dried under vacuum. The product was separated by silica gel column chromatography eluting with EtOAc/hexane (gradient from 1:1 to 3:1, R$_f$=0.13 in 2:1) to give the title compound as a white solid (0.31 g, 22% yield): mp 142-145° C.; $^1$H NMR (400 MHz, d$_6$-acetone) δ 8.16 (s, 1H), 7.28 (br s, 1H), 7.02 (s, 1H), 6.97 (br s, 1H), 6.69 (br s, 2H), 4.95-4.80 (m, 4H), 4.28 (br d, 2H), 3.43 (br t, 2H), 2.56 (br d, 2H), 1.89 (br t, 2H), 1.55 (s, 3H); $^{13}$C NMR (100 MHz, d$_6$-DMSO) δ 168.0, 145.3, 134.5, 128.4, 125.5, 117.4, 117.3, 74.4, 69.6, 44.9, 40.1, 35.7, 17.0; Mass Spectrum (API-TIS) m/z 573 (MH$^+$).

Example 24

6-Chloro-3-(5-hydroxypentyl)-3,4-dihydro-2H-1,2,4-benzothiadiazine-7-sulfonamide 1,1-dioxide

24a. Hexanoic acid, 6-oxo-, ethyl ester

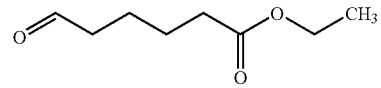

To a suspension of ethyl-6-hydroxyhexanoate (3.25 mL, 20 mmol) in anhydrous CH$_2$Cl$_2$ (400 mL) and alumina (30 g), was added pyridinium chlorochromate (21.56 g, 100 mmol) and the reaction mixture was stirred vigorously for 20 minutes under nitrogen. After filtration, the solution was filtered through silica gel to remove impurities. The solvent was partially removed under reduced pressure and the crude product was used without further purification 24b. 2H-1,2,4-Benzothiadiazine-3-pentanoic acid, 7-(aminosulfonyl)-6-chloro-3,4-dihydro-, ethyl ester, 1,1-dioxide

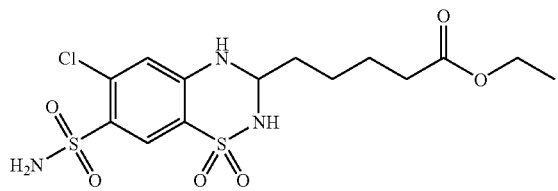

The title compound was prepared by the reaction of the product of Example 24a and 4-amino-6-chloro-1,3-benzenedisulfonamide following the procedure of Example 1c. The title compound was obtained as a white solid (2.51 g, 59% yield): mp 90° C.; $^1$H NMR (400 MHz, d$_6$-DMSO) δ 7.99 (s, 1H), 7.90 (s, 1H), 7.78 (d, J=11.6 Hz, 1H), 7.50 (s, 2H), 6.99 (s, 1H), 4.76-4.70 (m, 1H), 4.07 (q, J=7.1 Hz, 2H), 2.33 (t, J=7.2 Hz, 2H), 1.77 (q, J=7.2 Hz, 2H), 1.61-1.54 (m, 2H), 1.49-1.45 (m, 2H), 1.19 (t, J=7.0 Hz, 3H); Mass Spectrum (API-TIS) m/z 426 (MH)$^+$, 443 (MNH$_4$)$^+$.

24c. 2H-1,2,4-Benzothiadiazine-7-sulfonamide, 6-chloro-3,4-dihydro-3-(5-hydroxypentyl)-, 1,1-dioxide

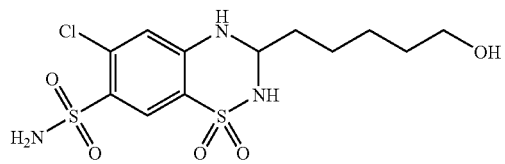

To a solution of the product of Example 24b (0.43 g, 1.0 mmol) in anhydrous THF (5 mL), a solution of 0.5 M AlH$_3$ (5 mL, 2.5 mmol) was added and the reaction mixture was stirred for 30 minutes at room temperature under nitrogen. The reaction mixture was quenched with saturated aqueous NH$_4$Cl, then acidified. After removal of solvent under reduced pressure, the residue was partitioned with EtOAc and water, and the aqueous layer was further extracted with EtOAc (2×). The combined organic layers were washed with brine, dried over Na$_2$SO$_4$, filtered, and the solvent was removed under reduced pressure. The residue obtained was purified by silica gel flash column chromatography eluting with 8% MeOH in CH$_2$Cl$_2$ to give the title compound (0.37 g, 95% yield) as a white solid: mp 190° C.; $^1$H NMR (400 MHz, d$_6$-DMSO) δ 7.99 (s, 1H), 7.89 (s, 1H), 7.78 (s, 1H), 7.50 (s, 2H), 6.99 (s, 1H), 4.74 (s, 1H), 4.38 (d, J=4.5 Hz, 1H), 3.41 (d, J=5.3 Hz, 2H), 1.77 (d, J=6.8 Hz, 2H), 1.45 (br s, 4H), 1.35 (d, J=4.7 Hz, 2H); $^{13}$C NMR (100.6 MHz, d$_6$-DMSO) δ 148.1, 136.4, 129.3, 127.4, 120.0, 118.3, 67.3, 62.6, 34.7, 33.3, 26.4, 25.3; Mass Spectrum (API-TIS) m/z 384 (MH)$^+$, 401 (MNH$_4$)$^+$.

Example 25

2H-1,2,4-Benzothiadiazine-7-sulfonamide, 3,4-dihydro-3-(5-hydroxypentyl)-6-(trifluoromethyl)-, 1,1-dioxide 25a. 2H-1,2,4-Benzothiadiazine-3-pentanoic acid, 7-(aminosulfonyl)-3,4-dihydro-6-(trifluoromethyl)-, ethyl ester, 1,1-dioxide

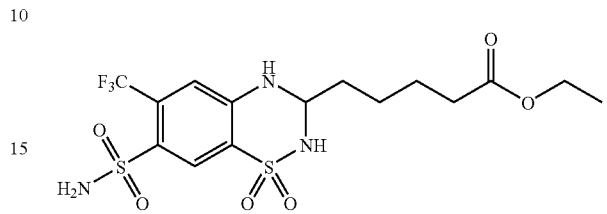

The title compound was prepared by the reaction of the product of the Example 24a and 2-amino-6-(trifluoromethyl) 1,3-benzenedisulfonamide following the procedure for Example 1c. The product was obtained as a white foam (0.66 g, 21% yield): $^1$H NMR (d$_6$-DMSO, 400 MHz) δ 8.21 (s, 1H), 8.12 (s, 1H), 7.86 (d, J=11.6 Hz, 1H), 7.57 (s, 2H), 7.34 (s, 1H), 4.79 (m, 1H), 4.07 (q, J=7.1 Hz, 2H), 2.33 (t, J=7.2 Hz, 2H), 1.79 (q, J=7.3 Hz, 2H), 1.66-1.55 (m, 2H), 1.51-1.46 (m, 2H), 1.19 (t, J=7.1 Hz, 3H); Mass Spectrum (API-TIS) m/z 460 (MH)$^+$, 477 (MNH$_4$)$^+$.

25b. 2H-1,2,4-Benzothiadiazine-7-sulfonamide, 3,4-dihydro-3-(5-hydroxypentyl)-6-(trifluoromethyl)-, 1,1-dioxide

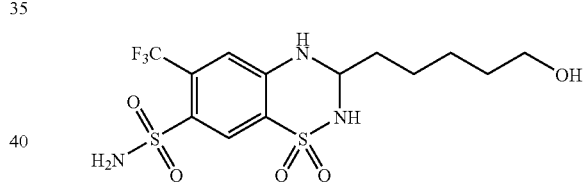

The title compound was prepared by the reduction of the product of the Example 25a following the procedure for Example 24c. The product was obtained as a white solid (0.34 g, 58% yield): mp 97° C. (shrinkage); $^1$H NMR (400 MHz, d$_6$-DMSO) δ 8.21 (s, 1H), 8.11 (s, 1H), 7.86 (br s, 1H), 7.57 (s, 2H), 7.36 (s, 1H), 4.79 (br s, 1H), 4.38 (t, J=5.1 Hz, 1H), 3.41 (q, J=5.9 Hz, 2H), 1.81-1.76 (m, 2H), 1.47-1.40 (m, 4H), 1.40-1.32 (m, 2H); $^{13}$C NMR (d$_6$-DMSO, 100.6 MHz) δ 147.5, 132.1 (d, J=33 Hz), 129.7, 128.8, 123.2, 117.1, 117.0, 67.5, 62.8, 34.7, 33.3, 26.5, 25.3; Mass Spectrum (API-TIS) m/z 418 (MH)$^+$, 435 (MNH$_4$)$^+$.

Example 26

2H-1,2,4-Benzothiadiazine-7-sulfonamide, 6-chloro-3,4-dihydro-3-(4-hydroxybutyl)-, 1,1-dioxide

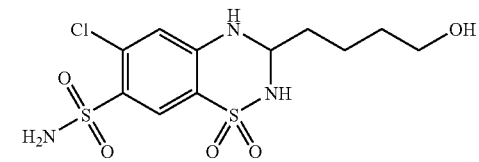

5-Hydroxy-1-pentanal (Acros Chemicals, 2.04 g, 20 mmol) and 2-amino-6-chloro-1,3-benzenedisulfonamide (2.87 g, 10 mmol) were mixed together in dioxane (75 mL) and concentrated hydrochloric acid (2 mL). The resulting mixture was refluxed for 1 hour, then cooled to room temperature, extracted with saturated brine, the organic layer separated and the solvent was evaporated at reduced pressure. The residue obtained was treated with ethyl acetate and washed with saturated aqueous sodium carbonate, water, brine, dried over sodium sulfate, filtered, and the filtrate was concentrated in vacuum to give the crude product. Purification by column chromatography over silica gel, eluting with 4% methanol in dichloromethane, gave 0.9 g of a white solid that was the undesired product (molecular ion peaks at 471 (MH)$^+$, and 471 (MNH$_4$)$^+$. The more polar fractions obtained by elution with 10% methanol in dichloromethane gave the title compound (1.2 g, 32.5% yield) as a white solid: mp 202-211° C.; $^1$H NMR (400 MHz, d$_6$-DMSO) δ 8.00 (s, 1H), 7.92 (s, 1H), 7.80 (d, J=11.2 Hz, 1H), 7.50 (s, 2H), 6.95 (s, 1H), 4.80-4.65 (m, 1H), 4.50-4.40 (m, 1H), 3.40 (br s, 2H), 1.80 (br s, 2H), 1.40 (br s, 4H); Mass Spectrum (API-TIS) m/z 387 (MNH$_4$)$^+$, 389 [(MNH$_4$)+2]$^+$.

Example 27

4H-1,2,4-Benzothiadiazine-7-sulfonamide, 6-chloro-3-[4-(nitrooxy)butyl]-, 1,1-dioxide 27a. Pentanamide, N-[2,4-bis(aminosulfonyl)-5-chlorophenyl]-5-bromo-

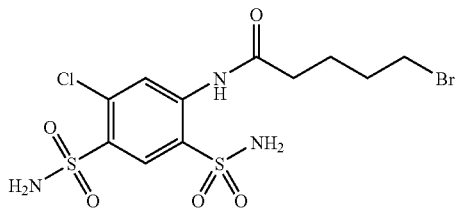

To a suspension of 2-amino-6-chloro-1,3-benzenedisulfonamide (2.85 g, 10 mmol) in dioxane (40 mL) was added 5-bromo valerylchloride (Aldrich Chemical Co., 1.4 mL, 1.05 equivalents). The reaction mixture was refluxed for 2 hours. The solvent was evaporated at reduced pressure and the residue was triturated with 5% ethyl acetate in ethyl ether to give the title compound as a white solid (4.39 g, 98% yield): mp>220° C.; $^1$H NMR (400 MHz, d$_6$-DMSO) δ 9.47 (s, 1H), 8.57 (s, 1H), 8.44 (s, 1H), 8.01 (s, 2H), 7.75 (s, 2H), 3.57 (dd, J=6.6 and 7.9 Hz, 2H), 2.53 (t, J=7.3 Hz, 2H), 1.95-1.85 (m, 2H), 1.85-1.70 (m, 2H); Mass Spectrum (API-TIS) m/z 448 (MH)$^+$, 450 (MH+2)$^+$, 465 (MNH$_4$)$^+$, 467 [(MNH$_4$)+2]$^+$.

27b. Pentanamide, N-[2,4-bis(aminosulfonyl)-5-chlorophenyl]-5-(nitrooxy)-

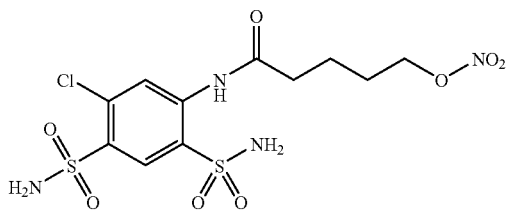

The product of the Example 27a (1.12 g, 2.6 mmol) was dissolved in acetonitrile (50 mL). To this solution was added silver nitrate (0.265 g, 1.56 mmol, 1.4 equivalents) and the resulting mixture was refluxed under nitrogen atmosphere for 2 hours. After filtration the solvent was evaporated under reduced pressure and the residue was extracted with ethyl acetate, washed with water, brine, dried over sodium sulfate. The product was purified by column chromatography over silica gel, eluting with 4% methanol in dichloromethane to give the title compound (0.64 g, 57% yield) as a white solid: mp 187-189° C.; $^1$H NMR (400 MHz, d$_6$-DMSO) δ 9.47 (s, 1H), 8.55 (s, 1H), 8.43 (s, 1H), 8.00 (s, 2H), 7.75 (s, 2H), 4.56 (t, J=6.1 Hz, 2H), 2.54 (t, J=7.0 Hz, 2H), 1.75-1.63 (m, 4H); Mass Spectrum (API-TIS) m/z 431 (MH)$^+$, 433 (MH+2)$^+$, 448 (MNH$_4$)$^+$, 450 [(MNH$_4$)+2]$^+$.

27c. 4H-1,2,4-Benzothiadiazine-7-sulfonamide, 6-chloro-3-[4-(nitrooxy)butyl]-, 1,1-dioxide

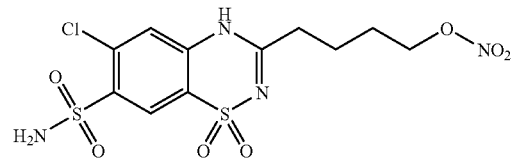

The product of the reaction 27b will be converted to the title compound following the procedure described in example 20c.

Example 28

Spiro[2H-1,2,4-benzothiadiazine-3(4H), 4'-piperidine]-7-sulfonamide, 6-chloro-1'-[3-[(nitrooxy)methyl]benzoyl]-, 1,1-dioxide

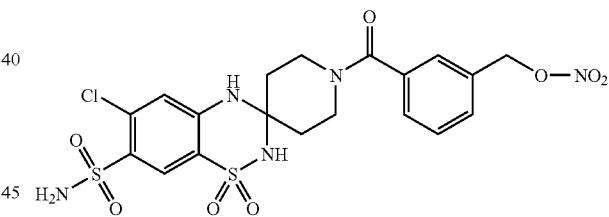

Triethylamine (0.88 mL, 6.3 mmol) was added to a mixture of the crude product of Example 15a (2.7 mmol) and the product of Example 18a (1.01 g, 2.5 mmol) in acetonitrile (50 mL) and stirred at room temperature for 3 hours. The reaction mixture was evaporated to dryness under reduced pressure. The residue was partitioned between 3N HCl (50 mL) and ethyl acetate (100 mL×2). The organic extract was washed with water, brine, dried over Na$_2$SO$_4$, filtered, concentrated and dried under vacuum. The product was separated by silica gel column chromatography eluting with EtOAc/hexane (gradient from 1:1 to 1:0, R$_f$=0.1 in ethyl acetate) to give the title compound as a white solid (0.24 g, 17% yield): mp>165 (dec.); $^1$H NMR (400 MHz, d$_6$-DMSO) δ 8.20 (br s, 1H), 8.04 (br s, 1H), 7.99 (s, 1H), 7.70-7.40 (m, 6H), 6.96 (s, 1H), 5.62 (s, 2H), 4.30-4.20 (br, 1H), 3.7-3.1 (br, 3H), 2.5-2.2 (br, 2H), 1.9-1.6 (br, 2H); $^{13}$C NMR (100 MHz, d$_6$-DMSO) δ 168.5, 145.2, 136.2, 134.5, 132.7, 130.4, 128.9, 128.4, 127.7, 125.5, 117.5, 117.3, 74.6, 69.8, 40.1, 37.7; Mass Spectrum (API-TIS) m/z 546 (MH$^+$). Anal. calcd for C$_{19}$H$_{20}$ClN$_5$O$_8$S$_2$: C, 41.80; H, 3.69; N, 12.83; Found: C, 41.77; H, 3.52; N, 12.58.

Example 29

4H-1,2,4-Benzothiadiazine-7-sulfonamide, 6-chloro-3-[[4-[(nitrooxy)methyl]phenyl]methyl]-, 1,1-dioxide

29a. Benzeneacetic acid, 4-[(nitrooxy)methyl]-

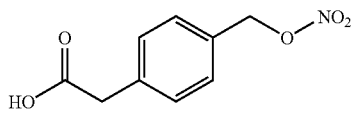

The title compound was prepared as a white solid (3.4 g, 74% yield) using AgNO$_3$ (4.06 g, 24 mmol) and 2-(4-(bromomethyl)phenyl)acetic acid (5 g, 21.8 mmol) in acetonitrile (50 mL) by following the procedure for Example 5a. mp 110° C.; $^1$H NMR (300 MHz, CDCl$_3$) δ 10.70 (bs, 1H), 7.31-7.39 (m, 4H), 5.41 (s, 2H), 3.67 (s, 2H); $^{13}$C NMR (75 MHz, CDCl$_3$) δ 177.8, 134.8, 131.6, 130.1, 129.6, 74.5, 40.9; Mass spectrum (API-TIS) m/z 229 (MNH$_4^+$), 211 (M-H).

29b. Benzeneacetyl chloride, 4-[(nitrooxy)methyl]-

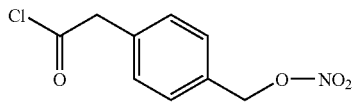

The title compound was prepared as a hygroscopic solid in quantitative yield from the product of Example 29a (1.5 g, 7.1 mmol), oxalyl chloride (0.95 mL, 1.35 g, 10.7 mmol) and DMF (35 μL) in CH$_2$Cl$_2$ (10 mL) by following the procedure for Example 20a. $^1$H NMR (400 MHz, CDCl$_3$) δ 7.28-7.40 (m, 4H), 5.41 (s, 2H), 4.15 (s, 2H). $^{13}$C NMR (100 MHz, CDCl$_3$) δ 171.7, 132.7, 132.4, 130.1, 129.7, 74.2, 52.7. Mass spectrum (API-TIS) m/z 229 (MH$^+$).

29c. N-(5-Chloro-2,4-disulfamoylphenyl)-2-{4-[(nitrooxy)methyl]phenyl}acetamide

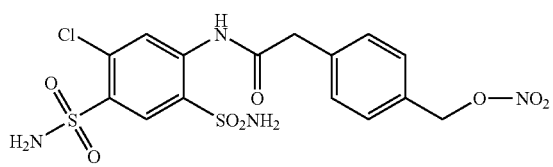

The title compound was prepared as a white solid (2.2 g, 81% yield) from the product of Example 29b (7.1 mmol) and 4-chloro-6-aminobenzene-1,3-disulfonamide (1.61 g, 5.68 mmol) in dioxane (10 mL) by following the procedure for Example 20b. Mp 163-165° C. $^1$H NMR (400 MHz, d$_6$-DMSO) δ 9.51 (br s, 1H), 8.48 (s, 1H), 8.41 (s, 1H), 8.00 (br s, 2H), 7.74 (br s, 2H), 7.34-7.48 (m, 4H), 5.54 (s, 2H), 3.87 (s, 2H). $^{13}$C NMR (100 MHz, d$_6$-DMSO) δ 170.2, 138.5, 136.0, 134.9, 131.4, 130.4, 129.9, 129.4, 124.6, 75.3, 43.7. Mass spectrum (API-TIS) m/z 477 (M-H), 479 (MH$^+$), 496 (MNH$_4^+$), 501 (MNa$^+$).

29d. 4H-1,2,4-Benzothiadiazine-7-sulfonamide, 6-chloro-3-[[4-[(nitrooxy)methyl]phenyl]methyl]-, 1,1-dioxide

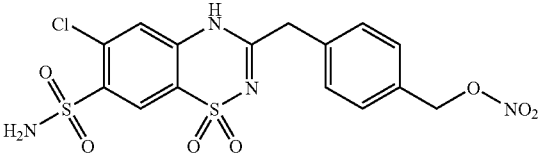

The title compound was prepared as a white solid (0.1 g, 13% yield) from the product of Example 29c (0.7 g, 1.5 mmol) and NaOH (0.12 g, 3 mmol) in water (9 mL) by following the procedure for Example 20c. Mp>260° C.; $^1$H NMR (400 MHz, d$_6$-DMSO) δ 12.64 (br s, 1H), 8.27 (s, 1H), 7.90 (s, 2H), 7.54 (s, 1H), 7.42-7.50 (m, 4H), 5.58 (s, 2H), 3.98 (s, 2H); $^{13}$C NMR (100 MHz, d$_6$-DMSO) δ 159.8, 139.2, 138.7, 136.1, 134.9, 131.9, 130.1, 130.0, 125.3, 120.8, 119.4, 75.3, 41.7; Mass spectrum (API-TIS) m/z 459 (M-H), 461 (MH$^+$), 478 (MNH$_4^+$).

Example 30

Spiro[2H-1,2,4-benzothiadiazine-3(4H), 4'-piperidine]-7-sulfonamide, 6-chloro-1'-[6-(nitrooxy)-1-oxohexyl]-, 1,1-dioxide

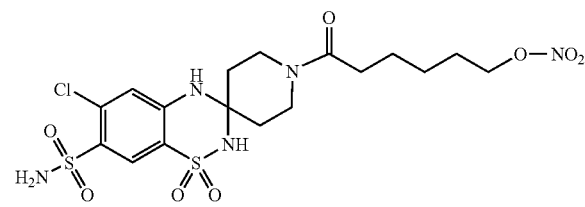

To the product of Example 5a (3.54 g, 20 mmol, N-(3-dimethylaminopropyl)-N'-ethylcarbodiimide hydrochloride (3.83 g, 20 mmol), 1-hydroxybenzotriazole hydrate (2.70 g, 20 mmol), and the product of Example 18a (8.05 g, 20 mmol) in acetonitrile (120 mL) was added triethylamine (18.36 mL, 132 mmol). The resulting mixture was stirred at room temperature for 7 hours, concentrated to remove the volatiles, taken up with EtOAc, washed with water, aqueous NaHCO$_3$, and aqueous NaCl. The organic layer was dried over Na$_2$SO$_4$, filtered, and concentrated to give a solid. Chromatography (silica gel, THF for loading, EtOAc for elution) of the crude product and subsequent recrystallization from THF:EtOAc (5:1) gave the title compound (3.60 g, 34% yield) as white needles: mp 159-162° C. (with decomposition); $^1$H NMR (400 MHz, d$_4$-MeOH) δ 8.14 (s, 1H), 6.89 (s, 1H), 4.47 (t, J=6.8 Hz, 2H), 4.38 (m, 1H), 3.76 (m, 1H), 3.47 (m, 1H), 3.09 (m, 1H), 2.54 (m, 1H), 2.43 (t, J=7.6 Hz, 2H), 1.76-1.67 (m, 7H), 1.44 (m, 2H); Mass spectrum (API-TIS) m/z 526.4 and 528.3 (MH$^+$ for $^{35}$Cl and $^{37}$Cl respectively).

Example 31

2H-1,2,4-Benzothiadiazine-2-acetic acid, 7-(aminosulfonyl)-6-chloro-3,4-dihydro-, (2R)-2,3-bis(nitrooxy)propyl ester, 1,1-dioxide

31a. 2H-1,2,4-Benzothiadiazine-2-acetic acid, 7-(aminosulfonyl)-6-chloro-3,4-dihydro-, 1,1-dioxide

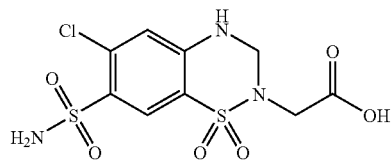

The title compound was prepared as described in U.S. Pat. No. 4,616,012 Example 7b.

31b. 2H-1,2,4-Benzothiadiazine-2-acetic acid, 7-(aminosulfonyl)-6-chloro-3,4-dihydro-, (2R)-2,3-bis(nitrooxy)propyl ester, 1,1-dioxide

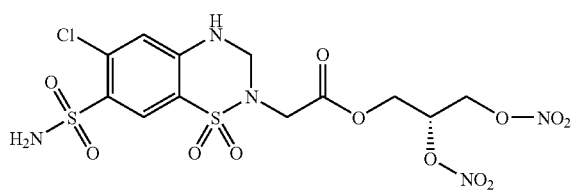

To a solution of the product of Example 31a (1.423 g, 4.0 mmol) and ((2R)-3-hydroxypropane-1,2-diyl dinitrate) (0.874 g, 4.8 mmol, prepared according to US 2004/0024057 Example 5d) in 25 mL of DMF was added N,N-dimethylaminopyridine (DMAP, 0.098 g, 0.8 mmol) and 1-(3-(dimethylamino)propyl)-3-ethylcarbodiimide hydrochloride (EDAC, 0.920 g, 4.8 mmol). The reaction mixture was stirred at room temperature for 16 hours. After evaporation of the solvent under reduced pressure, the residue was partitioned between ethyl acetate and water. The organic layer was washed with brine, and dried over magnesium sulfate. After evaporation of the solvent, the residue was purified via column chromatography on silica gel, 50 to 90% ethyl acetate in dichloromethane gradient. Evaporation of the solvent gave the title compound (0.88 g, 42% yield) as a white amorphous solid: $^1$H NMR (400 MHz, d$_6$-DMSO) δ 8.07 (s, 1H), 8.01 (s, 1H), 7.53 (s, 2H), 7.09 (s, 1H), 5.67 (m, 1H), 4.99-4.92 (m, 3H), 4.76 (dd, J=6.8, 12.6 Hz, 1H), 4.57 (dd, J=3.2, 12.6 Hz, 1H), 4.42 (dd, J=5.6, 12.6 Hz, 1H), 3.91 (s, 2H); $^{13}$C NMR (100 MHz, d$_6$-DMSO) δ 168.2, 146.5, 135.5, 129.5, 127.1, 118.2, 116.2, 77.8, 70.1, 61.9, 60.2, 48.2; Mass spectrum (API-TIS) m/z 537 (MNH$_4^+$), 1056 (2MNH$_4^+$)

Example 32

6-Chloro-2-(2-hydroxyethyl)-3,4-dihydro-2H-1,2,4-benzothiadiazine-7-sulfonamide 1,1-dioxide

32a. 2H-1,2,4-Benzothiadiazine-2-acetic acid, 7-(aminosulfonyl)-6-chloro-3,4-dihydro-, ethyl ester, 1,1-dioxide

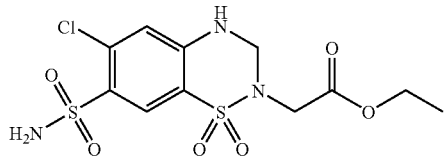

To a solution of hydrochlorothiazide (ONBIO, Inc., Ontario, Canada) (13.82 g, 46.4 mmol) in DMF (50 mL) was added cesium carbonate (7.51 g, 23.0 mmol) and ethyl bromoacetate (7.69 g, 46.1 mmol) and the mixture was stirred for 18 hours at room temperature. The solids were removed via suction filtration, and the solvent was evaporated under vacuum. The resulting residue was partitioned between ethyl acetate and water, and the organic layer was washed with water and brine, and dried over magnesium sulfate. After evaporation of the solvent, the residue was recrystallized from ethyl acetate/ether to give the title product (10.9 g, 61% yield) as white needles: mp 199-203° C.; $^1$H NMR (400 MHz, d$_6$-DMSO) δ 8.07 (s, 1H), 8.01 (s, 1H), 7.53 (s, 2H), 7.08 (s, 1H), 4.97 (s, 2H), 4.14 (q, J=7.1 Hz, 2H), 3.82 (s, 2H), 1.19 (t, J=7.1 Hz, 3H); Mass spectrum (API-TIS) m/z 384 (MH$^+$), 401 (MNH$_4^+$), 784 (2MNH$_4^+$).

32b. 2H-1,2,4-Benzothiadiazine-7-sulfonamide, 6-chloro-3,4-dihydro-2-(2-hydroxyethyl)-, 1,1-dioxide

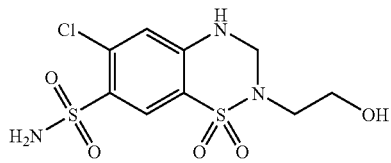

To a solution of the product of Example 32a (4.10 g, 10.68 mmol) in 70 mL of THF was added 0.3 mL of methanol, followed by lithium borohydride (2.0 M in THF, 10.68 mmol, 5.3 mL) at room temperature. After 30 minutes, another 2 mL of lithium borohydride solution was added. After another 30 minutes, the reaction was quenched with methanol and water. The reaction mixture was concentrated under reduced pressure, and the residue was partitioned between ethyl acetate and water. The pH of the aqueous layer was adjusted to 7-8, and the layer was removed. The organic layer was washed with water and brine, and dried over magnesium sulfate. After evaporation of the solvent, the residue was recrystallized from acetone/hexane to give the title product (2.784 g, 76% yield) as white prisms: mp 226-228° C.; $^1$H NMR (400 MHz, d$_6$-DMSO) δ 8.04 (s, 1H), 8.01 (s, 2H), 7.51 (s, 2H), 7.05 (s, 1H), 4.97 (s, 2H), 4.93 (t, J=5.0 Hz, 1H), 3.61 (q, J=5.4 Hz, 2H), 2.96 (t, J=5.7 Hz, 2H); Mass spectrum (API-TIS) m/z 342 (MH$^+$), 359 (MNH$_4^+$), 700 (2MNH$_4^+$)

32c. Alternative synthesis of 2H-1,2,4-benzothiadiazine-7-sulfonamide, 6-chloro-3,4-dihydro-2-(2-hydroxyethyl)-, 1,1-dioxide

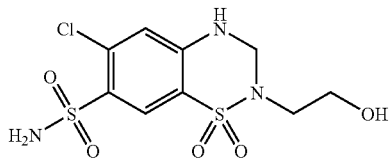

To a stirred solution of the product of Example 32a (4.10 g, 10.68 mmol) in 20 mL of THF and 11.5 mL of ethanol maintained at 10-15° C. was added sodium borohydride portionwise in order to keep the reaction temperature below 25° C. Thirty minutes after the addition was complete 3.75 mL of 6 N HCl was added slowly to the reaction mixture to maintain the temperature below 25° C. The quenched reaction mixture was filtered through a pad of Celite and the solids washed with a solution of THF/ethanol 1:1 (40 mL). The clear solution was concentrated under reduced pressure, and the residue was partitioned between ethyl acetate and water. The pH of the aqueous layer was adjusted to 7-8, and the layer was removed. The organic layer was washed with water and brine, and dried over magnesium sulfate. After evaporation of the solvent, the residue was recrystallized from acetone/hexane to give the title product (2.784 g, 76% yield) as white prisms: mp 226-228° C.; $^1$H NMR (400 MHz, d$_6$-DMSO) δ 8.04 (s, 1H), 8.01 (s, 1H), 7.51 (s, 2H), 7.05 (s, 1H), 4.97 (s, 2H), 4.93 (t, J=5.0 Hz, 1H), 3.61 (q, J=5.4 Hz, 2H), 2.96 (t, J=5.7 Hz, 2H); Mass spectrum (API-TIS) m/z 342 (MH$^+$), 359 (MNH$_4^+$), 700 (2MNH$_4^+$).

Example 33

2H-1,2,4-Benzothiadiazine-7-sulfonamide, 6-chloro-3,4-dihydro-2-[[3-[(nitrooxy)methyl]phenyl]methyl]-, 1,1-dioxide

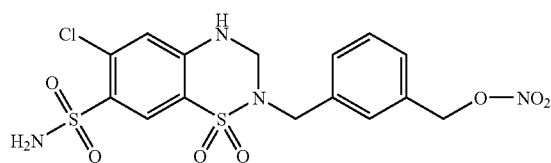

To a stirred solution of hydrochlorothiazide (3.80 g, 12.8 mmol) in DMF (60 mL) was added cesium carbonate (2.09 g, 6.4 mmol) and α,α'-dibromo-m-xylene (3.96 g, 15 mmol). After stirring at room temperature for 20 hours, the mixture was poured into water, and extracted with EtOAc. The organic layer was washed with brine, filtered through a pad of Na$_2$SO$_4$, and evaporated to dryness. The resulting white solid was dissolved in acetonitrile (80 mL), treated with silver nitrate (8.50 g, 50 mmol), and stirred at room temperature for 19 hours. The mixture was concentrated to remove the volatiles. The residue was taken up with EtOAc, and then stirred with aqueous NaCl for 10 minutes. After filtration, the organic layer was separated, filtered through a pad of Na$_2$SO$_4$, and concentrated. The crude product was purified by chromatography (silica gel, 0-50% EtOAc in CH$_2$Cl$_2$ gradient) and subsequent recrystallization from EtOAc:CH$_2$Cl$_2$ (1:3) gave the title compound (1.57 g, yield 27% over 2 steps) as a white solid: mp 136-139° C. (with decomposition); $^1$H NMR (400 MHz, d$_4$-MeOH) δ 8.21 (s, 1H), 7.44-7.40 (m, 4H), 6.95 (s, 1H), 5.46 (s, 2H), 4.73 (s, 2H), 4.16 (s, 2H); Mass spectrum (API-TIS) m/z 463.2 and 465.2 (MH$^+$ for $^{35}$Cl and $^{37}$Cl respectively).

Example 34

2H-1,2,4-Benzothiadiazine-2-acetamide, 7-(aminosulfonyl)-6-chloro-3,4-dihydro-N-[3-(nitrooxy)propyl]-, 1,1-dioxide

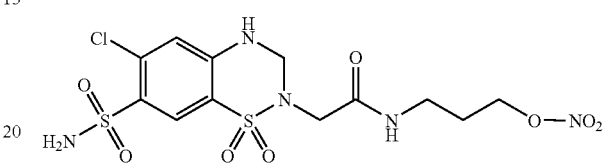

A solution of the product of Example 31a (0.767 g, 2.16 mmol), 3-(nitrooxy)propylamine nitric acid salt (0.426 g, 2.33 mmol, prepared as described in WO 2005/030135 A2, Example 8a), DMAP (142 mg, 1.16 mmol), EDAC (0.49 g, 2.56 mmol) and NEt$_3$ (0.9 mL, 6.46 mmol) in DMF (30 mL) were stirred at room temperature overnight. The reaction mixture was evaporated to dryness under vacuum. The residue was partitioned between 3N HCl (50 mL) and CH$_2$Cl$_2$ (100 mL). The organic extract was washed with 3N HCl, water, brine, dried over Na$_2$SO$_4$, filtered, concentrated and dried under vacuum. The product was purified by silica gel column chromatography eluting with EtOAc (R$_f$=0.1). The resulting solid was dissolved in EtOAc and triturated with CHCl$_3$. The solid was collected and dried under vacuum to give the title compound as a yellow solid (0.20 g, 20% yield): mp 138-141° C.; $^1$H NMR (400 MHz, d$_6$-acetone) δ 8.18 (s, 1H), 7.8 (br m, 1H), 7.26 (br s, 1H), 7.15 (s, 1H), 6.72 (br s, 2H), 5.13 (d, J=4.8 Hz, 2H), 4.64-4.60 (br t, 2H), 3.73 (s, 2H), 3.44-3.38 (br q, 2H), 2.00-1.95 (m, 2H); $^{13}$C NMR (100 MHz, d$_6$-acetone) δ 167.9, 147.0, 136.6, 130.4, 128.3, 118.8, 118.0, 72.4, 61.1, 50.1, 36.5, 27.6; Mass Spectrum (API-TIS) m/z 457 (M-H)$^-$.

Example 35

2H-1,2,4-Benzothiadiazine-7-sulfonamide, 6-chloro-3,4-dihydro-2-[3-(nitrooxy)propyl]-, 1,1-dioxide

35a. 1-Propanol, 3-bromo-, nitrate

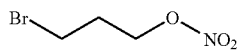

Nitric acid (90%, 39 mL) was added in portions to Ac$_2$O (98 mL) at 0° C. with stirring. After 25 minutes, 3-bromo-1-propanol (23 g, 165 mmol) in EtOAc (120 mL) was added, and the resulting mixture was stirred at the same temperature for 50 minutes. The reaction mixture was poured into a stirred mixture of ice water/EtOAc, basified carefully with solid NaHCO$_3$ to pH 8. The organic layer was separated, washed with aqueous NaHCO$_3$, filtered through a pad of Na$_2$SO$_4$, concentrated and vacuum-dried briefly to give the title compound (25.3 g, 84% yield) as a liquid: ¹H NMR (400 MHz, CDCl₃) δ 4.66-4.61 (m, 2H), 3.53-3.49 (m, 2H), 2.32-2.28 (m, 2H).

35b. 2H-1,2,4-Benzothiadiazine-7-sulfonamide, 6-chloro-3,4-dihydro-2-[3-(nitrooxy)propyl]-, 1,1-dioxide

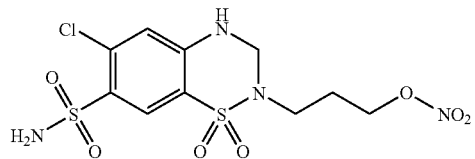

To a stirred solution of hydrochlorothiazide (41.1 g, 138 mmol) in DMF (400 mL) were added cesium carbonate (22.4 g, 68.75 mmol) and the product of Example 35a (25.3 g, 137.5 mmol). After being stirred at room temperature for 22 hours, the mixture was poured into water, and extracted with EtOAc. The organic layer was washed with aqueous NaCl, filtered through a pad of Na₂SO₄, and concentrated. The crude product was purified by chromatography (silica gel, 0-25% gradient of EtOAc in CH₂Cl₂) and subsequent recrystallization from EtOAc:CH₂Cl₂ (1:3) gave the title compound (18.6 g, 34% yield) as white prisms: mp 148-151° C. (with decomposition). ¹H NMR (400 MHz, d₄-MeOH) δ 8.19 (s, 1H), 6.99 (s, 1H), 4.95 (s, 2H), 4.60 (t, J=6.4 Hz, 2H), 3.13 (t, J=6.8 Hz, 2H), 2.09-2.03 (m, 2H); ¹³C NMR (100 MHz, d₆-DMSO) δ 145.99, 134.91, 128.75, 126.74, 117.34, 115.50, 71.02, 58.73, 43.20, 25.24; Mass spectrum (API-TIS) m/z 401.0 and 403.0 (MH⁺ for ³⁵Cl and ³⁷Cl respectively). Anal. Calcd. for C₁₀H₁₃ClN₄O₇S₂: C, 29.97; H, 3.27; N, 13.98. Found: C, 30.22; H, 2.93; N, 13.73.

Example 36

2H-1,2,4-Benzothiadiazine-7-sulfonamide, 6-chloro-3,4-dihydro-3-[[4-[2-(nitrooxy)ethyl]-1-piperidinyl]methyl]-, 1,1-dioxide, 2-hydroxy-1,2,3-propanetricarboxylate (1:1) (salt)

36a. 2H-1,2,4-Benzothiadiazine-7-sulfonamide, 3-(bromomethyl)-6-chloro-3,4-dihydro-, 1,1-dioxide

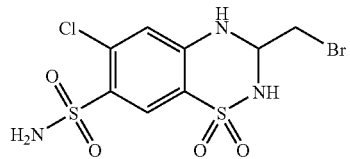

To a mixture of 4-chloro-6-aminobenzene-1,3-disulfonamide (Aldrich, 15.2 g, 53.3 mmol) and bromoacetaldehyde dimethylacetal (6.3 mL, 9 g, 53.3 mmol) in anhydrous dioxane (45 mL) at 120° C., was added dropwise 48% hydrobromic acid in H₂O (2 mL). The mixture was then heated at 100° C. for 20 minutes. The residue, after evaporation of the solvent, was diluted with water, the resultant precipitate was filtered, washed with water to give a sticky solid that was dissolved in EtOAc and dried over Na₂SO₄. The residue after evaporation of the solvent was recrystallized from EtOAc/hexane to give the title compound in quantitative yield as a white solid: mp 203-205° C.; ¹H NMR (400 MHz, d₆-DMSO) δ 8.16 (br s, 1H), 8.08 (br d, J=11.2 Hz, 1H), 7.99 (s, 1H), 7.53 (br s, 2H), 7.05 (s, 1H), 4.88-5.03 (m, 1H), 3.65-3.72 (m, 2H);

¹³C NMR (100 MHz, d₆-DMSO) δ 146.1, 134.7, 128.9, 125.3, 118.4, 117.4, 66.3, 31.5; Mass spectrum (API-TIS) m/z 387/389 (M-H), 407/409 (MNH₄⁺); Anal. calcd for C₈H₉BrClN₃O₄S₂.⅛ mol EtOAc: C, 25.41; H, 2.50; N, 10.46; Found: C, 25.35; H, 2.44; N, 10.46.

36b. 2H-1,2,4-Benzothiadiazine-7-sulfonamide, 6-chloro-3,4-dihydro-3-[[4-[2-(nitrooxy)ethyl]-1-piperidinyl]methyl]-, 1,1-dioxide

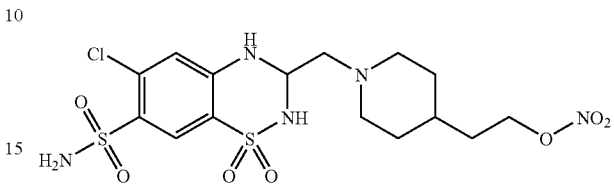

A mixture of nitrooxy(2-(4-piperidyl)ethyl), nitric acid salt (prepared as described in US 2004/0024057, Example 31a, 1.46 g, 6.2 mmol) and LiOH.H₂O (0.38 g, 8.9 mmol) in acetone (12 mL) at room temperature was treated with the product of Example 36a (1.2 g, 3.1 mmol). The reaction mixture was refluxed for 30 minutes. The residue after evaporation of the solvent was dissolved in EtOAc, washed with water, dried over Na₂SO₄, filtered and the solvent was evaporated. The crude material was chromatographed on silica gel eluting with CH₂Cl₂:EtOAc:MeOH (1:1:0.1) to give the title compound (0.4 g, 26% yield) as a white solid: mp 165-168° C.; ¹H NMR (400 MHz, d₆-DMSO) δ 7.96 (s, 1H), 7.56 (s, 2H), 7.40-7.60 (br s, 2H), 7.24 (s, 1H), 4.87 (br t, J=6.0 Hz, 1H), 4.56 (t, J=6.4 Hz, 2H), 2.85-2.93 (m, 1H), 2.75-2.82 (m, 1H), 2.55-2.68 (m, 2H), 2.15 (br t, J=10.8 Hz, 1H), 1.97 (br t, J=9.6 Hz, 1H), 1.55-1.68 (m, 4H), 1.20-1.38 (m, 3H); ¹³C NMR (100 MHz, d₆-DMSO) δ 146.3, 134.1, 128.1, 125.3, 118.4, 117.5, 72.0, 63.2, 60.1, 54.3, 52.6, 32.5, 31.9, 31.5, 31.2; Mass spectrum (API-TIS) m/z 482 (M-H), 484 (MH⁺); Anal. calcd for C₁₅H₂₂ClN₅O₇S₂.2 mol H₂O: C, 34.65; H, 4.26; N, 13.46; Found: C, 35.02; H, 4.15; N, 13.04.

36c. 2H-1,2,4-Benzothiadiazine-7-sulfonamide, 6-chloro-3,4-dihydro-3-[[4-[2-(nitrooxy)ethyl]-1-piperidinyl]methyl]-, 1,1-dioxide, 2-hydroxy-1,2,3-propanetricarboxylate (1:1) (salt)

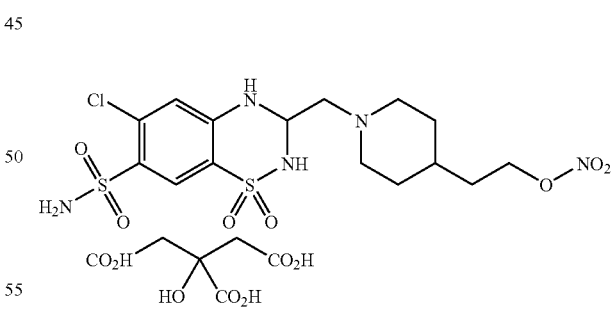

Citric acid (39.7 mg, 0.21 mmol) in MeOH (3 mL) was added to a solution of the product of Example 36b (0.1 g, 0.21 mmol) in EtOAc (3 mL). The reaction mixture was stirred at room temperature for 5 minutes. The solvent was evaporated, the solid was filtered and washed with EtOAc and hexane to give the title compound (96 mg, 69% yield) as an off-white solid: mp 118° C.; ¹H NMR (400 MHz, d₆-DMSO) δ 7.98 (s, 1H), 7.62 (br s, 1H), 7.50 (br s, 2H), 7.25 (s, 1H), 4.87-4.95 (br s, 1H), 4.57 (t, J=6.8 Hz, 2H), 2.80-3.00 (m, 2H), 2.55-2.72 (m, 6H), 2.20 (br t, J=10.8 Hz, 1H), 2.02 (br t, J=9.6 Hz, 1H), 1.56-1.68 (m, 4H), 1.20-1.38 (m, 3H); Mass spectrum (API-TIS) m/z 482 (M-H), 484 (MH$^+$); Anal. calcd for $C_{21}H_{30}ClN_5O_{14}S_2 \cdot 1$ mol EtOAc: C, 39.29; H, 5.00; N, 9.16; Found: C, 39.20; H, 4.86; N, 9.12.

Example 37

2H-1,2,4-Benzothiadiazine-7-sulfonamide, 6-chloro-3,4-dihydro-2-[(4-methyl-5-oxido-1,2,5-oxadiazol-3-yl)methyl]-, 1,1-dioxide

37a. 1,2,5-Oxadiazole-3-methanol, 4-methyl-, 5-oxide

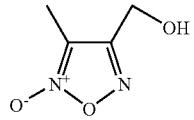

The title compound was prepared from the product of Example 9a as described by Di Stilo et al, *J. Med. Chem.*, 41: 5393-5401 (1998) as a colorless oil (3.4 g, 65% yield): $^1$H NMR (300 MHz, CDCl$_3$) δ 4.78 (d, J=6.2 Hz, 2H), 2.21-2.34 (br s, 1H), 2.24 (s, 3H); Mass spectrum (API-TIS) m/z 148 (MNH$_4^+$).

37b. 1,2,5-Oxadiazole, 4-(bromomethyl)-3-methyl-, 2-oxide

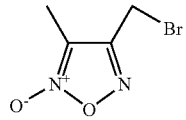

To a stirred solution of the product of Example 37a (1.65 g, 12.7 mmol) in CH$_2$Cl$_2$ (33 mL) was added polymer supported triphenylphosphine (6.6 g of resin, 3 mmol of P/g of resin, 19.8 mmol). The mixture was stirred at room temperature for 15 minutes under nitrogen. To this mixture, carbon tetrabromide (5 g, 15.1 mmol) was added portionwise. The resultant mixture was stirred at room temperature for 16 hours. The solid was filtered and washed with EtOAc. The residue, after evaporation of the solvent, was chromatographed on silica gel, eluting with EtOAc:Hexane (1:6) to give the title compound (1.7 g, 70% yield) as an oil: $^1$H NMR (300 MHz, CDCl$_3$) δ 4.39 (s, 2H), 2.25 (s, 3H); $^{13}$C NMR (75 MHz, CDCl$_3$) δ 149.2, 106.6, 13.5, 2.6.

37c. 2H-1,2,4-Benzothiadiazine-7-sulfonamide, 6-chloro-3,4-dihydro-2-[(4-methyl-5-oxido-1,2,5-oxadiazol-3-yl)methyl]-, 1,1-dioxide

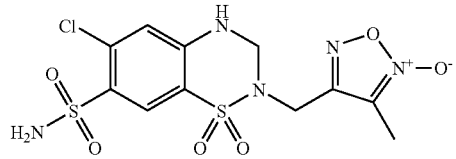

A mixture of the product of Example 37b (0.1 g, 0.52 mmol), hydrochlorothiazide (ONBIO Inc., 0.13 g, 0.43 mmol) and K$_2$CO$_3$ (0.14 g, 1 mmol) in CH$_3$CN (1 mL) was heated at 40-60° C. for 2.5 hours. The crude reaction mixture was chromatographed on silica gel, eluting with CH$_2$Cl$_2$: EtOAc:MeOH (1:1:0.1), to give the title compound (83 mg, 47% yield) as a white solid: mp 235-237° C.; $^1$H NMR (400 MHz, d$_6$-DMSO) δ 8.20-8.25 (br s, 1H), 8.06 (s, 1H), 7.52-7.60 (br s, 2H), 7.11 (s, 1H), 4.93 (s, 2H), 4.31 (s, 2H), 1.99 (s, 3H); $^{13}$C NMR (100 MHz, d$_6$-DMSO) δ 154.6, 145.9, 135.2, 129.1, 126.7, 117.7, 115.3, 113.3, 58.6, 41.5, 7.6; Mass spectrum (API-TIS) m/z 408 (M-H), 410 (MH$^+$), 427 (MNH$_4^+$), 432 (MNa$^+$); Anal. calcd for $C_{11}H_{12}ClN_5O_6S_2 \cdot \frac{1}{2}$ mol MeOH: C, 32.50; H, 3.32; N, 16.47; Found: C, 32.32; H, 2.96; N, 16.18.

Example 38

2H-1,2,4-Benzothiadiazine-2-acetamide, 7-(aminosulfonyl)-6-chloro-3,4-dihydro-N-methyl-N-[2-(nitrooxy)ethyl]-, 1,1-dioxide

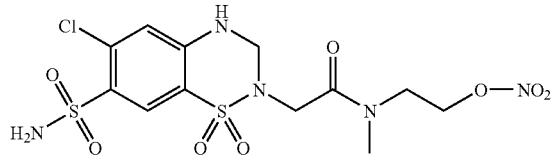

To a solution of the product of Example 31a (1.07 g, 3.0 mmol) and 2-(methylamino)ethyl nitrate (0.549 g, 3.0 mmol, prepared according to U.S. Patent No. 2004/0024057, Example 17c) in 30 mL of DMF was added 1-hydroxybenzotriazole (HOBt), (0.446 g, 3.3 mmol) and EDAC (0.633 g, 3.3 mmol). After the EDAC had dissolved, triethylamine (0.303 g, 3.0 mmol, 0.42 mL) was added and the mixture was stirred 2 hours at room temperature. The solvent was removed under vacuum, the residue was partitioned between ethyl acetate and water, and the organic layer was washed with water and brine, and dried over magnesium sulfate. After evaporation of the solvent, the crude product was purified via column chromatography on silica gel, eluting with 0 to 5% methanol in ethyl acetate gradient. Evaporation of the solvent gave the title compound (0.30 g, 22% yield) as a white solid: mp 160-165° C.; $^1$H NMR (400 MHz, d$_6$-DMSO) δ 8.04 (s, 1H), 8.02 (s, 1H), 7.53 (s, 2H), 7.07 (s, 1H), 4.94 (s, 2H), 4.64 (t, J=5.1 Hz, 2H), 3.89-3.85 (m, 2H), 3.67 (t, J=5.1 Hz, 2H), 2.96-2.88 (m, 3H); Mass spectrum (API-TIS) m/z 458 (MH$^+$), 475 (MNH$_4^+$), 915 (2 MH$^+$), 932 (2MNH$_4^+$).

Example 39

2H-1,2,4-Benzothiadiazine-2-acetamide, 7-(aminosulfonyl)-6-chloro-3,4-dihydro-N,N-bis[2-(nitrooxy)ethyl]-, 1,1-dioxide

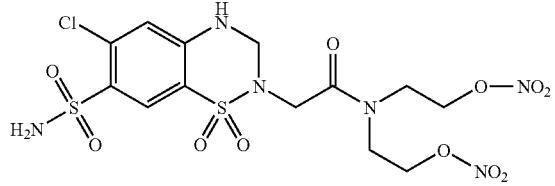

To a solution of the product of Example 31a (1.07 g, 3.0 mmol) and iminodiethane-2,1-diyl dinitrate nitrate (0.774 g, 3.0 mmol, prepared as described in Example 49a herein) in 30 mL of DMF was added 1-hydroxybenzotriazole (HOBt), (0.446 g, 3.3 mmol) and EDAC (0.633 g, 3.3 mmol). After the EDAC had dissolved, triethylamine (0.303 g, 3.0 mmol, 0.42 mL) was added and the mixture was stirred for 2 hours at room temperature. The solvent was removed under vacuum, the residue was partitioned between ethyl acetate and water, and the organic layer was washed with water and brine, and dried over magnesium sulfate. After evaporation of the solvent, the crude product was purified via column chromatography on silica gel, eluting with ethyl acetate. Evaporation of the solvent gave the title compound (0.20 g, 13% yield) as a white amorphous solid: $^1$H NMR (400 MHz, d$_6$-DMSO) δ 8.03 (s, 2H), 7.55 (s, 2H), 7.07 (s, 1H), 4.93 (s, 2H), 4.67-4.63 (m, 4H), 3.93 (s, 2H), 3.72-3.68 (m, 4H); Mass spectrum (API-TIS) m/z 533 (MH$^+$), 550 (MNH$_4^+$)

Example 40

2H-1,2,4-Benzothiadiazine-7-sulfonamide, 6-chloro-3,4-dihydro-2-[4-(nitrooxy)butyl]-, 1,1-dioxide 40a. 1-Butanol, 4-bromo-, nitrate

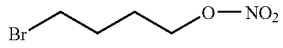

The title compound was prepared as described in *J. Med. Chem.* 1993, 36, 815-819.

40b. 2H-1,2,4-Benzothiadiazine-7-sulfonamide, 6-chloro-3,4-dihydro-2-[4-(nitrooxy)butyl]-, 1,1-dioxide

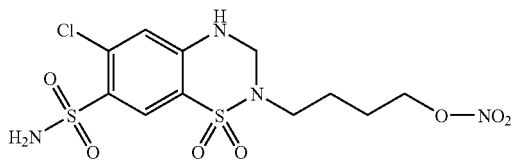

The title compound was synthesized as white prisms (1.26 g, 15% yield) from hydrochlorothiazide (5.95 g, 20 mmol), potassium carbonate (1.38 g, 10 mmol), and the product of Example 40a (4.30 g, 21.8 mmol) by following the procedure of Example 35b: mp 75-77° C.; $^1$H NMR (400 MHz, d$_4$-MeOH) δ 8.18 (s, 1H), 6.98 (s, 1H), 4.93 (s, 2H), 4.52 (t, J=6.4 Hz, 2H), 3.04 (t, J=6.8 Hz, 2H), 1.82-1.74 (m, 4H); Mass spectrum (API-TIS) m/z 415.2 and 417.1 (MH$^+$ for $^{35}$Cl and $^{37}$Cl respectively); Anal. Calcd. for C$_{11}$H$_{15}$ClN$_4$O$_7$S$_2$: C, 31.85; H, 3.64; N, 13.51; Found: C, 32.31; H, 3.32; N, 13.37.

Example 41

2H-1,2,4-Benzothiadiazine-7-sulfonamide, 6-chloro-3,4-dihydro-2-(4-hydroxybutyl)-, 1,1-dioxide

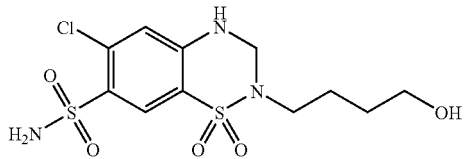

To a stirred solution of hydrochlorothiazide (3.65 g, 12.3 mmol) in DMF (50 mL) were added cesium carbonate (2.00 g, 6.15 mmol), and 4-bromo-1-butanol (1.88 g, 12.3 mmol). After stirring for 22 hours at room temperature, the reaction mixture was poured into water, and extracted with EtOAc. The organic layer was washed with aqueous NaCl, filtered through a pad of Na$_2$SO$_4$, and concentrated. Chromatography (silica gel; eluting with EtOAc, and then THF) and subsequent recrystallization from EtOAc:Hex (1:1) gave the title compound (0.66 g, 15% yield) as a white solid: mp 96-99° C.; $^1$H NMR (400 MHz, d$_4$-MeOH) δ 8.20 (s, 1H), 6.99 (s, 1H), 4.95 (m, 2H), 3.59 (m, 2H), 3.02 (m, 2H), 1.71 (m, 2H), 1.60 (m, 2H); Mass spectrum (API-TIS) m/z 370.1 and 372.0 (MH$^+$ for $^{35}$Cl and $^{37}$Cl respectively).

Example 42

Pentanoic acid, 4,5-bis(nitrooxy)-, 2-[7-(aminosulfonyl)-6-chloro-3,4-dihydro-1,1-dioxido-2H-1,2,4-benzothiadiazin-2-yl]ethyl ester

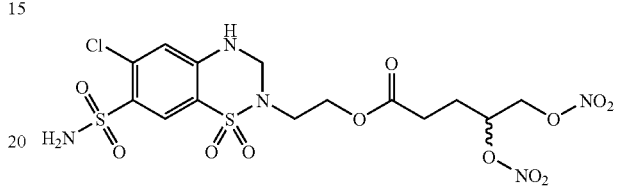

To the product of Example 32b (3.32 g, 9.73 mmol) and the product of Example 22a (2.61 g, 11.68 mmol) in 25 mL of DMF was added N,N-dimethylaminopyridine (DMAP, 0.234 g, 1.94 mmol) and 1-(3-(dimethylamino)propyl)-3-ethylcarbodiimide hydrochloride (EDAC, 2.41 g, 12.6 mmol). The reaction mixture was stirred at room temperature for 18 hours. After evaporation of the solvent under reduced pressure, the residue was partitioned between ethyl acetate and water. The organic layer was washed with brine, and dried over magnesium sulfate. After evaporation of the solvent, the residue was purified via column chromatography on silica gel, 3 to 20% methanol in dichloromethane gradient. Evaporation of the solvent gave the title compound (0.41 g, 8% yield) as a white amorphous solid: $^1$H NMR (400 MHz, d$_6$-DMSO) δ 8.05 (s, 1H), 8.02 (s, 1H), 7.52 (s, 2H), 7.07 (s, 1H), 5.48 (m, 1H), 4.96 (s, 2H), 4.93 (m, 1H), 4.73 (dd, J=5.8, 12.8 Hz, 1H), 4.23 (t, J=5.2 Hz, 2H), 3.19 (t, J=5.2 Hz, 2H), 2.51 (m, 2H), 2.09-1.94 (m, 2H); $^{13}$C NMR (100 MHz, d$_6$-DMSO) δ 172.4, 146.6, 135.4, 129.3, 127.2, 117.9, 116.4, 79.8, 72.2, 62.3, 59.5, 45.7, 29.4, 24.2; Mass spectrum (API-TIS) m/z 565 (MNH$_4^+$), 1112 (2MNH$_4^+$)

Example 43

2H-1,2,4-Benzothiadiazine-7-sulfonamide, 2-[4,5-bis(nitrooxy)pentyl]-6-chloro-3,4-dihydro-, 1,1-dioxide 43a. 1,2-Pentanediol, 5-bromo-, dinitrate

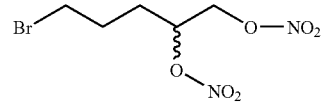

To a solution of 4,5-bis(nitrooxy)pentan-1-ol (1.88 g, 8.95 mmol, prepared as described in WO 2005/030135 A2, Example 27d) in Et$_2$O (20 mL) was added phosphorus tribromide (0.844 mL, 8.95 mmol). After stirring at room temperature for 16 hours, the mixture was poured onto ice, diluted with water, and extracted with Et$_2$O. The organic layer was washed with aqueous NaHCO₃, filtered through a pad of Na₂SO₄, and concentrated. Chromatography (1:5 and then 1:3 EtOAc:Hexane, silica gel) gave the title compound (1.28 g, 52% yield) as a colorless liquid: $^1$H NMR (400 MHz, CDCl₃) δ 5.34-5.30 (m, 1H), 4.77 (dd, J=13.2, 3.2 Hz, 1H), 4.52 (dd, J=12.8, 6.4 Hz, 1H), 3.47-3.42 (m, 2H), 2.07-1.93 (m, 4H).

43b. 2H-1,2,4-Benzothiadiazine-7-sulfonamide, 2-[4,5-bis(nitrooxy)pentyl]-6-chloro-3,4-dihydro-, 1,1-dioxide

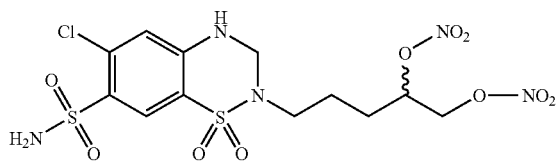

The title compound was synthesized as a white solid (1.66 g, 72% yield) from hydrochlorothiazide (1.49 g, 5.00 mmol), the product of Example 43a (1.28 g, 4.70 mmol), and cesium carbonate (0.815 g, 2.50 mmol) by following the procedure of Example 35b: mp 49-53° C.; $^1$H NMR (400 MHz, d₄-MeOH) δ 8.18 (s, 1H), 6.97 (s, 1H), 5.44 (m, 1H), 4.93 (s, 2H), 4.88 (m, 1H), 4.59 (dd, J=13.2, 6.4 Hz, 1H), 3.05 (t, J=6.4 Hz, 2H), 1.87-1.77 (m, 4H); Mass spectrum (API-TIS) m/z 490.2 and 492.2 (MH⁺ for ³⁵Cl and ³⁷Cl respectively).

Example 44

Pentanoic acid, 5-(nitrooxy)-, 2-[7-(aminosulfonyl)-6-chloro-3,4-dihydro-1,1-dioxido-2H-1,2,4-benzothiadiazin-2-yl]ethyl ester

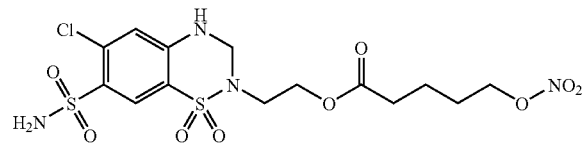

To the product of Example 32b (1.025 g, 3.0 mmol) and the product of Example 4a (0.489 g, 3.0 mmol) in 25 mL of DMF was added 1-hydroxybenzotriazole (HOBt), (0.446 g, 3.3 mmol) and EDAC (0.633 g, 3.3 mmol). The reaction mixture was stirred at room temperature for 18 hours. After evaporation of the solvent under reduced pressure, the residue was partitioned between ethyl acetate and water. The organic layer was washed with brine, and dried over magnesium sulfate. After evaporation of the solvent, the residue was purified via column chromatography on silica gel, eluting with 0 to 5% methanol in dichloromethane gradient. Evaporation of the solvent gave the title compound (0.08 g, 5% yield) as a white amorphous solid: $^1$H NMR (400 MHz, d₆-DMSO) δ 8.04 (s, 1H), 8.01 (s, 1H), 7.52 (s, 2H), 7.07 (s, 1H), 4.97 (s, 2H), 4.52 (t, J=6.2 Hz, 2H), 4.22 (t, J=5.2 Hz, 2H), 3.20 (t, J=5.2 Hz, 2H), 2.36 (t, J=7.2 Hz, 2H), 1.73-1.66 (m, 2H), 1.64-1.58 (m, 2H); Mass spectrum (API-TIS) m/z 504 (MNH₄⁺), 990 (2MNH₄⁺).

Example 45

2H-1,2,4-Benzothiadiazine-7-sulfonamide, 6-chloro-3,4-dihydro-3-[[methyl[2-(nitrooxy)ethyl]amino]methyl]-, 1,1-dioxide

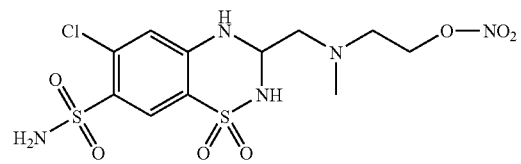

A mixture of methyl[2-(nitrooxy)ethyl]amine, nitric acid salt (prepared as described in U.S. Patent No. 2004/0024057, Example 17c, 72.6 mg, 0.39 mmol), the product of Example 36a (0.1 g, 0.25 mmol) and K₂CO₃ (70.6 mg, 0.51 mmol) in CH₃CN (1 mL) at room temperature was treated with LiOH.H₂O (30 mg, 0.71 mmol). The reaction mixture was heated at 50° C. for 1 hour. The residue, after evaporation of the solvent, was dissolved in EtOAc, washed with water, dried over Na₂SO₄, filtered and the solvent was evaporated. The crude material was chromatographed on silica gel, eluting with CH₂Cl₂:MeOH (1:0.1), to give the title compound (50 mg, 45% yield) as a white solid: mp 175-180° C.; $^1$H NMR (400 MHz, d₆-DMSO) δ 7.99 (s, 1H), 7.80 (br s, 2H), 7.51 (br s, 2H), 7.19 (s, 1H), 4.82-4.90 (br s, 1H), 4.60-4.68 (m, 2H), 2.71-2.92 (m, 4H), 2.36 (s, 3H); Mass spectrum (API-TIS) m/z 427 (M-H), 430 (MH⁺), 452 (MNa⁺).

Example 46

2H-1,2,4-Benzothiadiazine-7-sulfonamide, 6-chloro-3,4-dihydro-2-[5-(nitrooxy)pentyl]-, 1,1-dioxide 46a. 1-Pentanol, 5-bromo-, nitrate

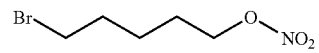

The title compound was prepared as a colorless liquid (6.32 g, 86% yield) from 5-bromo-1-pentanol (5.82 g, 35 mmol) by following the procedure of Example 35a: $^1$H NMR (400 MHz, CDCl₃) δ 4.46 (t, J=6.4 Hz, 2H), 3.41 (t, J=6.8 Hz, 2H), 1.93-1.85 (m, 2H), 1.79-1.71 (m, 2H), 1.60-1.53 (m, 2H).

46b. 2H-1,2,4-Benzothiadiazine-7-sulfonamide, 6-chloro-3,4-dihydro-2-[5-(nitrooxy)pentyl]-, 1,1-dioxide

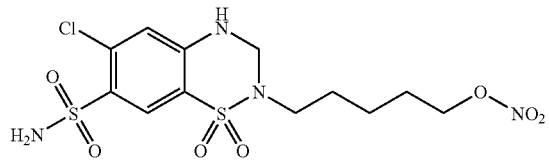

The title compound was synthesized as a white solid (8.72 g, 68% yield) from hydrochlorothiazide (8.93 g, 30 mmol), the product of Example 46a (6.32 g, 29.9 mmol), and cesium carbonate (4.89 g, 15 mmol) by the procedure of Example 35b: mp 120-123° C.; $^1$H NMR (400 MHz, d$_4$-MeOH) δ 8.17 (s, 1H), 6.97 (s, 1H), 4.92 (s, 2H), 4.50 (t, 6.4 Hz, 2H), 3.30 (m, 2H), 1.74 (m, 2H), 1.67 (m, 2H), 1.48 (m, 2H); Mass spectrum (API-TIS) m/z 429.1 and 431.1 (MH$^+$ for $^{35}$Cl and $^{37}$Cl respectively); Anal. Calcd. for $C_{12}H_{17}ClN_4O_7S_2$: C, 33.61; H, 4.00; N, 13.06; Found: C, 33.89; H, 3.74; N, 13.00.

Example 47

2H-1,2,4-Benzothiadiazine-7-sulfonamide, 6-chloro-3,4-dihydro-3-[6-(nitrooxy)hexyl]-, 1,1-dioxide

47a. 1,7-Heptanediol, mononitrate

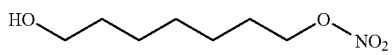

The title compound was obtained as a colorless oil (4.48 g, 99%) by the reaction of 7-bromoheptan-1-ol (5 g, 25.6 mmol) and silver nitrate (5.22 g, 30.7 mmol, 1.2 equivalents) by following the procedure of Example 1a: $^1$H NMR (400 MHz, CDCl$_3$) δ 4.45 (t, J=6.8 Hz, 2H), 3.65 (t, J=6.6 Hz, 2H), 1.73 (m, J=7.0 Hz, 2H), 1.56 (m, J=6.8 Hz, 2H), 1.46-1.36 (m, 7H); $^{13}$C NMR (75 MHz, CDCl$_3$) δ 73.4, 62.8, 32.6, 28.9, 26.7, 25.6, 25.5; Mass Spectrum (API-TIS) m/z 178 (MH)$^+$, 195 (MNH$_4$)$^+$.

47b. Heptanal, 7-(nitrooxy)-

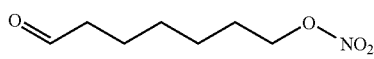

The product of Example 47a (1.77 g, 10 mmol) was treated with Dess-Martin periodinane reagent (4.17 g, 10 mmol) in dichloromethane (50 mL) and water (0.2 mL) following the procedure of Example 1b to give the title compound. The crude product obtained was used in the next step without further purification.

47c. 2H-1,2,4-Benzothiadiazine-7-sulfonamide, 6-chloro-3,4-dihydro-3-[6-(nitrooxy)hexyl]-, 1,1-dioxide

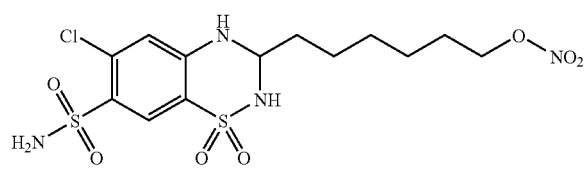

The crude product of Example 47b (10 mmol) was dissolved in dioxane (100 mL) and treated with 2-amino-6-chloro-1,3-benzenedisulfonamide (1.43 g, 5 mmol) and concentrated hydrochloric acid (1.0 mL) following the procedure for Example 1c. The product was purified by silica gel flash chromatography, eluting with 4% methanol in dichloromethane, to give the title compound (0.87 g, 39% yield) as a white solid: mp 161° C.; $^1$H NMR (400 MHz, d$_6$-DMSO) δ 7.98 (s, 1H), 7.88 (s, 1H), 7.77 (d, J=11.6 Hz, 1H), 7.49 (s, 2H), 6.99 (s, 1H), 4.74 (m, J=6.0 Hz, 1H), 4.53 (t, J=6.6 Hz, 2H), 1.79-1.74 (m, 2H), 1.70-1.67 (m, 2H), 1.47 (br s, 2H), 1.37 (br s, 4H); Mass Spectrum (API-TIS) m/z 443 (MH)$^+$, 460 (MNH$_4$)$^+$.

Example 48

2H-1,2,4-Benzothiadiazine-7-sulfonamide, 2-[(3S)-3,4-bis(nitrooxy)butyl]-6-chloro-3,4-dihydro-, 1,1-dioxide

48a. 1,2-Butanediol, 4-bromo-, dinitrate, (2S)—

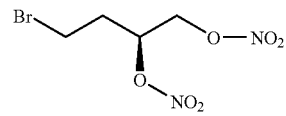

This compound was synthesized as a liquid (0.94 g, 53% yield) from (3S)-3,4-bis(nitrooxy)butan-1-ol (1.36 g, 6.93 mmol, prepared as described in WO 2005/030135 A2, Example 24d), and phosphorus tribromide (1.90 g, 7 mmol) by following the procedure of Example 43b. $^1$H NMR (400 MHz, CDCl$_3$) δ 5.56-5.52 (m, 1H), 4.88-4.83 (m, 1H), 4.54-4.49 (m, 1H), 3.52-3.43 (m, 2H), 2.41-2.31 (m, 1H), 2.25-2.17 (m, 1H).

48b. 2H-1,2,4-Benzothiadiazine-7-sulfonamide, 2-[(3S)-3,4-bis(nitrooxy)butyl]-6-chloro-3,4-dihydro-, 1,1-dioxide

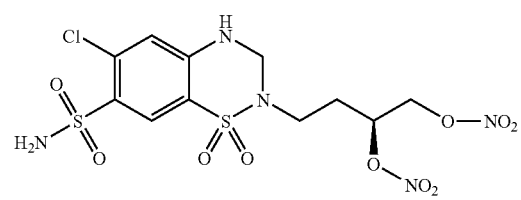

The title compound was synthesized as a white solid (1.05 g, 32% yield over 2 steps) from hydrochlorothiazide (1.19 g, 4 mmol), the product of Example 48a (0.94 g, 3.64 mmol), and cesium carbonate (0.593 g, 1.82 mmol) by following the procedure of Example 35b: mp 162-163° C.; $^1$H NMR (400 MHz, DMSO-d$_6$) δ 8.08 (s, br, 1H), 8.03 (s, 1H), 7.54 (s, 2H), 7.10 (s, 1H), 5.54 (m, 1H), 5.00 (m, 1H), 4.97 (s, 2H), 4.76 (dd, J=13.2, 5.6 Hz, 1H), 3.10 (m, 1H), 3.03 (m, 1H), 2.13 (m, 1H), 2.04 (m, 1H); Mass spectrum (API-TIS) m/z 476.1 and 478.1 (MH$^+$ for $^{35}$Cl and $^{37}$Cl respectively).

Example 49

2H-1,2,4-Benzothiadiazine-3-acetamide, 7-(aminosulfonyl)-6-chloro-3,4-dihydro-N,N-bis[2-(nitrooxy)ethyl]-, 1,1-dioxide

49a. Ethanol, 2,2'-iminobis-, dinitrate (ester), nitrate (1:1) (salt)

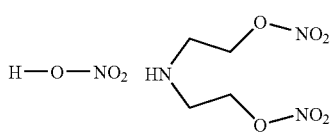

Diethanolamine (Aldrich, 5 g, 47.5 mmol) was added dropwise to a mixture of fuming $HNO_3$ (14.9 g, 9.9 mL, 0.24 mol) and $Ac_2O$ (38.8 g, 36 mL, 0.38 mol) at $-10°$ C. The reaction mixture was stirred at $-10°$ C. for 5 minutes then ice cold EtOAc (50 mL) was added. The reaction mixture was further stirred at $-10°$ C. for 25 minutes and diluted with hexane. The precipitate was collected by filtration and washed with hexane to give the title compound (10.5 g, 86%) as a white solid: mp 115-117° C.; $^1$H NMR (300 MHz, $d_6$-DMSO) δ 8.95 (br s, 1H), 4.80 (t, J=4.8 Hz, 4H), 3.44 (t, J=4.8 Hz, 4H); $^{13}$C NMR (75 MHz, $d_6$-DMSO) δ 68.8, 44.4; Mass spectrum (API-TIS) m/z 196 (MH$^+$); Anal. calcd for $C_4H_{10}N_4O_9$: C, 18.61; H, 3.90; N, 21.70. Found: C, 18.75; H, 3.67; N, 21.42.

49b. Ethanol, 2,2'-iminobis-, dinitrate (ester)

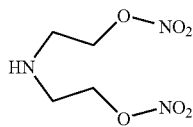

Saturated $NaHCO_3$ solution was added dropwise to a stirred suspension of the product of Example 49a (5 g, 19.4 mmol) in EtOAc (30 mL) to give a clear solution. The organic phase was washed with saturated $NaHCO_3$, water, dried over $Na_2SO_4$, filtered and evaporated in vacuo to give the title compound (3.6 g, 95% yield) as pale yellow oil, which was used immediately for the preparation of Example 49e. $^1$H NMR (300 MHz, $CDCl_3$) δ 4.55 (t, J=5.3 Hz, 4H), 3.00 (t, J=5.4 Hz, 4H). $^{13}$C NMR (75 MHz, $CDCl_3$) δ 72.6, 46.4. Mass spectrum (API-TIS) m/z 196 (MH$^+$).

49c. 2H-1,2,4-Benzothiadiazine-3-acetic acid, 7-(aminosulfonyl)-6-chloro-3,4-dihydro-, methyl ester, 1,1-dioxide

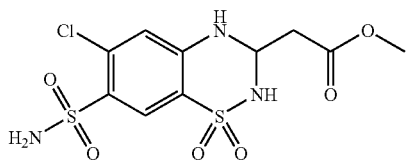

To a mixture of 4-chloro-6-aminobenzene-1,3-disulfonamide (Aldrich, 14.1 g, 49.3 mmol) and methyl 3,3-dimethoxypropionate (Aldrich, 9 mL, 9.4 g, 63.4 mmol) in anhydrous dioxane (50 mL) at 40° C., was added dropwise concentrated HCl (5 mL). The mixture was then heated at 70-90° C. for 30 minutes. The solvent was evaporated, the solid was washed with water, dissolved in EtOAc and dried over $Na_2SO_4$. The residue, after evaporation of the solvent, was recrystallized from EtOAc/hexane to give the title compound in quantitative yield as a white solid: mp 237-238° C.; $^1$H NMR (400 MHz, $d_6$-DMSO) δ 8.06 (br s, 2H), 8.00 (s, 1H), 7.53 (br s, 2H), 7.00 (s, 1H), 5.10-5.17 (m, 1H), 3.69 (s, 3H), 2.90-2.94 (m, 2H); $^{13}$C NMR (100 MHz, $d_6$-DMSO) δ 168.9, 146.2, 134.5, 128.6, 125.4, 118.1, 117.2, 62.9, 51.9, 38.2. Mass spectrum (API-TIS) m/z 367 (M-H), 370 (MH$^+$), 387 (MNH$_4^+$); Anal. calcd for $C_{10}H_{12}ClN_3O_6S_2$: C, 32.48; H, 3.27; N, 11.36. Found: C, 32.50; H, 3.09; N, 11.15.

49d. 2H-1,2,4-Benzothiadiazine-3-acetic acid, 7-(aminosulfonyl)-6-chloro-3,4-dihydro-, 1,1-dioxide

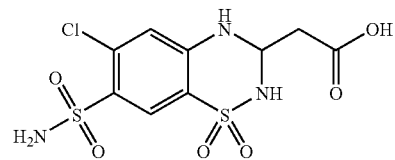

A mixture of the product of Example 49c (8.3 g, 22.4 mmol) and 1N NaOH (74 mL) in EtOH (265 mL) was stirred at room temperature for 1.5 hours. The reaction mixture was cooled to 0° C. and acidified with 1N HCl (80 mL). The solvent was evaporated and the resulting residue was extracted with EtOAc, washed with water, dried over $Na_2SO_4$. The crude solid was recrystallized from $CH_2Cl_2$:EtOAc to give the title compound (6.2 g, 77% yield) as a white solid: mp 160-162° C.; $^1$H NMR (400 MHz, $d_6$-DMSO) δ 12.80-12.90 (br s, 1H), 8.02 (br s, 2H), 7.99 (s, 1H), 7.51 (br s, 2H), 7.01 (s, 1H), 5.07-5.15 (m, 1H), 2.78-2.83 (m, 2H); $^{13}$C NMR (100 MHz, $d_6$-DMSO) δ 170.4, 146.3, 134.5, 128.5, 125.4, 118.1, 117.2, 59.8, 38.5; Mass spectrum (API-TIS) m/z 354 (M-H), 356 (MH$^+$), 373 (MNH$_4^+$); Anal. calcd for $C_9H_{10}ClN_3O_6S_2$: C, 30.38; H, 2.83; N, 11.81. Found: C, 30.61; H, 2.82; N, 11.47.

49e. 2H-1,2,4-Benzothiadiazine-3-acetamide, 7-(aminosulfonyl)-6-chloro-3,4-dihydro-N,N-bis[2-(nitrooxy)ethyl]-, 1,1-dioxide

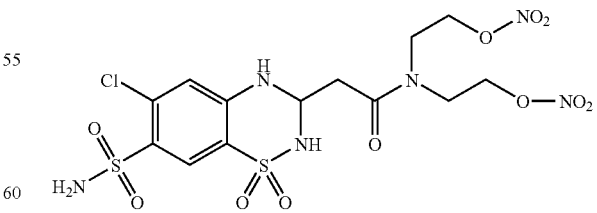

A mixture of the product of Example 49d (1 g, 2.81 mmol) and the product of Example 49b (1.64 g, 8.4 mmol) in a mixture of THF (5 mL) and DMF (3 mL) at 0° C. was treated with 1-{3-(dimethylamino)propyl}-3-ethylcarbodiimide hydrochloride (0.64 g, 3.3 mmol). The reaction mixture was stirred at 0° C. for 3 hours. The residue, after evaporation of the solvent, was chromatographed on silica gel, eluting with CH$_2$Cl$_2$:EtOAc:MeOH (1:1:0.1), to give the title compound (0.23 g, 15% yield) as an off-white solid: mp 94-97° C.; $^1$H NMR (400 MHz, d$_6$-DMSO) δ 8.27 (br s, 1H), 8.12 (br s, 1H), 7.87 (s, 1H), 7.54 (br s, 2H), 7.06 (s, 1H), 5.10-5.18 (m, 1H), 4.65-4.74 (m, 4H), 3.72-3.80 (m, 1H), 3.55-3.63 (m, 1H), 3.41 (br s, 2H), 3.03-3.10 (m, 2H); Mass spectrum (API-TIS) m/z 531 (M-H), 533 (MH$^+$), 550 (MNH$_4^+$); Anal. calcd for C$_{13}$H$_{17}$ClN$_6$O$_{11}$S$_2$: C, 29.30; H, 3.22; N, 15.77; Found: C, 29.58; H, 3.13; N, 15.49.

Example 50

2H-1,2,4-Benzothiadiazine-7-sulfonamide, 3-[3,5-bis[(nitrooxy)methyl]phenyl]-6-chloro-3,4-dihydro-, 1,1-dioxide 50a. 1,3,5-Benzenetrimethanol, 1,3-dinitrate

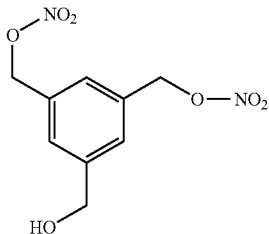

A solution of benzene-1,3,5-triyltrimethanol (2.3 g, 13.7 mmol, prepared as described in *J. Org. Chem.* 2001, 66, 5664) in THF (100 mL) was treated with a pre-mixed solution of fuming nitric acid (2.6 mL, 55.7 mol) in acetic anhydride (15 mL) and stirred at room temperature for 70 minutes. Water (20 mL) was added to the reaction mixture and THF was evaporated under reduced pressure. The resulting mixture was partitioned between EtOAc (100 mL×2) and water. The combined organic extracts were washed with saturated NaHCO$_3$, brine, dried over Na$_2$SO$_4$, filtered, and concentrated. The product was purified by silica gel column chromatography eluting with EtOAc/hexane (1:2, R$_f$=0.13) to give the title compound as a clear oil (1.18 g, 33% yield): $^1$H NMR (400 MHz, CDCl$_3$) δ 7.43 (s, 2H), 7.35 (s, 1H), 5.44 (s, 4H), 4.74 (s, 2H), 2.11 (br s, 1H); $^{13}$C NMR (100 MHz, CDCl$_3$) δ 142.6, 133.5, 128.3, 128.1, 73.9, 64.3.

50b. Benzaldehyde, 3,5-bis[(nitrooxy)methyl]-

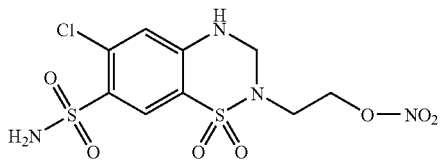

Pyridinium chlorochromate (1.20 g, 5.57 mmol) was added to a mixture of the product of Example 50a (1.295 g, 5.02 mmol) and Celite® (3.6 g) in CH$_2$Cl$_2$ (50 mL) and stirred at room temperature for 15 minutes. The reaction mixture was filtered through Celite® and washed with CH$_2$Cl$_2$ (100 mL). The filtrate was concentrated and the residue was purified by silica gel column chromatography eluting with EtOAc/hexane (1:3, R$_f$=0.25) to give the title compound as a clear oil (0.96 g, 75% yield): $^1$H NMR (400 MHz, CDCl$_3$) δ 10.05 (s, 1H), 7.95 (s, 2H), 7.72 (s, 1H), 5.53 (s, 4H); $^{13}$C NMR (100 MHz, CDCl$_3$) δ 190.6, 137.4, 134.6, 134.3, 130.4, 73.0; Mass Spectrum (API-TIS) m/z 274 (MNH$_4$)$^+$.

50c. 2H-1,2,4-Benzothiadiazine-7-sulfonamide, 3-[3,5-bis[(nitrooxy)methyl]phenyl]-6-chloro-3,4-dihydro-, 1,1-dioxide

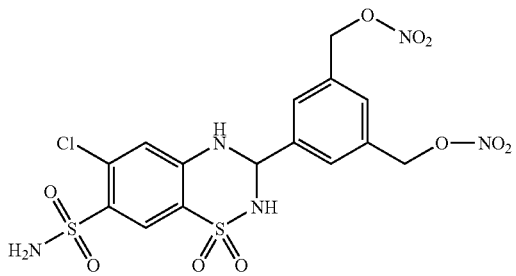

A solution of the product of Example 50b (0.71 g, 2.77 mmol), 4-amino-6-chlorobenzene-1,3-disulfonamide (0.78 g, 2.73 mmol) and p-toluenesulfonic acid monohydrate (0.311 g, 1.63 mmol) in 1,4-dioxane (25 mL) was heated to 100° C. for 4 hours. The reaction mixture was concentrated and the resulted material was separated by silica gel column chromatography eluting with EtOAc/hexane (3:2, R$_f$=0.6). The crude material was dissolved in EtOAc and triturated with CHCl$_3$. The solid was collected and dried under vacuum to give the title compound as a yellow solid (0.30 g, 21% yield): mp 121-124° C.; $^1$H NMR (400 MHz, d$_6$-DMSO) δ 8.41 (d, J=12 Hz, 1H), 8.38 (s, 1H), 8.07 (s, 1H), 7.82 (s, 2H), 7.68 (s, 1H), 7.56 (br s, 2H), 7.09 (s, 1H), 5.98 (d, J=12 Hz, 1H), 5.66 (s, 4H); $^{13}$C NMR (100 MHz, d$_6$-DMSO) δ 146.6, 137.4, 134.5, 133.8, 130.5, 128.9, 125.4, 118.7, 117.6, 74.2, 67.8; Mass Spectrum (API-TIS) m/z 541 (MNH$_4$)$^+$. Anal. calcd for C$_{15}$H$_{14}$ClN$_5$O$_{10}$S$_2$: C, 34.39; H, 2.69; N, 13.37; Found: C, 34.24; H, 2.46; N, 13.11.

Example 51

2H-1,2,4-Benzothiadiazine-7-sulfonamide, 6-chloro-3,4-dihydro-2-[2-(nitrooxy)ethyl]-, 1,1-dioxide Trifluoroacetic acid (4.9 mL, 63.60 mmol) was added to a solution of the product of Example 32b (10.68 g, 31.23 mmol) in THF (400 mL) followed by the addition of a pre-mixed solution of fuming nitric acid (4.4 mL, 94.27 mmol) in acetic anhydride (45 mL) and stirred at room temperature for 2 hours. The reaction was poured into water (100 mL) and adjust pH to 8 with saturated NaHCO$_3$. THF was evaporated under reduced pressure and the resulting aqueous mixture was extracted with EtOAc (450 mL). The organic extract was washed with water, 3N HCl, brine, dried over $Na_2SO_4$, filtered, and concentrated. The product was purified by silica gel column chromatography eluting with EtOAc/hexane (3:2, $R_f$=0.3) to obtain the title compound as a yellow solid (9.64 g, 80% yield); mp 161-163° C. (with decomposition). The analytical pure sample was obtained by triturating the product in EtOAc with $CHCl_3$. $^1H$ NMR (400 MHz, $d_6$-DMSO) δ 8.09 (s, 1H), 8.02 (s, 1H), 7.53 (br s, 2H), 7.09 (s, 1H), 5.98 (d, J=2.8 Hz, 2H), 4.73 (t, J=4.8 Hz, 2H), 3.32 (t, J=4.8 Hz, 2H); $^{13}C$ NMR (100 MHz, $d_6$-DMSO) δ 146.0, 135.0, 128.9, 126.7, 117.5, 115.7, 70.9, 591, 43.9; Mass Spectrum (API-TIS) m/z 404 $(MNH_4)^+$. Anal. calcd for $C_9H_{11}ClN_4O_7S_2$: C, 27.95; H, 2.87; N, 14.48; Found: C, 28.15; H, 2.86; N, 14.33.

51b. Alternative Synthesis of 2H-1,2,4-benzothiadiazine-7-sulfonamide, 6-chloro-3,4-dihydro-2-[2-(nitrooxy)ethyl]-, 1,1-dioxide

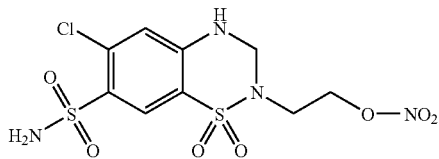

Trifluoroacetic acid (19.5 mL, 0.253 mol) was added to a solution of the product of Example 32b (43.1 g, 0.126 mol) in THF (1 L) followed by the addition of a pre-mixed solution of fuming nitric acid (17.8 mL, 0.381 mol) in acetic anhydride (180 mL) and stirred at room temperature for 2 hours. Water (300 mL) was added to the reaction and stirred for 1 hour. THF was evaporated under reduced pressure. The resulting residue was triturated with 20% ethanol (1 L) with vigorous stirring for 1 hour. The solid was collected and dried under vacuum to obtain the title compound as a yellow solid (39.4 g, 81% yield); mp 161-163° C. (with decomposition). $^1H$ NMR (400 MHz, $d_6$-DMSO) δ 8.09 (s, 1H), 8.02 (s, 1H), 7.53 (br s, 2H), 7.09 (s, 1H), 5.98 (d, J=2.8 Hz, 2H), 4.73 (t, J=4.8 Hz, 2H), 3.32 (t, J=4.8 Hz, 2H); $^{13}C$ NMR (100 MHz, $d_6$-DMSO) δ 146.0, 135.0, 128.9, 126.7, 117.5, 115.7, 70.9, 59.1, 43.9; Mass Spectrum (API-TIS) m/z 404 $(MNH_4)^+$. Anal. calcd for $C_9H_{11}ClN_4O_7S_2$: C, 27.95; H, 2.87; N, 14.48; Found: C, 28.15; H, 2.85; N, 14.33.

Example 52

2H-1,2,4-Benzothiadiazine-7-sulfonamide, 6-chloro-3,4-dihydro-4-nitro-2-[2-(nitrooxy)ethyl]-, 1,1-dioxide

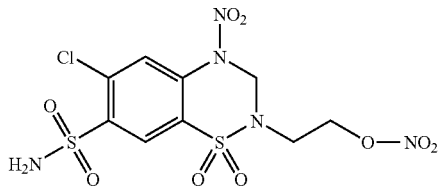

Trifluoroacetic acid (0.32 mL, 4.09 mmol) was added to a solution of the product of Example 32b (0.70 g, 2.05 mmol) in THF (30 mL) followed by the addition of a pre-mixed solution of fuming nitric acid (0.60 mL, 12.86 mmol) in acetic anhydride (6 mL) and stirred at room temperature for 2 hours. Water (2 mL) was added to the reaction mixture and THF was evaporated under reduced pressure. The resulting aqueous mixture was extracted with EtOAc (100 mL). The organic extract was washed with water, 3N HCl, brine, dried over $Na_2SO_4$, filtered, and concentrated. The product was purified by silica gel column chromatography eluting with EtOAc/hexane (3:2, $R_f$=0.1) to obtain the title compound as a yellow solid (0.27 g, 31% yield); mp 144° C. (with decomposition); $^1H$ NMR (400 MHz, $d_6$-DMSO) δ 8.36 (s, 1H), 8.30 (s, 1H), 8.03 (br s, 2H), 6.09 (br s, 2H), 4.76 (t, J=4.8 Hz, 2H), 3.63 (t, J=4.8 Hz, 2H); $^{13}C$ NMR (100 MHz, $d_6$-DMSO) δ 139.8, 135.4, 134.9, 128.6, 125.6, 125.0, 70.5, 64.4, 45.5; Mass Spectrum (API-TIS) m/z 449 $(MNH_4)^+$. Anal. calcd for $C_9H_{10}ClN_5O_9S_2$: C, 25.03; H, 2.33; N, 16.22; Found: C, 25.30; H, 2.30; N, 15.95.

Example 53

2H-1,2,4-Benzothiadiazine-2-butanoic acid, 7-(aminosulfonyl)-6-chloro-3,4-dihydro-, 1,1-dioxide 53a. Benzyl 4-bromobutanoate To a solution of 4-bromobutyryl chloride (Aldrich Chemical Company, Wisconsin), (10.27 g, 55.4 mmol) in 100 mL of dichloromethane was added benzyl alcohol (Aldrich Chemical Company, Wisconsin), (6.29 g, 58.1 mmol), followed by potassium carbonate (8.3 g, 60 mmol) in four portions. After 2 hours, water was added, and the layers were separated. The organic layer was washed with water, brine, and dried over magnesium sulfate. Evaporation of the solvent gave the title compound (11.87 g, 83% yield) as a colorless oil: $^1H$ NMR (400 MHz, $CDCl_3$) δ 7.36 (m, 5H), 5.14 (s, 2H), 3.46 (t, J=6.4 Hz, 2H), 2.56 (t, J=7.2 Hz, 2H), 2.20 (quin, J=6.6 Hz, 2H).

53b. Benzyl 4-[7-(aminosulfonyl)-6-chloro-1,1-dioxido-3,4-dihydro-2H-1,2,4-benzothiadiazin-2-yl] butanoate To a solution of hydrochlorothiazide (ONBIO, Inc., Ontario, Canada) (8.62 g, 29 mmol) in 30 mL of DMF was added cesium carbonate (4.68 g, 14.4 mmol) and the product of Example 53a (7.39 g, 28.7 mmol) and the mixture was stirred for 18 hours at room temperature. The solids were removed via filtration, and the solvent was removed under vacuum. The residue was partitioned between ethyl acetate and water, and the organic layer was washed with water and brine, and dried over magnesium sulfate. After evaporation of the solvent, the residue was purified via column chromatography on silica gel, 10 to 75% ethyl acetate in dichloromethane gradient. Evaporation of the solvent gave the title compound (8.71 g, 64% yield) as a white amorphous solid: $^1H$ NMR (400 MHz, $d_6$-DMSO) δ 8.02 (s, 2H), 7.52 (s, 2H), 7.36 (m, 5H), 7.06 (s, 1H), 5.09 (s, 2H), 4.90 (s, 2H), 2.94 (t, J=7.0 Hz, 2H), 2.45 (t, J=7.2 Hz, 2H), 1.87 (quin, J=7.1 Hz, 2H); Mass spectrum (API-TIS) m/z 474 $(MH^+)$, 491 $(MNH_4^+)$, 964 $(2MNH_4^+)$.

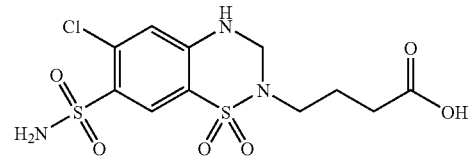

53c. 2H-1,2,4-Benzothiadiazine-2-butanoic acid, 7-(aminosulfonyl)-6-chloro-3,4-dihydro-, 1,1-dioxide The product of Example 53b (11.26 g, 23.76 mmol) was dissolved in 250 mL of ethyl acetate/tetrahydrofuran, 1:1 in a 500 mL Parr® bottle. Palladium on carbon (10% Pd/C, 1.0 g) was added, and the mixture was shaken under 15 psi of hydrogen for 30 minutes. The reaction mixture was filtered through Celite, and the solvent was removed under vacuum to obtain the crude product as a white solid. Recrystallization from acetone/ether provided the title compound (8.21 g, 90% yield) as white crystals: mp 72-78° C.; $^1$H NMR (400 MHz, $d_6$-DMSO) δ 12.11 (s, 1H), 8.01 (s, 2H), 7.51 (s, 2H), 7.06 (s, 1H), 4.90 (s, 2H), 2.92 (t, J=7.1 Hz, 2H), 2.29 (t, J=7.2 Hz, 2H), 1.81 (quin, J=7.1 Hz, 2H); Mass spectrum (API-TIS) m/z 384 (MH$^+$), 401 (MNH$_4^+$), 784 (2MNH$_4^+$).

Example 54

2H-1,2,4-Benzothiadiazine-7-sulfonamide, 6-chloro-3,4-dihydro-3-[4-(nitrooxy)-3,3-bis[(nitrooxy)methyl]butyl]-, 1,1-dioxide

54a. 2,2-Bis(hydroxymethyl)pentane-1,5-diol

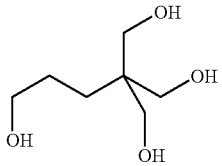

The title compound was prepared by following the procedure in U.S. Pat. No. 2,775,622. $^1$H NMR (400 MHz, $d_6$-DMSO) δ 4.28 (t, J=4.0 Hz, 1H), 4.18 (t, J=4.0 Hz, 3H), 3.31 (m, 2H), 3.25 (d, J=4.0 Hz, 6H), 1.37 (m, 2H), 1.12 (m, 2H).

54b. 2-(3-{[tert-Butyl(diphenyl)silyl]oxy}propyl)-2-(hydroxymethyl)propane-1,3-diol

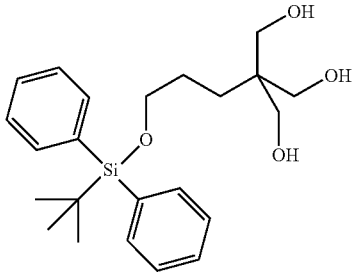

The product of Example 54a (1.0 g, 6.09 mmol) was dissolved in pyridine (25 mL) and cooled to 0° C. Tert-butylchlorodiphenylsilane (Aldrich Chemical Co., 1.59 g, 5.79 mmol) was added and the reaction mixture was stirred for 18 hours with slow warming to room temperature. The pyridine was removed in vacuo and the residue was re-dissolved in ethyl acetate, washed with water (20 mL), 3M hydrochloric acid (40 mL), and finally brine (20 mL). The organic layer was dried over sodium sulfate. Filtration and removal of solvent in vacuo gave the title compound (2.3 g, 93% yield) as a faint yellow oil: $^1$H NMR (400 MHz, $d_6$-DMSO) δ 7.60 (m, 4H), 7.38 (m, 6H), 4.17 (t, J=4.0 Hz, 3H), 3.57 (t, J=8.0 Hz, 2H), 3.25 (d, J=4.0 Hz, 6H), 1.53 (m, 2H), 1.19 (m, 2H), 0.97 (s, 9H).

54c. 2-[3-[[(1,1-Dimethylethyl)diphenylsilyl]oxy]propyl]-2-[(nitrooxy)methyl]-1,3-propanediol 1,3-dinitrate

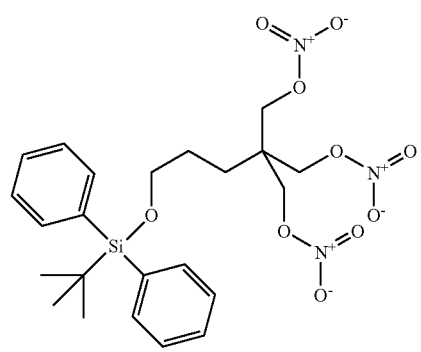

To the product of Example 54b (2.3 g, 5.71 mmol) slurried in dichloromethane (60 mL) and then cooled to 0° C., was added a mixture of nitric acid (90% fuming, 2.2 g, 34.3 mmol) and acetic anhydride (7.6 mL) at 0° C. The reaction mixture was stirred at 0° C. for 3 hours, poured directly onto 100 g of ice and allowed to stand overnight. The organic layer was separated, dried over sodium sulfate, filtered, and the solvent removed in vacuo to give the title compound (2.6 g, 85% yield) as a yellow oil: $^1$H NMR (400 MHz, CDCl$_3$) δ 7.60 (m, 4H), 7.37 (m, 6H), 4.39 (s, 6H), 3.65 (t, J=6.0 Hz, 2H), 1.58 (m, 2H), 1.48 (m, 2H), 1.05 (s, 9H).

54d. 1,5-Pentanediol, 2,2-bis[(nitrooxy)methyl]-, 1-nitrate

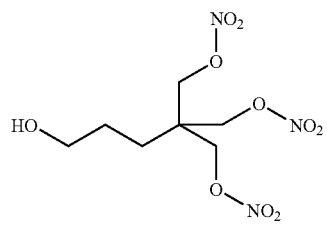

The product of Example 54c (2.6 g, 4.85 mmol) was dissolved in tetrahydrofuran (50 mL) and tetra-n-butylammonium fluoride (Aldrich Chemical Co., IM in tetrahydrofuran, 5.0 mmol) was added immediately. The reaction mixture was stirred for 45 minutes at room temperature and then immediately chromatographed on silica gel, eluting with a 10%-50% ethyl acetate/hexane gradient. The title compound (1.0 g, 71% yield) was obtained as a yellow solid: $^1$H NMR (400 MHz, CDCl$_3$) δ 4.48 (s, 6H), 3.70 (m, 2H), 1.69 (m, 2H), 1.63 (m, 2H), 1.36 (br t, J=4.0 Hz, 1H). Mass spectrum (API-TIS) m/z 317 (MNH$_4^+$).

54e.
5-(Nitrooxy)-4,4-bis[(nitrooxy)methyl]-pentanal

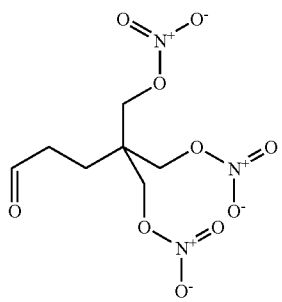

The product of Example 54d (1.1 g, 3.6 mmol) was dissolved in 30 mL of dichloromethane at room temperature. Celite® (4.5 g) was added followed by the addition of pyridinium dichromate (Aldrich Chemical Co., 4.5 g, 12.0 mmol). The reaction mixture was stirred for 20 hours, filtered through a short pad of silica gel and washed with ethyl acetate/hexanes (1:1). The solvent was removed in vacuo to give the title compound as a yellow oil that was used immediately without further purification: $^1$H NMR (400 MHz, $d_6$-DMSO) δ 9.80 (d, J=8 Hz, 1H), 4.46 (s, 6H), 1.95 (dt, J=8.0 and 6.0 Hz, 2H), 1.66 (m, 2H).

54f. 2H-1,2,4-Benzothiadiazine-7-sulfonamide, 6-chloro-3,4-dihydro-3-[4-(nitrooxy)-3,3-bis[(nitrooxy)methyl]butyl]-, 1,1-dioxide

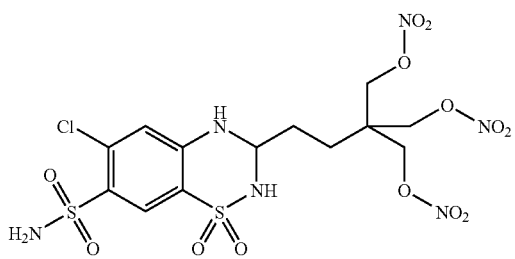

The product of Example 54e (524 mg, 1.84 mmol) was taken up into anhydrous 1,4-dioxane (10 mL). 4-Amino-6-chloro-1,3-benzenedisulfonamide (Aldrich Chemical Co., 600 mg, 2.02 mmol) was added followed by the addition of concentrated hydrochloric acid (0.5 mL). The reaction mixture was heated at reflux for 18 hours, cooled to room temperature and the solvent removed in vacuo. The resultant residue was purified by column chromatography on silica gel eluting with a methanol/dichloromethane gradient (0:100 to 35:65) to give the title compound (460 mg, 44% yield) as a yellow glassy solid: $^1$H NMR (400 MHz, $d_6$-DMSO) δ 7.99 (m, 2H), 7.51 (br s, 2H), 6.98 (br s, 1H), 4.75 (m, 1H), 4.69 (br s, 1H), 4.61 (s, 6H), 1.85 (m, 2H), 1.74 (m, 2H). Mass spectrum (API-TIS) m/z 582 (MNH$_4^+$).

Example 55

2H-1,2,4-Benzothiadiazine-7-sulfonamide, 3-[3,5-bis[(nitrooxy)methyl]phenyl]-3,4-dihydro-6-(trifluoromethyl)-, 1,1-dioxide

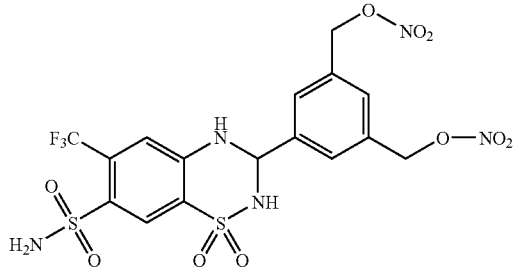

A solution of the product of Example 50b (1.09 g, 4.25 mmol), 4-amino-6-(trifluoromethyl)benzene-1,3-disulfonamide (1.25 g, 3.92 mmol) and p-toluenesulfonic acid monohydrate (0.39 g, 2.05 mmol) in 1,4-dioxane (40 mL) were heated to reflux for 5 hours. The reaction mixture was concentrated and the resulted material was separated by silica gel column chromatography, eluting with EtOAc/hexane (2:3, R$_f$=0.2). The crude material was dissolved in EtOAc and triturated with CHCl$_3$. The solid was collected and dried under vacuum to give the title compound as a yellow solid (1.06 g, 45% yield); mp>113° C. (with decomposition); $^1$H NMR (400 MHz, $d_6$-DMSO) δ 8.58 (s, 1H), 8.49 (d, J=11.6 Hz, 1H), 8.30 (s, 1H), 7.83 (s, 2H), 7.69 (s, 1H), 7.65 (br s, 2H), 7.47 (s, 1H), 6.04 (d, J=11.6 Hz, 1H), 5.67 (s, 4H); $^{13}$C NMR (100 MHz, $d_6$-DMSO) δ 145.7, 137.2, 133.8, 130.5, 129.6 (q, J$_{CF}$=32 Hz), 129.2, 128.8, 126.5, 122.3 (q, J$_{CF}$=273 Hz), 121.8, 116.0 (q, J$_{CF}$=7 Hz), 74.2, 67.8; Mass Spectrum (API-TIS) m/z 575 (MNH$_4$). Anal. calcd for C$_{16}$H$_{14}$F$_3$N$_5$O$_{10}$S$_2$: C, 34.48; H, 2.53; N, 12.56; Found: C, 34.51; H, 2.30; N, 12.28.

Example 56

2H-1,2,4-Benzothiadiazine-7-sulfonamide, 6-chloro-3,4-dihydro-2-[5-(nitrooxy)-4,4-bis[(nitrooxy)methyl]pentyl]-, 1,1-dioxide

56a. 2-(3-Bromopropyl)-2-[(nitrooxy)methyl]-1,3-propanediol 1,3-dinitrate

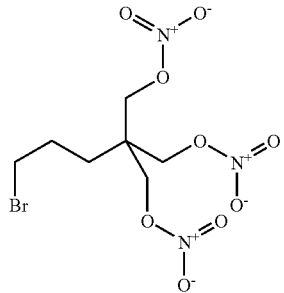

The product of Example 54d (1.1 g, 3.7 mmol) was dissolved in dry tetrahydrofuran (15 mL), then carbon tetrabromide (Aldrich Chemical Co., 3.1 g, 9.4 mmol) was added followed by the addition of triphenylphosphine (Aldrich Chemical Co., 1.5 g, 5.6 mmol). The exothermic reaction was stirred at room temperature for 2.5 hours. The solvent was removed in vacuo to give a yellow oily residue. Hexanes were added to the residue, the solids removed by filtration and the filtrate concentrated in vacuo to give a yellow oil. The oil was chromatographed on silica gel eluting with an ethyl acetate/hexanes gradient (5:95 to 35:65). The title compound (1.1 g, 81% yield) was obtained as a faint yellow oil which slowly solidified: $^1$H NMR (400 MHz, CDCl$_3$) δ 4.47 (s, 6H), 3.41 (t, J=8 Hz, 2H), 1.92 (m, 2H), 1.75 (m, 2H).

56b. 2H-1,2,4-Benzothiadiazine-7-sulfonamide, 6-chloro-3,4-dihydro-2-[5-(nitrooxy)-4,4-bis[(nitrooxy)methyl]pentyl]-, 1,1-dioxide

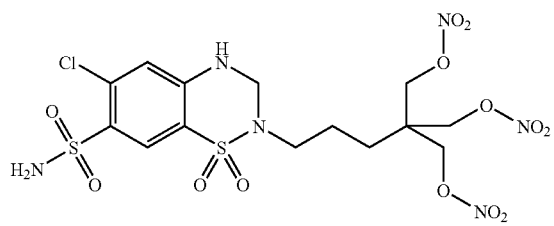

The product of Example 56a (1.1 g, 3.0 mmol) was dissolved in N,N-dimethylformamide (10 mL). 6-Chloro-3,4-dihydro-2H-1,2,4-benzothiadiazine-7-sulfonamide 1,1-dioxide (ONBIO, 1.0 g, 3.3 mmol) was added followed by cesium carbonate (0.5 g, 1.5 mmol) and the resulting mixture was stirred at room temperature for 48 hours. The reaction mixture was poured into 100 mL of water and extracted with ethyl acetate (20 mL×2). The combined organic layers were washed with brine, dried over sodium sulfate, filtered and the solvent removed in vacuo to give a yellow oil. Column chromatography using a methanol/dichloromethane gradient (0:100 to 35:65) gave the title compound (0.8 g, 41% yield) as a white glassy solid: $^1$H NMR (400 MHz, d$_6$-DMSO) δ 7.95 (br s, 2H), 7.51 (br s, 2H), 1.07 (br s, 1H), 4.92 (br d, J=2.4 Hz, 2H), 4.59 (s, 6H), 3.32 (s, 2H), 1.67 (m, 2H), 1.53 (m, 2H). Mass spectrum (API-TIS) m/z 596 (MNH$_4$$^+$).

Example 57

Acetamide, N-[[7-(aminosulfonyl)-6-chloro-3,4-dihydro-1,1-dioxido-2H-1,2,4-benzothiadiazin-3-yl]methyl]-2-[bis[2-(nitrooxy)ethyl]amino]-

57a. 2H-1,2,4-Benzothiadiazine-7-sulfonamide, 3-(aminomethyl)-6-chloro-3,4-dihydro-, 1,1-dioxide

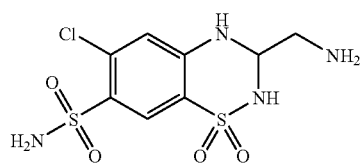

To a solution of aminoacetaldehyde dimethylacetal (2.18 mL, 2.13 g, 20.2 mmol) in EtOAc (25 mL) at 0° C. was added dropwise a solution of HCl in ether (13 mL, 2N solution in ether). The mixture was stirred at 0° C. for 5 minutes. To this solution, 4-chloro-6-aminobenzene-1,3-disulfonamide (Aldrich, 5.8 g, 20.3 mmol) in diethylene glycol dimethylether (30 mL) was added. The reaction mixture was then heated at 60-90° C. for 1 hour. The solvent was decanted and the solid was dissolved in water. An aqueous solution of Na$_2$CO$_3$ (10%) was added to adjust the pH 7-8, extracted with EtOAc, dried over Na$_2$SO$_4$, filtered and the solvent was evaporated. The crude material was chromatographed on silica gel eluting with CH$_2$Cl$_2$:EtOAc:MeOH (1:1:0.2 to 1:1:1) to give the title compound (3 g, 53% yield) as a white solid: mp 157-160° C. $^1$H NMR (400 MHz, d$_6$-DMSO) δ 7.97 (s, 1H), 7.05 (s, 1H), 5.65-4.70 (m, 1H), 2.88-2.96 (m, 1H), 2.77-2.84 (m, 1H); $^{13}$C NMR (100 MHz, d$_6$-DMSO) δ 147.1, 134.8, 128.4, 125.9, 118.7, 117.6, 68.1, 44.9. Mass spectrum (API-TIS) m/z 325 (M-H), 327 (MH$^+$); Anal. calcd for C$_8$H$_{11}$ClN$_4$O$_4$S$_2$0: C, 30.06; H, 3.54; N, 16.70. Found: C, 30.26; H, 3.40; N, 16.38.

57b. Acetamide, N-[[7-(aminosulfonyl)-6-chloro-3,4-dihydro-1,1-dioxido-2H-1,2,4-benzothiadiazin-3-yl]methyl]-2-bromo-

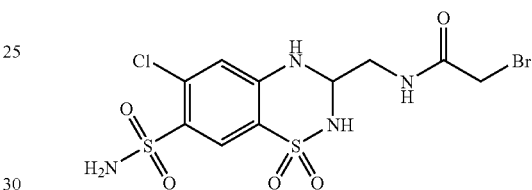

To a suspension of the product of Example 57a (1.3 g, 3.98 mmol) in anhydrous dioxane (2 mL) was added dropwise bromoacetyl chloride (0.93 g, 0.49 mL, 6.0 mmol). The reaction mixture was heated at 60-90° C. for 45 minutes. The solvent was evaporated and diluted with CH$_2$Cl$_2$. The solid was filtered and recrystallized from CH$_2$Cl$_2$:EtOAc to give the title compound (1.5 g, 84%) as an off-white solid: mp 204-207° C.; Mass spectrum (API-TIS) m/z 445/447 (M-H), 447/449 (MH$^+$).

57c. Acetamide, N-[[7-(aminosulfonyl)-6-chloro-3,4-dihydro-1,1-dioxido-2H-1,2,4-benzothiadiazin-3-yl]methyl]-2-[bis[2-(nitrooxy)ethyl]amino]-

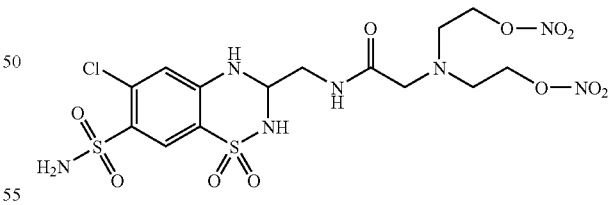

A mixture of the product of Example 57b (0.5 g, 1.12 mmol), the product of Example 49a (0.87 g, 3.4 mmol) and NaHCO$_3$ (0.31 g, 3.7 mmol) in DMF (6 mL) was stirred at room temperature for 28 hours. The residue, after evaporation of the solvent, was dissolved in a minimum amount of MeOH, the solid filtered and the filtrate was chromatographed on silica gel, eluting with CH$_2$Cl$_2$:MeOH (1:0.01 to 1:0.2) to give the title compound (0.2 g, 32% yield) as a white solid: mp 118° C. (with decomposition); $^1$H NMR (400 MHz, d$_6$-DMSO) δ 8.21 (s, 1H), 7.00 (s, 1H), 4.96-5.10 (m, 1H), 4.60-4.67 (m, 4H), 3.71-3.78 (m, 1H), 3.56-3.62 (m, 1H), 3.41 (s, 2H), 3.07 (br t, J=5.6 Hz, 4H); $^{13}$C NMR (100 MHz, d$_6$-DMSO) δ 174.4, 148.0, 136.9, 130.3, 127.7, 120.7, 118.9, 72.4, 66.9, 59.3, 53.1, 42.4; Mass spectrum (API-TIS) m/z 562 (MH$^+$); Anal. calcd for C$_{14}$H$_{20}$ClN$_7$O$_{11}$S$_2$: C, 29.92; H, 3.59; N, 17.45. Found: C, 29.65; H, 3.41; N, 17.20.

Example 58

2H-1,2,4-Benzothiadiazine-7-sulfonamide, 6-chloro-3,4-dihydro-2-[6-(nitrooxy)hexyl]-, 1,1-dioxide 58a. 1-Hexanol, 6-bromo-, nitrate

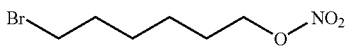

The title compound was prepared as a liquid (10 g, 98% yield) from 6-bromo-1-hexanol (8.15 g, 45 mmol) by following the procedure of Example 35a. $^1$H NMR (400 MHz, CDCl$_3$) δ 4.43 (t, J=6.8 Hz, 2H), 3.39 (t, J=6.8 Hz, 2H), 1.89-1.81 (m, 2H), 1.76-1.69 (m, 2H), 1.51-1.38 (m, 4H).

58b. 2H-1,2,4-Benzothiadiazine-7-sulfonamide, 6-chloro-3,4-dihydro-2-[6-(nitrooxy)hexyl]-, 1,1-dioxide

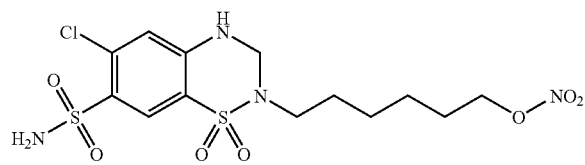

The title compound was synthesized as white prisms (12.3 g, 63% yield) from hydrochlorothiazide (13.1 g, 44 mmol), the product of Example 58a (10 g, 44 mmol), and cesium carbonate (7.17 g, 22 mmol) by following the procedure of Example 35b: mp 158-160° C.; $^1$H NMR (400 MHz, d$_4$-MeOH) δ 8.18 (s, 1H), 6.97 (s, 1H), 4.92 (s, 2H), 4.48 (t, J=6.4 Hz, 2H), 2.99 (t, J=6.8 Hz, 2H), 1.71 (m, 2H), 1.67 (m, 2H), 1.44 (m, 4H); Mass spectrum (API-TIS) m/z 443.2 and 445.3 (MH$^+$ for $^{35}$Cl and $^{37}$Cl respectively); Anal. Calcd. for C$_{13}$H$_{19}$ClN$_4$O$_7$S$_2$: C, 35.25; H, 4.32; N, 12.65; Found: C, 33.45; H, 4.26; N, 12.41.

Example 59

2H-1,2,4-Benzothiadiazine-7-sulfonamide, 6-chloro-3,4-dihydro-2-(3-hydroxypropyl)-, 1,1-dioxide

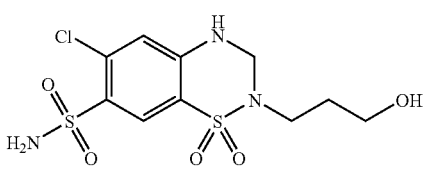

To a stirred solution of hydrochlorothiazide (3.15 g, 10.6 mmol) in DMF (30 mL) were added potassium carbonate (0.732 g, 5.3 mmol), and 3-bromo-1-propanol (1.47 g, 10.6 mmol). After being stirred for 22 hours at room temperature, the mixture was poured into water, and extracted with EtOAc. The organic layer was washed with aqueous NaCl, filtered through a pad of Na$_2$SO$_4$, and concentrated. Chromatography (silica gel; EtOAc, and then THF) and subsequent recrystallization from EtOAc: CH$_2$Cl$_2$ (1:1) gave the title compound (1.02 g, 27% yield) as white prisms: mp 160° C.; $^1$H NMR (400 MHz, d$_4$-MeOH) δ 8.18 (s, 1H), 6.97 (s, 1H), 4.93 (s, 2H), 3.63 (t, J=6.0 Hz, 2H), 3.09 (t, J=6.8 Hz, 2H), 1.84 (m, 2H); Mass spectrum (API-TIS) m/z 356.2 and 358.1 (MH$^+$ for $^{35}$Cl and $^{37}$Cl respectively).

Example 60

2H-1,2,4-Benzothiadiazine-7-sulfonamide, 6-chloro-3,4-dihydro-2-(5-hydroxypentyl)-, 1,1-dioxide

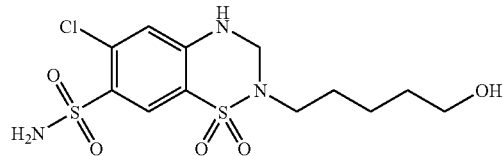

To a stirred solution of hydrochlorothiazide (3.65 g, 12.3 mmol) in DMF (30 mL) were added cesium carbonate (2.00 g, 6.15 mmol), and 5-bromo-1-pentanol (2.05 g, 12.3 mmol). After being stirred for 66 hours at room temperature, the mixture was poured into water, and extracted with EtOAc. The organic layer was washed with aqueous NaCl, filtered through a pad of Na$_2$SO$_4$, and concentrated. Chromatography (silica gel; EtOAc, and then THF) and subsequent recrystallization from EtOAc:CH$_2$Cl$_2$:Hexane (1:1:1) gave the title compound (2.21 g, 47% yield) as a white solid: mp 177-179° C.; $^1$H NMR (400 MHz, d$_4$-MeOH) δ 8.17 (s, 1H), 6.96 (s, 1H), 4.91 (s, 2H), 3.54 (t, J=6.4 Hz, 2H), 2.98 (t, J=7.6 Hz, 2H), 1.65 (m, 2H), 1.53 (m, 2H), 1.42 (m, 2H); Mass spectrum (API-TIS) m/z 384.3 and 386.2 (MH$^+$ for $^{35}$Cl and $^{37}$Cl respectively).

Example 61

2H-1,2,4-Benzothiadiazine-7-sulfonamide, 3,4-dihydro-3-[4-(nitrooxy)butyl]-6-(trifluoromethyl)-, 1,1-dioxide 61a. 1,3-Dioxane-2-butanol, 5,5-dimethyl-, nitrate

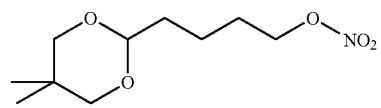

2-(4-Bromobutyl)-5,5-dimethyl-1,3-dioxane (34.8 g, 150 mmol, prepared by the reaction of neopentyl glycol and 3,4-dihydro-2H-pyran following the procedure in U.S. Pat. No. 4,847,391) was treated with silver nitrate (35.5 g, 210 mmol) in anhydrous acetonitrile. The resulting mixture was refluxed for 2 hours, cooled to room temperature and the precipitate was removed by filtration. The filtrate was evaporated at reduced pressure, and then extracted with ethyl acetate (2×). The combined extracts were washed with distilled water 61b. 2H-1,2,4-Benzothiadiazine-7-sulfonamide, 3,4-dihydro-3-[4-(nitrooxy)butyl]-6-(trifluoromethyl)-, 1,1-dioxide

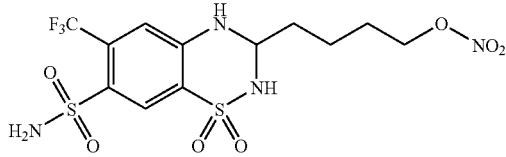

The crude product of Example 61a (2.36 g, 11 mmol) and 2-amino-6-(trifluoromethyl)-1,3-benzenedisulfonamide (1.595 g, 5 mmol) were mixed together in dioxane (75 mL) and concentrated hydrochloric acid (1 mL). The reaction mixture was refluxed overnight, cooled to room temperature, washed with saturated brine. The organic layer was separated and the solvent was evaporated at reduced pressure. The resulting residue was treated with water, swirled; water was decanted off and discarded. The residue was then extracted with ethyl acetate (2×). The combined extracts were washed with saturated aqueous sodium carbonate, water, brine, dried over sodium sulfate, filtered, and the filtrate was concentrated in vacuo to give the crude product. Purification by column chromatography over silica gel, eluting with 4% methanol in dichloromethane, gave an oil (1 g) that was crystallized from 40% ethyl acetate in hexane to give the title compound (850 mg, 38% yield) as a white solid: mp 171-177° C.; $^1$H NMR (400 MHz, d$_6$-DMSO) δ 8.22 (s, 1H), 8.15 (s, 1H), 7.89 (d, J=11.6 Hz, 1H), 7.58 (s, 2H), 6.35 (s, 1H), 4.85-4.79 (m, 1H), 4.56 (t, J=6.4 Hz, 2H), 1.90-1.65 (m, 4H), 1.60-1.45 (m, 2H); $^{13}$C NMR (d$_6$-DMSO) 6147.0, 134.8, 128.7, 126.0, 118.8, 117.5, 74.1, 66.2, 33.0, 26.1, 21.0; Mass Spectrum (API-TIS) m/z 449 (MH)$^+$, 466 (MNH$_4$)$^+$.

Example 62

2H-1,2,4-Benzothiadiazine-7-sulfonamide, 3,4-dihydro-3-(4-hydroxybutyl)-6-(trifluoromethyl)-, 1,1-dioxide

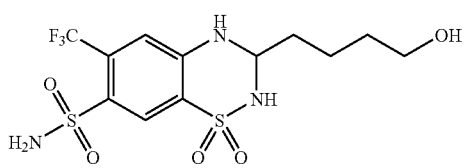

The title compound will be prepared by the reaction of 5-hydroxy-1-pentanal (2.04 g, 20 mmol) and 2-amino-6-(trifluoromethyl)-1,3-benzenedisulfonamide (2.87 g, 10 mmol) following the procedure for Example 26.

Example 63

Acetamide, N-[[7-(aminosulfonyl)-6-chloro-3,4-dihydro-1,1-dioxido-2H-1,2,4-benzothiadiazin-3-yl]methyl]-2-[bis[2-(nitrooxy)ethyl]amino]-N-methyl- 63a. 2H-1,2,4-Benzothiadiazine-7-sulfonamide, 6-chloro-3,4-dihydro-3-[(methylamino)methyl]-, 1,1-dioxide

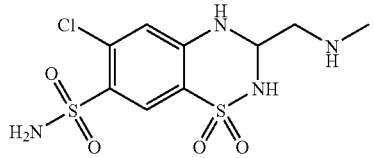

The title compound was prepared as a white solid (3.4 g, 49%) from 4-chloro-6-aminobenzene-1,3-disulfonamide (Aldrich) by following the procedure for Example 57a: mp 145-147° C.; $^1$H NMR (400 MHz, d$_6$-DMSO) δ 7.98 (s, 1H), 7.75-7.95 (br s, 2H), 7.30-7.60 (br s, 2H), 7.17 (s, 1H), 4.83-4.87 (m, 1H), 2.75-2.90 (m, 2H), 2.35 (s, 3H); $^{13}$C NMR (100 MHz, d$_6$-DMSO) δ 146.5, 134.3, 128.0, 125.4, 118.2, 117.3, 64.6, 53.4, 35.8. Mass spectrum (API-TIS) m/z 339 (M-H), 341 (MH$^+$); Anal. calcd for C$_9$H$_{13}$ClN$_4$O$_4$S$_2$: C, 31.72; H, 3.84; N, 16.44; Found: C, 31.64; H, 3.85; N, 16.19.

63b. N-{[7-(Aminosulfonyl)-6-chloro-1,1-dioxido-3,4-dihydro-2H-1,2,4-benzothiadiazin-3-yl]methyl}-2-bromo-N-methylacetamide

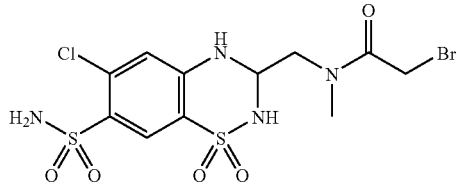

The title compound was prepared as a white solid (1.3 g, 96%) from the product of Example 63a by following the procedure for Example 57b: mp 150-152° C.; Mass spectrum (API-TIS) m/z 461/463 (MH$^+$).

63c. Acetamide, N-[[7-(aminosulfonyl)-6-chloro-3,4-dihydro-1,1-dioxido-2H-1,2,4-benzothiadiazin-3-yl]methyl]-2-[bis[2-(nitrooxy)ethyl]amino]-N-methyl-

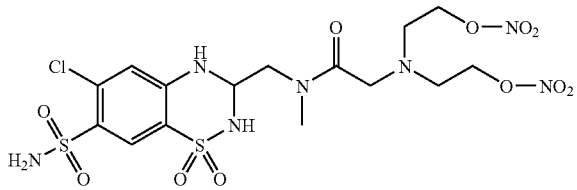

The title compound was prepared as an off-white solid (0.15 g, 24%) from the product of Example 63b by following the procedure for Example 57c: mp 183-185° C. (with decomposition); $^1$H NMR (400 MHz, d$_4$-MeOH) δ 8.20 (s, 1H), 7.00 (s, 1H), 5.07-5.13 (m, 1H), 4.60 (br t, J=5.2 Hz, 4H), 3.97-4.05 (m, 1H), 3.67 (br s, 2H), 3.46-3.55 (m, 1H), 3.23 (br s, 3H), 3.10 (br t, J=5.2 Hz, 4H); $^{13}$C NMR (100 MHz, d$_4$-MeOH) δ 163.9, 138.0, 126.9, 120.2, 117.6, 110.5, 108.9, 62.9, 56.0, 47.2, 42.8, 41.8, 27.4; Mass spectrum (API-TIS) m/z 574 (M-H), 576 (MH$^+$); Anal. calcd for C$_{15}$H$_{22}$ClN$_7$O$_{11}$S$_2$.0.3 mol EtOAc: C, 32.30; H, 4.05; N, 16.28; Found: C, 32.00; H, 3.66; N, 15.89.

Example 64

Spiro[2H-1,2,4-benzothiadiazine-3(4H), 4'-piperidine]-7-sulfonamide, 1'-[6 (nitrooxy)-1-oxohexyl]-6-(trifluoromethyl)-, 1,1-dioxide

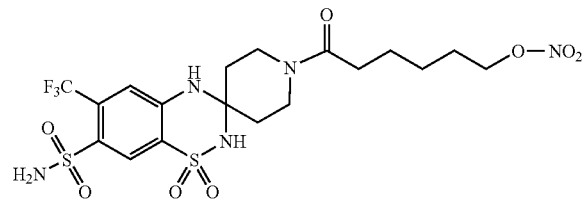

To a stirred mixture of the product of Example 5a (0.354 g, 2 mmol), N-(3-dimethylaminopropyl)-N'-ethylcarbodiimide hydrochloride (0.383 g, 2 mmol), 1-hydroxybenzotriazole hydrate (0.270 g, 2 mmol), and the product of Example 12b (0.780 g, 1.78 mmol) in a mixture of DMF (1 mL) and acetonitrile (20 mL) was added triethylamine (1.40 mL, 10 mmol). After the addition, the mixture was stirred at room temperature for 1 hour. The mixture was concentrated to remove the volatiles, taken up with EtOAc, washed with water, aqueous NaHCO$_3$, and aqueous NaCl. The organic layer was dried over Na$_2$SO$_4$, filtered, and concentrated to give a solid. Chromatography (silica gel, THF for loading, EtOAc for eluting) of the crude product and subsequent recrystallization from EtOAc:Hexane (5:1) gave the title compound (0.460 g, yield 46%) as white prisms: mp 162-165° C. (with decomposition; $^1$H NMR (400 MHz, d$_4$-MeOH) δ 8.33 (s, 1H), 7.22 (s, 1H), 4.48 (t, J=8.0 Hz, 2H), 4.37 (m, 1H), 3.85 (m, 1H), 3.48 (m, 1H), 3.09 (m, 1H), 2.52 (m, 1H), 2.46 (t, J=8.0 Hz, 2H), 2.32 (m, 1H), 1.76-1.60 (m, 6H), 1.49-1.43 (m, 2H). Mass spectrum (API-TIS) m/z 560.1 (MH$^+$).

Example 65

(5-{[{[7-(Aminosulfonyl)-6-chloro-1,1-dioxido-3,4-dihydro-2H-1,2,4-benzothiadiazin-3-yl]methyl}(methyl)amino]carbonyl}-1,3-phenylene)bis(methylene) dinitrate 65a. 3,5-Bis[(nitrooxy)methyl]benzoic acid

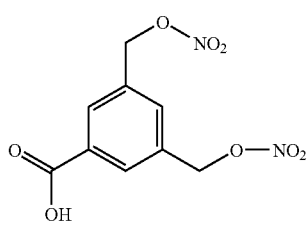

A solution of 3,5-bis(hydroxymethyl)benzoic acid (1.7 g, 9.3 mmol, prepared as described in *Tetrahedron* 49: 8761, 1993) in THF (100 mL) was treated with a pre-mixed solution of fuming nitric acid (2.2 mL, 47.1 mol) in acetic anhydride (25 mL) and stirred at room temperature for 1 hour. The reaction mixture was evaporated to dryness under reduced pressure and the product was purified by silica gel column chromatography eluting with EtOAc/hexane (3:2, R$_f$=0.2) to obtained the title compound (1.28 g, 51% yield) as a white solid: mp 39-41° C.; $^1$H NMR (400 MHz, CDCl$_3$) δ 12.46 (br, 1H), 8.17 (s, 2H), 7.75 (s, 1H), 5.52 (s, 4H); $^{13}$C NMR (100 MHz, CDCl$_3$) δ 170.6, 134.1, 133.9, 131.2, 130.4, 73.2; Mass Spectrum (API-TIS) m/z 271 (M-H)$^-$.

65b. [5-(Chlorocarbonyl)-1,3-phenylene]bis(methylene)dinitrate

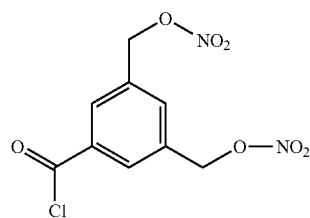

Oxalyl chloride (0.4 mL, 4.4 mmol) was added to a solution of the product of Example 65a (0.9 g, 3.4 mmol) in CH$_2$Cl$_2$ (50 mL) and DMF (50 µL) and stirred at room temperature for 1 hour. The reaction mixture was evaporated to dryness and dried under vacuum to give the title compound as a light colored oil. The product was use in the next step without purification. $^1$H NMR (400 MHz, CDCl$_3$) δ 8.18 (s, 2H), 7.82 (s, 1H), 5.55 (s, 4H); $^{13}$C NMR (100 MHz, CDCl$_3$) δ 167.2, 135.3, 134.6, 134.4, 131.9, 72.7.

65c. (5-{[(2,2-Dimethoxyethyl)(methyl)amino]carbonyl}-1,3-phenylene)bis(methylene) dinitrate

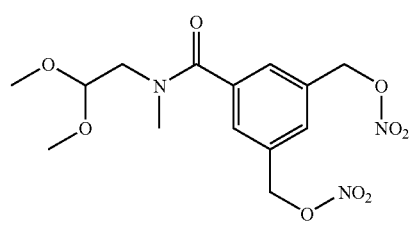

(Methylamino)acetaldehyde dimethyl acetal (0.5 mL, 3.9 mmol) and NEt$_3$ (0.5 mL, 3.6 mmol) was added to the crude product of Example 65b in CH$_2$Cl$_2$ (50 mL) and stirred at room temperature for 5 hours. The reaction was partitioned between CH$_2$Cl$_2$ (100 mL) and 3N HCl (50 mL). The organic extract was washed with water, brine, dried over Na$_2$SO$_4$, filtered, concentrated and dried under vacuum. The product was separated by silica gel column chromatography eluting with EtOAc/hexane (R$_f$=0.23 in 3:2) to give the title compound as a mixture of the Z, E isomers (1.1 g, 84% yield) as an oil: Mass Spectrum (API-TIS) m/z 374 (MH)$^+$.

65d. (5-{[{[7-(Aminosulfonyl)-6-chloro-1,1-di-oxido-3,4-dihydro-2H-1,2,4-benzothiadiazin-3-yl]methyl}(methyl)amino]carbonyl}-1,3-phenylene)bis(methylene)dinitrate

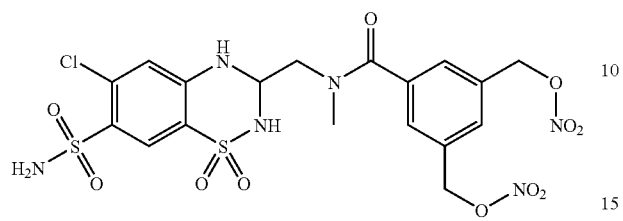

A mixture of 4-amino-6-chloro-1,3-benzenedisulfonamide (0.8 g, 2.8 mmol), the product of Example 65c (1.1 g, 2.8 mmol) and concentrated HCl (0.25 mL, 3.0 mmol) in dioxane (30 mL) was heated to 90° C. for 1.5 hours. The reaction mixture was evaporated to dryness under reduced pressure. The resulting material was partitioned between EtOAc (100 mL×2) and 3N HCl (50 mL). The organic extract was washed with water, brine, dried over $Na_2SO_4$, filtered, concentrated and dried under vacuum. The product was purified by silica gel column chromatography eluting with EtOAc/hexane ($R_f$=0.25 in 5:1) to give the title compound as a mixture of the Z, E isomers, as a white solid (0.7 g, 41% yield): mp 137° C. (with decomposition); $^1H$ NMR (400 MHz, $d_6$DMSO, 350.1° K) δ 8.06 (s, 1H), 8.0-7.8 (m, 2H), 7.65 (s, 1H), 7.59 (s, 2H), 7.28 (br, 2H), 6.98 (s, 1H), 5.66 (s, 4H), 5.1-5.0 (m, 1H), 4.1-4.0 (m, 1H), 3.6-3.5 (m, 1H), 2.98 (s, 3H); Mass Spectrum (API-TIS) m/z 595 (MH)$^+$. Anal. calcd for $C_{18}H_{19}ClN_6O_{11}S_2$: C, 36.34; H, 3.22; N, 14.13; Found: C, 36.06; H, 3.00; N, 13.83.

Example 66

2H-1,2,4-Benzothiadiazine-7-sulfonamide, 6-chloro-3,4-dihydro-2-(6-hydroxyhexyl)-, 1,1-dioxide

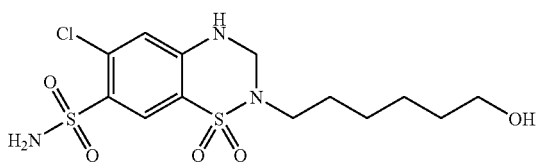

To a stirred solution of hydrochlorothiazide (6.25 g, 21 mmol) in DMF (60 mL) were added cesium carbonate (3.32 g, 10.2 mmol), and 6-bromo-1-hexanol (3.70 g, 20.4 mmol). After stirring for 25 hours at room temperature, the mixture was poured into water, and extracted with EtOAc. The organic layer was washed with aqueous NaCl, filtered through a pad of $Na_2SO_4$, and concentrated. Chromatography (silica gel; EtOAc, and then THF) and subsequent recrystallization from EtOAc: $CH_2Cl_2$ (1:3) gave the title compound (3.02 g, 37% yield) as a white solid: mp 176-179° C.; $^1H$ NMR (400 MHz, $d_4$-methanol) δ 8.17 (s, 1H), 6.96 (s, 1H), 3.54 (t, J=6.8 Hz, 2H), 2.98 (t, J=6.8 Hz, 2H), 1.65-1.62 (m, 2H), 1.54-1.51 (m, 2H), 1.39-1.38 (m, 4H). Mass spectrum (API-TIS) m/z 398.2 and 400.3 (MH$^+$ for $^{35}$Cl and $^{37}$Cl respectively).

Example 67

2H-1,2,4-Benzothiadiazine-7-sulfonamide, 6-chloro-3,4-dihydro-2-[(2E)-4-(nitrooxy)-2-butenyl]-, 1,1-dioxide 67a. 2-Buten-1-ol, 4-bromo-, nitrate, (2E)-

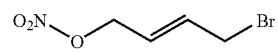

To a stirred solution of trans-1,4-dibromo-2-butene (ACROS, 7 g, 32.7 mmol) in $CH_3CN$ (40 mL) at room temperature, was added silver nitrate (5.6 g, 32.7 mmol). The reaction mixture was stirred at room temperature for 16 hours. The residue after filtration and evaporation of the solvent was chromatographed on silica gel eluting with EtOAc:Hexane (0.1:1) to give the title compound (3 g, 47% yield) as an oil. $^1H$ NMR (400 MHz, $CDCl_3$) δ 6.06-6.16 (m, 1H), 5.79-5.88 (m, 1H), 4.92 (d, J=6.4 Hz, 2H), 3.93 (d, J=7.2 Hz, 2H). $^{13}C$ NMR (100 MHz, $CDCl_3$) δ 134.2, 125.0, 72.0, 30.4.

67b. 2H-1,2,4-Benzothiadiazine-7-sulfonamide, 6-chloro-3,4-dihydro-2-[(2E)-4-(nitrooxy)-2-butenyl]-, 1,1-dioxide

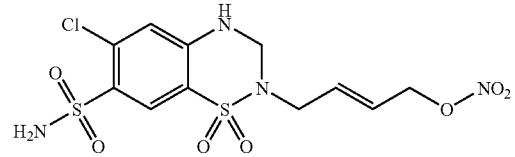

A mixture of the product of Example 67a (0.78 g, 4.0 mmol), hydrochlorothiazide (ONBIO Inc., 1 g, 3.4 mmol) and $K_2CO_3$ (0.46 g, 3.3 mmol) in anhydrous DMF (5 mL) was stirred at room temperature for 3 hours. The reaction mixture was then diluted with EtOAc, filtered and evaporated. The residue was re-dissolved in EtOAc, washed with ice cold 0.1 N HCl, dried over $Na_2SO_4$. The residue after filtration and evaporation of the solvent was chromatographed on silica gel eluting with $CH_2Cl_2$:MeOH (1:0.1) to give the title compound (0.39 g, 28% yield) as a white solid: mp 160-162° C. (with decomposition); $^1H$ NMR (400 MHz, $d_6$-DMSO) δ 8.01-8.03 (br s, 2H), 7.51 (s, 2H), 7.05 (s, 1H), 5.94-6.02 (m, 1H), 5.83-5.91 (m, 1H), 5.05 (d, J=6.4 Hz, 2H), 4.82 (d, J=2.8 Hz, 2H), 3.58 (d, J=6.0 Hz, 2H); $^{13}C$ NMR (100 MHz, $d_6$-DMSO) δ 146.0, 134.9, 132.1, 128.8, 126.6, 125.3, 117.4, 115.6, 72.9, 57.8, 47.4. Mass spectrum (API-TIS) m/z 411 (M-H), 413 (MH$^+$), 430 (MNH$_4^+$). Anal. calcd for $C_{11}H_{13}ClN_4O_7S_2 \cdot$¼ mol $CH_2Cl_2$: C, 31.13; H, 3.13; N, 12.90. Found: C, 31.51; H, 2.93; N, 12.56.

Example 68

2H-1,2,4-Benzothiadiazine-7-sulfonamide, 2-[[3-(4-bromobutoxy)-5-[(nitrooxy)methyl]phenyl]methyl]-6-chloro-3,4-dihydro-, 1,1-dioxide

68a. 1,3-Benzenedimethanol, 5-hydroxy-

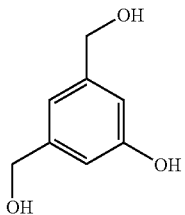

To a solution of LiAlH$_4$ (95 mL, 1 M in THF, 95 mmol) at 0° C. was added dropwise a solution of 5-hydroxyisophthalic acid dimethylester (Aldrich, 5 g, 24 mmol) in THF (100 mL). The reaction mixture was stirred at room temperature for 3 hours and then at 70° C. for 1.5 hours. The reaction mixture was carefully acidified with an aqueous solution of 10% H$_2$SO$_4$ at 0° C. The solid was filtered and extracted with a mixture of CH$_2$Cl$_2$:MeOH (1:1). The combined organic extracts were dried over Na$_2$SO$_4$, filtered and evaporated. The crude product was chromatographed on silica gel eluting with CH$_2$Cl$_2$:MeOH (9:1 to 7:3) to give the title compound (3.6 g, 98% yield) as a white solid: mp 70-72° C. $^1$H NMR (400 MHz, d$_3$-MeOD) δ 6.80 (s, 1H), 6.70 (s, 2H), 4.52 (s, 4H). $^{13}$C NMR (100 MHz, d$_3$-MeOD) δ 158.7, 144.3, 117.6, 113.7, 65.1. Mass spectrum (API-TIS) m/z 155 (MH$^+$), 153 (M-H), 172 (MNH$_4^+$).

68b. 1,3-Benzenedimethanol, 5-(4-bromobutoxy)-

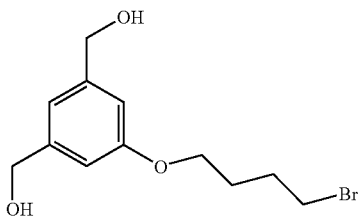

A mixture of the product from Example 68a (2 g, 13 mmol), dibromobutane (11.5 mL, 20.6 g, 95 mmol) and K$_2$CO$_3$ (1.9 g, 13.8 mmol) in anhydrous DMF (15 mL) was stirred at room temperature for 2 days. The residue after filtration and evaporation was chromatographed on silica gel eluting with CH$_2$Cl$_2$:MeOH (9:1 to 7:3 to 1:1) to give the title compound (1.6 g, 43% yield) as an off-white solid: mp 46-48° C. $^1$H NMR (400 MHz, CDCl$_3$) δ 6.89 (s, 1H), 6.79 (s, 2H), 4.60 (s, 4H), 3.98 (t, J=6.0 Hz, 2H), 3.47 (t, J=6.4 Hz, 2H), 2.25-2.40 (br s, 2H), 1.95-2.08 (m, 2H), 1.85-1.98 (m, 2H). $^{13}$C NMR (100 MHz, CDCl$_3$) δ 159.5, 142.9, 117.7, 112.2, 67.1, 65.1, 33.6, 29.6, 28.0. Mass spectrum (API-TIS) m/z 289/291 (MH$^+$), 306/308 (MNH$_4^+$), 271/273 (M-OH). Anal. calcd. for C$_{12}$H$_{17}$BrO$_3$: C, 49.84; H, 5.93. Found: C, 50.09; H, 5.97.

68c. 1,3-Benzenedimethanol, 5-(4-bromobutoxy)-, dinitrate

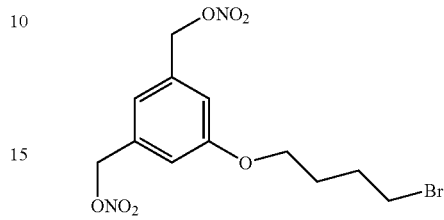

Fuming HNO$_3$ (1.2 g, 0.8 mL, 19 mmol) was added dropwise to Ac$_2$O (3 g, 2.8 mL, 29.7 mmol) at 0° C. The reaction mixture was stirred at 0° C. for 1 hour. A solution of the product from Example 68b (1.1 g, 3.8 mmol) in EtOAc (15 mL) was then added dropwise over 15 minutes. The resulting mixture was stirred at 0° C. for 1 hour, diluted with EtOAc, washed with an ice cold solution of 10% NaHCO$_3$, water and dried over Na$_2$SO$_4$. The residue after filtration and evaporation of the solvent was chromatographed on silica gel eluting with hexane:EtOAc (9:1 to 7:3) to give the title compound (0.9 g, 63% yield) as a semi-solid. $^1$H NMR (400 MHz, CDCl$_3$) δ 7.00 (s, 1H), 6.93 (s, 2H), 5.40 (s, 4H), 4.03 (t, J=6.0 Hz, 2H), 3.50 (t, J=6.4 Hz, 2H), 2.02-2.12 (m, 2H), 1.90-2.02 (m, 2H). $^{13}$C NMR (100 MHz, CDCl$_3$) δ 159.7, 134.7, 121.3, 115.8, 74.1, 67.4, 33.4, 29.5, 27.9. Mass spectrum (API-TIS) m/z 396 (MNH$_4^+$).

68d. 2H-1,2,4-Benzothiadiazine-7-sulfonamide, 2-[[3-(4-bromobutoxy)-5[(nitrooxy)methyl]phenyl]methyl]-6-chloro-3,4-dihydro-, 1,1-dioxide

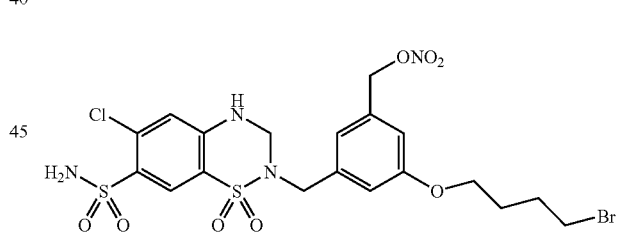

A mixture of the product of Example 68c (0.82 g, 2.2 mmol), hydrochlorothiazide (ONBIO Inc., 0.77 g, 2.6 mmol) and K$_2$CO$_3$ (0.29 g, 2.1 mmol) in anhydrous DMF (5 mL) was stirred at 0° C. for 30 minutes. Then the resulting mixture was gradually warm to room temperature, and stirred at room temperature for 3 hours. The reaction mixture was then diluted with EtOAc, filtered and evaporated. The residue was re-dissolved in EtOAc, washed with ice cold 0.1 N HCl, water and dried over Na$_2$SO$_4$. The crude product was chromatographed on silica gel eluting with CH$_2$Cl$_2$:EtOAc:MeOH (1:1:0.1) to give the title compound (0.4 g, 30% yield) as a white solid: mp 80° C. $^1$H NMR (400 MHz, CDCl$_3$) δ 8.06 (s, 2H), 7.54 (s, 2H), 6.90-7.10 (m, 4H), 5.53 (s, 2H), 4.77 (d, J=2.4 Hz, 2H), 4.07 (s, 2H), 4.02 (t, J=6.0 Hz, 2H), 3.60 (t, J=5.6 Hz, 2H), 1.90-2.02 (m, 2H), 1.78-1.90 (m, 2H). $^{13}$C NMR (100 MHz, CDCl$_3$) δ 158.8, 146.0, 137.5, 135.0, 134.1, 128.9, 126.7, 121.2, 117.5, 115.6, 114.5, 74.7, 66.8, 58.0, 49.5, 34.8, 29.0, 27.3. Mass spectrum (API-TIS) m/z 613 (MH$^+$). Anal. calcd. for $C_{19}H_{22}BrClN_4O_8S_2$: C, 37.17; H, 3.61; N, 9.13. Found: C, 37.32; H, 3.42; N, 8.88.

Example 69

2H-1,2,4-Benzothiadiazine-7-sulfonamide, 2-[4-[3,5-bis[(nitrooxy)methyl]phenoxy]butyl]-6-chloro-3,4-dihydro-, 1,1-dioxide 69a. 2H-1,2,4-Benzothiadiazine-7-sulfonamide, 2-[4-[3,5-bis(hydroxymethyl)phenoxy]butyl]-6-chloro-3,4-dihydro-, 1,1-dioxide

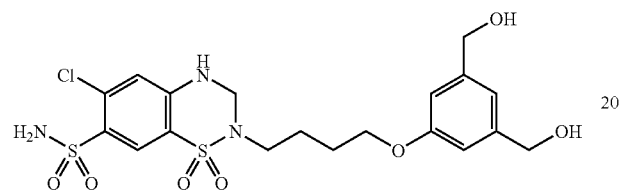

A mixture of the product of Example 68b (2.74 g, 9.5 mmol), hydrochlorothiazide (ONBIO Inc., 3.38 g, 11.4 mmol) and $K_2CO_3$ (1.3 g, 9.4 mmol) in anhydrous DMF (20 mL) was stirred at room temperature for 16 hours. The solvent was evaporated. The residue was suspended in EtOAc, washed with ice cold 0.1 N HCl, water and dried over $Na_2SO_4$. The crude product was chromatographed on silica gel eluting with $CH_2Cl_2$:MeOH (9:1 to 7:3 to 1:1) to give the title compound (1.2 g, 25% yield) as a white solid: mp 78-80° C. $^1$H NMR (400 MHz, $d_6$-DMSO) δ 7.98-8.02 (m, 2H), 7.50 (br s, 2H), 7.05 (s, 1H), 6.83 (br s, 1H), 6.72 (br s, 2H), 5.12 (br t, J=6.0 Hz, 2H), 4.92 (d, J=2.8 Hz, 2H), 4.44 (d, J=5.2 Hz, 4H), 3.92-3.98 (m, 2H), 2.90-3.00 (m, 2H), 1.70-1.80 (m, 4H). $^{13}$C NMR (100 MHz, $d_6$-DMSO) δ 158.5, 146.0, 143.8, 134.8, 128.6, 126.7, 117.3, 116.5, 115.7, 110.6, 66.8, 62.8, 58.2, 45.9, 25.9, 24.3. Mass spectrum (API-TIS) m/z 504 (M-H), 506 (MH$^+$), 523 (MNa$^+$), 488 (M-OH), 470 (M-2× OH). Anal. calcd. for $C_{19}H_{24}ClN_3O_7S_2$: C, 45.10; H, 4.78; N, 8.30. Found: C, 44.90; H, 4.59; N, 8.16.

69b. 2H-1,2,4-Benzothiadiazine-7-sulfonamide, 2-[4-[3,5-bis[(nitrooxy)methyl]phenoxy]butyl]-6-chloro-3,4-dihydro-, 1,1-dioxide

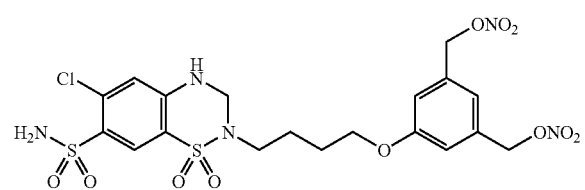

To a mixture of fuming HNO$_3$ (0.44 g, 0.29 mL, 6.9 mmol) and Ac$_2$O (1.1 g, 1 mL, 11.1 mmol) at –10° C. was added dropwise a solution of the product from Example 69a (0.7 g, 1.4 mmol) in THF (6 mL) over a period of 15 minutes. The reaction mixture was stirred at –10 to 0° C. for 2 hours, diluted with EtOAc, washed with an ice-cold solution of 10% NaHCO$_3$, water and dried over Na$_2$SO$_4$. The residue after filtration and evaporation of the solvent was chromatographed on silica gel eluting with CH$_2$Cl$_2$:MeOH (9:1 to 7:3 to 1:1) to give the title compound (0.9 g, 63% yield) as a white solid: mp 65-67° C. $^1$H NMR (400 MHz, $d_6$-DMSO) δ 7.98-8.02 (m, 2H), 7.50 (s, 2H), 7.11 (s, 1H), 7.08 (s, 2H), 7.05 (s, 1H), 5.55 (s, 4H), 4.92 (br s, 2H), 3.95-4.02 (m, 2H), 2.90-2.98 (m, 2H), 1.70-1.80 (m, 4H). $^{13}$C NMR (100 MHz, $d_6$-DMSO) δ 158.8, 146.0, 134.8, 134.4, 128.6, 126.7, 121.5, 117.3, 115.9, 74.5, 67.3, 58.2, 45.9, 25.7, 24.2. Mass spectrum (API-TIS) m/z 594 (M-H). Anal. calcd. for $C_{19}H_{22}ClN_5O_{11}S_2$: C, 38.29; H, 3.72; N, 11.75. Found: C, 38.58; H, 3.79; N, 11.55.

Example 70

2H-1,2,4-Benzothiadiazine-7-sulfonamide, 2-[3-[3,5-bis[(nitrooxy)methyl]phenoxy]propyl]-6-chloro-3,4-dihydro-, 1,1-dioxide 70a. 1,3-Benzenedimethanol, 5-(3-bromopropoxy)-

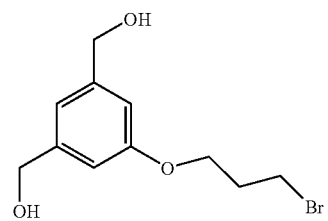

The title compound was prepared as a white solid (1.1 g, 31%) from the product of Example 68a (2 g, 13 mmol), dibromopropane (7.9 g, 39.1 mmol) and K$_2$CO$_3$ (1.9 g, 13.8 mmol) in anhydrous DMF (8 mL) by following the procedure for Example 68b. Mp 70-71° C. $^1$H NMR (400 MHz, $d_3$-MeOD) δ 7.63 (br s, 1H), 7.55 (br s, 2H), 5.24 (s, 4H), 4.84 (t, J=5.6 Hz, 2H), 4.42 (t, J=6.4 Hz, 2H), 2.95-3.05 (m, 2H). $^{13}$C NMR (100 MHz, $d_3$-MeOD/$d_6$-DMSO) δ 159.1, 144.4, 117.5, 111.4, 65.6, 63.5, 32.5, 31.2. Mass spectrum (API-TIS) m/z 275/277 (MH$^+$), 292/294 (MNH$_4^+$), 257/259 (M-OH).

70b. 2H-1,2,4-Benzothiadiazine-7-sulfonamide, 2-[3-[3,5-bis(hydroxymethyl)phenoxy]propyl]-6-chloro-3,4-dihydro-, 1,1-dioxide

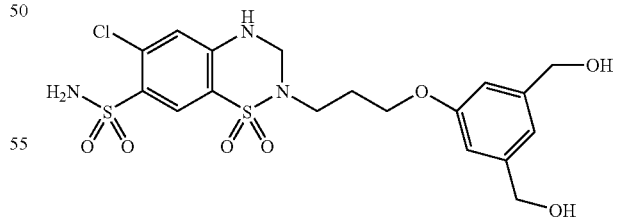

The title compound was prepared as a white solid (1.24 g, 63%) from the product of Example 70a (1.1 g, 4 mmol), hydrochlorothiazide (ONBIO Inc., 1.4 g, 4.7 mmol) and K$_2$CO$_3$ (0.55 g, 4 mmol) in anhydrous DMF (10 mL) by following the procedure for Example 69a. Mp 155-157° C. $^1$H NMR (400 MHz, $d_6$-DMSO) δ 7.98-8.05 (m, 2H), 7.51 (s, 2H), 7.07 (s, 1H), 6.84 (s, 1H), 6.73 (s, 2H), 5.13 (t, J=6.0 Hz, 2H), 4.94 (d, J=2.4 Hz, 2H), 4.44 (d, J=5.6 Hz, 4H), 3.95-4.05

(m, 2H), 3.08 (t, J=6.8 Hz, 2H), 2.04 (t, J=6.8 Hz, 2H). $^{13}$C NMR (100 MHz, d$_6$-DMSO) δ 158.3, 146.0, 143.9, 134.8, 128.7, 126.7, 117.3, 116.6, 115.6, 110.6, 66.6, 64.4, 62.8, 58.5, 43.4, 28.8, 27.6, 23.5. Mass spectrum (API-TIS) m/z 490 (M-H), 509 (MNH$_4^+$), 474 (M-OH), 457 (M-2×OH). Anal. calcd. for C$_{18}$H$_{22}$ClN$_3$O$_7$S$_2$.¼ mol EtOAc: C, 44.44; H, 4.70; N, 8.18. Found: C, 44.59; H, 4.49; N, 7.97.

70c. 2H-1,2,4-Benzothiadiazine-7-sulfonamide, 2-[3-[3,5-bis[(nitrooxy)methyl]phenoxy]propyl]-6-chloro-3,4-dihydro-, 1,1-dioxide

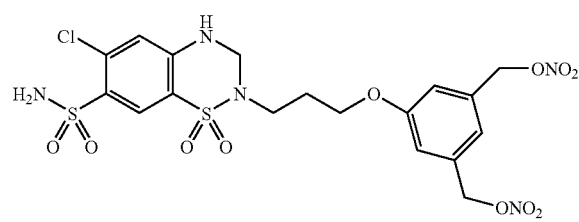

The title compound was prepared as a white foam (0.5 g, 60%) from the product of Example 70b (0.7 g, 1.4 mmol), fuming HNO$_3$ (0.45 g, 0.3 mL, 7.1 mmol) and Ac$_2$O (1.2 g, 1 mL, 11.4 mmol) in THF (5 mL) by following the procedure for Example 69b. Mp 70-72° C. $^1$H NMR (400 MHz, d$_6$-DMSO) δ 8.01 (s, 2H), 7.49 (s, 2H), 7.12 (s, 1H), 7.08 (s, 2H), 7.05 (s, 1H), 5.74 (s, 4H), 4.93 (d, J=2.4 Hz, 2H), 4.05 (t, J=6.0 Hz, 2H), 3.07 (t, J=6.8 Hz, 2H), 1.95-2.10 (m, 2H). $^{13}$C NMR (100 MHz, d$_6$-DMSO) δ 158.7, 146.0, 134.9, 134.4, 128.7, 126.8, 121.7, 117.3, 116.0, 115.6, 74.5, 65.0, 58.5, 43.4, 27.5. Mass spectrum (API-TIS) m/z 599 (MNH$_4^+$). Anal. calcd. for C$_{18}$H$_{20}$ClN$_5$O$_{11}$S$_2$: C, 37.15; H, 3.46; N, 12.03. Found: C, 37.35; H, 3.61; N, 11.76.

Example 71

2H-1,2,4-Benzothiadiazine-7-sulfonamide, 2-[2-[3,5-bis[(nitrooxy)methyl]phenoxy]ethyl]-6-chloro-3,4-dihydro-, 1,1-dioxide 71a. 1,3-Benzenedimethanol, 5-(2-bromoethoxy)-

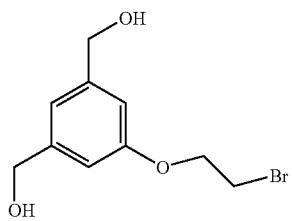

The title compound was prepared as a white foam (1.6 g, 38%) from the product of Example 68a (2.5 g, 16.2 mmol), dibromoethane (9.1 g, 4.2 mL, 48.6 mmol) and K$_2$CO$_3$ (2.4 g, 17 mmol) in anhydrous DMF (12 mL) by following the procedure for Example 68b. Mass spectrum (API-TIS) m/z 262 (MH$^+$).

71b. 2H-1,2,4-Benzothiadiazine-7-sulfonamide, 2-[2-[3,5-bis(hydroxymethyl)phenoxy]ethyl]-6-chloro-3,4-dihydro-, 1,1-dioxide

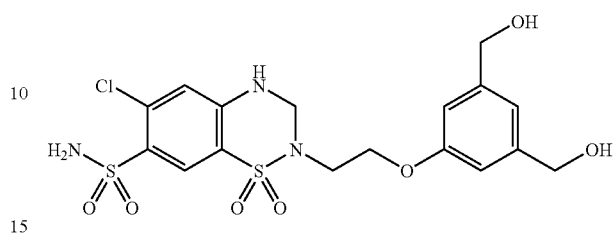

The title compound was prepared as a white solid (1.1 g, 60%) from the product of Example 71a (1 g, 3.8 mmol), hydrochlorothiazide (ONBIO Inc., 1.36 g, 4.6 mmol) and K$_2$CO$_3$ (0.53 g, 3.8 mmol) in anhydrous DMF (10 mL) by following the procedure for Example 69a. Mp 80-82° C. $^1$H NMR (400 MHz, d$_6$-DMSO) δ 7.09 (s, 1H), 8.04 (s, 1H), 7.52 (s, 2H), 7.06 (s, 1H), 6.87 (s, 1H), 6.75 (s, 2H), 5.15 (t, J=6.0 Hz, 2H), 5.03 (d, J=2.4 Hz, 2H), 4.44 (d, J=5.6 Hz, 4H), 4.17 (t, J=5.2 Hz, 2H), 3.27-3.34 (m, 2H). $^{13}$C NMR (100 MHz, d$_6$-DMSO) δ 158.0, 146.0, 144.0, 134.9, 128.7, 126.6, 117.4, 116.9, 115.9, 110.6, 66.0, 62.8, 59.3, 45.7. Mass spectrum (API-TIS) m/z 476 (M-H), 495 (MNH$_4^+$), 460 (M-OH), 443 (M-2×OH). Anal. calcd. for C$_{17}$H$_{20}$ClN$_3$O$_7$S$_2$.0.3 mol EtOAc: C, 43.34; H, 4.48; N, 8.33. Found: C, 43.36; H, 4.22; N, 7.92.

71c. 2H-1,2,4-Benzothiadiazine-7-sulfonamide, 2-[2-[3,5-bis[(nitrooxy)methyl]phenoxy]ethyl]-6-chloro-3,4-dihydro-, 1,1-dioxide

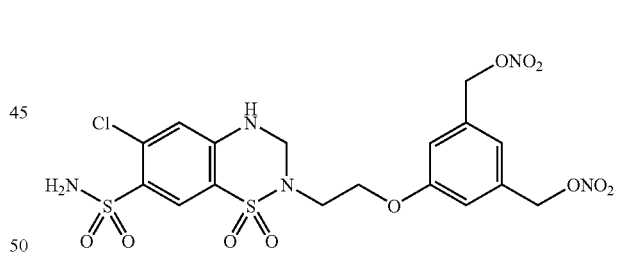

The title compound was prepared as a white foam (0.5 g, 84%) from the product of Example 71b (0.5 g, 1 mmol), fuming HNO$_3$ (0.32 g, 0.22 mL, 5.2 mmol) and Ac$_2$O (0.85 g, 0.8 mL, 8.4 mmol) in THF (5 mL) by following the procedure for Example 69b. Mp 72-75° C. $^1$H NMR (400 MHz, d$_6$-DMSO) δ 8.08 (s, 1H), 8.04 (s, 1H), 7.52 (s, 2H), 7.15 (s, 1H), 7.08 (s, 1H), 7.04 (s, 1H), 5.56 (s, 4H), 5.03 (br s, 2H), 4.21 (t, J=4.8 Hz, 2H), 3.36 (t, J=4.8 Hz, 2H). $^{13}$C NMR (100 MHz, d$_6$-DMSO) δ 158.3, 146.1, 134.9, 134.5, 128.7, 126.5, 121.9, 117.4, 116.0, 115.9, 74.4, 66.3, 59.2, 45.8. Mass spectrum (API-TIS) m/z 585 (MNH$_4^+$), 566 (M-H). Anal. calcd. for C$_{17}$H$_{18}$ClN$_5$O$_{11}$S$_2$.0.3 mol EtOAc: C, 37.04; H, 3.54; N, 11.61. Found: C, 37.27; H, 3.24; N, 11.66.

Example 72

2H-1,2,4-Benzothiadiazine-2-acetamide, 7-(aminosulfonyl)-6-chloro-3,4-dihydro-N,N-bis[3-(nitrooxy)propyl]-, 1,1-dioxide

72a. 3,3'-Iminobis-1-propanol, dinitrate (ester), nitrate (1:1) (salt)

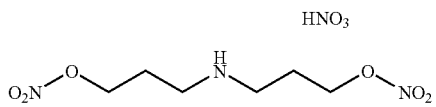

Fuming nitric acid (90%; 10.1 mL, 200 mmol) was added to ice-cold acetic anhydride (30 mL) and stirred in the ice bath for 15 minutes. Meanwhile, a solution of 3,3'-iminobis-1-propanol (Karl Industries, 6.66 g, 50 mmol) in ethyl acetate (50 mL) and THF (50 mL) was treated with concentrated nitric acid (3.13 mL, 50 mmol) at room temperature. The mixture was cooled to 0° C., and the solution of fuming nitric acid/acetic anhydride was added dropwise via addition funnel. After stirring at 0° C. for 1 hour, ether (100 mL) was added. The white solid was collected via filtration, and washed with additional ether. The solid was quickly dried under vacuum to give the title compound as a white solid (11.21 g, 78% yield): mp 102-104° C.; $^1$H NMR (400 MHz, $d_6$-DMSO) δ 8.43 (br s, 2H), 4.61 (t, J=7.0 Hz, 4H), 3.05 (br s, 4H), 2.02 (quin, J=7.0 Hz, 4H); $^{13}$C NMR (100 MHz, $CDCl_3$) δ 71.5, 44.2, 23.6; Mass spectrum (API-TIS) m/z 224 ($MH^+$).

72b. 2H-1,2,4-Benzothiadiazine-2-acetamide, 7-(aminosulfonyl)-6-chloro-3,4-dihydro-N,N-bis[3-(nitrooxy)propyl]-, 1,1-dioxide

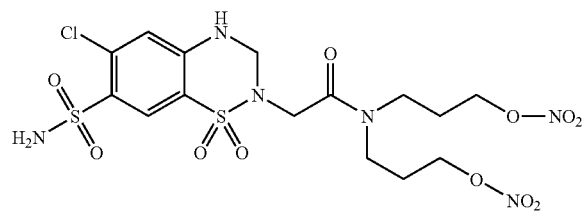

To a suspension of the product of Example 72a (9.0 mmol, 2.58 g) in 50 mL ethyl acetate was added an excess of saturated sodium bicarbonate until bubbling had stopped and both layers were clear. The organic layer was separated, washed with brine, and dried over sodium sulfate. The solvent was removed via rotary evaporation, and the pale yellow residue was dissolved in 5 mL DMF. This solution was added to a mixture of the product of Example 31a and 1-(3-(dimethylamino)propyl)-3-ethylcarbodiimide hydrochloride (EDAC, 0.690 g, 3.6 mmol) in DMF (25 mL) at 0° C. The reaction mixture was stirred at 0° C. for 4 hours. After evaporation of the solvent under reduced pressure, the residue was partitioned between ethyl acetate and water. The organic layer was washed with 2N HCl, water, brine, and dried over magnesium sulfate. After evaporation of the solvent, the residue was purified via column chromatography on silica gel, 25 to 75% ethyl acetate in dichloromethane gradient. Evaporation of the solvent gave a white amorphous solid, which was recrystallized from acetone/chloroform/ether to give the title compound as white crystals (0.366 g, 22% yield): mp 157-160° C. $^1$H NMR (400 MHz, $d_6$-DMSO) δ 8.03 (s, 1H), 8.02 (s, 1H), 7.53 (s, 2H), 7.07 (s, 1H), 4.95 (d, J=2.5 Hz, 2H), 4.52 (t, J=6.2 Hz, 4H), 3.85 (s, 2H), 3.39-3.34 (m, 4H), 1.95-1.88 (m, 4H); C NMR (100 MHz, $d_6$-DMSO) δ 166.9, 146.6, 135.5, 129.3, 127.0, 118.1, 116.9, 72.4, 71.7, 59.3, 47.1, 43.7, 42.5, 25.9, 25.0; Mass spectrum (API-TIS) m/z 561 ($MH^+$), 578 ($MNH_4^+$), 1121 (2 $MH^+$), 1138 ($2MNH_4^+$). Anal. calcd for $C_{15}H_{21}ClN_6O_{11}S_2$: C, 32.12; H, 3.77; N, 14.98. Found: C, 32.06; H, 3.65; N, 14.79.

Example 73

2H-1,2,4-Benzothiadiazine-7-sulfonamide, 2-[(3R)-3,4-bis(nitrooxy)butyl]-6-chloro-3,4-dihydro-, 1,1-dioxide

73a. 1,3-Dioxolane, 4-(2-bromoethyl)-2,2-dimethyl-, (4R)—

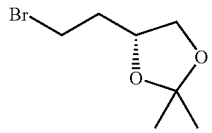

To a stirred solution of (4R)-4-(2-hydroxyethyl)-2,2-dimethyl-1,3-dioxolane (Aldrich, 10 g, 68 mmol) and triethylamine 919 mL, 136 mmol) in tetrahydrofuran (500 mL) at 0° C. was added methanesulfonyl chloride (6.6 mL, 85 mmol) via a pipette. The resulting mixture was stirred at the same temperature for 30 minutes before the addition of lithium bromide (59 g, 680 mmol). The reaction mixture was stirred at room temperature for 21 hours and then concentrated by rotary evaporation to remove most of the volatiles. The residue was partitioned between ethyl acetate and water. The organic layer was separated, and the aqueous layer was extracted with ethyl acetate. The combined organic extracts were washed with water twice, dried over sodium sulfate, filtered, and concentrated. The residue was purified by flash chromatography (silica gel, 0-20% EtOAc in hexane gradient) to give the title compound (11.3 g, 80% yield) as an oil. $^1$H NMR (400 MHz, $CDCl_3$) δ 4.24 (m, 1H), 4.08 (m, 1H), 3.57 (m, 1H), 3.49 (m, 2H), 2.20-1.90 (m, 2H), 1.39 (s, 3H), 1.34 (s, 3H). $^{13}$C NMR (100 MHz, $CDCl_3$) δ 108.77, 73.70, 68.61, 36.87, 29.13, 26.73, 25.31.

73b. 2H-1,2,4-Benzothiadiazine-7-sulfonamide, 2-[(3R)-3,4-bis(nitrooxy)butyl]-6-chloro-3,4-dihydro-, 1,1-dioxide

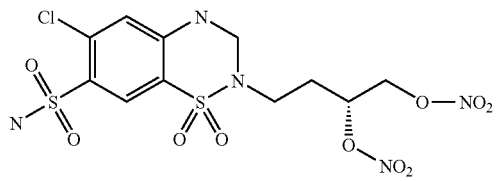

To a stirred solution of the product of Example 73a (5.43 g, 26.1 mmol) in methanol (120 mL) was added p-toluenesulfonic acid monohydrate (1 g). After stirring at ambient temperature for 69 hours, the mixture was concentrated by rotary evaporation. The residue was chromatographed (EtOAc, silica gel) twice to give the crude diol-bromide (1.20 g, 27% yield) as a colorless liquid. Nitric acid (90%, 2.7 mL, 57 mmol) was added to acetic anhydride (7 mL) at 0° C. with stirring. After 15 minutes, the crude diol-bromide (1.20 g, 7.12 mmol) in ethyl acetate (80 mL) was added, and the stirring was continued for one hour. The mixture was poured into a stirred mixture of 400 mL ethyl acetate and ice water (1:1), solid sodium bicarbonate (30 g) was added in portions over 10 minutes. The organic layer was separated, washed with aqueous sodium bicarbonate, dried over sodium sulfate, filtered, and concentrated. The residue was chromatographed (silica gel, 1:3 EtOAc:Hexane) to give the crude dinitrate-bromide (1.35 g, 73% yield) as a yellow oil. To a stirred solution of the crude dinitrate-bromide (1.35 g, 5.22 mmol), hydrochlorothiazide (1.79 g, 6 mmol) in DMF (20 mL) was added cesium carbonate (0.85 g, 2.61 mmol). After stirring at room temperature for 25 hours, the mixture was taken up with EtOAc (200 mL), washed with water and aqueous NaCl, filtered slowly through a pad of sodium sulfate, and concentrated. The residue was purified by column chromatography (0-30% EtOAc in $CH_2Cl_2$) to give a solid. Recrystallization of the solid from EtOAc:$CH_2Cl_2$ (1:2) gave the title compound (157 mg, 6.3% yield) as a white solid: mp 158-162° C. $^1$H NMR (400 MHz, $d_6$ DMSO) δ 8.06 (br, s, 1H), 8.03 (s, 1H), 7.56 (br, s, 2H), 7.10 (s, 1H), 5.56 (m, 1H), 5.04 (m, 1H), 5.02 (s, 2H), 4.78 (m, 1H), 3.18-3.01 (m, 2H), 2.19-2.00 (m, 2H). $^{13}$C NMR (100 MHz, $d_6$-DMSO) δ 147.03, 136.00, 129.71, 127.68, 118.51, 116.30, 78.48, 72.99, 59.59, 43.29, 28.18. Mass spectrum (API-TIS) m/z 476.0 and 478.1 (MH$^+$ for $^{35}$Cl and $^{37}$Cl respectively). Anal. Calcd. for $C_{11}H_{14}ClN_5O_{10}S_2$: C, 27.77; H, 2.97; N, 14.72. Found: C, 27.94; H, 2.75; N, 14.46.

Example 74

2H-1,2,4-Benzothiadiazine-7-sulfonamide, 6-chloro-3,4-dihydro-3-[2-(nitrooxy)ethyl]-, 1,1-dioxide 74a. 1,3-Dioxolane-2-ethanol, nitrate

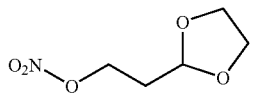

To a suspension of 2-(2-bromoethyl)-1,3-dioxolane (Aldrich Chemical Co., 7.24 g, 40 mmol) in acetonitrile (125 mL) was added silver nitrate (8.49 g, 50 mmol) and the reaction mixture was refluxed under nitrogen atmosphere for 3 hours. After filtration to remove the solid, the solvent was evaporated under reduced pressure and the residue was extracted with ethyl acetate, washed with water, brine, dried over sodium sulfate, filtered, and concentrated in vacuo to give the title compound in nearly quantitative yield and was used without further purification. $^1$H NMR (CDCl$_3$) δ 5.01 (t, J=4.4 Hz, 1H), 4.62 (t, J=6.6 Hz, 2H), 4.14-4.10 (m, 2H), 4.01-3.95 (m, 2H), 2.13-2.09 (m, 2H).

74b. 2H-1,2,4-Benzothiadiazine-7-sulfonamide, 6-chloro-3,4-dihydro-3-[2-(nitrooxy)ethyl]-, 1,1-dioxide

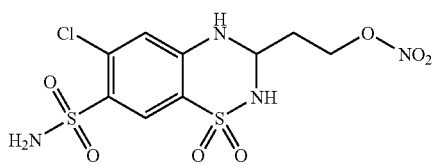

To the product of Example 74a (1.63 g, 10 mmol) and 2-amino-6-chloro-1,3-benzenedisulfonamide (Aldrich Chemical Co., 1.439 g, 5 mmol) in anhydrous dioxane (50 mL) was added Amberlyst (15) wet strongly acidic resin (3 g). The reaction mixture was stirred gently at room temperature for 2 days, then decanted into another flask. The resin was washed with dioxane (2 mL) and the washings added to the reaction mixture. Fresh Amberlyst (15) wet strongly acidic resin (2 g) was added to the reaction mixture and the stirring was continued at room temperature for 24 hours. The resin was removed by filtration and the filtrate was concentrated under reduced pressure. The resulting residue was treated with ethyl acetate and washed with saturated aqueous sodium carbonate, water, brine, dried over sodium sulfate, filtered, and concentrated in vacuo to give the crude product. Purification by column chromatography over silica gel, eluting with 3% methanol in dichloromethane gave 1.3 g of an oil that was triturated with 20% ethyl acetate in hexane to give the title compound (1.1 g, 54% yield) as a white solid: mp 113-117° C.; $^1$H NMR (d$_6$-DMSO) δ 8.03 (s, 1H), 8.01 (s, 1H), 7.97 (s, 1H), 7.52 (s, 2H), 6.98 (s, 1H), 4.96-4.89 (m, 1H), 4.77-4.65 (m, 2H), 2.28-2.15 (m, 2H); $^{13}$C NMR (d$_6$-DMSO) δ 146.3, 134.2, 128.6, 125.4, 118.2, 117.1, 69.1, 63.3, 30.4. Mass spectrum (API-TIS) m/z 404 (MH)$^+$, 406 (MH+2)$^+$.

Example 75

2H-1,2,4-Benzothiadiazine-7-sulfonamide, 2-[2,3-bis(nitrooxy)propyl]-6-chloro-3,4-dihydro-, 1,1-dioxide; 2H-1,2,4-benzothiadiazine-7-sulfonamide, 2-[2,3-bis(nitrooxy)propyl]-6-chloro-3,4-dihydro-4-nitro-, 1,1-dioxide; and 2H-1,2,4-benzothiadiazine-7-sulfonamide, 6-chloro-3,4-dihydro-2-[2-hydroxy-3-(nitrooxy)propyl]-4-nitro-, 1,1-dioxide 75a. 2H-1,2,4-Benzothiadiazine-7-sulfonamide, 6-chloro-3,4-dihydro-2-(2-propenyl)-, 1,1-dioxide

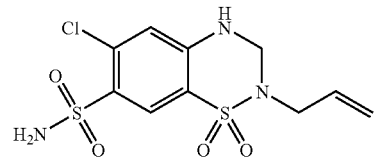

To a solution of hydrochlorothiazide (ONBIO, Inc., Ontario, Canada) (21.63 g, 72.7 mmol) in 60 mL DMF was added cesium carbonate (14.2 g, 44 mmol) and the suspension was cooled to 0° C. Allyl bromide (9.67 g, 6.76 mL, 79.9 mmol) was added as a neat liquid, and the mixture was stirred for 18 hours at room temperature. The solids were removed via filtration, and the solvent was removed under vacuum. The resulting residue was partitioned between ethyl acetate and water, and the organic layer was washed with water and brine, and dried over magnesium sulfate. After evaporation of the solvent, the residue was purified via column chromatography on silica gel, 25 to 50% ethyl acetate in dichloromethane gradient. The solvent was removed via rotary evaporation, and the residue was recrystallized from acetone/chloroform/ether to give the title compound (13.39 g, 55% yield) as off-white needles: mp 178-180° C.; $^1$H NMR (400 MHz, d$_6$-DMSO) δ 8.03 (s, 2H), 7.53 (s, 2H), 7.06 (s, 1H), 5.89-5.83 (m, 1H), 5.34 (dd, J=1.4 and 17.1 Hz, 1H), 5.29 (dd, J=1.1 and 10.2 Hz, 1H), 4.84 (s, 2H), 3.55 (d, J=6.2 Hz, 2H); C NMR (100 MHz, DMSO-d$_6$) δ 146.5, 135.4, 132.6, 129.2, 127.1, 120.3, 117.9, 116.2, 57.9, 49.3; Mass spectrum (API-TIS) m/z 338 (MH$^+$), 355 (MNH$_4^+$), 692 (2MNH$_4^+$)

75b. 2H-1,2,4-Benzothiadiazine-7-sulfonamide, 6-chloro-2-(2,3-dihydroxypropyl)-3,4-dihydro-, 1,1-dioxide

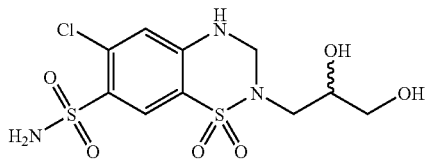

To a solution of the product of Example 75a (1.69 g, 5.0 mmol) in acetone (25 mL) at room temperature was added osmium tetroxide (Aldrich, 0.3 mL, 4% in water, 0.05 mmol), followed by pyridine (catalytic, 0.01 mL) and N-methylmorpholine N-oxide (TCI, 12.5 mmol, 50% in water, 2.59 mL). The reaction mixture was stirred overnight at room temperature. The next day, additional N-methylmorpholine N-oxide (0.5 mL) was added, and stirring was continued overnight. The reaction mixture was quenched with saturated sodium thiosulfate (2 mL) and some solid sodium sulfite. After 2 hours, the reaction was extracted with ethyl acetate (3×). The organic layer was washed with water and brine, and dried over magnesium sulfate. After evaporation of the solvent, the residue was recrystallized from ethyl acetate/methanol/ether to give the title compound (0.972 g, 52% yield) as white prisms: mp 189-194° C.; $^1$H NMR (400 MHz, d$_6$-DMSO) δ 8.06 (s, 1H), 8.01 (s, 1H), 7.50 (s, 2H), 7.05 (s, 1H), 5.04 (d, J=5.2 Hz, 2H), 4.98 (dd, J=3.0 and 5.0 Hz, 1H), 4.66 (t, J=5.6 Hz, 1H), 3.72-3.68 (m, 1H), 3.39-3.34 (m, 1H), 3.31-3.25 (m, 1H), 3.05 (dd, J=3.8 and 13.6 Hz, 1H); 2.78 (dd, J=7.8 and 13.6 Hz, 1H); $^{13}$C NMR (100 MHz, d$_6$-DMSO) δ 146.1, 134.8, 128.5, 126.7, 117.2, 115.8, 70.5, 63.5, 59.6, 48.8; Mass spectrum (API-TIS) m/z 372 (MH$^+$), 389 (MNH$_4^+$), 760 (2MNH$_4^+$)

75c. 2H-1,2,4-Benzothiadiazine-7-sulfonamide, 2-[2,3-bis(nitrooxy)propyl]-6-chloro-3,4-dihydro-, 1,1-dioxide

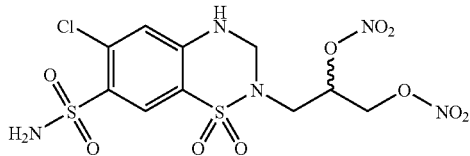

Trifluoroacetic acid (1.6 mL, 20.8 mmol) was added to a solution of the product of Example 75b (3.53 g, 9.49 mmol) in THF (95 mL) followed by the addition of a pre-mixed solution of fuming nitric acid (2.9 mL, 57.2 mmol) in acetic anhydride (15 mL) and the resulting mixture was stirred at room temperature for 4.5 hours. The reaction mixture was poured into water (30 mL) and THF was evaporated under reduced pressure. The resulting aqueous mixture was extracted with EtOAc (150 mL). The organic extract was washed with water, 3N HCl, brine, dried over Na$_2$SO$_4$, filtered, and concentrated. The product was purified by silica gel column chromatography eluting with EtOAc/hexane (gradient from 25 to 65%, R$_f$=0.22 in 60%) to obtain the title compound as a light yellow solid (1.7 g, 39% yield): mp 80-95° C. (with decomposition). $^1$H NMR (400 MHz, d$_6$-DMSO) δ 8.11 (br s, 1H), 8.02 (s, 1H), 7.54 (br s, 2H), 7.10 (s, 1H), 5.72-5.70 (m, 1H), 5.00-4.90 (m, 3H), 4.85-4.70 (m, 1H), 3.45-3.35 (m, 2H); $^{13}$C NMR (100 MHz, d$_6$-DMSO) δ 145.9, 135.1, 129.0, 126.7, 117.5, 115.4, 77.6, 70.1, 59.9, 45.2; Mass Spectrum (API-TIS) m/z 479 (MNH$_4$)$^+$. Anal. calcd. for C$_{10}$H$_{12}$ClN$_5$O$_{10}$S$_2$: C, 26.01; H, 2.62; N, 15.16. Found: C, 26.02; H, 2.60; N, 14.91.

75d 2H-1,2,4-benzothiadiazine-7-sulfonamide, 2-[(2R)-2,3-bis(nitrooxy)propyl]-6-chloro-3,4-dihydro-, 1,1-dioxide (enantiomer 1) and 2H-1,2,4-benzothiadiazine-7-sulfonamide, 2-[(2S)-2,3-bis(nitrooxy)propyl]-6-chloro-3,4-dihydro-, 1,1-dioxide (enantiomer 2)

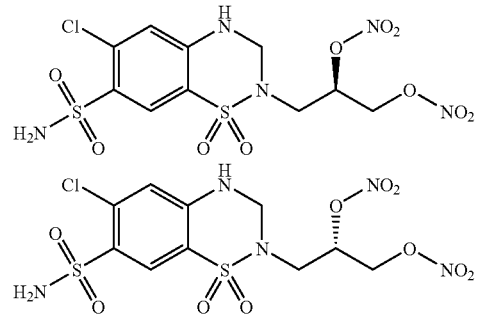

The product of Example 75c (0.98 g) was separated by Chiral Technologies, West Chester, Pa. on a ChiralPak AD column, using ethanol as the eluant. Enantiomer 1 (0.46 g) had a retention time of 4.93 minutes, Enantiomer 2 (0.46 g) had a retention time of 6.24 minutes when analyzed on a ChiralPak AD-H 4.6 mm×25 cm column, eluted with ethanol.

75e. 2H-1,2,4-Benzothiadiazine-7-sulfonamide, 2-[2,3-bis(nitrooxy)propyl]-6-chloro-3,4-dihydro-4-nitro-, 1,1-dioxide

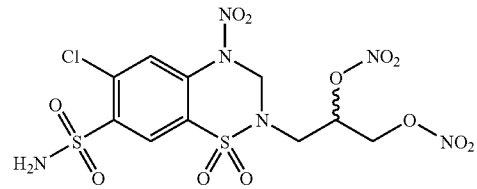

The title compound was the by-product of the reaction of Example 75c and was separated by column chromatography. The fractions of R$_f$=0.45 (in 60% EtOAc/hexane) were collected to give the title compound as a yellow solid (1.0 g, 21% yield): mp>100° C. (with decomposition). $^1$H NMR (400 MHz, d$_6$-DMSO) δ 8.38 (s, 1H), 8.30 (s, 1H), 8.03 (br s, 2H), 6.14 (d, J=15.0 Hz, 1H), 5.99 (d, J=15.0 Hz, 1H), 5.80-5.70 (m, 1H), 5.00-4.90 (m, 1H), 4.85-4.70 (m, 1H), 3.69 (d, J=5.6 Hz, 2H), 3.65-3.50 (br s, 1H); $^{13}$C NMR (100 MHz, d$_6$-DMSO) δ 139.8, 135.5, 135.2, 128.5, 125.3, 125.2, 77.4, 69.8, 65.3, 46.8; Mass Spectrum (API-TIS) m/z 524 (MNH$_4$)$^+$.

75f. 2H-1,2,4-Benzothiadiazine-7-sulfonamide, 6-chloro-3,4-dihydro-2-[2-hydroxy-3-(nitrooxy)propyl]-4-nitro-, 1,1-dioxide

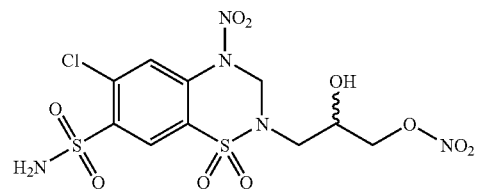

The title compound was the by-product in the reaction of Example 75c and was separated by column chromatography.

The fractions of R$_f$=0.33 (in 60% EtOAc/hexane) were collected to obtain the title compound as a yellow solid (0.33 g, 8% yield): $^1$H NMR (400 MHz, d$_6$-DMSO) δ 8.34 (s, 1H), 8.31 (s, 1H), 8.00 (br s, 2H), 6.10 (d, J=14.8 Hz, 1H), 6.02 (d, J=14.8 Hz, 1H), 4.70-4.40 (m, 2H), 4.10-4.00 (m, 1H), 3.45-3.30 (m, 2H); $^{13}$C NMR (100 MHz, d$_6$-DMSO) δ 139.7, 135.5, 135.0, 128.6, 125.7, 125.1, 74.3, 65.7, 65.6, 50.6; Mass Spectrum (API-TIS) m/z 479 (MNH$_4$)$^+$.

Example 76

1-Piperidinyloxy, 4-[[7-(aminosulfonyl)-6-chloro-3,4-dihydro-1,1-dioxido-2H-1,2,4-benzothiadiazin-3-yl]methyl]-2,2,6,6-tetramethyl- 76a. 1-Piperidinyloxy, 2,2,6,6-tetramethyl-4-(2-oxoethyl)-

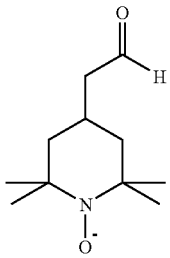

The title compound was prepared from 4-oxo-2,2,6,6-tetramethyl-1-oxy-piperidine (tempone) (Aldrich) as described by Smith, P. et al, *J. Am. Chem. Soc.*, 106(7):1986-1991 (1984). The product was a red oil. Mass spectrum (API-TIS) m/z 199 (MH$^+$). IR (neat) 1728 (C=O) cm$^{-1}$.

76b. 1-Piperidinyloxy, 4-[[7-(aminosulfonyl)-6-chloro-3,4-dihydro-1,1-dioxido-2H-1,2,4-benzothiadiazin-3-yl]methyl]-2,2,6,6-tetramethyl-

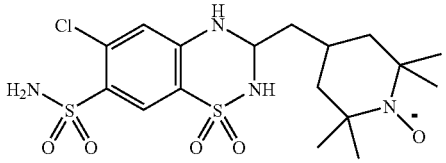

To a mixture of 4-chloro-6-aminobenzene-1,3-disulfonamide (Aldrich, 1 g, 3.5 mmol) and the product of Example 76a (1.4 g, 7.0 mmol) in anhydrous dioxane (10 mL) at 55-60° C., was added dropwise concentrated HCl (10 drops) over a period of 30 minutes. The mixture was then heated at 60° C. for 1 hour. The solvent was evaporated. The residue was neutralized with 10% NaHCO$_3$, and the product was extracted with EtOAc. The combined organic layers were washed with water, dried over Na$_2$SO$_4$, filtered. The residue after evaporation of the solvent was chromatographed on silica gel eluting with hexane:EtOAc:MeOH (4.5:5:0.5) to give the title compound (0.26 g, 16% yield) as a pale orange-red solid: mp 238-240° C. $^1$H NMR (400 MHz, d$_6$-DMSO) δ 7.70-8.10 (br s, 3H), 7.35-7.55 (br s, 2H), 6.88-7.05 (br s, 1H), 3.25 (s, 2H). Mass spectrum (API-TIS) m/z 464 (M-H), 465 (M$^+$). Anal. calcd for C$_{17}$H$_{26}$ClN$_4$O$_5$S$_2$.¼ mol EtOAc C, 44.30; H, 5.78; N, 11.48. Found: C, 44.43; H, 5.68; N, 11.43.

Example 77

2H-1,2,4-Benzothiadiazine-7-sulfonamide, 6-chloro-3,4-dihydro-3-[(1-hydroxy-2,2,6,6-tetramethyl-4-piperidinyl)methyl]-, 1,1-dioxide

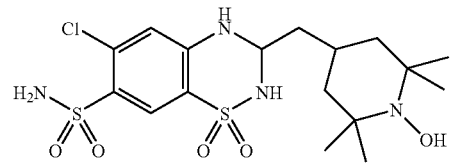

The residue after workup from Example 76b was chromatographed on silica gel eluting with CH$_2$Cl$_2$:EtOAc:MeOH (4.5:4.5:1) to give the title compound (0.4 g, 24% yield) as a white solid: mp 174-176° C. $^1$H NMR (400 MHz, d$_6$-DMSO) δ 7.97 (s, 1H), 7.77-7.90 (br s, 1H), 7.47 (br s, 2H), 7.06 (br s, 1H), 6.97 (s, 1H), 4.75-4.85 (br s, 1H), 3.29 (s, 2H), 1.95-2.00 (m, 1H), 1.42-1.70 (m, 3H), 1.10-1.22 (m, 1H), 1.04 (s, 6H), 1.02 (s, 6H). Mass spectrum (API-TIS) m/z 465 (M-H), 467 (MH$^+$).

Example 78

2H-1,2,4-benzothiadiazine-7-sulfonamide, 6-chloro-3,4-dihydro-2-[2-hydroxy-1-(hydroxymethyl)ethyl]-, 1,1-dioxide 78a. Propanedioic acid, [7-(aminosulfonyl)-6-chloro-3,4-dihydro-1,1-dioxido-2H-1,2,4-benzothiadiazin-2-yl]-, dimethyl ester

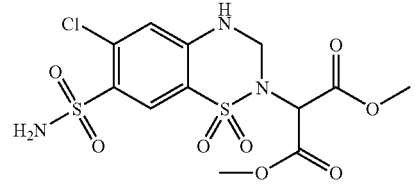

To a stirred mixture of hydrochlorothiazide (15.0 g, 50.38 mmol) and cesium carbonate (8.21 g, 25.19 mmol) in DMF (120 mL) was added dimethyl bromomalonate (tech., 90%; 6.60 mL, 50.38 mmol) via a syringe. The reaction mixture was stirred at room temperature for 18 hours, poured into water, and extracted with ethyl acetate twice. The combined organic extracts were washed with aqueous NaCl, dried over Na$_2$SO$_4$, filtered, and concentrated by rotary evaporation. The residue was purified by column chromatography (silica gel, 0-30% gradient of ethyl acetate in methylene chloride) to give the title compound (3.06 g, 14% yield) as a white solid. $^1$H NMR (400 MHz, d$_4$-MeOH) δ 8.17 (s, 1H), 6.92 (s, 1H), 5.22 (s, 2H), 3.85 (s, 1H), 3.65 (s, 6H). Mass spectrum (API-TIS) m/z 428.0 and 430.0 (MH$^+$ for $^{35}$Cl and $^{37}$Cl respectively).

78b. 2H-1,2,4-Benzothiadiazine-7-sulfonamide, 6-chloro-3,4-dihydro-2-[2-hydroxy-1-(hydroxymethyl)ethyl]-, 1,1-dioxide

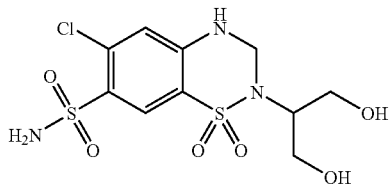

To a stirred solution of the product of Example 78a (1.00 g, 2.34 mmol) in a mixture of ethanol (15 mL) and THF (15 mL) at 0° C. was added NaBH$_4$ in portions. The reaction mixture was stirred at 0° C. for 2 hours, and then at room temperature for 18 hours. Hydrochloric acid (6 N, 3 mL) was added dropwise, and the resulting milky white suspension was filtered. The filter cake was washed thoroughly with ethanol and THF, and the filtrate was concentrated by rotary evaporation. Column chromatography (silica gel, 0-30% gradient of THF in EtOAc) and subsequent crystallization from MeOH gave the title compound (62 mg, yield 7%) as a white solid. Mp 139-143° C. $^1$H NMR (400 MHz, d$_4$-MeOH) δ 8.17 (s, 1H), 6.92 (s, 1H), 4.77 (s, 2H), 3.60-3.55 (m, 2H), 3.49-3.44 (m, 2H), 2.88-2.84 (m, 1H). $^{13}$C NMR (100 MHz, (CD$_3$)$_2$SO) δ 147.72, 135.24, 128.74, 126.54, 119.78, 118.00, 64.32, 55.59, 55.55. Mass spectrum (API-TIS) m/z 372.3 and 374.0 (MH$^+$ for $^{35}$Cl and $^{37}$Cl respectively).

Example 79

2H-1,2,4-Benzothiadiazine-7-sulfonamide, 3-[2-[3,5-bis(hydroxymethyl)phenyl]ethyl]-6-chloro-3,4-dihydro-, 1,1-dioxide

79a. 1,3-Benzenedicarboxylic acid, 5-(3-oxopropyl)-, dimethyl ester

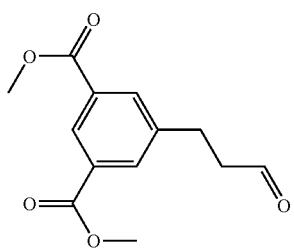

A mixture of 5-bromodimethylisophthalate (11.2 g, 41.0 mmol), allyl alcohol (3.62 mL, 53.2 mmol), sodium carbonate (11.0 g, 104 mmol), benzyltriethylammonium chloride (10.2 g, 45 mmol) and palladium diacetate (0.45 g, 2.0 mmol) in DMF (80 mL) was heated to 80° C. for 1.5 hours. The reaction mixture was filtered through Celite and washed with EtOAc (100 mL). The combined filtrate was evaporated to dryness under vacuum. The residue was partition between EtOAc (150 mL) and water (150 mL×3). The organic extract was washed with brine, dried over Na$_2$SO$_4$, filtered, and concentrated. The product was purified by silica gel column chromatography eluting with EtOAc/hexane (gradient from 20 to 40% EtOAc/hexane; R$_f$=0.15 in 25%) to obtain the title compound as a crystalline solid (7.13 g, 70% yield): mp 70-71° C.; $^1$H NMR (400 MHz, CDCl$_3$) δ 9.84 (t, J=1.0 Hz, 1H), 8.50 (t, J=1.5 Hz, 1H), 8.07 (d, J=1.5 Hz, 2H), 3.94 (s, 6H), 3.06 (t, J=7.5 Hz, 2H), 2.88 (t, J=7.5 Hz, 2H); $^{13}$C NMR (100 MHz, CDCl$_3$) δ 200.3, 165.9, 141.2, 133.5, 130.7, 128.5, 52.2, 44.5, 27.4; Mass Spectrum (API-TIS) m/z 251 (MH)$^+$.

79b. 1,3-Benzenedicarboxylic acid, 5-(3,3-dimethoxypropyl)-, dimethyl ester

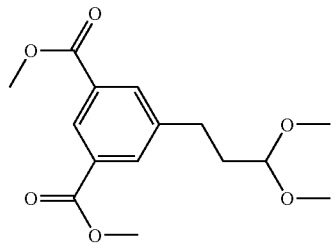

The product of Example 79a (6.14 g, 24.5 mmol), trimethyl orthoformate (5.5 mL, 50.3 mmol) and concentrated sulfuric acid (0.07 mL, 1.3 mmol) in MeOH (50 mL) was heated to reflux for 1.5 hours, then cooled to room temperature and Na$_2$CO$_3$ (0.48 g, 4.5 mmol) was added. The resulting mixture and stirred at room temperature for 20 minutes and then evaporated to dryness. The residue was dissolved in EtOAc (100 mL), dried over Na$_2$SO$_4$, filtered, concentrated and dried under vacuum. The product was purified by silica gel column chromatography, eluting with EtOAc/hexane (gradient from 20 to 35% EtOAc/hexane; R$_f$=0.25 in 25%) to give the title compound as a white crystalline solid (6.77 g, 93% yield): mp 59-61° C.; $^1$H NMR (400 MHz, CDCl$_3$) δ 8.52 (t, J=1.6 Hz, 1H), 8.07 (d, J=1.6 Hz, 2H), 4.36 (t, J=5.8 Hz, 1H), 3.94 (s, 6H), 3.34 (s, 6H), 2.81-2.75 (m, 2H), 2.00-1.90 (m, 2H); $^{13}$C NMR (100 MHz, CDCl$_3$) δ 166.3, 142.5, 133.8, 130.7, 128.4, 103.5, 52.8, 52.3, 33.8, 30.4; Mass Spectrum (API-TIS) m/z 265 (M-OCH$_3$)$^+$.

79c. 1,3-Benzenedimethanol, 5-(3,3-dimethoxypropyl)-

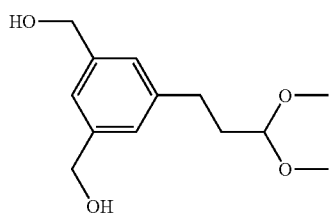

Super-hydride (1 M in THF, 8.6 mL, 8.6 mmol) was added to the product of Example 79b (0.553 g, 1.9 mmol) in THF (20 mL) and stirred at room temperature overnight. The reaction mixture was quenched with water (5 mL) and THF, and evaporated under reduced pressure. The residue was partitioned between EtOAc (100 mL) and water (50 mL). The organic layer was washed with brine, dried over Na$_2$SO$_4$, filtered and concentrated. The product was purified by silica gel column chromatography eluting with EtOAc/hexane (gradient from 30% to 70% EtOAc/hexane, R$_f$=0.15 in 67%)

to give the title compound as a clear oil (0.33 g, 74% yield). $^1$H NMR (400 MHz, CDCl$_3$) δ 7.08 (s, 1H), 7.01 (s, 2H), 4.50 (d, J=4.8 Hz, 4H), 4.31 (t, J=5.8 Hz, 1H), 3.77 (br t, 1H), 3.27 (s, 6H), 2.61-2.50 (m, 2H), 1.90-1.80 (m, 2H); $^{13}$C NMR (100 MHz, CDCl$_3$) δ 141.8, 141.3, 125.9, 123.0, 103.6, 64.5, 52.6, 33.8, 30.5; Mass Spectrum (API-TIS) m/z 258 (MNH$_4$)$^+$.

79d. 2H-1,2,4-Benzothiadiazine-7-sulfonamide, 3-[2-[3,5-bis(hydroxymethyl)phenyl]ethyl]-6-chloro-3,4-dihydro-, 1,1-dioxide

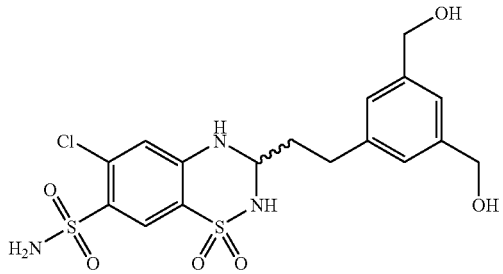

A solution of the product of Example 79c (0.65 g, 2.71 mmol), p-toluenesulphonic acid monohydrate (0.524 g, 2.75 mmol) and 4-amino-6-chloro-1,3-benzenedisulfonamide (0.77 g, 2.69 mmol) in 1,4-dioxane (27 mL) was heated to reflux for 1 hour. The reaction mixture was evaporated to dryness under reduced pressure. The resulting residue was dissolved in acetone (50 mL) and stirred with sodium acetate (0.32 g, 3.9 mmol) for 30 min. The mixture was dried over Na$_2$SO$_4$, filtered and concentrated. The product was purified by silica gel column chromatography eluting with EtOAc/hexane (gradient from 40 to 100% EtOAc/hexane, R$_f$=0.13 in 100%) to give the title compound as a white solid (0.6 g, 48% yield): mp 218° C.; $^1$H NMR (400 MHz, d$_6$-DMSO) δ 8.00 (s, 1H), 7.97 (s, 1H), 7.91 (d, J=11.6 Hz, 1H), 7.50 (s, 2H), 7.11 (s, 1H), 7.07 (s, 2H), 6.99 (s, 1H), 5.50-4.80 (br, 2H), 4.80-4.70 (m, 1H), 4.47 (s, 4H), 2.80-2.70 (m, 2H), 2.10-2.00 (m, 2H); $^{13}$C NMR (100 MHz, d$_6$-DMSO) δ 146.5, 142.5, 140.2, 134.3, 128.2, 125.5, 124.8, 122.4, 118.3, 117.0, 65.3, 62.9, 35.0, 30.0; Mass Spectrum (API-TIS) m/z 460 (M-H)$^-$. Anal. Calcd. for C$_{17}$H$_{20}$ClN$_3$O$_6$S$_2$: C, 44.20; H, 4.36; N, 9.10. Found: C, 44.12; H, 4.26; N, 8.87.

Example 80

2H-1,2,4-Benzothiadiazine-7-sulfonamide, 3-[2-[3,5-bis[(nitrooxy)methyl]phenyl]ethyl]-6-chloro-3,4-dihydro-, 1,1-dioxide 80a. Benzenepropanal, 3,5-bis[(nitrooxy)methyl]-

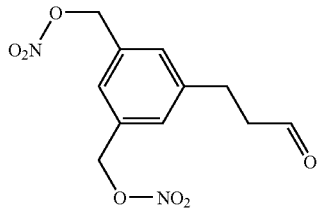

A pre-mixed solution of fuming nitric acid (90%, 1.4 mL, 27.0 mmol) in acetic anhydride (15 mL) was added to the product of Example 79c (2.04 g, 8.5 mmol) in EtOAc (50 mL) and stirred at room temperature for 25 minutes. The reaction mixture was stirred with 3N HCl (50 mL) for 1 hour and then evaporated under reduced pressure. The resulting mixture was extracted with EtOAc (200 mL). The organic extract was washed with brine, dried over Na$_2$SO$_4$, filtered and concentrated. The product was purified by silica gel column chromatography eluting with EtOAc/hexane (gradient from 20 to 50% EtOAc/hexane, R$_f$=0.35 in 40%) to give the title compound as a light yellow oil (1.64 g, 68% yield). $^1$H NMR (400 MHz, CDCl$_3$) δ 9.80 (t, J=1.0 Hz, 1H), 7.28 (s, 3H), 5.41 (s, 4H), 2.98 (t, J=7.3 Hz, 2H), 2.82 (t, J=7.3 Hz, 2H); $^{13}$C NMR (100 MHz, CDCl$_3$) δ 200.6, 142.2, 133.3, 129.9, 127.4, 74.0, 44.6, 27.4.

80b. 2H-1,2,4-Benzothiadiazine-7-sulfonamide, 3-[2-[3,5-bis[(nitrooxy)methyl]phenyl]ethyl]-6-chloro-3,4-dihydro-, 1,1-dioxide

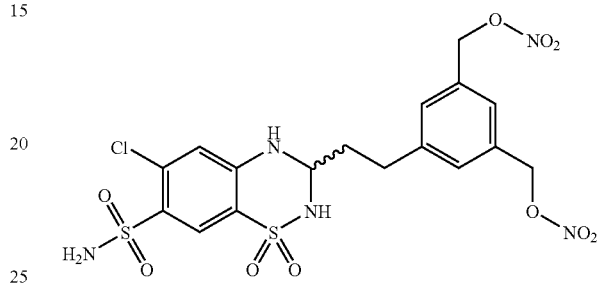

The product of Example 80a (0.5 g, 1.76 mmol), p-toluenesulphonic acid monohydrate (0.34 g, 1.79 mmol) and 4-amino-6-chloro-1,3-benzenedisulfonamide (0.51 g, 1.78 mmol) in 1,4-dioxane (15 mL) was heated to reflux for 1 hour. The reaction mixture was evaporated to dryness under reduced pressure. The residue was dissolved in acetone (50 mL) and stirred with sodium acetate (0.23 g, 2.74 mmol) for 30 min. The resulting mixture was dried over Na$_2$SO$_4$, filtered and concentrated. The product was purified by silica gel column chromatography eluting with EtOAc/hexane (gradient from 50 to 80%, R$_f$=0.35 in 67%) to give the title compound as a white solid (0.34 g, 35% yield): mp 101-104° C.; $^1$H NMR (400 MHz, d$_6$-DMSO) δ 8.00 (s, 1H), 7.97 (s, 1H), 7.93 (d, J=11.6 Hz, 1H), 7.51 (s, 2H), 7.43 (s, 1H), 7.41 (s, 2H), 6.99 (s, 1H), 5.59 (s, 4H), 4.82-4.70 (m, 1H), 2.90-2.80 (m, 2H), 2.10-2.00 (m, 2H); $^{13}$C NMR (100 MHz, d$_6$-DMSO) δ 146.5, 142.0, 134.4, 133.2, 129.8, 128.3, 127.5, 125.5, 118.3, 117.0, 74.6, 65.3, 34.6, 29.6; Mass Spectrum (API-TIS) m/z 550 (M-H)$^-$.

Example 81

2H-1,2,4-benzothiadiazine-7-sulfonamide, 6-chloro-3,4-dihydro-2-(oxiranylmethyl)-, 1,1-dioxide

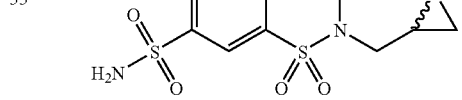

Cesium carbonate (1.297 g, 3.98 mmol) was added as a solid, followed by epibromohydrin (0.604 ml, 7.30 mmol) hydrochlorothiazide (1.976 g, 6.64 mmol) in DMF. The reaction mixture was stirred overnight at room temperature. The reaction mixture was filtered through a medium glass frit, and concentrated via rotary evaporation under high vacuum. The residue was partitioned between ethyl acetate and water. The organic layer was washed with water, brine and dried over magnesium sulfate. LCMS analysis showed that desired product was present. After evaporation of the solvent, the residue was purified via column chromatography on silica gel, 5 to 10% methanol in dichloromethane gradient (product $R_f$=0.35 in 10% methanol in dichloromethane). The appropriate fractions were combined, concentrated and the residue was recrystallized from acetone/chloroform/ether to give the title product (0.710 g, 2.01 mmol, 30% yield) as white prisms: mp 192-197° C.; $^1$H NMR (400 MHz, $d_6$-DMSO) δ 8.11 (s, 1H), 8.01 (s, 1H), 7.52 (s, 2H), 7.05 (s, 1H), 5.02-4.92 (m, 2H), 3.33 (dd, J=3.1, 14.2 Hz, 1H), 3.23-3.19 (m, 1H), 2.86 (dd, J=6.4, 14.3 Hz, 1H), 2.77 (dd, J=4.3, 4.8 Hz, 1H), 2.59 (dd, J=2.6, 4.9 Hz, 1H); $^{13}$C NMR (100 MHz, DMSO-$d_6$) δ 146.0, 134.9, 128.7, 126.6, 117.3, 115.7, 59.1, 49.6, 48.5, 44.1; Mass spectrum (API-TIS) m/z 354 (MH$^+$), 371 (MNH$_4^+$), 724 (2MNH$_4^+$) Anal. calcd for $C_{10}H_{12}ClN_3O_5S_2$: C, 33.95; H, 3.42; N, 11.88. Found: C, 33.99; H, 3.19; N, 11.74.

Example 82

2H-1,2,4-Benzothiadiazine-7-sulfonamide, 6-chloro-3,4-dihydro-4-methyl-3-[4-(nitrooxy)butyl]-, 1,1-dioxide 82a. 1,3-Benzenedisulfonyl dichloride, 4-chloro-6-(methylamino)-

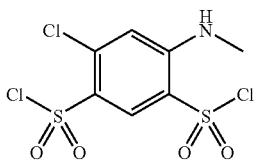

Chlorosulfonic acid (75 ml, 1130 mmol) was cooled to 0° C. and stirred during the slow addition of N-methyl-3-chloroaniline (10.0 g, 70.6 mmol). The reaction mixture was heated between 118-135° C. for 4.5 hours and allowed to stand at room temperature overnight. The mixture was slowly poured into a bath of ice water and the resulting semi-solid was extracted with hot chloroform (2×200 mL). The combined organic extracts were dried over MgSO$_4$, and the solvent removed to near dryness under reduced pressure. The product was used in the next step without purification or analysis.

82b. 1,3-Benzenedisulfonamide, 4-chloro-6-(methylamino)-

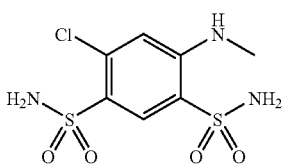

Ammonium hydroxide (37.9 ml, 282 mmol) was cooled to 0° C. in an ice bath and the product of Example 82a (23.91 g, 70.6 mmol) was added dropwise. The mixture was allowed to warm to room temperature for 4 hours. The resulting solid was collected via filtration and triturated in MeOH/H$_2$O. The solid was collected via filtration to give the title compound (1.0 g, 4.72% yield) as a pale grey solid: $^1$H NMR (400 MHz, CDCl$_3$) δ 8.20 (s, 1H), 7.40 (br s, 4H), 6.88 (s, 1H), 6.44-6.41 (m, 1H), 2.90 (d, J=4.8 Hz, 3H). Mass spectrum (API-TIS) m/z 300 (MH$^+$).

82c. 2H-1,2,4-Benzothiadiazine-7-sulfonamide, 6-chloro-3,4-dihydro-4-methyl-, 1,1-dioxide

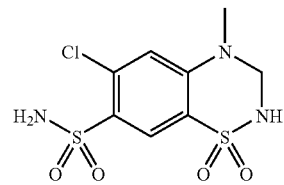

The product of Example 82b (1.00 g, 3.34 mmol) was taken up in water (15 mL) and heated to reflux. To this was added a solution of formaldehyde (0.323 ml, 4.34 mmol) and ammonium chloride (0.196 g, 3.67 mmol) in 5 mL of water. The mixture was heated and stirred at reflux for 5 hours, cool to room temperature and left to stir over the weekend. The solid was removed via filtration and recrystallized from acetone/chloroform/ether to give the title compound (0.62 g, 59.2% yield) as a white solid: $^1$H NMR (400 MHz, CDCl$_3$) δ 8.33 (t, J=8.1, NH), 8.01 (s, 1H), 7.52 (s, 2H), 7.04 (s, 1H), 4.78 (d, J=8.1, 2H), 3.07 (s, 3H). Mass spectrum (API-TIS) m/z 312 (MH$^+$) and 329 (MNH$_4^+$).

82d. 2H-1,2,4-Benzothiadiazine-7-sulfonamide, 6-chloro-3,4-dihydro-4-methyl-3-[4-(nitrooxy)butyl]-, 1,1-dioxide

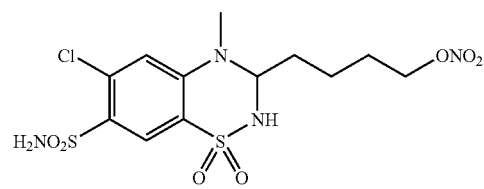

The product of Example 82b (1.5 g, 5.00 mmol) and the product of Example 17a (0.810 g, 5.50 mmol) were combined in dioxane (50 mL) and concentrated HCl (2 mL) and the reaction mixture was heated at reflux for 1 hour. The mixture was cooled to room temperature, washed with brine, and the organic layer separated. The solvent was removed under reduced pressure and the residue was taken up in EtOAc, washed with sodium carbonate, water, and brine, and dried over MgSO$_4$. The solvent was removed under reduced pressure to give the crude product. Purification via column chromatography (1:1 THF/hexane to 100% THF gradient) gave the title compound (0.41 g, 19.10% yield) as a white foam: $^1$H NMR (400 MHz, CDCl$_3$) δ 8.36 (d, J=7.2 Hz, 1H), 8.00 (s, 1H), 7.51 (s, 2H), 7.02 (s, 1H), 4.78-4.72 (m, 1H), 4.52 (t, J=6.4, 2H), 3.03 (s, 3H), 1.95-1.86 (m, 2H), 1.69-1.66 (m, 2H), 1.58-1.54 (m, 1H), 1.44-1.41 (m, 1H). Mass spectrum (API-TIS) m/z 429 (MH$^+$).

Example 83

2H-1,2,4-Benzothiadiazine-7-sulfonamide, 3-[(1R)-1,2-bis(nitrooxy)ethyl]-6-chloro-3,4-dihydro-4-methyl-, 1,1-dioxide

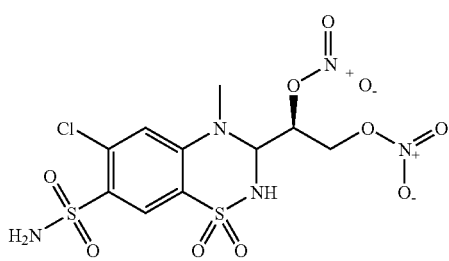

The title compound will be synthesized by the condensation of the product of Example 82b with (R)-(+)-2,2-dimethyl-1,3-dioxolane-4-carboxaldehyde following the procedure of Example 79d. The product will be hydrolyzed to 2H-1,2,4-benzothiadiazine-7-sulfonamide, 6-chloro-3-[(1R)-1,2-dihydroxyethyl]-3,4-dihydro-4-methyl-, 1,1-dioxide in aqueous methanol under acidic condition. The resulting compound will be nitrated following the procedure of Example 75c to give the title compound.

Example 84

2H-1,2,4-Benzothiadiazine-7-sulfonamide, 3-[(1S)-1,2-bis(nitrooxy)ethyl]-6-chloro-3,4-dihydro-4-methyl-, 1,1-dioxide

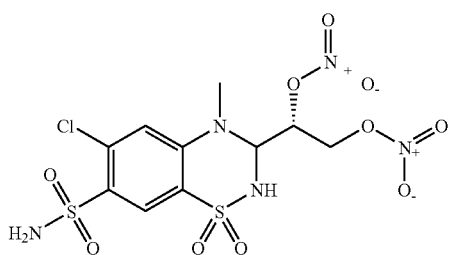

The title compound will be synthesized by following the same procedure as Example 84 except (S)-(+)-2,2-dimethyl-1,3-dioxolane-4-carboxaldehyde will be used as the starting material.

Example 85

Determination of the Diuresis

Procedures were approved by the Institutional Animal Care and Use Committee of NitroMed, Inc. Male Wistar rats (180-200 g) were purchased from Charles River Laboratories (Kingston, N.Y. or Raleigh, N.C.) and allowed to acclimate in the facility for a period of at least 72 h. Rats were randomly housed 2-3 per cage in a light-controlled room with a 12 hour light/dark cycle and allowed ad libitum access to food and water.

Prior to the experiment, each rat was placed in a metabolic cage and allowed to acclimate for a period of 24-48 hours with food and water ad libitum. During this acclimation period, rats received mash food instead of pellet food to prevent contamination of the urine samples. All rats were fasted for 18 hours prior to experimentation. In addition, water was removed 90 minutes prior to oral dosing with test compound or vehicle.

The test compounds were prepared immediately prior to dosing in 0.5% Methocel (F4M Premium Hydroxypropyl Methylcellulose, lot # PF12012N12; Dow Chemical Company, USA) and homogenized with a glass/Teflon pestle motorized homogenizer. Gently vortexed test compounds were administered intragastrically (p.o.; 30 mg/kg or 3 mg/kg) at a dose volume of 3 ml per rat using an 18 gauge gavage needle. Urine volume (ml) was monitored and urine was collected for subsequent electrolyte analysis over a 6 hours period. Table 1 gives the urine volume collected over a period of 6 hours. Data are expressed as mean ±SEM; n=6 or 7.

TABLE 1

| Example No. | Urine collected in 6 hours (mL) (30 mg/kg) | Urine collected in 6 hours (mL) (3 mg/kg) |
| --- | --- | --- |
| 1c | 7.6 ± 0.5 | 6.6 ± 0.4 |
| 2 | 5.7 ± 0.7 | Not determined |
| 3d | 5.3 ± 0.8 | Not determined |
| 4b | Not determined | 4.0 ± 0.5 |
| 4c | 3.8 ± 0.7 | Not determined |
| 5b | 4.5 ± 0.5 | Not determined |
| 6b | 6.8 ± 0.5 | Not determined |
| 7 | 5.7 ± 0.4 | Not determined |
| 8 | 6.2 ± 0.7 | Not determined |
| 9b | 6.7 ± 0.8 | Not determined |
| 10 | 6.9 ± 0.9 | Not determined |
| 11 | 3.7 ± 0.3 | Not determined |
| 12a | 4.0 ± 0.4 | Not determined |
| 12c | 5.5 ± 0.4 | 2.8 ± 0.4 |
|  | 8.7 ± 0.5 | 3.9 ± 0.6 |
| 13 | 2.2 ± 0.5 | Not determined |
| 14 | 4.0 ± 0.4 | Not determined |
| 15b | 4.5 ± 0.2 | Not determined |
| 16c | 4.3 ± 0.3 | Not determined |
| 17b | 5.8 ± 0.7 | 6.5 ± 0.3 |
|  | 6.3 ± 0.4 | 5.2 ± 0.5 |
| 17c (enantiomer 1) | 7.0 ± 0.6 | Not determined |
| 17c (enantiomer 2) | 7.8 ± 0.5 | Not determined |
| 18b | 3.0 ± 0.4 | Not determined |
|  | 3.2 ± 0.5 |  |
| 19b | 2.5 ± 0.4 | Not determined |
| 20c | 3.0 ± 0.9 | Not determined |
| 21b | 2.7 ± 0.3 | Not determined |
| 22b | 2.5 ± 0.2 | Not determined |
| 23 | 1.7 ± 0.6 | Not determined |
| 24c | 7.2 ± 0.7 | 8.6 ± 0.4 |
| 26 | 6.0 ± 0.4 | Not determined |
| 31a | Not determined | 2.5 ± 0.3 |
| 31b | Not determined | 2.0 ± 0.3 |
| 32b | Not determined | 5.1 ± 0.2 |
| 33 | Not determined | 3.0 ± 0.4 |
| 34 | Not determined | 2.8 ± 0.3 |
| 35b | Not determined | 7.2 ± 0.3 |
|  |  | 7.3 ± 0.9 |
| 36a | Not determined | 5.5 ± 0.6 |
| 36c | Not determined | 3.0 ± 0.4 |
| 37c | Not determined | 2.1 ± 0.6 |
| 38 | Not determined | 4.5 ± 0.6 |
| 39 | Not determined | 2.5 ± 0.5 |
| 40b | Not determined | 6.0 ± 0.7 |
| 41 | Not determined | 5.5 ± 0.6 |
| 42 | Not determined | 6.2 ± 0.3 |
| 43b | Not determined | 3.0 ± 0.6 |
| 44 | Not determined | 2.5 ± 0.3 |
| 45 | Not determined | 4.8 ± 1.3 |
| 46b | Not determined | 7.3 ± 0.7 |
| 47c | Not determined | 8.3 ± 0.6 |
| 48b | Not determined | 4.8 ± 0.8 |

TABLE 1-continued

| Example No. | Urine collected in 6 hours (mL) (30 mg/kg) | Urine collected in 6 hours (mL) (3 mg/kg) |
|---|---|---|
| 49e | Not determined | 2.5 ± 0.5 |
| 50c | Not determined | 3.3 ± 0.6 |
| 51 | Not determined | 8.0 ± 1.1 |
| 52 | Not determined | 5.7 ± 0.8 |
| 53c | Not determined | 3.7 ± 0.4 |
| 54 | Not determined | 5.0 ± 0.4 |
|  |  | 5.5 ± 0.3 |

(Day 0). Terminal plasma was collected on day 29 for analysis of aldosterone and plasma renin levels. Plasma renin and aldosterone were measured utilizing commercially available kits (Cayman Chemical; Ann Arbor, Mich. and Alpha Diagnostics; San Antonio, Tex., respectively).

Table 2 shows that the plasma aldosterone and renin measured on day 29 were significantly lowered following Example 51 treatment as compared to vehicle or HCT treated rats indicating that administration of Example 51 appeared to have beneficial effects on the renin-angiotensin system by reducing plasma aldosterone and renin levels when compared to hydrochlorothiazide.

TABLE 2

| TEST CONDITION | RENIN (Relative Units) | | ALDOSTERONE (pg/ml) | | N |
|---|---|---|---|---|---|
| | DAY 0 | Day 29 | DAY 0 | Day 29 | |
| Vehicle | 6.1 ± 0.4 | 15.1 ± 2.9 | 403.4 ± 33.9 | 1852.5 ± 166.9 | 8 |
| HCT | 5.0 ± 0.6 | 24.6 ± 1.0 | 411.5 ± 41.8 | 2081.0 ± 232.1 | 8 |
| Example 51 | 6.1 ± 0.3 | 9.5 ± 0.5$^{a,b}$ | 540.8 ± 38.9 | 1326.6 ± 118.7$^c$ | 8 |

$^a$P < 0.05 versus vehicle controls Example 51
$^b$P < 0.001 versus HCT treated animals.
$^c$P < 0.05 versus HCT treated animals TABLE 1-continued

| Example No. | Urine collected in 6 hours (mL) (30 mg/kg) | Urine collected in 6 hours (mL) (3 mg/kg) |
|---|---|---|
| 55 | Not determined | 3.3 ± 0.4 |
| 56 | Not determined | 4.3 ± 0.6 |
|  |  | 4.1 ± 0.5 |
| 57c | Not determined | 3.6 ± 0.6 |
| 58b | Not determined | 6.3 ± 0.2 |
| 59 | Not determined | 6.7 ± 0.6 |
| 65d | Not determined | 4.6 ± 0.3 |
| 67b | Not determined | 6.7 ± 0.6 |
| 69a | Not determined | 2.7 ± 0.6 |
| 69b | Not determined | 2.5 ± 0.5 |
| 70b | Not determined | 2.8 ± 0.7 |
| 70c | Not determined | 3.3 ± 0.4 |
| 71b | Not determined | 2.1 ± 0.5 |
| 71c | Not determined | 1.3 ± 0.6 |
| 72b | Not determined | 1.8 ± 0.2 |
| 73b | Not determined | 3.8 ± 0.5 |
| 75b | Not determined | 4.6 ± 0.6 |
| 75c | Not determined | 5.4 ± 0.6 |
| 75d (enantiomer 1) | Not determined | 5.3 ± 0.3 |
| 75d (enantiomer 2) | Not determined | 5.5 ± 0.4 |
| 75e | Not determined | 3.3 ± 0.6 |
| 76b | Not determined | 2.2 ± 0.4 |
| 77 | Not determined | 2.3 ± 0.4 |
| 78b | Not determined | 2.7 ± 0.8 |
| 80b | Not determined | 3.9 ± 0.5 |

Example 86

Rat Aldosterone and Renin Inhibition Under In Vivo Conditions

The effect of chronic administration of Example 51 and hydrochlorothiazide (HCT) on plasma aldosterone and renin levels was tested in male Wistar rats. Compounds were administered via mini-osmotic pumps implanted subcutaneously in the scapular area of the rats using aseptic techniques. Molar equivalent doses of HCT and Example 51 (10 mg/kg/day) in 50% DMSO/PEG300 were delivered for 28 days via Alzet mini-pumps and compared to vehicle treated animals. A 250 µl blood sample was obtained from tail vein cannulae for analysis of aldosterone and plasma renin levels Example 87

In Vitro Relaxant Effect in Rat Aorta

Male Wistar rats (250-400 g) were anesthetized with ketamine (10 mg/kg i.p.), exsanguinated and their abdominal aorta were removed. After the removal of fat and connective tissue, the aorta was cut into rings, 3-4 mm in length, and suspended in 10 ml organ baths containing a modified Krebs' solution (composition, mM: NaCl 119, $CaCl_2$ 2.5, KCl 4.5, $NaHCO_3$ 25, $MgCl_2$ 1.25, $NaHPO_4$ 1.0, D-glucose 11.1). The Krebs' solution was maintained at 37° C. and gassed with 5% $CO_2$ in $O_2$. The aortic rings were suspended at an initial resting tension of 1.5 g and washed every 15 minutes during a 60 minute equilibration period. After the equilibration period, the rings were contracted with 1 µM phenylephrine, and the contraction was allowed to reach a plateau before test compounds dissolved in DMSO were administered in a cumulative fashion (1-30,000 nM). Results were calculated as a percentage of the maximum relaxation produced by 10 mM papaverine added at the end of the experiment.

The ability of Example 46b to relax isolated rat aorta pre-contracted with phenylephrine (1 µM) was studied. Example 46b was an efficacious relaxant agent in the rat aorta with an $EC_{50}$ value of ~7 µM. The vasorelaxant response elicited by Example 46b was abolished in the presence of ODQ, a potent and selective inhibitor of nitric oxide (NO)-sensitive guanylyl cyclase.

Example 88

Angiotensin II-Induced Contractions in Rat Aorta

Male Wistar rats (250-300 g) were anesthetized with ketamine (10 mg/kg i.p.), exsanguinated and their abdominal aorta were removed. After the removal of fat and connective tissue, the aorta was cut into rings, 3-4 mm in length, and suspended in 10 ml organ baths containing a modified Krebs' solution (composition, mM: NaCl 119, $CaCl_2$ 2.5, KCl 4.5, $NaHCO_3$ 25, $MgCl_2$ 1.25, $NaHPO_4$ 1.0, D-glucose 11.1). The Krebs' solution was maintained at 37° C. and gassed with 5% $CO_2$ in $O_2$. The aortic rings were suspended at an initial resting tension of 1.5 g and washed every 15 minutes during a 60 minute equilibration period. After the equilibration period, the rings were contracted with 1 µM phenylephrine. Once the contraction to the phenylephrine had reached a plateau tissues were washed 3 times over a 15 min. period. Test articles or vehicle (DMSO) were added to the tissues and 20 min. later each tissue was contracted with angiotensin II (100 nM) and the contraction to angiotensin II was allowed to reach its maximum before the experiment was terminated. Results were calculated as a percentage of the maximum contraction produced by 100 nM angiotensin II in tissues which received only the DMSO vehicle.

The ability of HCT, Example 17b, Example 51, Example 56b, and the des-NO metabolite of Example 17b, Example 26, to inhibit contractions elicited by 100 nM angiotensin II in isolated rat aorta was studied. Neither HCT nor the des-NO compound Example 26 significantly inhibited the angiotensin-II-induced contractions whereas Example 17b, Example 51 and Example 56b produced significant inhibition (Table 3). The difference in their activity is likely to be due to the ability of Example 17b, Example 51 and Example 56b to release bioavailable NO in the rat aorta.

TABLE 3

| TEST CONDITION | % INHIBITION | N |
|---|---|---|
| HCT (1 × $10^{-6}$ M) | 0 | 6 |
| HCT (1 × $10^{-5}$ M) | 12 | 6 |
| Example 17b (1 × $10^{-6}$ M) | 36 | 6 |
| Example 17b (1 × $10^{-5}$ M) | 58 | 6 |
| Example 26 (1 × $10^{-6}$ M) | 8 | 6 |
| Example 51 (1 × $10^{-6}$ m) | 51 | 2 |
| Example 56b (1 × $10^{-6}$ M) | 64 | 2 |

Example 89

Blood Pressure Determination Under In Vivo Conditions in the Dahl Salt Sensitive Rat The effect of subchronic administration of Example 1c and hydrochlorothiazide (HCT) on blood pressure was assessed in telemeterized male Dahl salt sensitive rats (5-6 weeks old; 125-150 g) fed a high salt (8%) diet for 4 weeks. Compounds were administered twice a day for 7 eight days via gavage at 30 mg/kg HCT equivalent in a 0.5% methylcellulose vehicle. Blood pressure was continuously monitored by telemetry and reported as a change in mean arterial blood pressure (MABP) over a 24 h period.

Salt diet-induced hypertension (~ a 10 mm Hg change in mean arterial blood pressure) was noted in vehicle treated animals during the treatment period. FIG. 1 shows that animals orally treated twice a day with Example 1c but not HCT at 30 mg/kg exhibited reductions in blood pressure (approximately 5 mm Hg) during the treatment period.

Example 90

Blood Pressure Determination Under In Vivo Conditions in the Spontaneously Hypertensive Rat The effect of subchronic administration of Example 17b and hydrochlorothiazide (HCT) on blood pressure was assessed in telemeterized male Spontaneously Hypertensive rats (SHR; 9-10 weeks old; 250-300 g). Compounds were administered twice a day for 7 eight days via gavage at 30 mg/kg HCT equivalent in a 0.5% methylcellulose vehicle. Blood pressure was continuously monitored by telemetry and reported as a change in mean arterial blood pressure (MABP) over a 24 h period.

Figure 2:
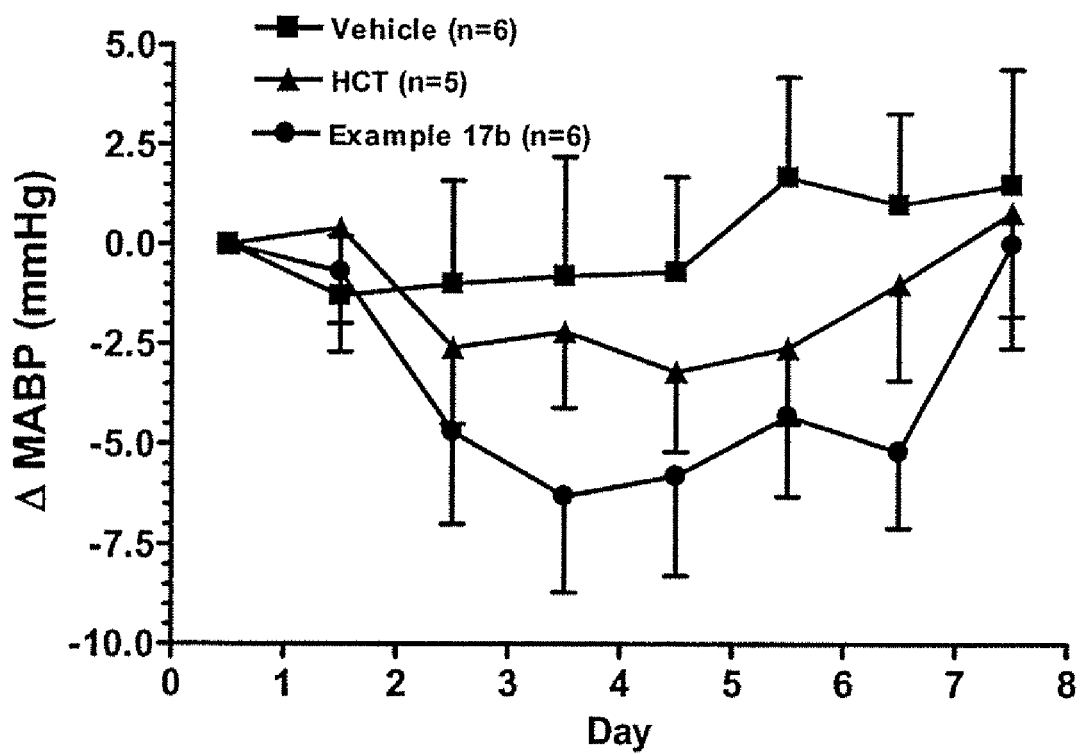
FIG. 2 shows the blood pressure lowering effects of hydrochlorothiazide and Example 17b in Spontaneous Hypertensive rats.

FIG. 2 shows that animals orally treated twice a day with Example 17b exhibited larger reductions in blood pressure (approximately 5-6 mm Hg) during the treatment period than animals treated with HCT.

The disclosure of each patent, patent application and publication cited or described in the present specification is hereby incorporated by reference herein in its entirety.

Although the invention has been set forth in detail, one skilled in the art will appreciate that numerous changes and modifications can be made to the invention, and that such changes and modifications can be made without departing from the spirit and scope of the invention.

What is claimed is:

1. A compound of Formula (I), or a pharmaceutically acceptable salt thereof:
wherein the compound of Formula (I) is:

(I)

wherein:
$X_2$ is $—S(O)_2$;
$Y_2$ is chlorine or $CF_3$;
$—V_2—U_2—W_2—$ is:
(i) $—NH—(C(R_q)(R_r))—NR_q—$; or
(ii) $—NH—C(R_q)=N—$;
$R_q$ and $R_r$ at each occurrence are independently a hydrogen, a lower alkyl group, a substituted alkyl group, a benzyl group, an aryl group, an alkylaryl group, $—CH_2—S—CH—CH=CH_2$; $—CH_2—S—CF_3$, $—CH_2—S—CH_2—C_6H_5$ or K' with the proviso that $(R_q)$ and/or $(R_r)$with the carbon atom to which they are attached form a spiro ring;
K' is $-G-E_c-(C(R_e)(R_f))_x—W_d—(C(R_e)(R_f))_y—W_i-E_j-W_g—(C(R_e)(R_f))_z—V_4$;
K is $—(W)_a-E_b-(C(R_e)(R_f))_{p1}-E_c-(C(R_e)(R_f))_x—(W)_d—(C(R_e)(R_f))_y—(W)_i-E_j-(W)_g—(C(R_e)(R_f))_z—V_4$;
a, b, c, d, g, i and j are each independently an integer from 0 to 3;
$p_1$, x, y and z are each independently an integer from 0 to 10;
G is a heterocyclic ring;
$V_4$ is $V_3$, $R_e$, $—U_3—V_5$ or $V_6$;
$V_3$ is:

(1)

(2) 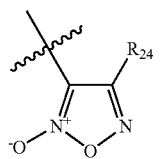
(3) 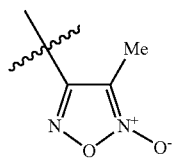
(4) 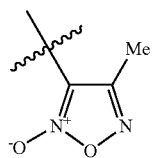
(5) 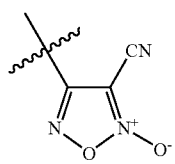
(6) 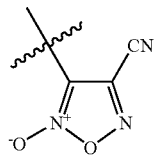
(7) 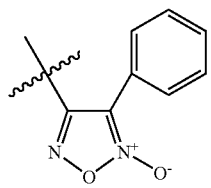
(8) 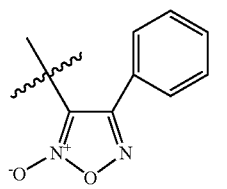
(9) 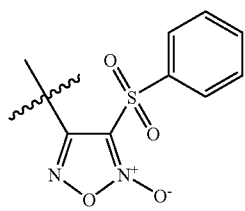
(10) 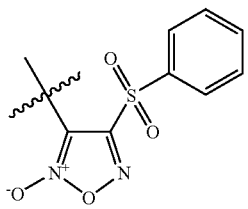
(11) 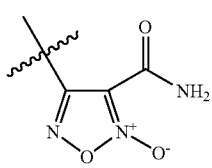
(12) 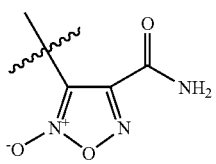
(13) 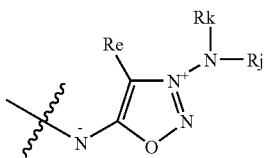
(14) 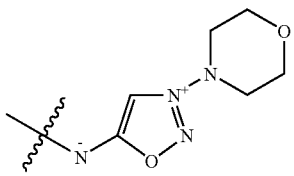
(15) 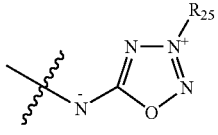
(16) 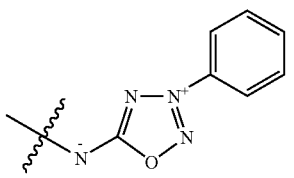
(17) 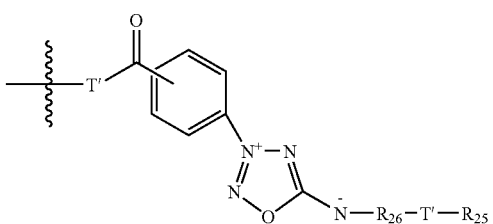

-continued

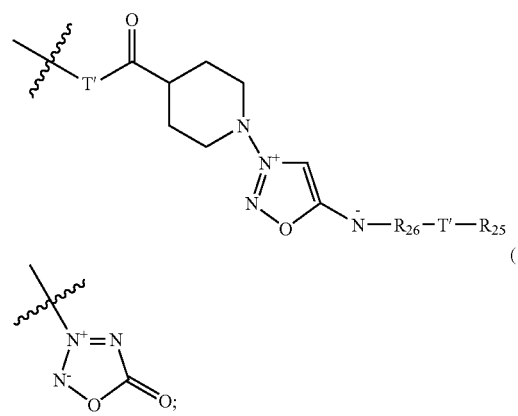

(18)

(19)

$R_{24}$ is —$C_6H_4R_{29}$, —CN, —$S(O)_2$—$C_6H_4R_{29}$, —C(O)—N($R_a$)($R_i$), —$NO_2$, —C(O)—$OR_{25}$ or —$S(O)_2$—$R_{25}$;

$R_{25}$ is an aryl group, a lower alkyl group, a haloalkyl group, a hydroxyalkyl group or an arylalkyl group;

$R_{26}$ is —C(O)— or —$S(O)_2$—;

$R_{29}$ is a hydrogen, —CN, —$S(O)_2$—$R_{25}$, —C(O)—N($R_a$)($R_i$), —$NO_2$ or —C(O)—$OR_{25}$;

T' is oxygen, sulfur or $NR_6$;

$R_6$ is a hydrogen, a lower alkyl group or an aryl group;

$V_6$ is:

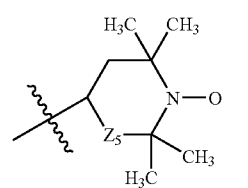 (1)

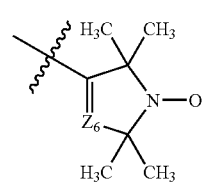 (2)

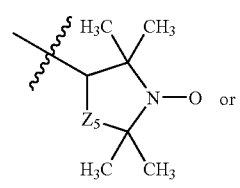 (3)

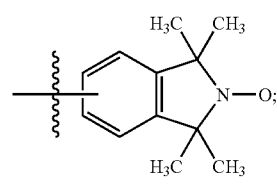 (4)

$Z_5$ is —$CH_2$ or oxygen;

$Z_6$ is —CH or nitrogen;

$k_1$ is an integer from 1 to 3;

W at each occurrence is independently —C(O)—, —C(S)—, -$T_3$-, —(C($R_e$)($R_f$))$_h$—, —N($R_a$)$R_i$, an alkyl group, an aryl group, a heterocyclic ring, an arylheterocyclic ring, —(CH$_2$CH$_2$O)$_{q1}$— or a heterocyclic nitric oxide donor;

E at each occurrence is independently -$T_3$-, an alkyl group, an aryl group, —(C($R_e$)($R_f$))$_h$—, a heterocyclic ring, an arylheterocyclic ring, —(CH$_2$CH$_2$O)$_{q1}$— or $Y_4$;

$Y_4$ is:

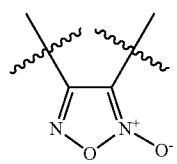 (1)

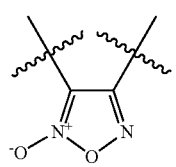 (2)

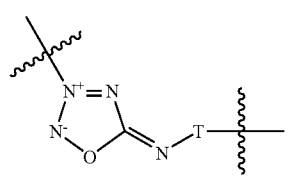 (3)

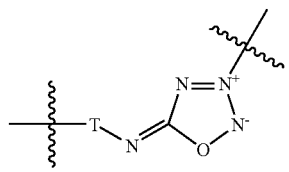 (4)

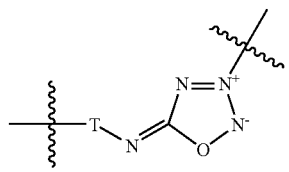 (5)

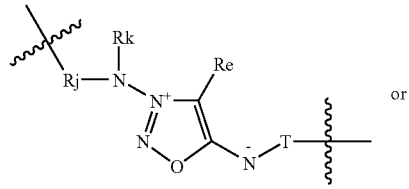 (6)

T is a —$S(O)_o$—; a carbonyl or a covalent bond;

o is an integer from 0 to 2;

$R_j$ and $R_k$ are independently selected from an alkyl group, an aryl group, or $R_j$ and $R_k$ taken together with the nitrogen atom to which they are attached are a heterocyclic ring;

$T_3$ at each occurrence is independently a covalent bond, a carbonyl, an oxygen, —$S(O)_o$— or —N($R_a$)$R_i$;

h is an integer form 1 to 10;

$q_1$ is an integer from 1 to 5;

$R_e$ and $R_f$ are each independently a hydrogen, an alkyl, a cycloalkoxy, a halogen, a hydroxy, an hydroxyalkyl, an alkoxyalkyl, an arylheterocyclic ring, an alkylaryl, an alkylcycloalkyl, an alkylheterocyclic ring, a cycloalkylalkyl, a cycloalkylthio, an arylalklythio, an arylalklythioalkyl, an alkylthioalkyl, a cycloalkenyl, an heterocyclicalkyl, an alkoxy, a haloalkoxy, an amino, an alkylamino, a dialkylamino, an arylamino, a diarylamino, an alkylarylamino, an alkoxyhaloalkyl, a sulfonic acid, a sulfonic ester, an alkylsulfonic acid, an arylsulfonic acid, an arylalkoxy, an alkylthio, an arylthio, a cyano, an aminoalkyl, an aminoaryl, an aryl, an arylalkyl, an alkylaryl, a carboxamido, an alkylcarboxamido, an arylcarboxamido, an amidyl, a carboxyl, a carbamoyl, an alkylcarboxylic acid, an arylcarboxylic acid, an alkylcarbonyl, an arylcarbonyl, an ester, a carboxylic ester, an alkylcarboxylic ester, an arylcarboxylic ester, a sulfonamido, an alkylsulfonamido, an arylsulfonamido, an alkylsulfonyl, an alkylsulfonyloxy, an arylsulfonyl, arylsulphonyloxy, a sulfonic ester, an alkyl ester, an aryl ester, a urea, a phosphoryl, a nitro, $-U_3-V_5$, $V_6$, $-(C(R_o)(R_p))_{k1}-U_3-V_5$, $-(C(R_o)(R_p))_{k1}-U_3-V_3$, $-(C(R_o)(R_p))_{k1}-U_3-V_6$, $-(C(R_o)(R_p))_{k1}-U_3-C(O)-V_6$, or $R_e$ and $R_f$ taken together with the carbons to which they are attached form a carbonyl, a methanthial, a heterocyclic ring, a cycloalkyl group, an aryl group, an oxime, an imine, a hydrazone, a bridged cycloalkyl group,

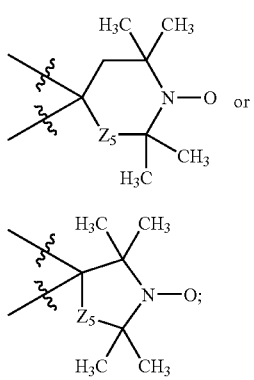

$R_o$ and $R_p$ are each independently a hydrogen, an alkyl, a cycloalkoxy, a halogen, a hydroxy, an hydroxyalkyl, an alkoxyalkyl, an arylheterocyclic ring, an alkylaryl, an alkylcycloalkyl, an alkylheterocyclic ring, a cycloalkylalkyl, a cycloalkylthio, an arylalklythio, an arylalklythioalkyl, an alkylthioalkyl a cycloalkenyl, an heterocyclicalkyl, an alkoxy, a haloalkoxy, an amino, an alkylamino, a dialkylamino, an arylamino, a diarylamino, an alkylarylamino, an alkoxyhaloalkyl, a sulfonic acid, a sulfonic ester, an alkylsulfonic acid, an arylsulfonic acid, an arylalkoxy, an alkylthio, an arylthio, a cyano an aminoalkyl, an aminoaryl, an aryl, an arylalkyl, an alkylaryl, a carboxamido, an alkylcarboxamido, an arylcarboxamido, an amidyl, a carboxyl, a carbamoyl, an alkylcarboxylic acid, an arylcarboxylic acid, an alkylcarbonyl, an arylcarbonyl, an ester, a carboxylic ester, an alkylcarboxylic ester, an arylcarboxylic ester, a sulfonamido, an alkylsulfonamido, an arylsulfonamido, an alkylsulfonyl, an alkylsulfonyloxy, an arylsulfonyl, arylsulphonyloxy, a sulfonic ester, an alkyl ester, an aryl ester, a urea, a phosphoryl, a nitro, $-U_3-V_5$, $V_6$, or $R_o$ and $R_p$ taken together with the carbons to which they are attached form a carbonyl, a methanthial, a heterocyclic ring, a cycloalkyl group, an aryl group, an oxime, an imine, a hydrazone a bridged cycloalkyl group,

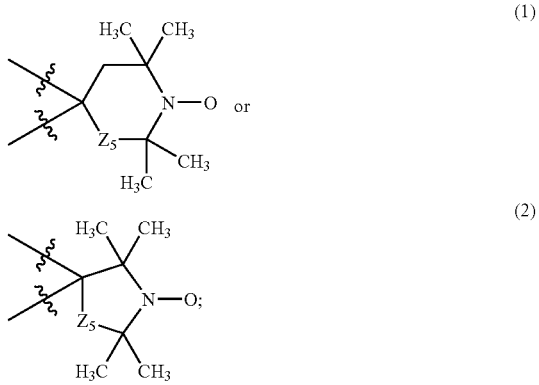

$U_3$ is an oxygen, sulfur or $-N(R_a)R_i$;

$V_5$ is $-NO$ or $-NO_2$ (i.e. an oxidized nitrogen);

$k_1$ is an integer from 1 to 3;

$R_a$ is a lone pair of electrons, a hydrogen or an alkyl group;

$R_i$ is a hydrogen, an alkyl, an aryl, an alkylcarboxylic acid, an arylcarboxylic acid, an alkylcarboxylic ester, an arylcarboxylic ester, an alkylcarboxamido, an arylcarboxamido, an alkylaryl, an alkylsulfinyl, an alkylsulfonyl, an alkylsulfonyloxy, an arylsulfinyl, an arylsulfonyl, an arylsulphonyloxy, a sulfonamido, a carboxamido, a carboxylic ester, an aminoalkyl, an aminoaryl, $-CH_2-C-(U_3-V_5)(R_e)(R_f)$, a bond to an adjacent atom creating a double bond to that atom or $-(N_2O_2-).M_1^+$, wherein $M_1^+$ is an organic or inorganic cation; and with the proviso that the compound of Formula (I) must contain at least one group selected from a $-ONO$ group, a $-SNO$ group, a $-NNO$ group, a $-ONO_2$ group, -a $SNO_2$ group, a $-NNO_2$ group, a $-(N_2O_2-).M_1^+$ group, a heterocyclic nitric oxide donor group and a nitroxide group where the group is linked to the compound of Formula (I) through a carbon, oxygen or nitrogen atom via a bond that cannot be hydrolyzed.

2. A composition comprising the compound of claim 1 and a pharmaceutically acceptable carrier.

3. The compound of claim 1, wherein the compound of Formula (I) is a hydrochlorothiazide, a hydroflumethiazide, that contains at least one group selected from a $-ONO$ group, a $-SNO$ group, a $-NNO$ group, a $-ONO_2$ group, -a $SNO_2$ group, a $-NNO_2$ group, a $-(N_2O_2-).M_1^+$ group, a heterocyclic nitric oxide donor group and a nitroxide group where the group is linked to the hydrochlorothiazide or hydroflumethiazide through a carbon, oxygen or nitrogen atom via a bond that cannot be hydrolyzed; or a pharmaceutically acceptable salts thereof.

4. A compound selected from the following Formulas, or a pharmaceutically acceptable salt thereof

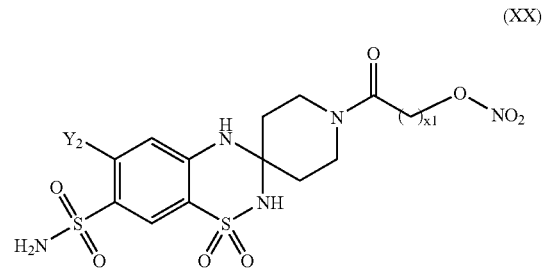

-continued (XXI)

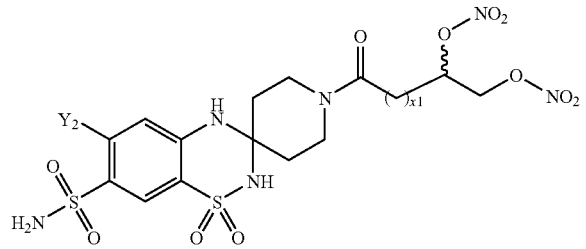

(XXII)

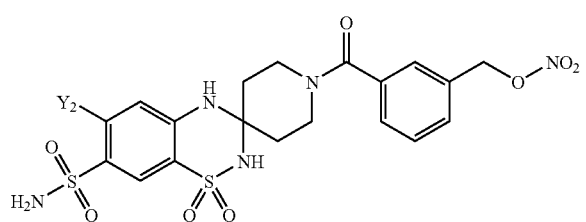

$Y_2$ is chlorine or $CF_3$;

$x_1$ is an integer from 1 to 6;

$y_1$ is an integer from 0 to 3

$R_{30}$ is a hydrogen, a lower alkyl group, $-(CH_2)_{x1}-O-NO_2$; and $R_{31}$ is a hydrogen or a lower alkyl group.

5. A method for treating a condition resulting from excessive water and/or electrolyte retention in a patient in need thereof comprising administering to the patient a therapeutically effective amount of the composition of claim 2, wherein the condition resulting from excessive water and/or electrolyte retention is a result of lower extremity swelling, fatigue, body fluid retention, a cardiac enlargement, a pulmonary edema, a cerebral edema, cirrhosis of the liver, poor blood circulation, a lymphatic system failure, chronic nephritis, malnutrition, premenstrual syndrome, sunburn, hypertension, Meniere's disease, glaucoma, cystic fibrosis and/or an imbalance of sodium and potassium.

6. A method for treating a cardiovascular disease in a patient in need thereof comprising administering to the patient a therapeutically effective amount of the composition of claim 2, wherein the cardiovascular disease is heart failure, restenosis, hypertension, diastolic dysfunction, a coronary artery disease, myocardial infarction, cerebral infarction, atherosclerosis, atherogenesis, cerebrovascular disease, angina, aneurysm, ischemic heart disease, cerebral ischemia, myocardial ischemia, thrombosis, platelet aggregation, platelet adhesion, smooth muscle cell proliferation, vascular or non-vascular wall damage, peripheral vascular disease, neointimal hyperplasia following percutaneous transluminal coronary angiograph, vascular grafting, coronary artery bypass surgery, a thromboembolic event, post-angioplasty restenosis, coronary plaque inflammation, hypercholesterolemia, embolism, stroke, shock, arrhythmia, atrial fibrillation or atrial flutter, or thrombotic occlusion and reclusion cerebrovascular incident.

7. The method of claim 6, wherein the cardiovascular disease is hypertension, heart failure or diastolic dysfunction.

8. A method for treating a renovascular disease in a patient in need thereof comprising administering to the patient a therapeutically effective amount of the composition of claim 2, wherein the renovascular disease is renal failure, renal insufficiency, renal deterioration associated with severe hypertension or renovascular hypertension.

9. The method of claims 5, 6, or 8, further comprising administering (i) at least one therapeutic agent; (ii) at least one nitric oxide enhancing compound (iii) at least one therapeutic agent and at least one nitric oxide enhancing compound.

10. The method of claim 9, wherein the therapeutic agent is an aldosterone antagonist, an alpha adrenergic receptor agonists, an alpha-adrenergic receptor antagonist, an angiotensin II antagonist, an angiotensin-converting enzyme inhibitor, an antidiabetic compound, an anti-hyperlipidemic compound, an antimicrobial compound, an antioxidant, an antithrombotic and vasodilator compound, a β-adrenergic antagonist, a calcium channel blocker, a carbonic anhydrase inhibitor, a digitalis, a diuretic, an endothelin antagonist, a hydralazine compound, a $H_2$ receptor antagonist, a neutral endopeptidase inhibitor, a nonsteroidal antiinflammatory compound, a phosphodiesterase inhibitor, a potassium channel blocker, a platelet reducing agent, a prostaglandin, a proton pump inhibitor, a renin inhibitor, a selective cyclooxygenase-2 inhibitor, a steroid, or a combination of two or more thereof.

11. The method of claim 9, wherein the nitric oxide donor compound is selected from the group consisting of a S-nitrosothiol, a nitrite, a nitrate, a S-nitrothiol, a sydnonimine, a NONOate, a N-nitrosoamine, a N-hydroxyl nitrosamine, a nitrosimine, a diazetine dioxide, an oxatriazole 5-imine, an oxime, a hydroxylamine, a N-hydroxyguanidine compound, a hydroxyurea, a furoxan or a nitroxide.

12. A compound selected from the group consisting of:
   spiro[2H-1,2,4-benzothiadiazine-3(4H), 4'-piperidin]-1'-yloxy, 7-(aminosulfonyl)-6-chloro-2',2',6',6'-tetramethyl-1,1-dioxido-;
   spiro[2H-1,2,4-benzothiadiazine-3(4H), 4'-piperidine]-7-sulfonamide, 1'-[5-(nitrooxy)-1-oxopentyl]-6-(trifluoromethyl)-, 1,1-dioxide;
   spiro[2H-1,2,4-benzothiadiazine-3(4H), 4'-piperidine]-7-sulfonamide, 1'-[3-[(nitrooxy)methyl]benzoyl]-6-(trifluoromethyl)-, 1,1-dioxide;
   spiro[2H-1,2,4-benzothiadiazine-3(4H), 4'-piperidine]-7-sulfonamide, 1'-[2-methyl-3-(nitrooxy)-2-[(nitrooxy)methyl]-1-oxopropyl]-6-(trifluoromethyl)-, 1,1-dioxide;
   spiro[2H-1,2,4-benzothiadiazine-3(4H), 4'-piperidine]-7-sulfonamide, 1'-[2,2-dimethyl-3-(nitrooxy)-1-oxopropyl]-6-(trifluoromethyl)-, 1,1-dioxide; and pharmaceutically acceptable salts thereof.

* * * * *